United States Patent
Suzuki et al.

(10) Patent No.: US 10,207,992 B2
(45) Date of Patent: Feb. 19, 2019

(54) DIBENZOCARBAZOLE COMPOUND, LIGHT-EMITTING ELEMENT, LIGHT-EMITTING DEVICE, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Hiroki Suzuki, Kanagawa (JP); Satoshi Seo, Kanagawa (JP); Tsunenori Suzuki, Kanagawa (JP); Naoaki Hashimoto, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 169 days.

(21) Appl. No.: 15/334,929

(22) Filed: Oct. 26, 2016

(65) Prior Publication Data

US 2017/0125703 A1 May 4, 2017

(30) Foreign Application Priority Data

Oct. 30, 2015 (JP) .................................. 2015-214392

(51) Int. Cl.
| | | |
|---|---|---|
| C07D 209/80 | (2006.01) | |
| H01L 51/00 | (2006.01) | |
| C09K 11/02 | (2006.01) | |
| C09K 11/06 | (2006.01) | |
| H05B 33/14 | (2006.01) | |
| H05B 33/20 | (2006.01) | |
| H01L 51/50 | (2006.01) | |

(52) U.S. Cl.
CPC ............ *C07D 209/80* (2013.01); *C09K 11/02* (2013.01); *C09K 11/06* (2013.01); *H01L 51/0052* (2013.01); *H01L 51/0072* (2013.01); *H05B 33/14* (2013.01); *H05B 33/20* (2013.01); *C09K 2211/1007* (2013.01); *C09K 2211/1011* (2013.01); *C09K 2211/1014* (2013.01); *H01L 51/5016* (2013.01); *Y02P 20/582* (2015.11)

(58) Field of Classification Search
CPC .................................................... C07D 209/80
See application file for complete search history.

(56) References Cited

U.S. PATENT DOCUMENTS

| | | | |
|---|---|---|---|
| 8,178,217 | B2 | 5/2012 | Nomura et al. |
| 8,183,793 | B2 | 5/2012 | Egawa et al. |
| 8,986,857 | B2 | 3/2015 | Suzuki et al. |
| 9,240,558 | B2 | 1/2016 | Suzuki et al. |
| 9,257,655 | B2 | 2/2016 | Suzuki et al. |
| 9,412,962 | B2 | 8/2016 | Hamada et al. |
| 9,419,237 | B2 | 8/2016 | Shitagaki et al. |
| 2007/0031701 | A1 | 2/2007 | Nakashima et al. |
| 2007/0080630 | A1 | 4/2007 | Egawa et al. |
| 2007/0215889 | A1 | 9/2007 | Kawakami et al. |
| 2008/0122344 | A1 | 5/2008 | Shin et al. |
| 2016/0126463 | A1 | 5/2016 | Kadoma et al. |
| 2016/0233437 | A1 | 8/2016 | Suzuki et al. |
| 2017/0125704 | A1 | 5/2017 | Suzuki et al. |

FOREIGN PATENT DOCUMENTS

| | | | | |
|---|---|---|---|---|
| JP | 62-147463 | * | 7/1987 | ............ G03G 5/06 |
| KR | 2011-0014752 | | 2/2011 | |
| KR | 2012-0081539 | | 7/2012 | |
| KR | 2015-0034665 | | 4/2015 | |
| WO | WO 2010-114264 A2 | | 7/2010 | |

* cited by examiner

*Primary Examiner* — Joseph R Kosack
(74) *Attorney, Agent, or Firm* — Husch Blackwell LLP

(57) ABSTRACT

A novel dibenzocarbazole compound with which a light-emitting element having low power consumption, high reliability, and high color purity can be fabricated is provided. In the dibenzocarbazole compound, an aryl group which has 14 to 30 carbon atoms and at least an anthracene skeleton is bonded to nitrogen of a dibenzo[a,g]carbazole skeleton or a dibenzo[a,i]carbazole skeleton. Furthermore, a light-emitting element including the dibenzocarbazole compound is provided.

29 Claims, 49 Drawing Sheets

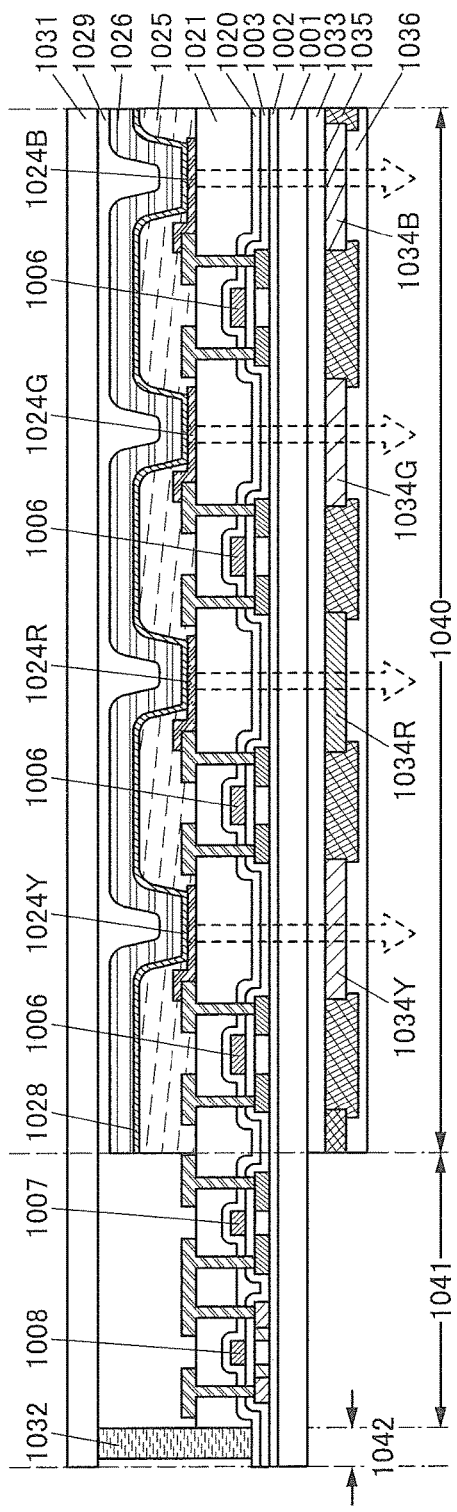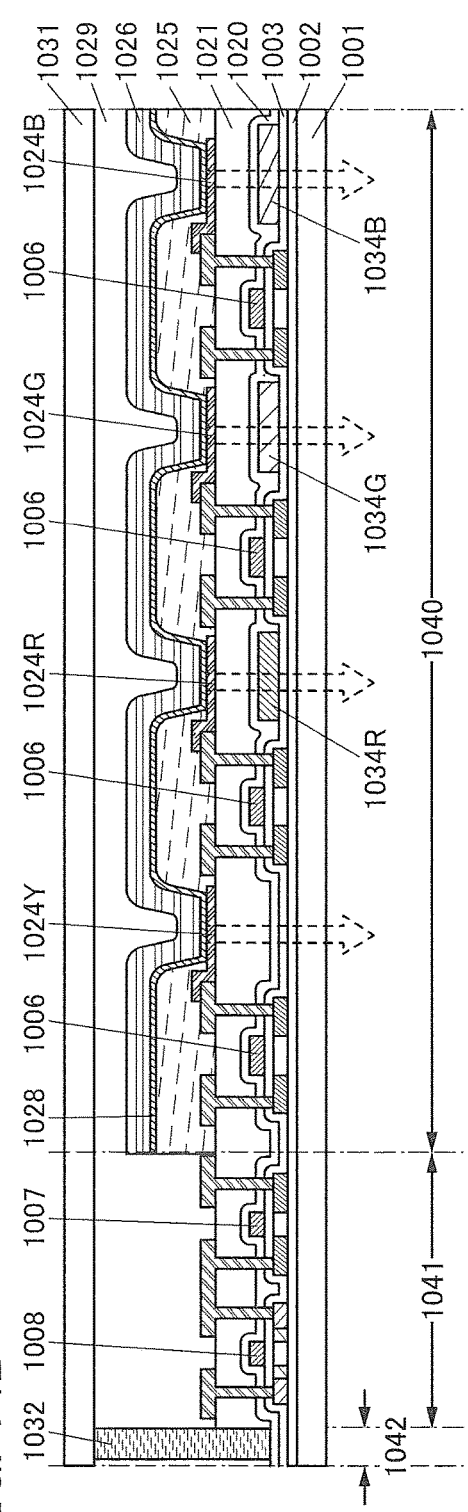

DIBENZOCARBAZOLE COMPOUND, LIGHT-EMITTING ELEMENT, LIGHT-EMITTING DEVICE, DISPLAY DEVICE, ELECTRONIC DEVICE, AND LIGHTING DEVICE

BACKGROUND OF THE INVENTION

1. Field of the Invention

One embodiment of the present invention relates to a dibenzocarbazole compound. One embodiment of the present invention also relates to a light-emitting element, and a light-emitting device, a display device, an electronic device, and a lighting device each including the light-emitting element.

Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, a method for driving any of them, and a method for manufacturing any of them.

2. Description of the Related Art

In recent years, research and development have been extensively conducted on light-emitting elements using electroluminescence (EL). In a basic structure of such a light-emitting element, a layer containing a light-emitting material (an EL layer) is interposed between a pair of electrodes. By applying a voltage between the pair of electrodes of this element, light emission from the light-emitting material can be obtained.

Since the above light-emitting element is of a self-luminous type, a display device using this light-emitting element has advantages such as high visibility, no necessity of a backlight, low power consumption, and the like. Furthermore, the display device also has advantages in that it can be formed to be thin and lightweight, and has high response speed.

In a light-emitting element (e.g., an organic EL element) whose EL layer contains an organic material as a light-emitting material and is provided between a pair of electrodes, application of a voltage between the pair of electrodes causes injection of electrons from a cathode and holes from an anode into the EL layer having a light-emitting property and thus a current flows. By recombination of the injected electrons and holes, the organic material having a light-emitting property is brought into an excited state to provide light emission.

Note that an excited state formed by an organic material can be a singlet excited state (S*) or a triplet excited state (T*). Light emission from the singlet excited state is referred to as fluorescence, and light emission from the triplet excited state is referred to as phosphorescence. The statistical generation ratio of the excited states in the light-emitting element is considered to be S*:T*=1:3. In other words, a light-emitting element including a material that emits phosphorescence (a phosphorescent material) has higher emission efficiency than a light-emitting element including a material that emits fluorescence (a fluorescent material). Therefore, light-emitting elements containing phosphorescent materials capable of converting energy of the triplet excited state into light emission have been actively developed in recent years.

Among light-emitting elements including phosphorescent materials, a light-emitting element that emits blue light has not been put into practical use yet because it is difficult to develop a stable material having a high triplet excitation energy level. For this reason, a light-emitting element including a more stable fluorescent material has been developed for a light-emitting element that emits blue light and a material for increasing the emission efficiency and lifetime of a light-emitting element including a fluorescent material has been searched.

Note that the performance of a light-emitting element, such as emission efficiency or lifetime, is significantly affected by not only the performance of a light-emitting material but also the performance of a host material for exciting the light-emitting material or a carrier-transport material for transporting a carrier. Therefore, materials having a variety of molecular structures have been proposed in order to increase the emission efficiency and the lifetime of a light-emitting element (for example, Patent Documents 1 and 2).

In particular, as for a light-emitting element that emits deep blue light, not only a light-emitting material but also a host material for exciting the light-emitting material needs to have high excitation energy. Accordingly, development of a highly stable host material which can excite a light-emitting material efficiently has been required.

REFERENCE

Patent Document

[Patent Document 1] United States Published Patent Application No. 2008/0122344
[Patent Document 2] PCT International Publication No. 2010/114264

SUMMARY OF THE INVENTION

As an example of a material which can be used as a host material of a light-emitting element that emits blue fluorescence, 9-[4-(10-phenyl-9-anthryl)phenyl]-9H-carbazole (abbreviation: CzPA) can be given. By using CzPA as a host material, a light-emitting element that emits blue fluorescence and has excellent characteristics in terms of emission efficiency and driving lifetime can be fabricated.

However, in recent years, display devices with low power consumption and high color reproducibility have been required with demand for higher performance. Therefore, light-emitting elements that emits light with higher color purity and has higher emission efficiency have been required. In particular, light-emitting elements that have high efficiency and long lifetime and emit deep blue light have been required. Note that although many light-emitting element materials have been proposed so far, it is difficult to develop a material with which a light-emitting element having high emission efficiency and long lifetime and emitting deep blue light can be achieved.

An object of one embodiment of the present invention is to provide a novel compound. Another object of one embodiment of the present invention is to provide a novel compound with which a light-emitting element having high emission efficiency can be achieved. Another object of one embodiment of the present invention is to provide a novel compound with which a light-emitting element having lower power consumption can be achieved. Another object of one embodiment of the present invention is to provide a novel compound with which a light-emitting element having long lifetime can be achieved. Another object of one embodiment of the present invention is to provide a novel compound with which a novel light-emitting element can be achieved. Another object of one embodiment of the present invention is to provide a light-emitting element including a novel compound. Another object of one embodiment of the present invention is to provide a light-emitting element with high emission efficiency. Another object of one embodiment of the present invention is to provide a light-emitting element which emits blue light with high emission efficiency. Another object of one embodiment of the present invention is to provide a light-emitting element with long lifetime. Another object of one embodiment of the present invention is to provide a novel light-emitting device. Another object of one embodiment of the present invention is to provide a novel display device. Another object of one embodiment of the present invention is to provide a novel electronic device. Another object of one embodiment of the present invention is to provide a novel lighting device.

Note that the description of the above objects does not disturb the existence of other objects. In one embodiment of the present invention, there is no need to achieve all the objects. Other objects are apparent from and can be derived from the description of the specification and the like.

The present inventors synthesized a novel dibenzocarbazole compound including a dibenzo[a,g]carbazole skeleton or a dibenzo[a,i]carbazole skeleton and an anthracene skeleton and have found that a light-emitting element having excellent characteristics can be provided when the dibenzocarbazole compound is used.

That is, one embodiment of the present invention is a dibenzocarbazole compound in which an aryl group is bonded to a dibenzo[a,g]carbazole skeleton or a dibenzo[a,i]carbazole skeleton and the aryl group is an aryl group which has 14 to 30 carbon atoms and at least an anthracene skeleton.

Another embodiment of the present invention is a dibenzocarbazole compound in which an aryl group is bonded to the 7-position of a dibenzo[a,g]carbazole skeleton or the 11-position of a dibenzo[a,i]carbazole skeleton and the aryl group is an aryl group which has 14 to 30 carbon atoms and at least an anthracene skeleton.

Another embodiment of the present invention is a dibenzocarbazole compound in which the 7-position of a dibenzo[a,g]carbazole skeleton or the 11-position of a dibenzo[a,i]carbazole skeleton is bonded to an anthracene skeleton through a phenylene group.

Another embodiment of the present invention is a dibenzocarbazole compound in which the 7-position of a dibenzo[a,g]carbazole skeleton or the 11-position of a dibenzo[a,i]carbazole skeleton is bonded to the 9-position of an anthracene skeleton through a phenylene group.

Another embodiment of the present invention is a dibenzocarbazole compound in which the 7-position of a dibenzo[a,g]carbazole skeleton or the 11-position of a dibenzo[a,i]carbazole skeleton is bonded to a substituted or unsubstituted anthryl phenyl group having 20 to 30 carbon atoms.

Another embodiment of the present invention is a dibenzocarbazole compound in which the 7-position of a dibenzo[a,g]carbazole skeleton or the 11-position of a dibenzo[a,i]carbazole skeleton is bonded to a substituted or unsubstituted (9-anthryl)phenyl group having 20 to 30 carbon atoms.

Another embodiment of the present invention is a dibenzocarbazole compound represented by General Formula (G1).

[Chemical formula 1]

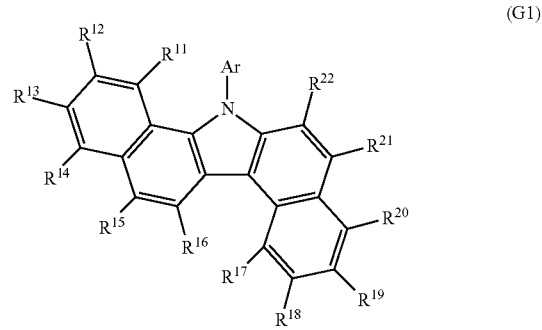

(G1)

In General Formula (G1), $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and Ar represents a substituted or unsubstituted aryl group which has 14 to 30 carbon atoms and at least an anthracene skeleton.

Another embodiment of the present invention is a dibenzocarbazole compound represented by General Formula (G2).

[Chemical Formula 2]

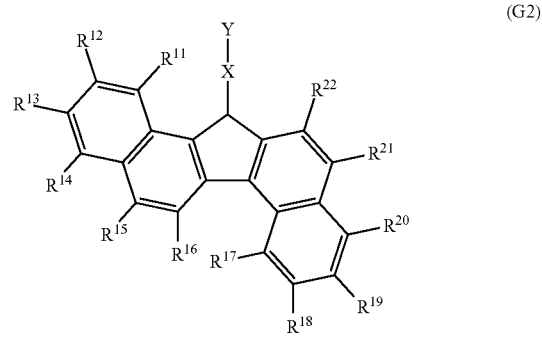

(G2)

In General Formula (G2), $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; X represents a substituted or unsubstituted arylene group having 6 to 13 carbon atoms; and Y represents a substituted or unsubstituted anthryl group.

In the above structure, the total number of carbon atoms of X and Y is preferably 20 to 30.

Another embodiment of the present invention is a dibenzocarbazole compound represented by General Formula (G3).

[Chemical Formula 3]

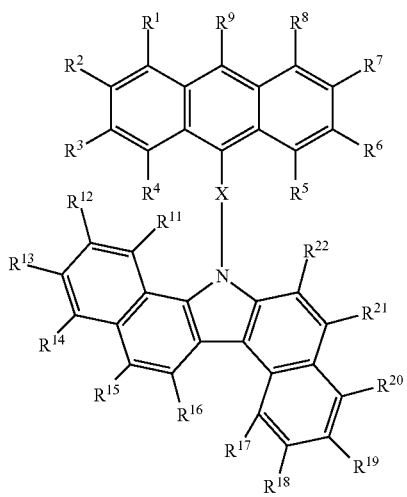

(G3)

In General Formula (G3), $R^1$ to $R^8$ each independently represent hydrogen or an alkyl group having 1 to 4 carbon atoms; $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and X represents a substituted or unsubstituted arylene group having 6 to 13 carbon atoms.

In the above structure, the total number of carbon atoms of $R^1$ to $R^9$ and X is preferably 6 to 16.

In any of the above structures, X preferably represents a substituted or unsubstituted phenylene group.

Another embodiment of the present invention is a dibenzocarbazole compound represented by General Formula (G4).

[Chemical Formula 4]

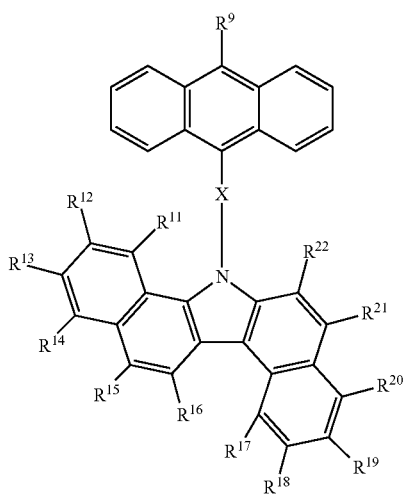

(G4)

In General Formula (G4), $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and X represents a substituted or unsubstituted phenylene group.

Another embodiment of the present invention is a dibenzocarbazole compound represented by General Formula (G5).

[Chemical Formula 5]

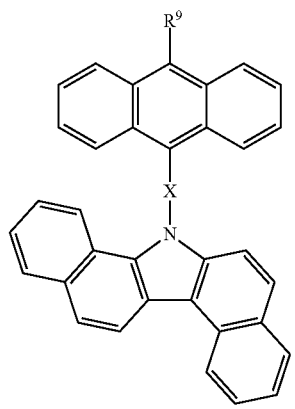

(G5)

In General Formula (G5), $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted phenylene group.

In any of the above structures, the total number of carbon atoms of $R^9$ and X is preferably 6 to 16.

Another embodiment of the present invention is a dibenzocarbazole compound represented by Structural Formula (100).

[Chemical Formula 6]

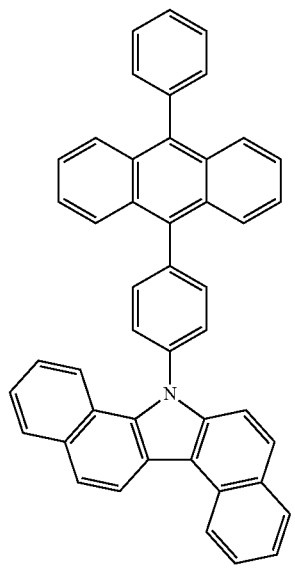

(100)

Another embodiment of the present invention is a dibenzocarbazole compound represented by General Formula (G6).

[Chemical Formula 7]

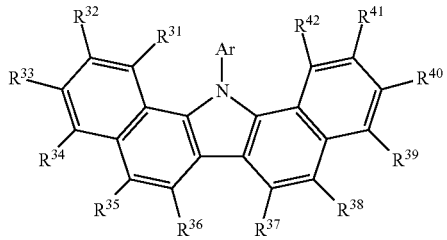

(G6)

In General Formula (G6), $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and Ar represents a substituted or unsubstituted aryl group which has 14 to 30 carbon atoms and at least an anthracene skeleton.

Another embodiment of the present invention is a dibenzocarbazole compound represented by General Formula (G7).

[Chemical Formula 8]

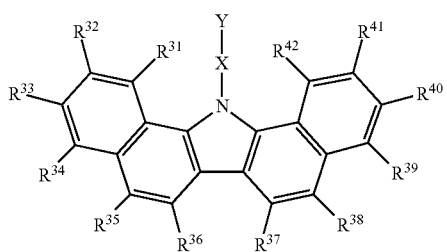

(G7)

In General Formula (G7), $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; X represents a substituted or unsubstituted arylene group having 6 to 13 carbon atoms; and Y represents a substituted or unsubstituted anthryl group.

In the above structure, the total number of carbon atoms of X and Y is preferably 20 to 30.

Another embodiment of the present invention is a dibenzocarbazole compound represented by General Formula (G8).

[Chemical Formula 9]

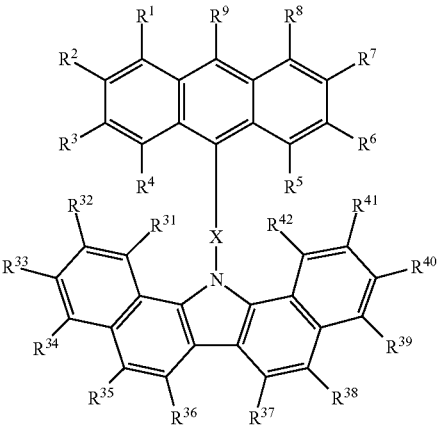

(G8)

In General Formula (G8), $R^1$ to $R^8$ each independently represent hydrogen or an alkyl group having 1 to 4 carbon atoms; $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and X represents a substituted or unsubstituted arylene group having 6 to 13 carbon atoms.

In the above structure, the total number of carbon atoms of $R^1$ to $R^9$ and X is preferably 6 to 16.

In any of the above structures, X preferably represents a substituted or unsubstituted phenylene group.

Another embodiment of the present invention is a dibenzocarbazole compound represented by General Formula (G9).

[Chemical Formula 10]

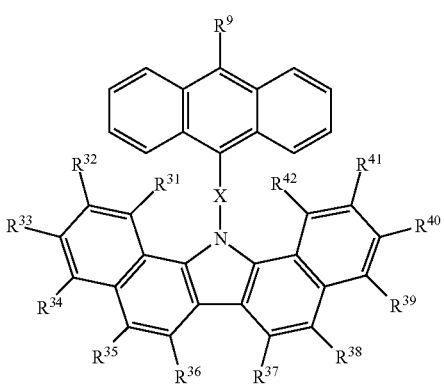

(G9)

In General Formula (G9), $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and X represents a substituted or unsubstituted phenylene group.

Another embodiment of the present invention is a dibenzocarbazole compound represented by General Formula (G10).

[Chemical Formula 11]

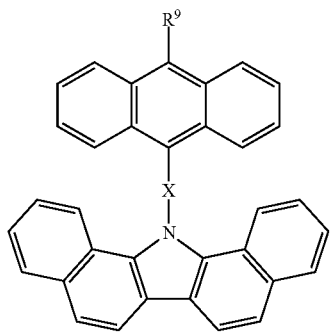

(G10)

In General Formula (G10), $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted phenylene group.

In any of the above structures, the total number of carbon atoms of $R^9$ and X is preferably 6 to 16.

Another embodiment of the present invention is a dibenzocarbazole compound represented by Structural Formula (136).

[Chemical Formula 12]

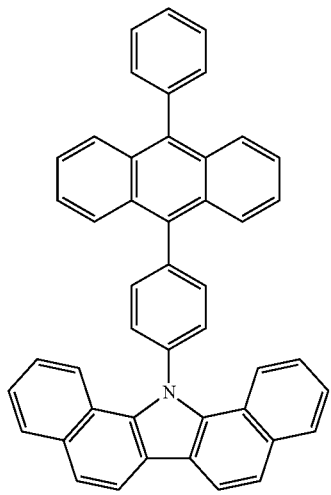

(136)

Another embodiment of the present invention is a light-emitting element including the dibenzocarbazole compound having any of the above structures.

Another embodiment of the present invention is a light-emitting element that includes a light-emitting layer and an electron-transport layer each including the dibenzocarbazole compound having any of the above structures.

Another embodiment of the present invention is a light-emitting element that includes a host material and a guest material. The host material is the dibenzocarbazole compound having any of the above structures.

In the above structure, the guest material preferably has a function of emitting fluorescence. Fluorescence emitted from the guest material is preferably blue. The guest material preferably emits light whose chromaticity y in CIE 1931 chromaticity coordinates is greater than or equal to 0.01 and less than or equal to 0.15.

In any of the above structures, it is preferable that the weight ratio of the guest material to the host material be greater than 0 and less than 0.03.

Another embodiment of the present invention is a light-emitting device including the light-emitting element with any of the above structures and a transistor. Another embodiment of the present invention is a display device including the light-emitting element with any of the above structures and a driving circuit. Another embodiment of the present invention is an electronic device including the light-emitting element with any of the above structures and at least one of a sensor, an operation button, a speaker, and a microphone. Another embodiment of the present invention is a lighting device including the light-emitting element with any of the above structures and at least one of a housing and a touch sensor. The category of one embodiment of the present invention includes not only a light-emitting device including a light-emitting element but also an electronic device including a light-emitting device. Accordingly, a light-emitting device in this specification refers to an image display device or a light source (including a lighting device). A display module in which a connector such as a flexible printed circuit (FPC) or a tape carrier package (TCP) is connected to a light-emitting device, a display module in which a printed wiring board is provided on the tip of a TCP, and a display module in which an integrated circuit (IC) is directly mounted on a light-emitting element by a chip on glass (COG) method are also embodiments of the present invention.

One embodiment of the present invention can provide a novel compound. One embodiment of the present invention can provide a novel compound with which a light-emitting element having high emission efficiency can be achieved. One embodiment of the present invention can provide a novel compound with which a light-emitting element having lower power consumption can be achieved. One embodiment of the present invention can provide a novel compound with which a light-emitting element having long lifetime can be achieved. One embodiment of the present invention can provide a novel compound with which a novel light-emitting element can be achieved. One embodiment of the present invention can provide a light-emitting element including the novel compound. One embodiment of the present invention can provide a light-emitting element with high emission efficiency. One embodiment of the present invention can provide a light-emitting element that emits blue light with high emission efficiency. One embodiment of the present invention can provide a light-emitting element with long lifetime. One embodiment of the present invention can provide a novel light-emitting device. One embodiment of the present invention can provide a novel display device. One embodiment of the present invention can provide a novel electronic device. One embodiment of the present invention can provide a novel lighting device.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 14A and 14B are schematic cross-sectional views each illustrating a display device of one embodiment of the present invention.

DETAILED DESCRIPTION OF THE INVENTION

Figure 1A:
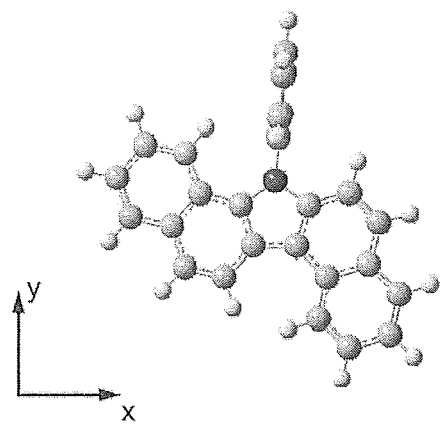
FIGS. 1A to 1F are diagrams illustrating structures of substituents of a compound which is one embodiment of the present invention.

Embodiments of the present invention will be described in detail below with reference to the drawings. However, the present invention is not limited to description to be given below, and modes and details thereof can be variously modified without departing from the purpose and the scope of the present invention. Accordingly, the present invention should not be interpreted as being limited to the content of the embodiments and examples below.

Note that the position, the size, the range, or the like of each structure illustrated in drawings and the like is not accurately represented in some cases for simplification. Therefore, the disclosed invention is not necessarily limited to the position, the size, the range, or the like disclosed in the drawings and the like.

Note that the ordinal numbers such as "first", "second", and the like in this specification and the like are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

In the description of modes of the present invention in this specification and the like with reference to the drawings, the same components in different diagrams are commonly denoted by the same reference numeral in some cases.

In this specification and the like, the terms "film" and "layer" can be interchanged with each other. For example, the term "conductive layer" can be changed into the term "conductive film" in some cases. Also, the term "insulating film" can be changed into the term "insulating layer" in some cases.

In this specification and the like, a singlet excited state (S*) refers to a singlet state having excited energy. Among singlet excited states, an excited state having the lowest energy is referred to as the lowest singlet excited state. Furthermore, a singlet excited energy level means an energy level in a singlet excited state. Among singlet excited energy levels, the lowest excited energy level is referred to as the lowest singlet excited energy ($S_1$) level. Note that in this specification and the like, simple expressions "singlet excited state" and "singlet excitation energy level" mean the lowest singlet excited state and the $S_1$ level, respectively, in some cases.

In this specification and the like, a triplet excited state (T*) means a triplet state having excited energy. Among triplet excited states, an excited state having the lowest energy is referred to as the lowest triplet excited state. Furthermore, a triplet excitation energy level means an energy level in a triplet excited state. Among triplet excitation energy levels, the lowest excitation energy level is referred to as the lowest triplet excitation energy ($T_1$) level. Note that in this specification and the like, simple expressions "triplet excited state" and "triplet excitation energy level" mean the lowest triplet excited state and the $T_1$ level, respectively, in some cases.

In this specification and the like, a fluorescent material refers to a material that emits light in the visible light region when the relaxation from the singlet excited state to the ground state occurs. A phosphorescent material refers to a material that emits light in the visible light region at room temperature when the relaxation from the triplet excited state to the ground state occurs. That is, a phosphorescent material refers to a material that can convert triplet excitation energy into visible light.

Note that in this specification and the like, "room temperature" refers to a temperature higher than or equal to 0° C. and lower than or equal to 40° C.

In this specification and the like, a wavelength range of blue refers to a wavelength range of greater than or equal to 400 nm and less than or equal to 550 nm, and blue light has at least one peak in that range in an emission spectrum.

Embodiment 1

In this embodiment, a compound that can suitably be used in a light-emitting element of one embodiment of the present invention is described below.

A compound of one embodiment of the present invention is a dibenzocarbazole compound in which an aryl group having at least an anthracene skeleton is bonded to a dibenzo[a,g]carbazole skeleton or a dibenzo[a,i]carbazole skeleton. The dibenzo[a,g]carbazole skeleton, the dibenzo[a,i]carbazole skeleton, and the aryl group including an anthracene skeleton have a high carrier-transport property, and thus a light-emitting element including the dibenzocarbazole compound can have a low driving voltage. Furthermore, the dibenzocarbazole compound has a wide band gap, and thus a light-emitting element including the dibenzocarbazole compound can have high emission efficiency. In particular, a light-emitting element that emits blue light with high emission efficiency can be fabricated. In addition, since the dibenzocarbazole compound is highly resistant to repetition of oxidation and reduction, a light-emitting element including the dibenzocarbazole compound can have a long lifetime, in particular, a long driving lifetime. As described above, a light-emitting element including the compound of one embodiment of the present invention can have excellent emission characteristics and high performance.

When the number of carbon atoms of the aryl group is 14 to 30, the dibenzocarbazole compound is a low molecular compound with a relatively low molecular weight and accordingly has a structure suitable for vacuum evaporation (capable of being vacuum-evaporated at relatively low temperature). In general, a lower molecular weight tends to diminish heat resistance after film formation. However, the dibenzocarbazole compound has an advantage in that sufficient heat resistance can be ensured even with a low molecular weight because of the effect of the rigid dibenzo[a,g]carbazole skeleton, dibenzo[a,i]carbazole skeleton, and anthracene skeleton. Note that the dibenzo[a,g]carbazole skeleton or the dibenzo[a,i]carbazole skeleton is preferably bonded to the anthracene skeleton through an arylene group such as a phenylene group or a naphthylene group.

When nitrogen included in the dibenzo[a,g]carbazole skeleton and the dibenzo[a,i]carbazole skeleton is bonded to a substituent, the dibenzo[a,g]carbazole skeleton and the dibenzo[a,i]carbazole skeleton each have a wider band gap and thus can be favorably used for a light-emitting element that emits high-energy light such as blue light. Accordingly, a dibenzocarbazole compound in which the 7-position of a dibenzo[a,g]carbazole skeleton or the 11-position of the dibenzo[a,i]carbazole skeleton is bonded to an anthracene skeleton through an arylene group can be favorably used for a light-emitting element that emits blue light. Note that it is preferable that a phenylene group be used as the arylene group because the dibenzocarbazole compound can be stable and have a low molecular weight.

When the dibenzo[a,g]carbazole skeleton or the dibenzo [a,i]carbazole skeleton is bonded to the 9-position of an anthracene skeleton through an arylene group, the dibenzocarbazole compound has a high carrier-transport property. Accordingly, a light-emitting element including the dibenzocarbazole compound can be driven at low voltage. Note that it is preferable that a phenylene group be used as the arylene group because of its stability and its low molecular weight.

For the above reason, the dibenzocarbazole compound in which the 7-position of the dibenzo[a,g]carbazole skeleton or the 11-position of the dibenzo[a,i]carbazole skeleton is bonded to the 9-position of an anthracene skeleton through an arylene group has a wide band gap and a high carrier-transport property, and thus a light-emitting element including the dibenzocarbazole compound can have low driving voltage and emit blue light with high emission efficiency. Note that it is preferable that a phenylene group be used as the arylene group because of its stability and its low molecular weight.

In other words, the above dibenzocarbazole compound is a dibenzocarbazole compound in which an arylanthracene derivative is bonded to the dibenzo[a,g]carbazole skeleton or the dibenzo[a,i]carbazole skeleton. The dibenzocarbazole compound can be easily synthesized with high purity, so that element deterioration due to impurities can be suppressed. Note that the number of carbon atoms of the arylanthracene derivative bonded to the dibenzo[a,g]carbazole skeleton or the dibenzo[a,i]carbazole skeleton is preferably 20 to 30 in terms of stability of element characteristics and driving lifetime. In this case, the dibenzocarbazole compound can be vacuum-evaporated at relatively low temperature as described above and accordingly is unlikely to deteriorate due to pyrolysis or the like at evaporation. In addition, the compound is excellent in not only driving lifetime but also drive voltage. This is also because of electrochemical stability and high carrier-transport property owing to the molecular structure of the dibenzocarbazole compound in which an anthracene skeleton is bonded to the 7-position of the dibenzo[a,g]carbazole skeleton or the 11-position of the dibenzo[a,i]carbazole skeleton through an arylene group. Note that it is preferable that an anthrylphenyl group be used as the arylanthracene derivative because the dibenzocarbazole compound can be stable and have a low molecular weight.

Furthermore, for the above reason, a dibenzocarbazole compound in which the 9-position of an anthracene skeleton is bonded to the 7-position of the dibenzo[a,g]carbazole skeleton or the 11-position of the dibenzo[a,i]carbazole skeleton through an arylene group is more preferable. It can also be said that a dibenzocarbazole compound in which a (9-anthryl)aryl group is bonded to the 7-position of the dibenzo[a,g]carbazole skeleton or the 11-position of the dibenzo[a,i]carbazole skeleton is more preferable. Note that the number of carbon atoms of a (9-anthryl)aryl group bonded to the 7-position of the dibenzo[a,g]carbazole skeleton or the 11-position of the dibenzo[a,i]carbazole skeleton is preferably 20 to 30 in terms of stability of the compound and the light-emitting element. Thus, the dibenzocarbazole compound has a wide band gap which is a feature due to the effect of the skeleton of the (9-anthryl)aryl group, in addition to the high suitability for evaporation, electrochemical stability, and carrier-transport property described above. Hence, this compound is effective in a structure of a light-emitting element in which the dibenzocarbazole compound is used as a host material of a light-emitting layer and a light-emitting material is added as a guest material to the light-emitting layer. This compound is suitably used as a host material particularly in a blue light-emitting element. Note that it is preferable that a phenyl group be used as an aryl group of the (9-anthryl)aryl group because the dibenzocarbazole compound can be stable and have a low molecular weight. That is, it is preferable that a (9-anthryl) phenyl group be used as the (9-anthryl)aryl group.

<Quantum Chemical Calculation>

The most stable molecular structures of compounds including the dibenzo[a,g]carbazole skeleton or the dibenzo [a,i]carbazole skeleton which is one embodiment of the present invention were derived from quantum chemistry calculation. For comparison, a compound including a dibenzo[c,g]carbazole skeleton was also subjected to quantum chemistry calculation. The compounds which were subjected to the calculation were 7-phenyl-7H-dibenzo[a,g] carbazole (abbreviation: agDBCz), 11-phenyl-11H-dibenzo [a,i]carbazole (abbreviation: aiDBCz), and 7-phenyl-7H-dibenzo[c,g]carbazole (abbreviation: cgDBCz). Molecular structures of the compounds are shown below.

[Chemical Formula 13]

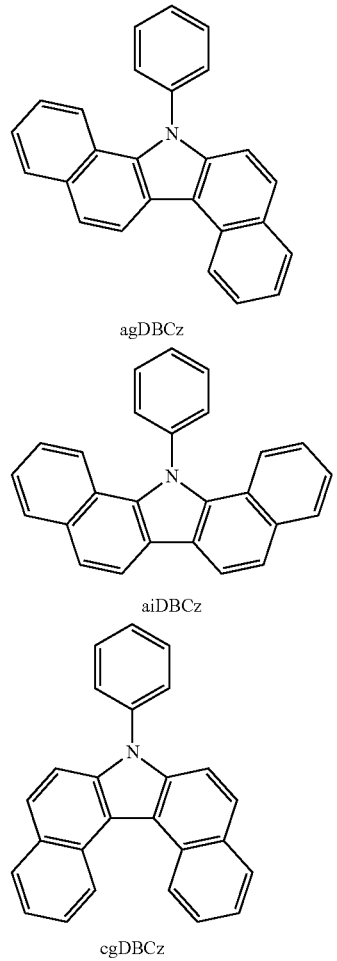

agDBCz aiDBCz cgDBCz

The most stable structure of each of the compounds in a singlet ground state was calculated using the density functional theory (DFT). Note that Gaussian 09 was used as the quantum chemistry computational program. A high performance computer (ICE X, manufactured by SGI Japan, Ltd.) was used for the calculation. As a basis function, 6-311G (d,p) was used, and as a functional, B3LYP was used. In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable high-accuracy calculations.

Figure 1B:
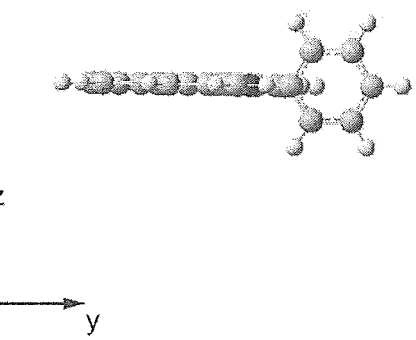
Figure 1C:
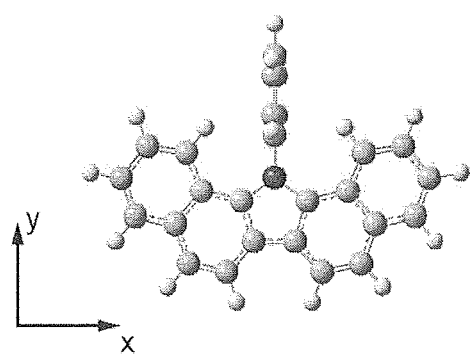
Figure 1D:
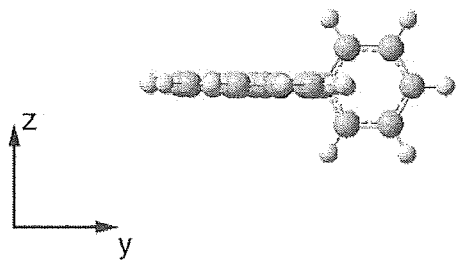
Figure 1E:
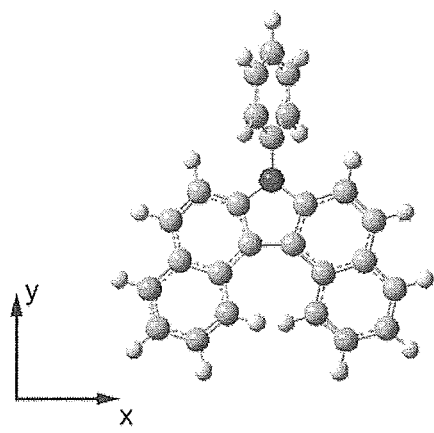
Figure 1F:
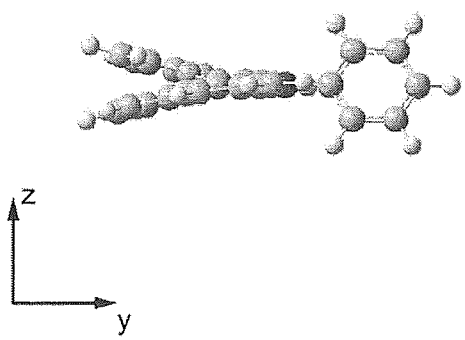

FIGS. 1A to 1F show calculation results. FIGS. 1A and 1B show the result of agDBCz, FIGS. 1C and 1D show the result of aiDBCz, and FIGS. 1E and 1F show the result of cgDBCz. Note that in FIGS. 1A to 1F, a pyrrole ring included in each of the compounds is shown so as to be provided on an x-y plane. FIGS. 1A, 1C, and 1E show the most stable structures of the compounds seen from the x-y plane. FIGS. 1B, 1D, and 1F show the most stable structures of the compounds seen from a y-z plane.

As shown in FIGS. 1B and 1D, the dibenzo[a,g]carbazole skeleton in agDBCz is provided over the x-y plane and the dibenzo[a,i]carbazole skeleton in aiDBCz is provided over the x-y plane. As shown in FIG. 1F, in cgDBCz, hydrogen at the 1-position and hydrogen at the 12-position of the dibenzo[c,g]carbazole skeleton encounter steric hindrance, and thus the dibenzo[c,g]carbazole skeleton on the x-y plane is distorted in the z-axis direction.

That is, it can be said that the molecular structure distortion of the dibenzo[a,g]carbazole skeleton and the dibenzo [a,i]carbazole skeleton is smaller than that of the dibenzo [c,g]carbazole skeleton, and thus the dibenzo[a,g]carbazole skeleton and the dibenzo[a,i]carbazole skeleton are stable skeletons. Accordingly, the dibenzo[a,g]carbazole skeleton or the dibenzo[a,i]carbazole skeleton is used, whereby a stable dibenzocarbazole compound can be formed. A light-emitting element including the dibenzocarbazole compound can have long driving lifetime.

Furthermore, the lowest triplet excitation energy levels (T1 levels) of the above compounds were calculated. For the calculation of the T1 levels of the compounds, the most stable structures of the compounds in a singlet excited state and a triplet excited state were calculated using the density functional theory (DFT). As a basis function, 6-311G(d,p) was used, and as a functional, B3LYP was used. In addition, vibrational levels were calculated, and energy in electron transition between the lowest vibrational levels (0-0 transition) in the singlet excited state and the triplet excited state was calculated, whereby the T1 levels were calculated.

As a result of the calculation, the triplet excitation energy levels of agDBCz, aiDBCz, and cgDBCz were 2.44 eV, 2.60 eV, and 2.28 eV, respectively. That is, agDBCz and aiDBCz have higher triplet excitation energy than cgDBCz. Accordingly, the dibenzo[a,g]carbazole skeleton and the dibenzo [a,i]carbazole skeleton are favorably combined with a benzo [a]anthracene skeleton or the like having higher triplet excitation energy than an anthracene skeleton.

Example 1 of Compound

The above dibenzocarbazole compound which is one embodiment of the present invention is a dibenzocarbazole compound represented by General Formula (G1).

[Chemical Formula 14]

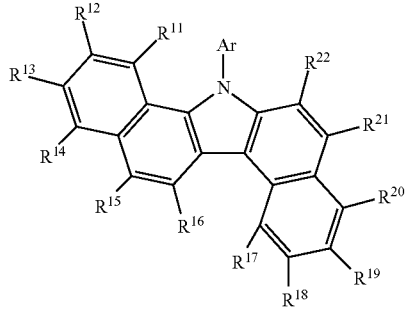

(G1)

In General Formula (G1), Ar represents a substituted or unsubstituted aryl group which has 14 to 30 carbon atoms and at least an anthracene skeleton. In the case where the aryl group has a substituent, as the substituent, an alkyl group having 1 to 6 carbon atoms, a substituted or unsubstituted cycloalkyl group having 3 to 6 carbon atoms, or a substituted or unsubstituted aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Furthermore, $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Example 2 of Compound

A dibenzocarbazole compound of one embodiment of the present invention, in which the 7-position of the dibenzo[a, g]carbazole skeleton is bonded to the aryl group having at least an anthracene skeleton, has a wide band gap and thus can be favorably used for a light-emitting element that emits high-energy light such as blue light, which is preferable. Furthermore, since the dibenzocarbazole compound has a high carrier-transport property, a light-emitting element including the compound can be driven at low voltage, which is preferable. The above dibenzocarbazole compound is a dibenzocarbazole compound represented by General Formula (G2).

[Chemical Formula 15]

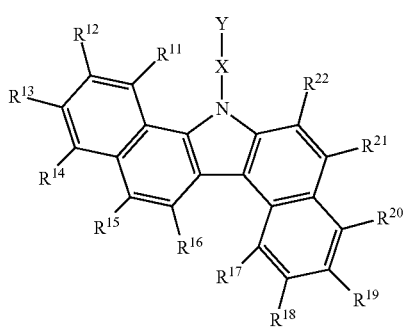

(G2)

In General Formula (G2), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a substituted or unsubstituted cycloalkyl group having 3 to 6 carbon atoms, or a substituted or unsubstituted aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

Y represents a substituted or unsubstituted anthryl group. In the case where the anthryl group has a substituent, as the substituent, an alkyl group having 1 to 6 carbon atoms, a substituted or unsubstituted cycloalkyl group having 3 to 6 carbon atoms, or a substituted or unsubstituted aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

Furthermore, $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above alkyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Note that the total number of carbon atoms of X and Y is preferably 20 to 30 in General Formula (G2), in which case the dibenzocarbazole compound is a low molecular compound with a relatively low molecular weight and accordingly has a structure suitable for vacuum evaporation (capable of being vacuum-evaporated at a relatively low temperature).

X is preferably a substituted or unsubstituted phenylene group in General Formula (G2), in which case the dibenzocarbazole compound is stable and has a low molecular weight.

Example 3 of Compound

A dibenzocarbazole compound of one embodiment of the present invention, in which the 7-position of the dibenzo[a,g]carbazole skeleton is bonded to the 9-position of an anthracene skeleton through an arylene group, has a high carrier-transport property, and thus a light-emitting element including the compound can be driven at low voltage, which is preferable. The above dibenzocarbazole compound is a dibenzocarbazole compound represented by General Formula (G3).

[Chemical Formula 16]

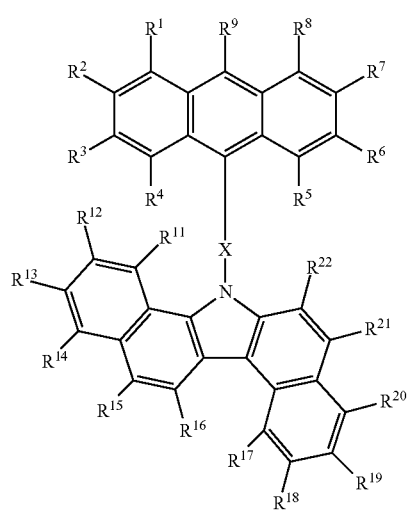

(G3)

In General Formula (G3), X represents a substituted or unsubstituted arylene group having 6 to 13 carbon atoms.

Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a cycloalkyl group having 3 to 6 carbon atoms, or an aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

$R^1$ to $R^8$ each independently represent hydrogen or an alkyl group having 1 to 4 carbon atoms. Specific examples of the alkyl group having 1 to 4 carbon atoms include a methyl group, an ethyl group, a propyl group, an isopropyl group, a butyl group, an isobutyl group, and a tert-butyl group.

$R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group. The above aryl group may include a substituent. An alkyl group having 1 to 4 carbon atoms can be selected as the substituent. Specific examples of the alkyl group having 1 to 4 carbon atoms include a methyl group, an ethyl group, a propyl group, an isopropyl group, a butyl group, an isobutyl group, and a tert-butyl group.

Furthermore, $R^{11}$ to $R^{22}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, a fluorenyl group, and the like. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, a biphenyl group, and the like.

Note that the total number of carbon atoms of $R^1$ to $R^9$ and X is preferably 6 to 16 in General Formula (G3), in which case the dibenzocarbazole compound is a low molecular compound with a relatively low molecular weight and accordingly has a structure suitable for vacuum evaporation (capable of being vacuum-evaporated at a relatively low temperature).

X is preferably a substituted or unsubstituted phenylene group in General Formula (G3), in which case the dibenzocarbazole compound is stable and has a low molecular weight.

Example 4 of Compound

In the case where each of $R^1$ to $R^8$ represents hydrogen in General Formula (G3), the compound is advantageous in terms of easiness of synthesis and material cost and has a relatively low molecular weight to be suitable for vacuum evaporation, which is particularly preferable. The dibenzocarbazole compound is a dibenzocarbazole compound represented by General Formula (G4).

[Chemical Formula 17]

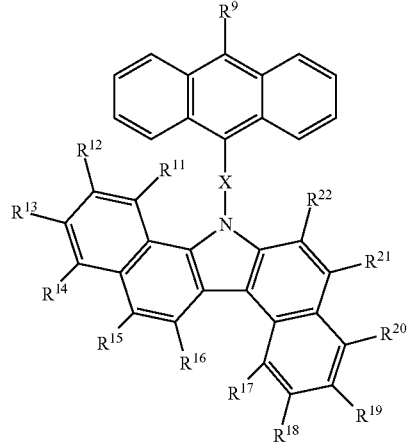

(G4)

In General Formula (G4), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a cycloalkyl group having 3 to 6 carbon atoms, or an aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

$R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group. The above aryl group may include a substituent. An alkyl group having 1 to 4 carbon atoms can be selected as the substituent. Specific examples of the alkyl group having 1 to 4 carbon atoms include a methyl group, an ethyl group, a propyl group, an isopropyl group, a butyl group, an isobutyl group, and a tert-butyl group.

Furthermore, $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Note that X is preferably a substituted or unsubstituted phenylene group in General Formula (G4), in which case the dibenzocarbazole compound is stable and has a low molecular weight.

Note that the total number of carbon atoms of $R^9$ and X is preferably 6 to 16 in General Formula (G4), in which case the dibenzocarbazole compound is a low molecular compound with a relatively low molecular weight and accordingly has a structure suitable for vacuum evaporation (capable of being vacuum-evaporated at a relatively low temperature).

Example 5 of Compound

In the case where each of $R^{11}$ to $R^{22}$ represents hydrogen in General Formula (G4), the compound is advantageous in terms of easiness of synthesis and material cost and has a relatively low molecular weight to be suitable for vacuum evaporation, which is particularly preferable. The dibenzocarbazole compound is a dibenzocarbazole compound represented by General Formula (G5).

[Chemical Formula 18]

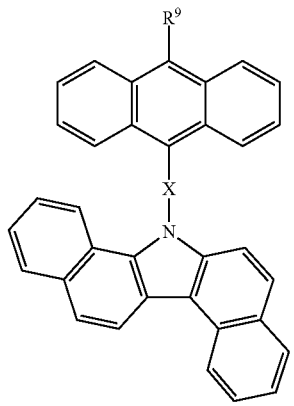

(G5)

In General Formula (G5), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a cycloalkyl group having 3 to 6 carbon atoms, or an aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

$R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group. The above aryl group may include a substituent. An alkyl group having 1 to 4 carbon atoms can be selected as the substituent. Specific examples of the alkyl group having 1 to 4 carbon atoms include a methyl group, an ethyl group, a propyl group, an isopropyl group, a butyl group, an isobutyl group, and a tert-butyl group.

Note that X is preferably a substituted or unsubstituted phenylene group in General Formula (G5), in which case the dibenzocarbazole compound is stable and has a low molecular weight.

Note that the total number of carbon atoms of $R^9$ and X is preferably 6 to 16 in General Formula (G5), in which case the dibenzocarbazole compound is a low molecular compound with a relatively low molecular weight and accordingly has a structure suitable for vacuum evaporation (capable of being vacuum-evaporated at a relatively low temperature).

Note that each of $R^9$ and X is preferably a phenylene group in General Formula (G5), in which case the dibenzocarbazole compound is stable and has a low molecular weight. Furthermore, the compound is advantageous in terms of easiness of synthesis and material cost.

Example 6 of Compound

The above dibenzocarbazole compound which is one embodiment of the present invention is a dibenzocarbazole compound represented by General Formula (G6).

[Chemical Formula 19]

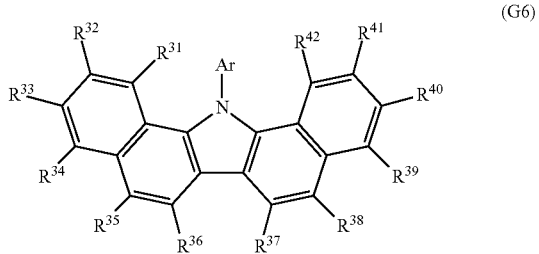

(G6)

In General Formula (G1), Ar represents a substituted or unsubstituted aryl group which has 14 to 30 carbon atoms and at least an anthracene skeleton. In the case where the aryl group has a substituent, as the substituent, an alkyl group having 1 to 6 carbon atoms, a substituted or unsubstituted cycloalkyl group having 3 to 6 carbon atoms, or a substituted or unsubstituted aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Furthermore, $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Example 7 of Compound

A dibenzocarbazole compound of one embodiment of the present invention, in which the 11-position of the dibenzo [a,i]carbazole skeleton is bonded to the aryl group having at least an anthracene skeleton, has a wide band gap and thus can be favorably used for a light-emitting element which emits high-energy light such as blue light, which is preferable. Furthermore, since the dibenzocarbazole compound has a high carrier-transport property, a light-emitting element including the compound can be driven at low voltage, which is preferable. The above dibenzocarbazole compound is a dibenzocarbazole compound represented by General Formula (G7).

[Chemical Formula 20]

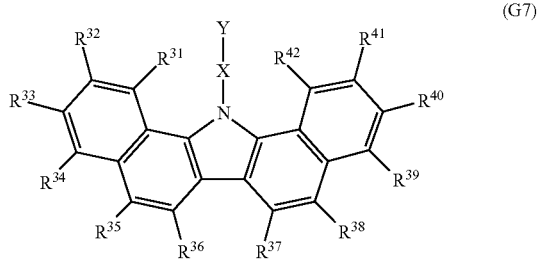

(G7)

In General Formula (G7), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a substituted or unsubstituted cycloalkyl group having 3 to 6 carbon atoms, or a substituted or unsubstituted aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

Y represents a substituted or unsubstituted anthryl group. In the case where the anthryl group has a substituent, as the substituent, an alkyl group having 1 to 6 carbon atoms, a substituted or unsubstituted cycloalkyl group having 3 to 6 carbon atoms, or a substituted or unsubstituted aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

Furthermore, $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Note that the total number of carbon atoms of X and Y is preferably 20 to 30 in General Formula (G7), in which case the dibenzocarbazole compound is a low molecular compound with a relatively low molecular weight and accordingly has a structure suitable for vacuum evaporation (capable of being vacuum-evaporated at a relatively low temperature).

Note that X is preferably a substituted or unsubstituted phenylene group in General Formula (G7), in which case the dibenzocarbazole compound is stable and has a low molecular weight.

Example 8 of Compound

A dibenzocarbazole compound of one embodiment of the present invention, in which the 11-position of the dibenzo[a,i]carbazole skeleton is bonded to the 9-position of an anthracene skeleton through an arylene group, has a high carrier-transport property, and thus a light-emitting element including the compound can be driven at low voltage, which is preferable. The above dibenzocarbazole compound is a dibenzocarbazole compound represented by General Formula (G8).

[Chemical Formula 21]

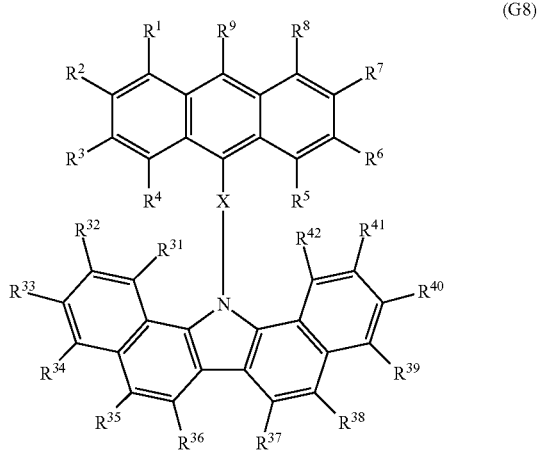

(G8)

In General Formula (G8), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a cycloalkyl group having 3 to 6 carbon atoms, or an aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

$R^1$ to $R^8$ each independently represent hydrogen or an alkyl group having 1 to 4 carbon atoms. Specific examples of the alkyl group having 1 to 4 carbon atoms include a methyl group, an ethyl group, a propyl group, an isopropyl group, a butyl group, an isobutyl group, and a tert-butyl group.

$R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group. The above aryl group may include a substituent. An alkyl group having 1 to 4 carbon atoms can be selected as the substituent. Specific examples of the alkyl group having 1 to 4 carbon atoms include a methyl group, an ethyl group, a propyl group, an isopropyl group, a butyl group, an isobutyl group, and a tert-butyl group.

Furthermore, $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

Note that the total number of carbon atoms of $R^1$ to $R^9$ and X is preferably 6 to 16 in General Formula (G8), in which case the dibenzocarbazole compound is a low molecular compound with a relatively low molecular weight and accordingly has a structure suitable for vacuum evaporation (capable of being vacuum-evaporated at a relatively low temperature).

X is preferably a substituted or unsubstituted phenylene group in General Formula (G8), in which case the dibenzocarbazole compound is stable and has a low molecular weight.

Example 9 of Compound

In the case where each of $R^1$ to $R^8$ represents hydrogen in General Formula (G8), the compound is advantageous in terms of easiness of synthesis and material cost and has a relatively low molecular weight to be suitable for vacuum evaporation, which is particularly preferable. The dibenzocarbazole compound is a dibenzocarbazole compound represented by General Formula (G9).

[Chemical Formula 22]

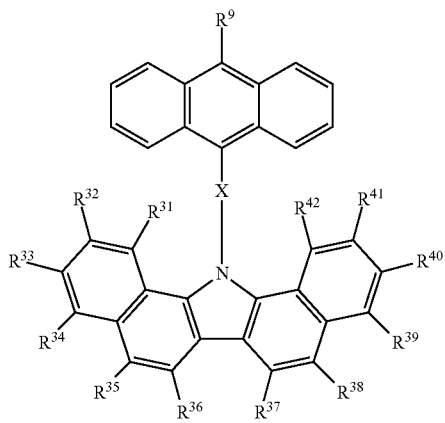

(G9)

In General Formula (G9), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a cycloalkyl group having 3 to 6 carbon atoms, or an aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

$R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group. The above aryl group may include a substituent. An alkyl group having 1 to 4 carbon atoms can be selected as the substituent. Specific examples of the alkyl group having 1 to 4 carbon atoms include a methyl group, an ethyl group, a propyl group, an isopropyl group, a butyl group, an isobutyl group, and a tert-butyl group.

Furthermore, $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of a cycloalkyl group having 3 to 6 carbon atoms include a cyclopropyl group, a cyclobutyl group, a cyclopentyl group, and a cyclohexyl group. Specific examples of the aryl group having 6 to 13 carbon atoms include a phenyl group, a naphthyl group, a biphenyl group, and a fluorenyl group. The above aryl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 12 carbon atoms include a phenyl group, a naphthyl group, and a biphenyl group.

X is preferably a substituted or unsubstituted phenylene group in General Formula (G9), in which case the dibenzocarbazole compound is stable and has a low molecular weight.

Note that the total number of carbon atoms of $R^9$ and X is preferably 6 to 16 in General Formula (G9), in which case the dibenzocarbazole compound is a low molecular compound with a relatively low molecular weight and accordingly has a structure suitable for vacuum evaporation (capable of being vacuum-evaporated at a relatively low temperature).

Example 10 of Compound

In the case where each of $R^{31}$ to $R^{42}$ represents hydrogen in General Formula (G9), the compound is advantageous in terms of easiness of synthesis and material cost and has a relatively low molecular weight to be suitable for vacuum evaporation, which is particularly preferable. The dibenzocarbazole compound is a dibenzocarbazole compound represented by General Formula (G10).

[Chemical Formula 23]

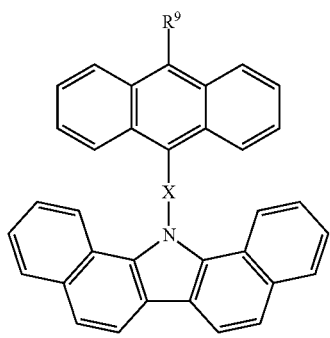

(G10)

In General Formula (G10), X represents a substituted or unsubstituted arylene group having 6 to 13 carbon atoms. Specific examples of the arylene group having 6 to 13 carbon atoms include a phenylene group, a naphthylene group, a biphenylene group, and a fluorenylene group. In the case where the arylene group has a substituent, as the substituent, an alkyl group having 1 to 6 carbon atoms, a cycloalkyl group having 3 to 6 carbon atoms, or an aryl group having 6 to 10 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group.

$R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms. Specific examples of the alkyl group having 1 to 6 carbon atoms include a methyl group, an ethyl group, a propyl group, an isopropyl group, a butyl group, an isobutyl group, a tert-butyl group, and an n-hexyl group. Specific examples of the cycloalkyl group having 3 to 6 carbon atoms include a cyclopropyl group, a cyclobutyl group, a cyclopentyl group, and a cyclohexyl group. Specific examples of the aryl group having 6 to 10 carbon atoms include a phenyl group and a naphthyl group. The above aryl group may include a substituent. An alkyl group having 1 to 4 carbon atoms can be selected as the substituent. Specific examples of the alkyl group having 1 to 4 carbon atoms include a methyl group, an ethyl group, a propyl group, an isopropyl group, a butyl group, an isobutyl group, and a tert-butyl group.

X is preferably a substituted or unsubstituted phenylene group in General Formula (G10), in which case the dibenzocarbazole compound is stable and has a low molecular weight.

Note that the total number of carbon atoms of $R^9$ and X is preferably 6 to 16 in General Formula (G10), in which case the dibenzocarbazole compound is a low molecular compound with a relatively low molecular weight and accordingly has a structure suitable for vacuum evaporation (capable of being vacuum-evaporated at a relatively low temperature).

Note that each of $R^9$ and X is preferably a phenylene group in General Formula (G10), in which case the dibenzocarbazole compound is stable and has a low molecular weight. Furthermore, the compound is advantageous in terms of easiness of synthesis and material cost.

Examples of Substituents

As an aryl group represented by Ar in General Formulae (G1) and (G6), which has 14 to 30 carbon atoms and at least an anthracene skeleton, and is, any of groups represented by Structural Formulae (Ant-1) to (Ant-53) can be used, for example. Note that the group Ar may include a substituent and is not limited to the following.

[Chemical Formula 24]

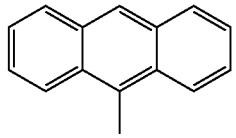

(Ant-1)

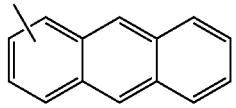

(Ant-2)

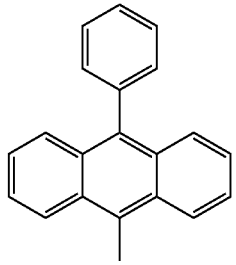

(Ant-3)

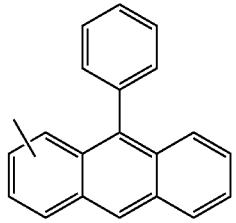

(Ant-4)

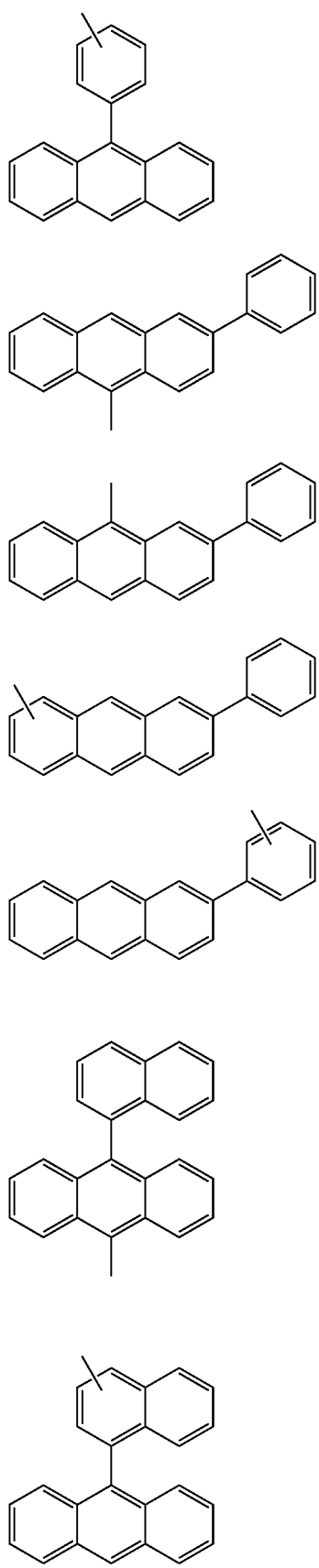
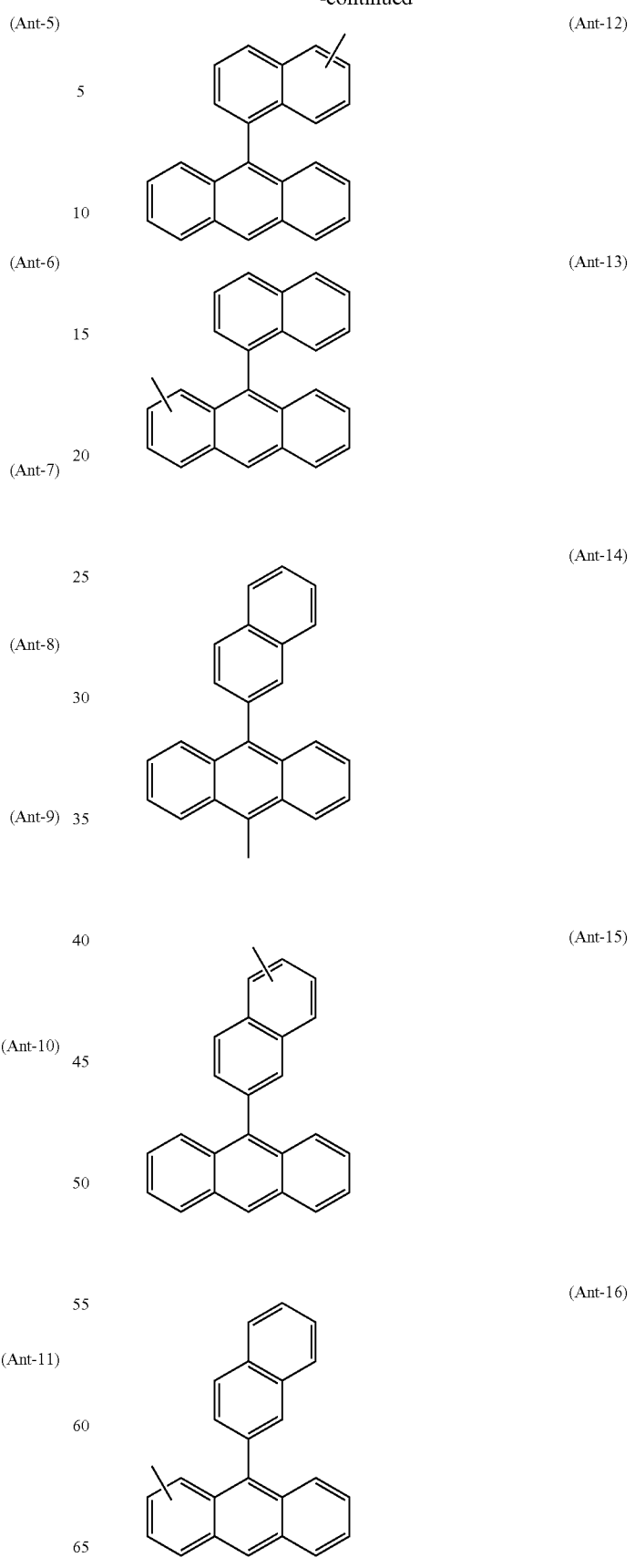

[Chemical Formul 25]
(Ant-17) 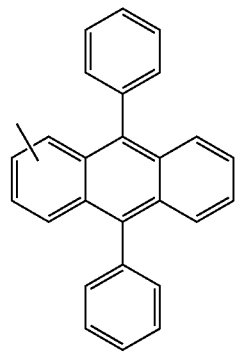
(Ant-21) 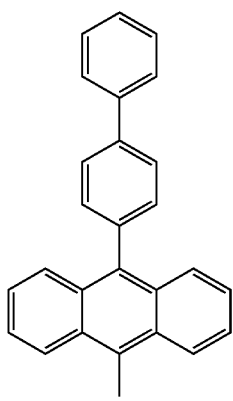
(Ant-18) 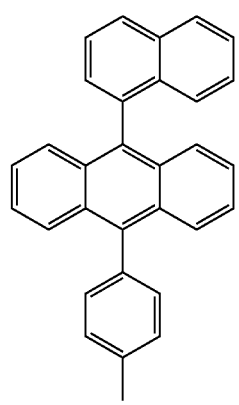
(Ant-22) 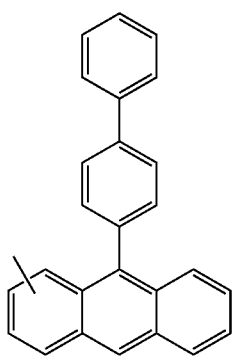
(Ant-19) 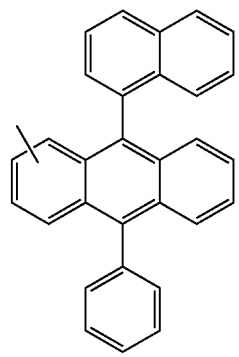
(Ant-23) 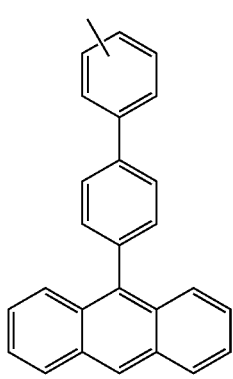
(Ant-20) 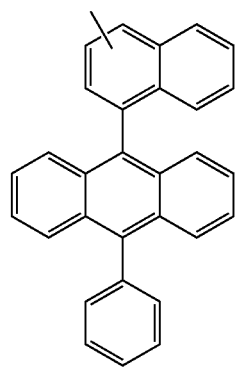
(Ant-24) 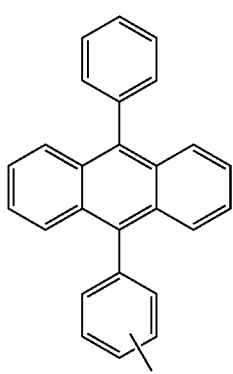

(Ant-25)
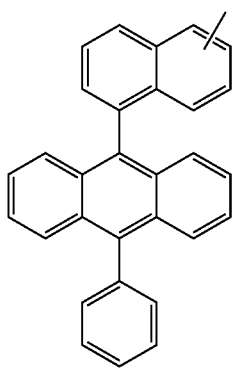
(Ant-26)
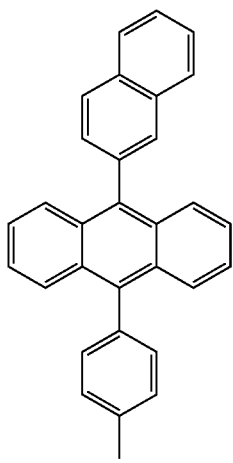
(Ant-27)
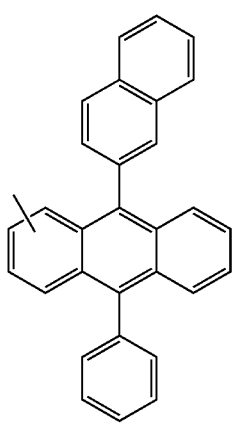
(Ant-28)
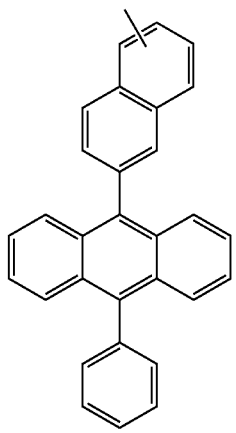
[Chemical Formula 26]
(Ant-29)
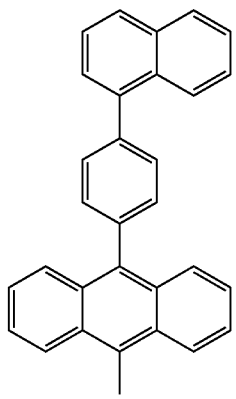
(Ant-30)
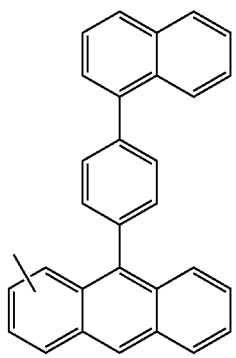
(Ant-31)
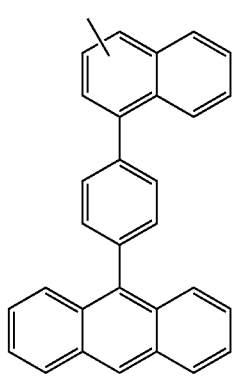

(Ant-32)
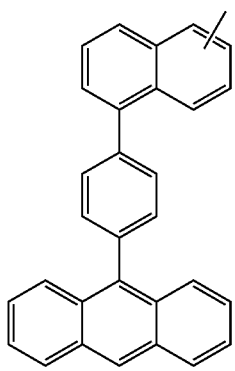
(Ant-33)
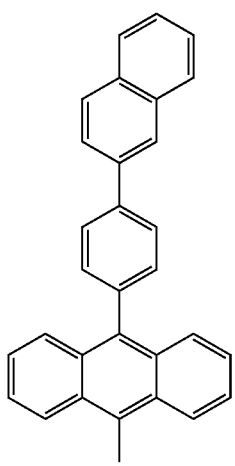
(Ant-34)
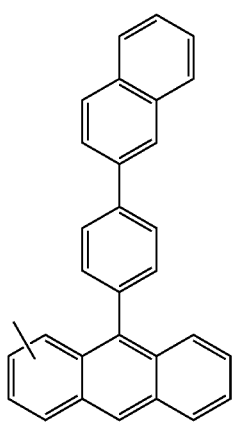
(Ant-35)
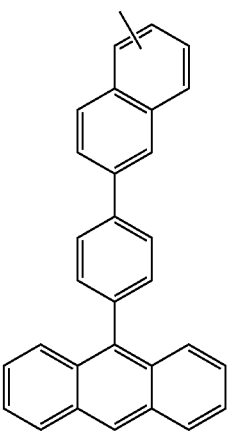
(Ant-36)
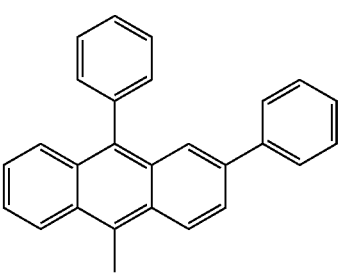
(Ant-37)
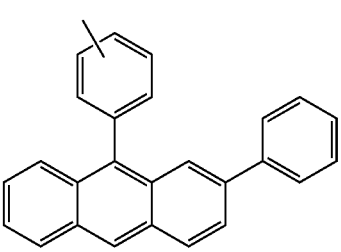
(Ant-38)
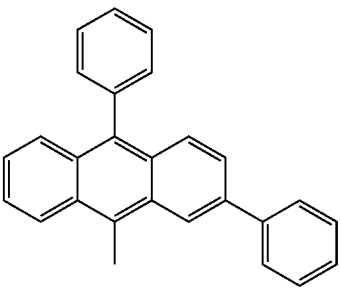
(Ant-39)

(Ant-40)
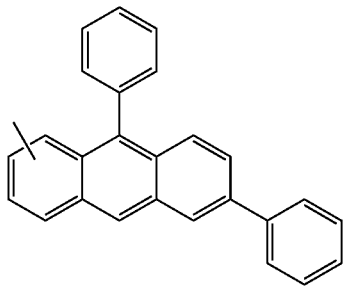
(Ant-41)
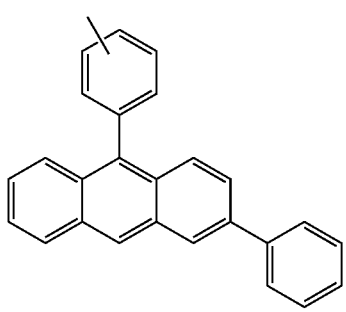
[Chemical Formula 27]
(Ant-42)
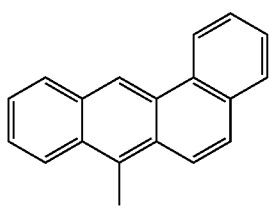
(Ant-43)
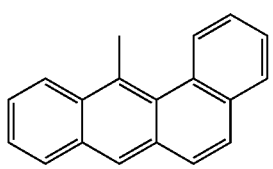
(Ant-44)
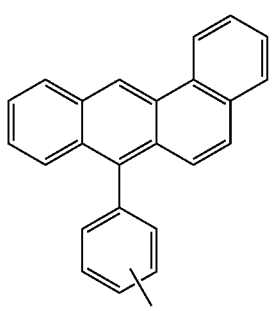
(Ant-45)
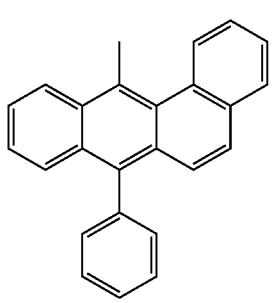
(Ant-46)
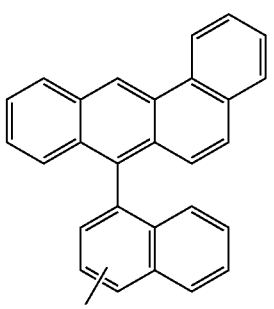
(Ant-47)
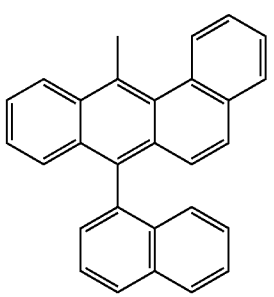
(Ant-48)
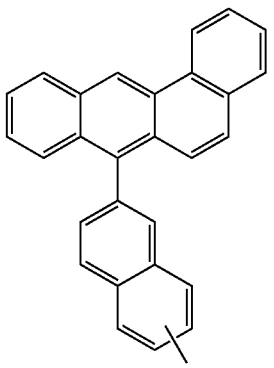
(Ant-49)
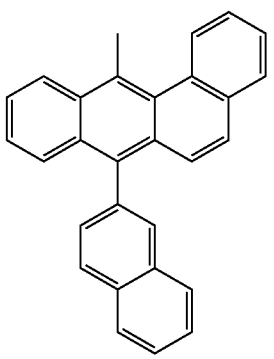

-continued

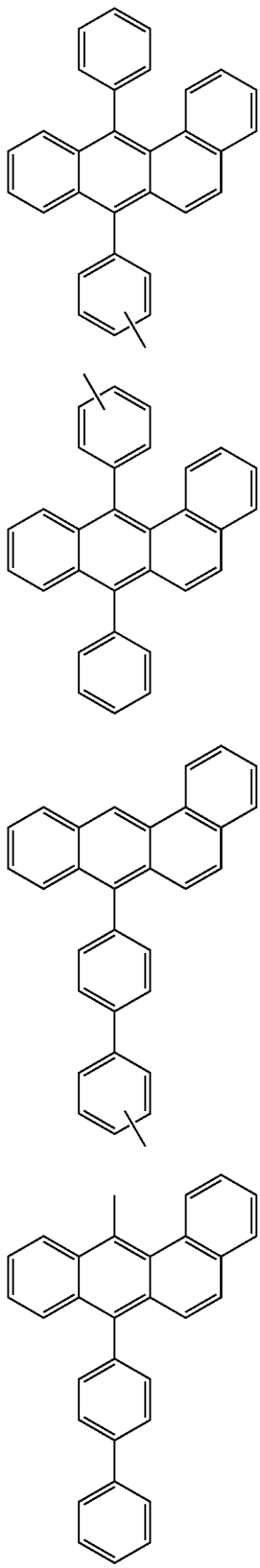

(Ant-50)

(Ant-51)

(Ant-52)

(Ant-53)

In General Formulae (G2) and (G7), as an anthryl group represented by Y, any of groups represented by Structural Forumlae (Ant-1) to (Ant-16) and (Ant-42) to (Ant-45) can be used, for example. Note that the group Y may include a substituent and is not limited to the following.

In General Formulae (G2) to (G5) and General Formulae (G7) to (G10), as an arylene group represented by X, any of groups represented by Structural Formulae (Ar-1) to (Ar-15) can be used, for example. Note that the group X may include a substituent and is not limited to the following.

[Chemical Formula 28]

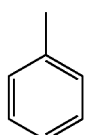
(Ar-1)

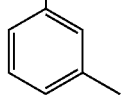
(Ar-2)

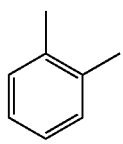
(Ar-3)

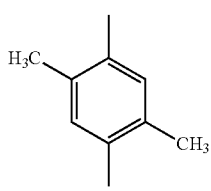
(Ar-4)

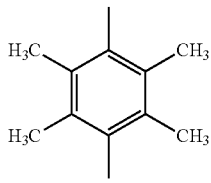
(Ar-5)

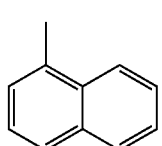
(Ar-6)

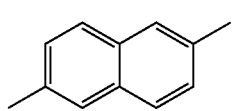
(Ar-7)

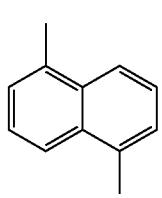
(Ar-8)

-continued (Ar-9) 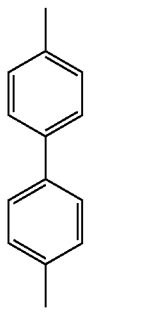

(Ar-10) 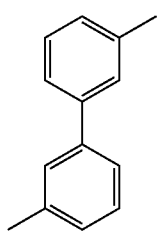

(Ar-11) 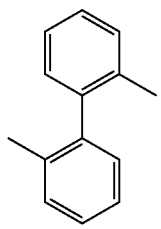

(Ar-12) 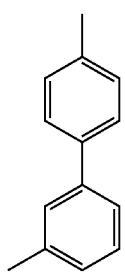

(Ar-13) 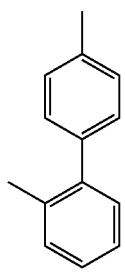

(Ar-14) 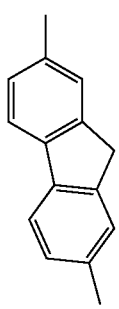

(Ar-15) 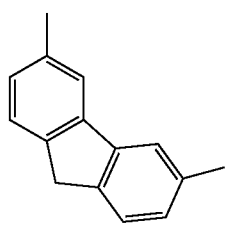

As hydrogen, an alkyl group, or an aryl group represented by $R^{11}$ to $R^{22}$ in General Formulae (G1) to (G4) and $R^{31}$ to $R^{42}$ in General Formulae (G6) and (G9), any of groups represented by Structural Formulae (R-1) to (R-29) can be used, for example. Note that the alkyl group or the aryl group may include a substituent and is not limited to the following.

[Chemical Formula 29]

(R-1) 

(R-2) 

(R-3) 

(R-4) 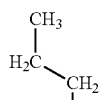

(R-5) 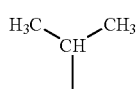

(R-6) 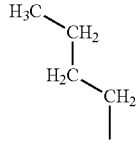

(R-7) 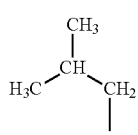

(R-8) 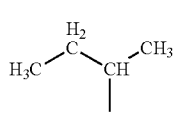

(R-9) 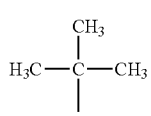

-continued
(R-10) 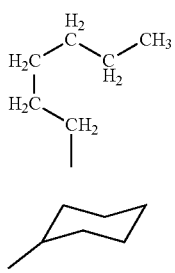
(R-11) 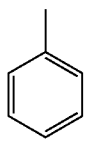
(R-12) 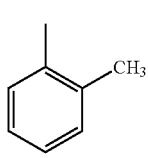
(R-13) 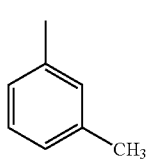
(R-14) 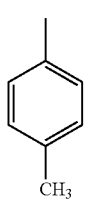
(R-15)
(R-16) 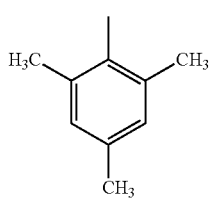
(R-17) 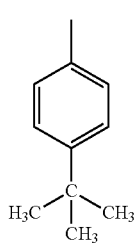
(R-18) 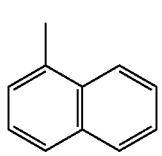
(R-19) 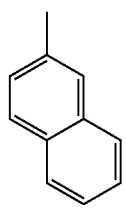
(R-20) 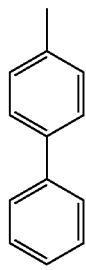
(R-21) 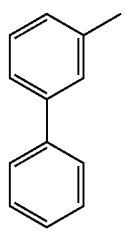
(R-22) 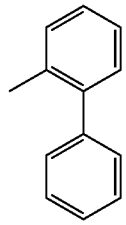
(R-23) 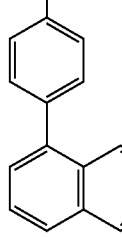
(R-24) 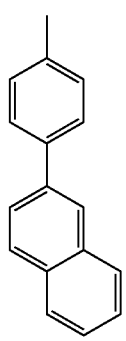

-continued (R-25)
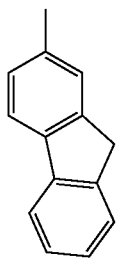

(R-26)
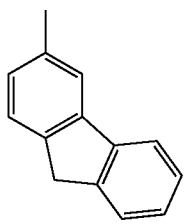

(R-27)
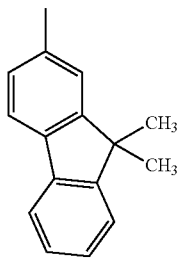

(R-28)
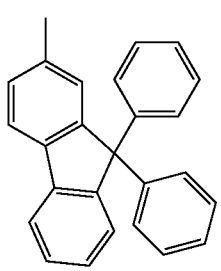

(R-29)
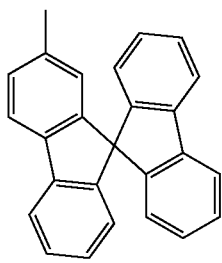

As an alkyl group or an aryl group represented by $R^9$ in General Formulae (G3) to (G5) and General Formulae (G8) to (G10), any of the groups represented by Structural Formulae (R-1) to (R-19) can be used, for example. Note that the alkyl group or the aryl group may include a substituent and is not limited to the following.

As hydrogen or an alkyl group represented by $R^1$ to $R^8$ in General Formulae (G3) and (G8), any of the groups represented by Structural Formulae (R-1) to (R-9) can be used, for example. Note that the alkyl group is not limited to the above.

Specific Examples of Compounds

Specific examples of structures of the dibenzocarbazole compounds represented by General Formulae (G1) to (G10) are compounds represented by Structural Formulae (100) to (171). Note that the dibenzocarbazole compounds represented by General Formulae (G1) to (G10) are not limited to the following examples.

[Chemical Formula 30]

(100)
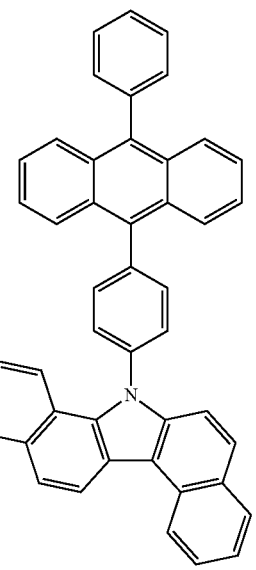

(101)
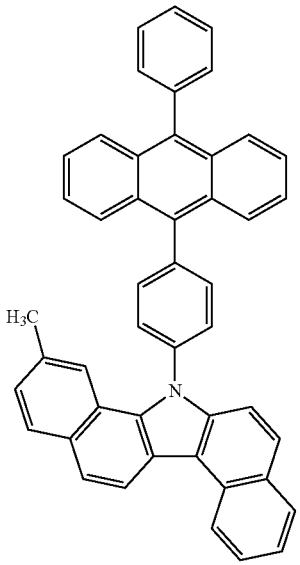

(102)
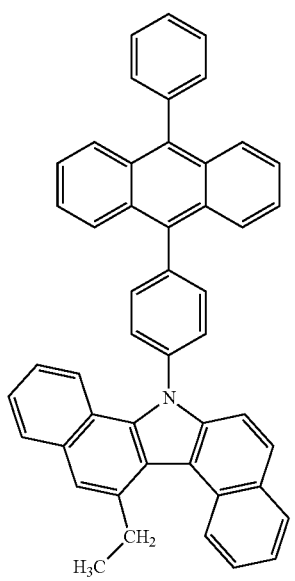
(103)
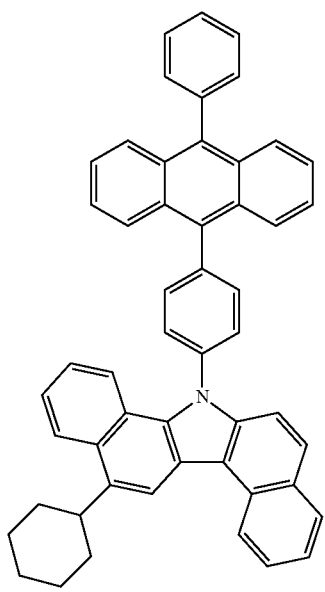
(104)
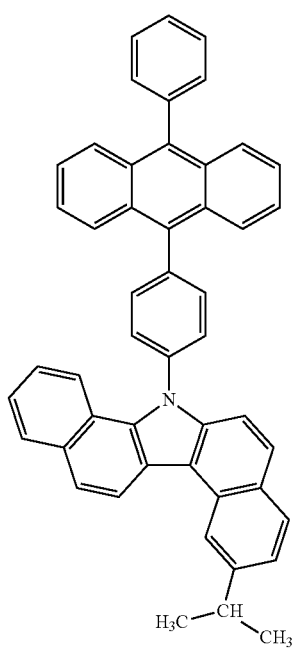
(105)
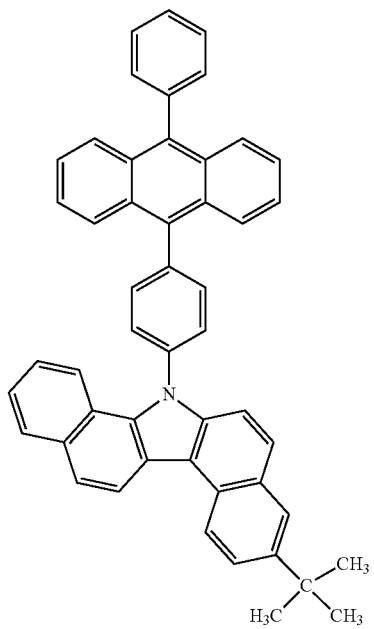

[Chemical Formula 31]
(106)
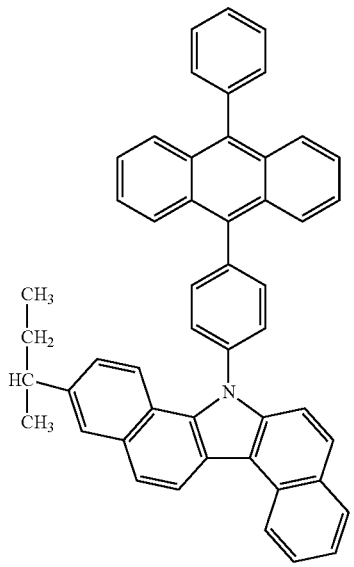
(107)
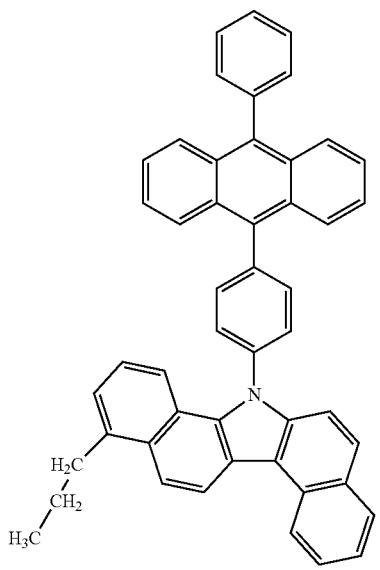
(108)
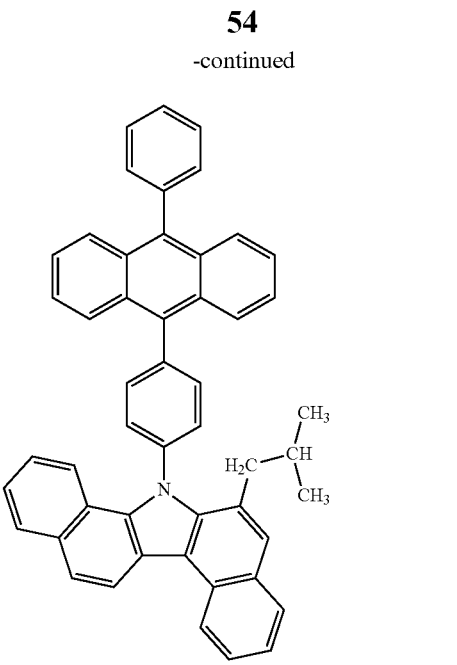
(109)
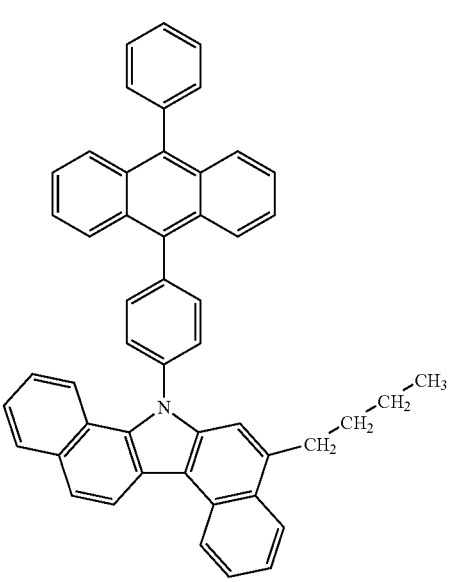

(110)
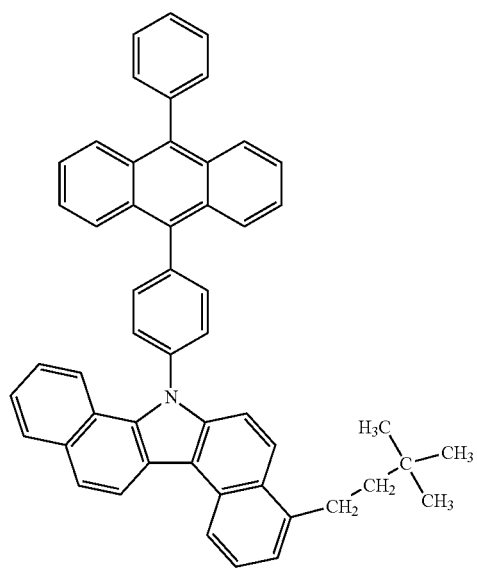
(111)
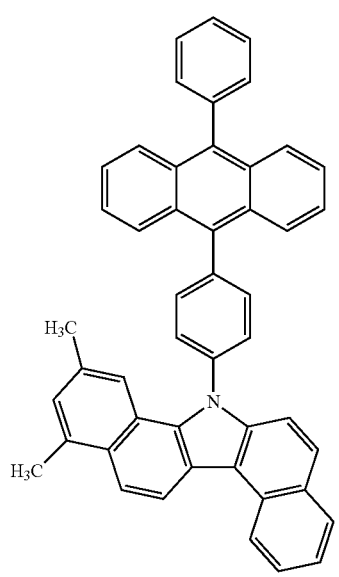
[Chemical Formula 32]
(112)
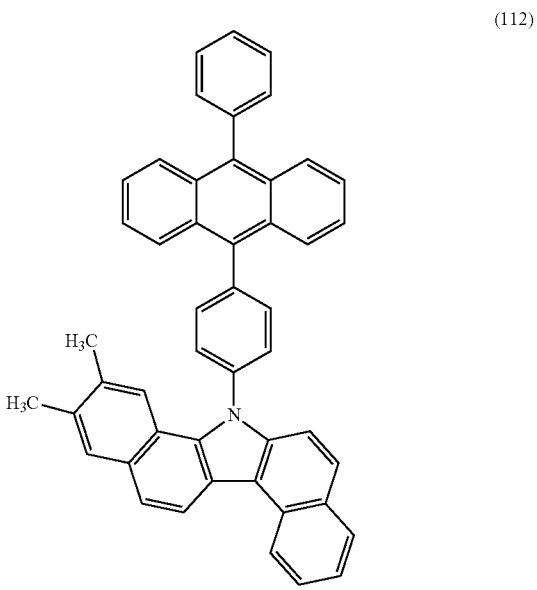
(113)
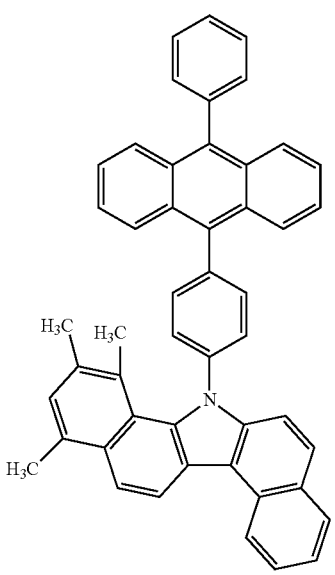

(114)
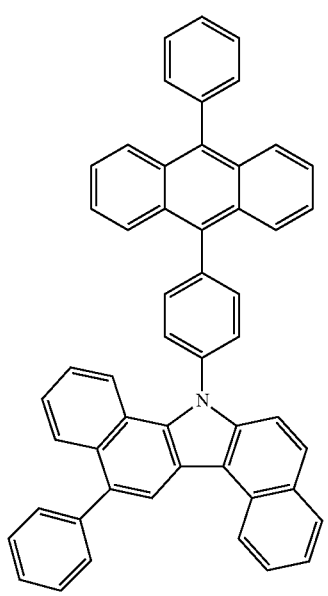
(116)
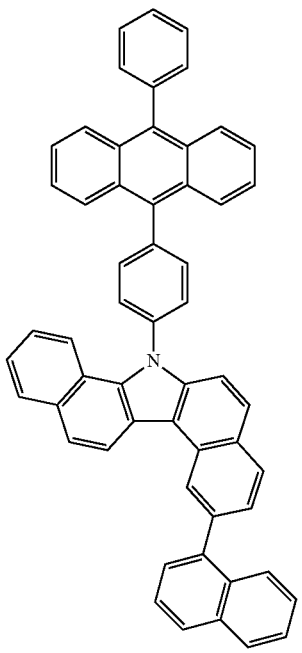
(115)
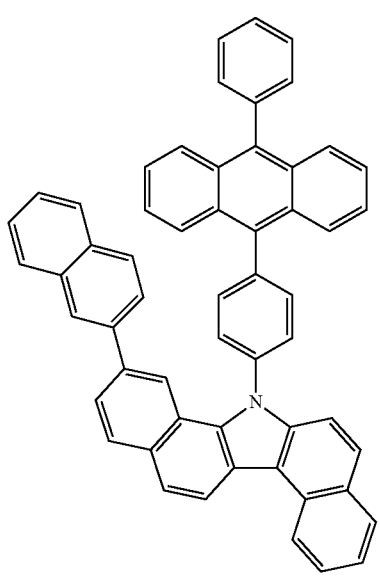
(117)
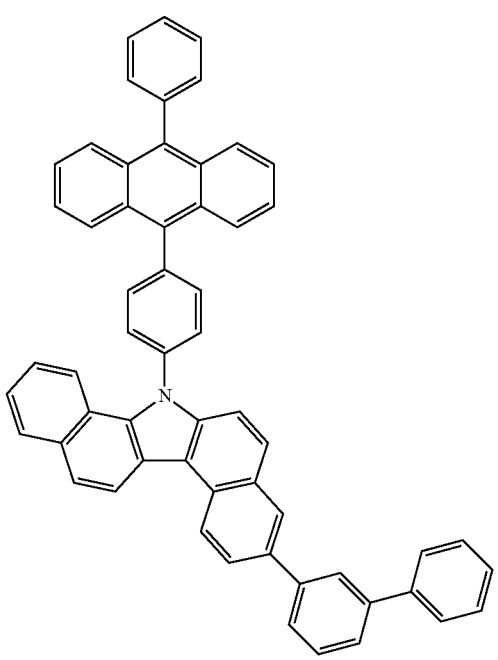

[Chemical Formula 33]
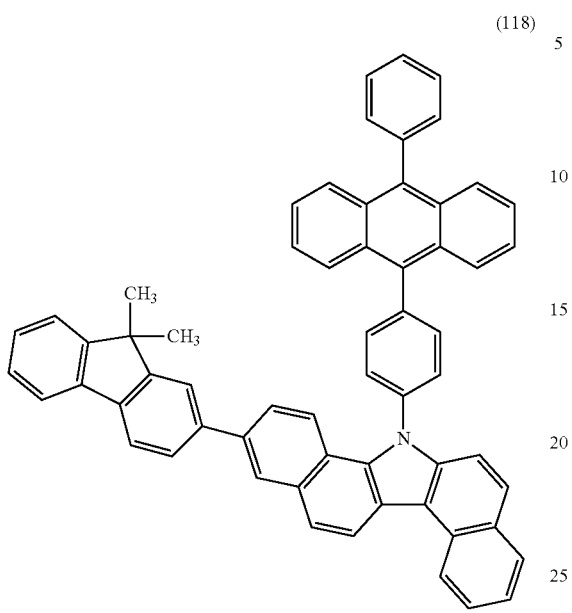
(118)
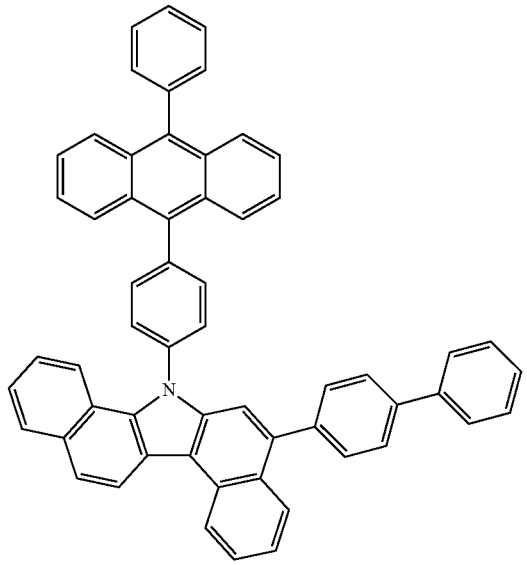
(120)
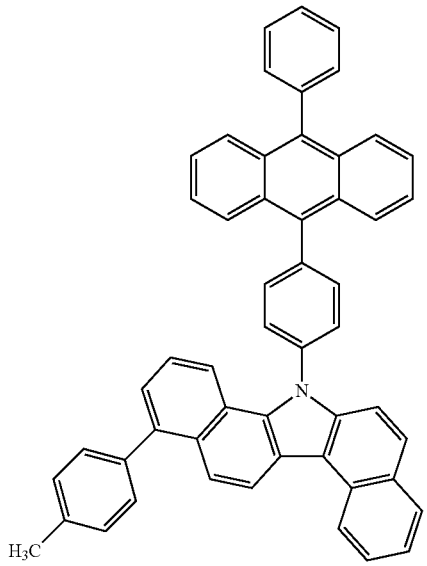
(119)
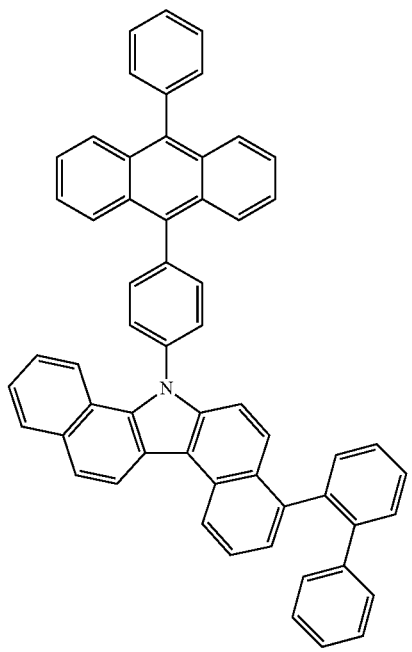
(121)

(122)
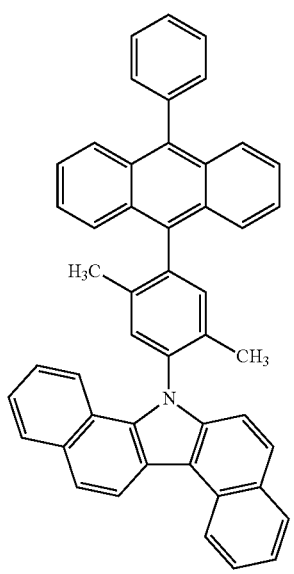
[Chemical Formula 34]
(124)
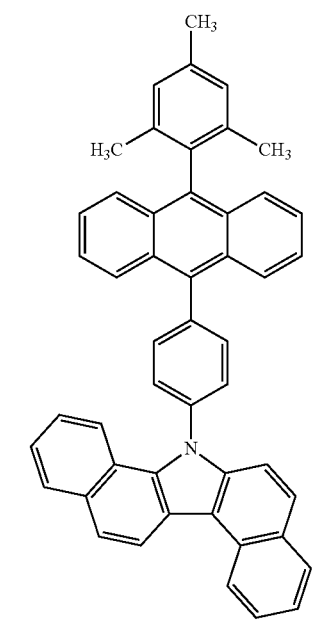
(123)
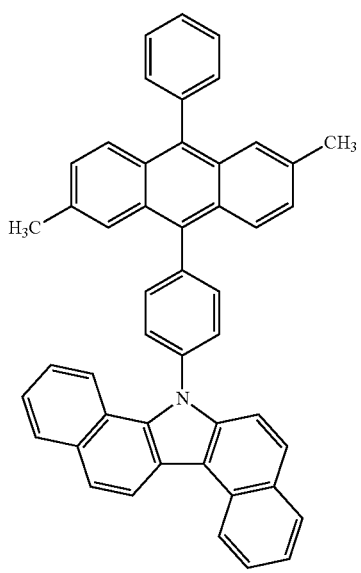
(125)
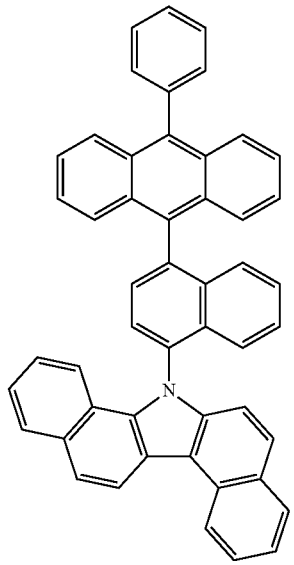

(126)
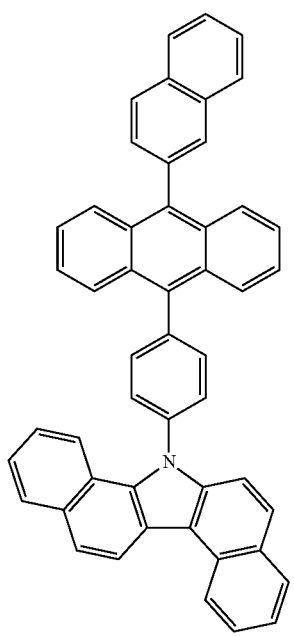
(127)
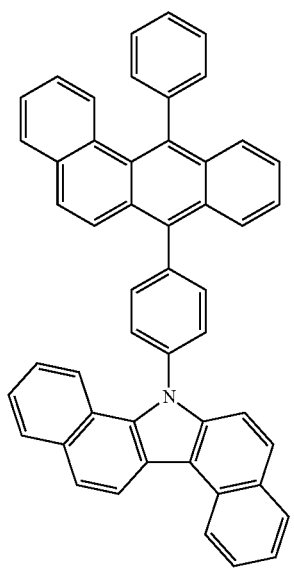
(128)
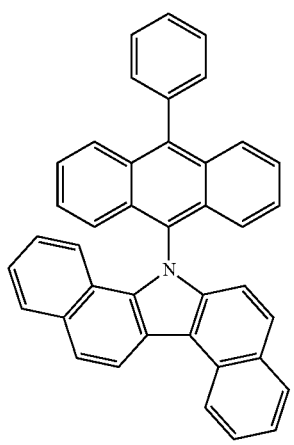
(129)
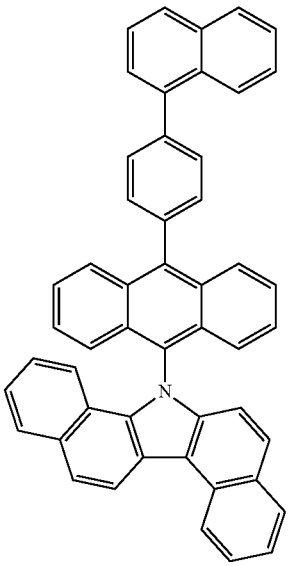
[Chemical Formula 35]
(130)
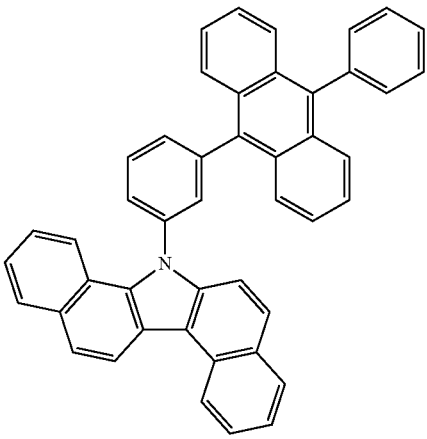
(131)
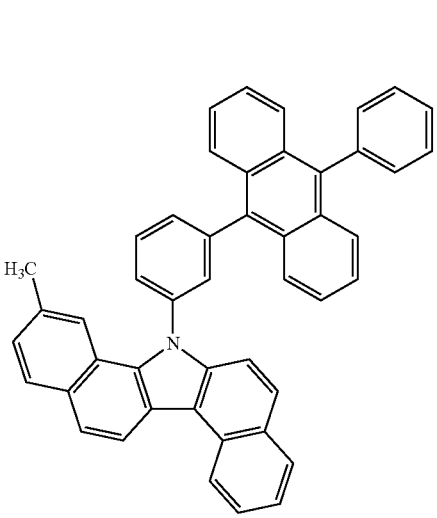

(132)
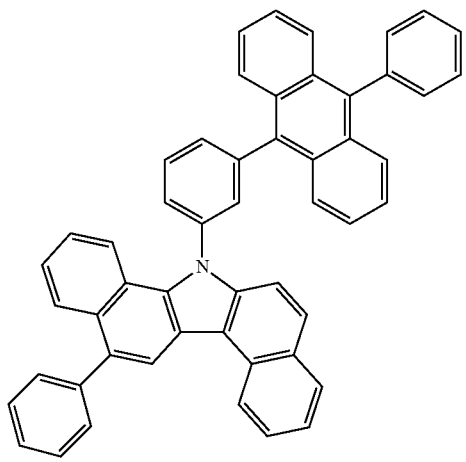
(133)
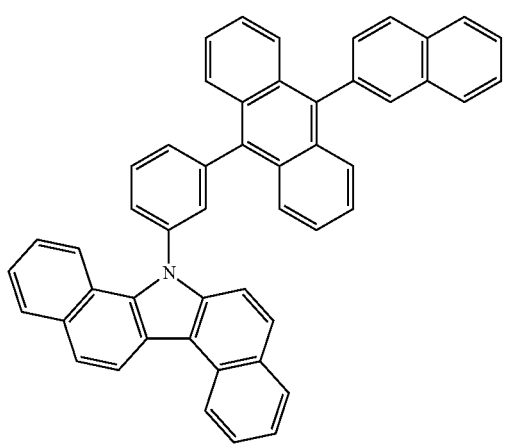
(134)
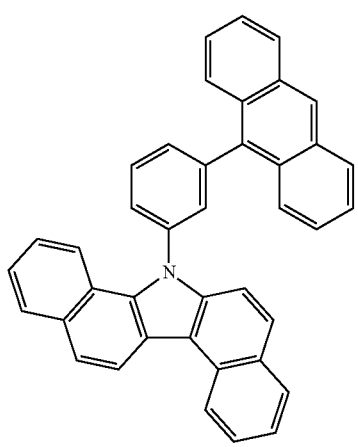
(135)
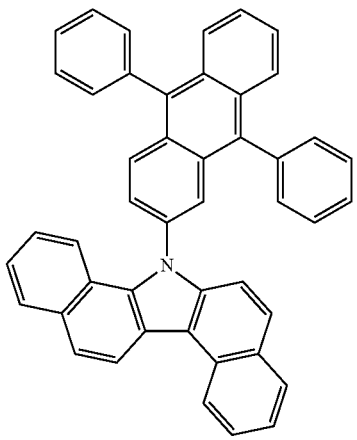
[Chemical Formula 36]
(136)
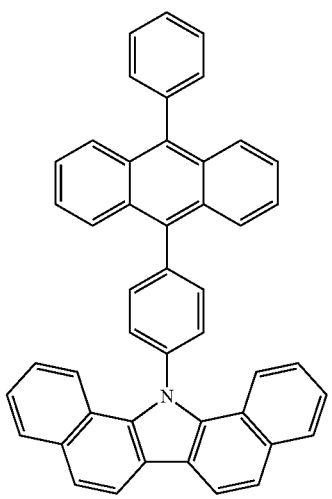
(137)
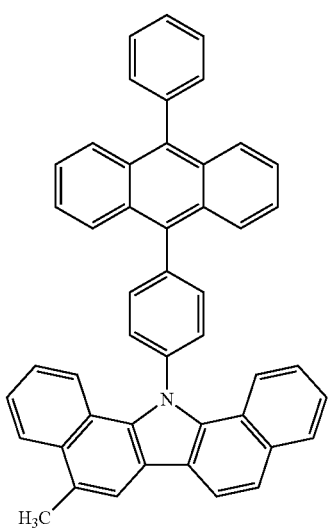

(138)
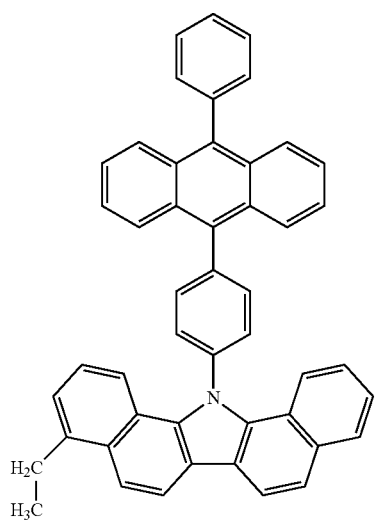
(139)
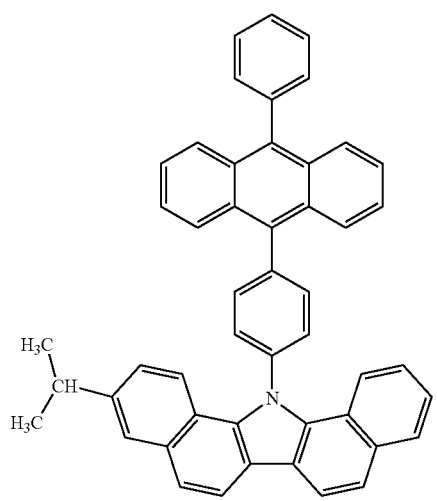
(140)
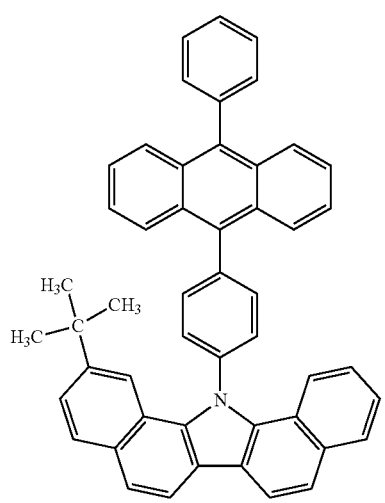
(141)
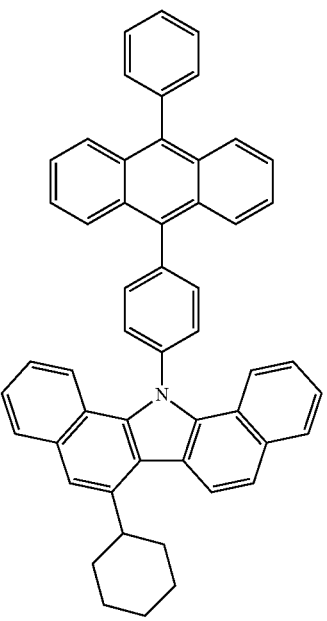
[Chemical Formula 37]
(142)
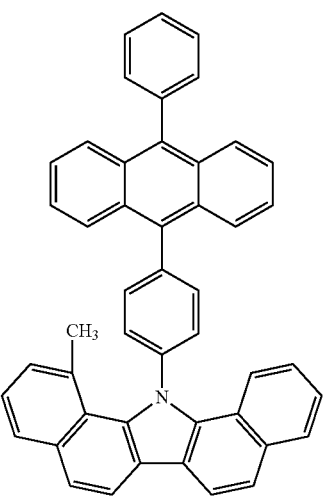
(143)
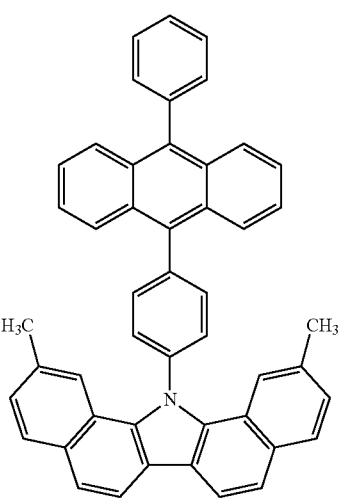

-continued
(144)
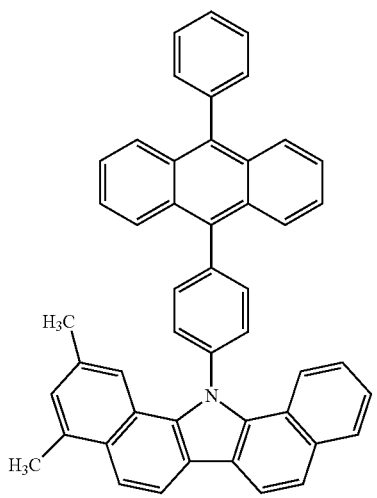
(145)
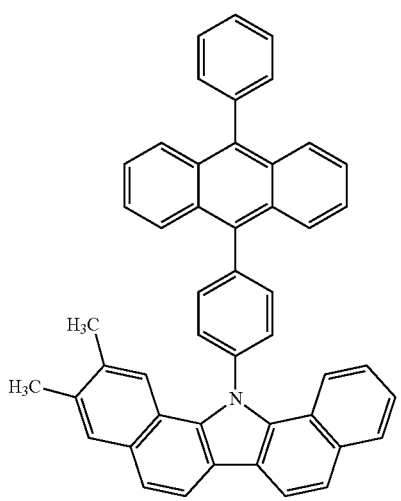
(146)
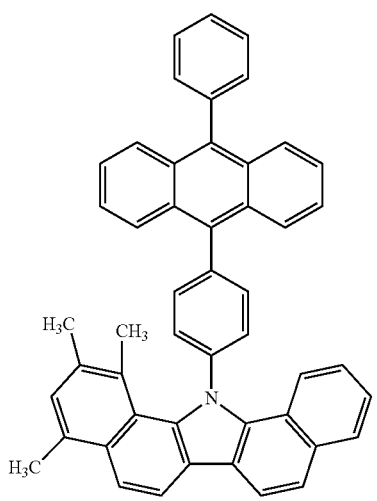
-continued
(147)
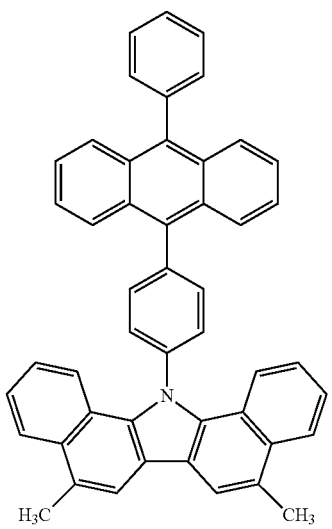
[Chemical Formula 38]
(148)
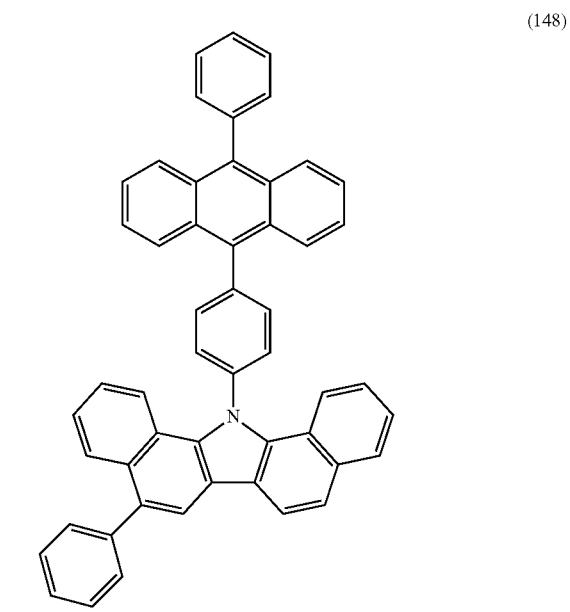
(149)
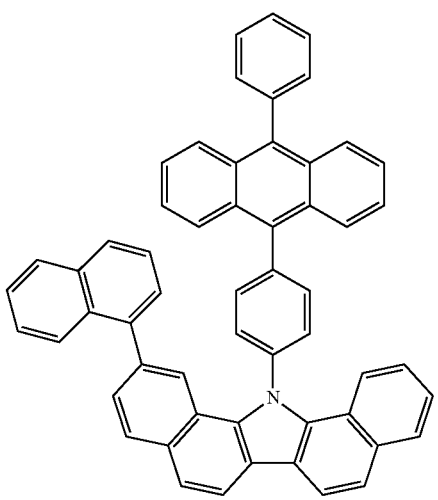

-continued
(150)
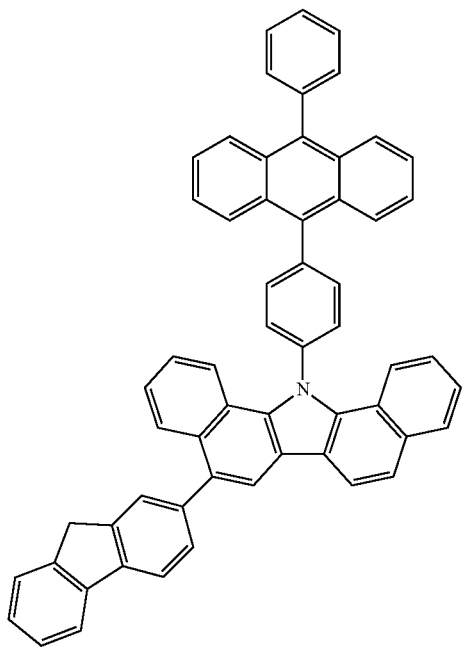
(151)
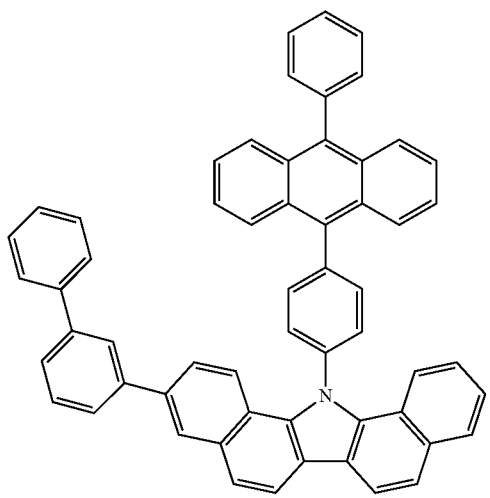
(152)
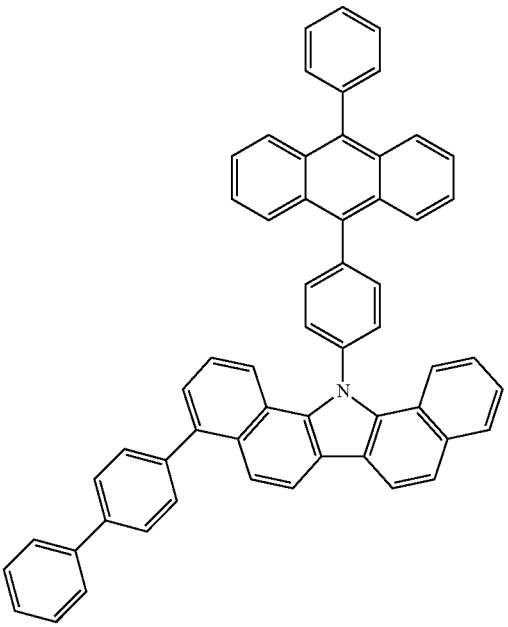
(153)
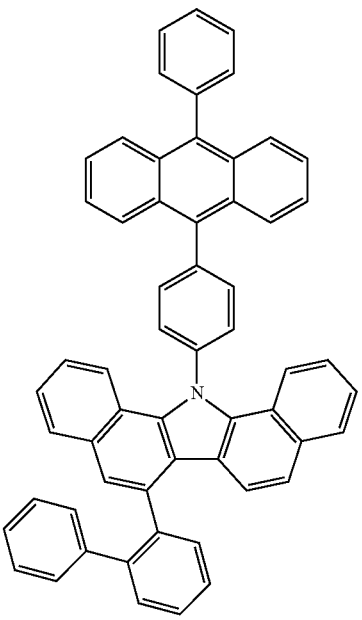

[Chemical Formula 39]
(154)
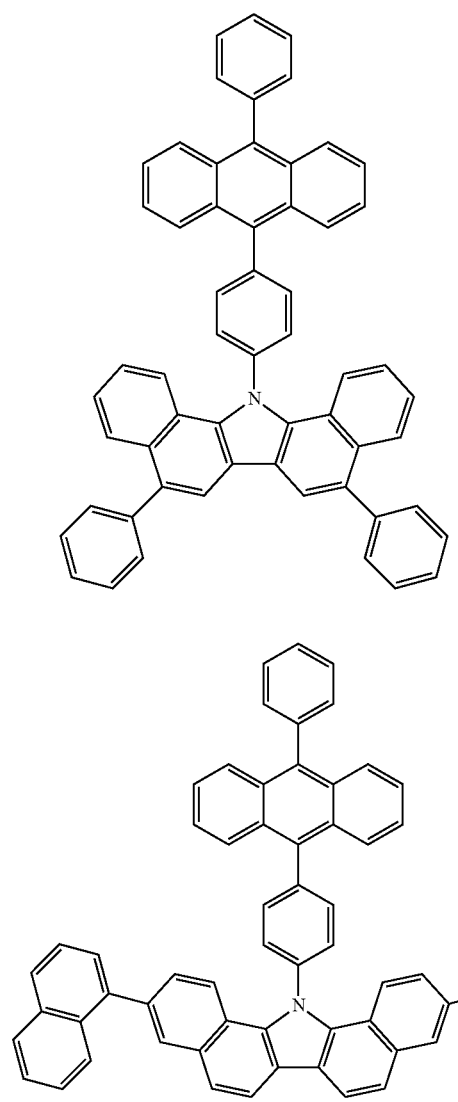
(155)
(156)
[Chemical Formula 40]
(157)
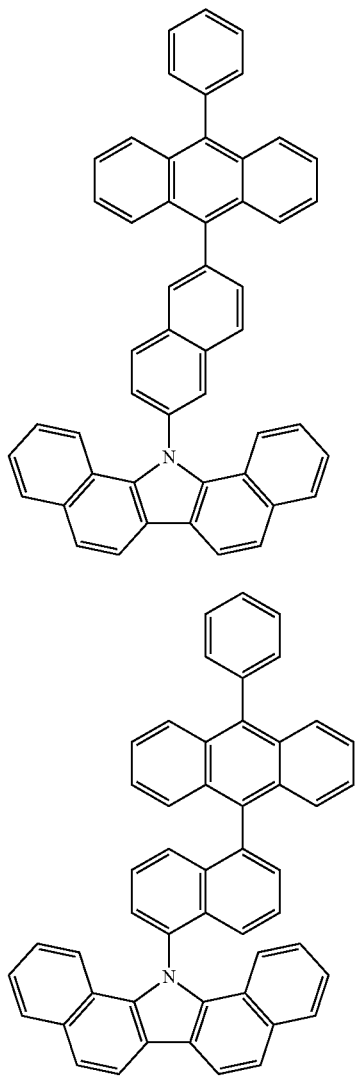
(158)
(159)
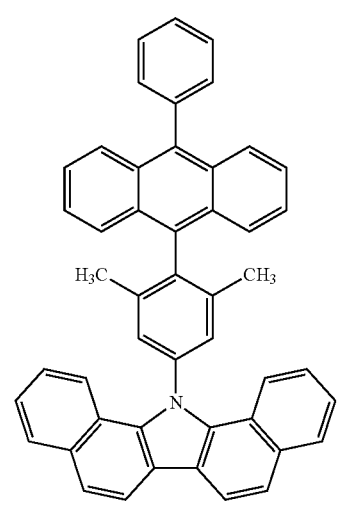
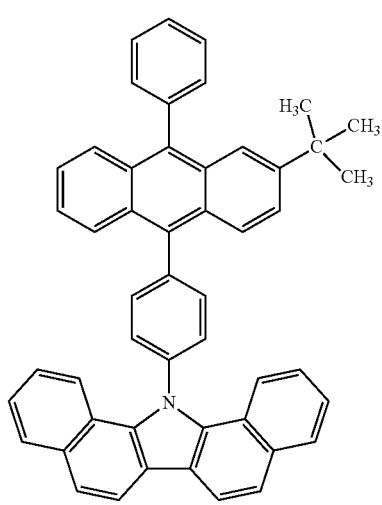

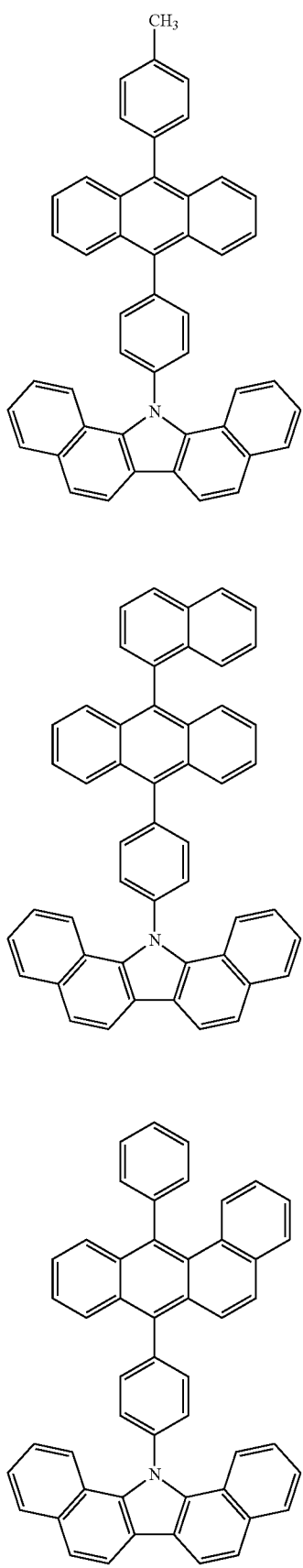
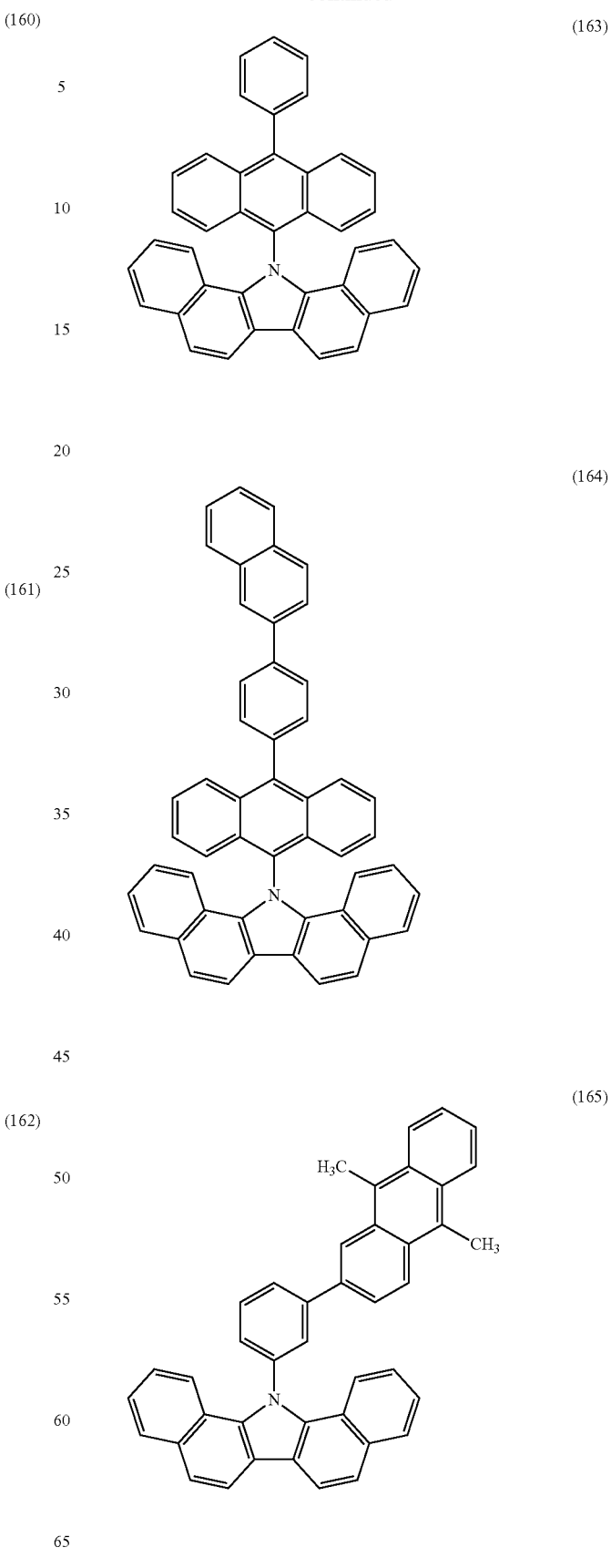

[Chemical Formula 41]

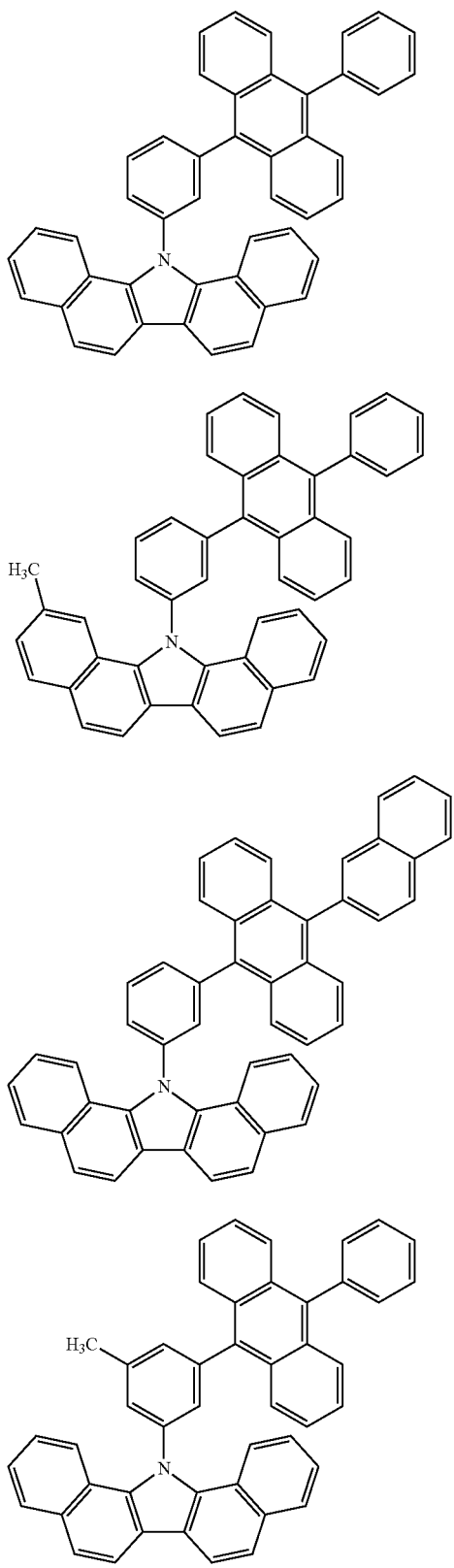

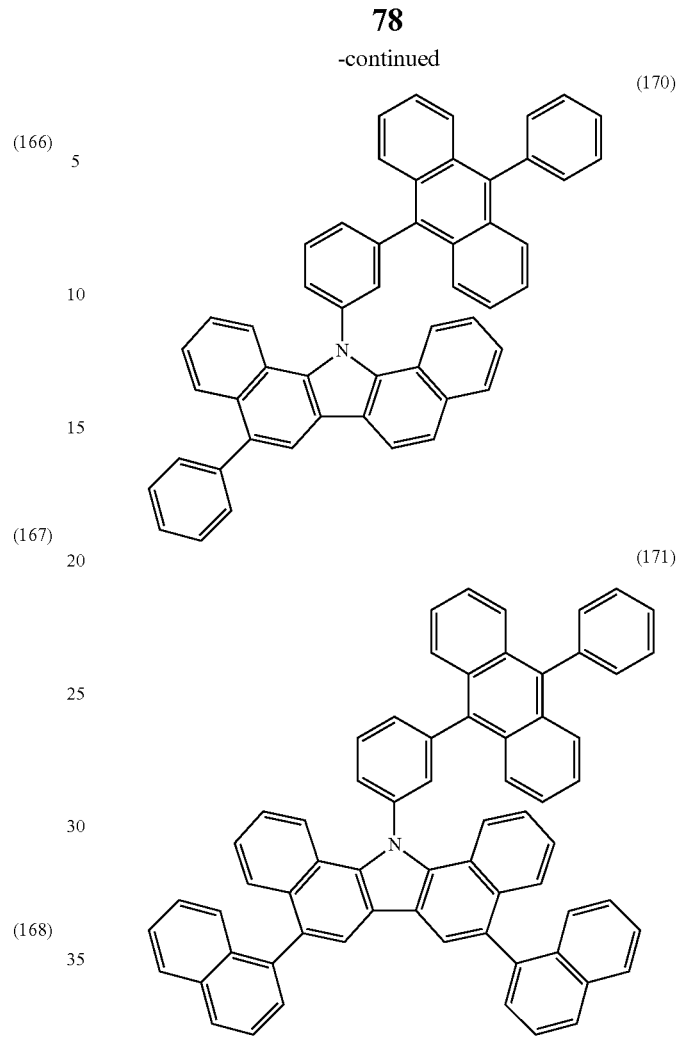

As described above, the dibenzocarbazole compound which is one embodiment of the present invention has a wide band gap and thus is preferably used as a host material or a carrier-transport material particularly in a light-emitting element that emits blue light. In that case, the blue light-emitting element can have high emission efficiency. Furthermore, the dibenzocarbazole compound which is one embodiment of the present invention has a high carrier-transport property and thus is preferably used as a host material or a carrier-transport material in a light-emitting element. Accordingly, a light-emitting element with low drive voltage can be manufactured. Moreover, since the dibenzocarbazole compound which is one embodiment of the present invention is highly resistant to repetition of oxidation and reduction, a light-emitting element including the dibenzocarbazole compound can have a long lifetime. Therefore, the dibenzocarbazole compound which is one embodiment of the present invention is a material suitably used in a light-emitting element.

Note that the dibenzocarbazole compound which is one embodiment of the present invention can be deposited by an evaporation method (including a vacuum evaporation method), an ink-jet method, a coating method, a gravure printing method, or the like.

Note that the compound described in this embodiment can be used in combination with any of the structures described in the other embodiments as appropriate.

Embodiment 2

In this embodiment, methods for synthesizing the dibenzocarbazole compounds represented by General Formulae (G1) and (G6) are described. A variety of reactions can be applied to each of the methods for synthesizing the dibenzocarbazole compounds. For example, synthesis reactions described below enable the synthesis of the dibenzocarbazole compounds represented by General Formulae (G1) and (G6). Note that the methods for synthesizing the dibenzocarbazole compound which is one embodiment of the present invention are not limited to the following.

<Example of Method for Synthesizing Dibenzo[a,g]Carbazole Compound Represented by General Formula (G1)>

The dibenzo[a,g]carbazole compound represented by General Formula (G1) can be synthesized as in Synthesis Scheme (A-1). That is, a halide of an anthracene derivative (a1) is coupled with a dibenzo[a,g]carbazole derivative (a2) by using a metal catalyst, a metal, or a metal compound in the presence of a base, whereby the dibenzo[a,g]carbazole compound represented by General Formula (G1) can be obtained.

[Chemical Formula 42]

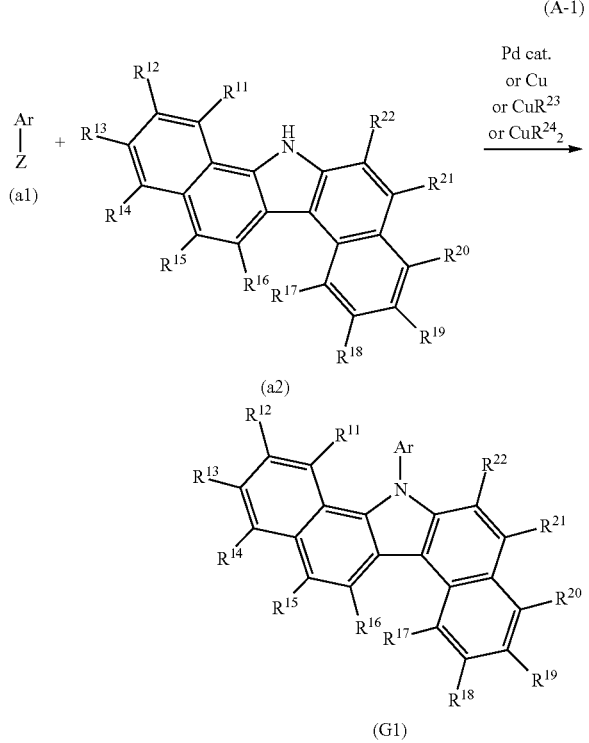

In Synthesis Scheme (A-1), $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and Ar represents a substituted or unsubstituted aryl group which has 14 to 30 carbon atoms and at least an anthracene skeleton.

In the case where the Hartwig-Buchwald reaction is performed in Synthesis Scheme (A-1), Z represents a halogen or a triflate group. As the halogen, iodine, bromine, or chlorine is preferable. In this reaction, a palladium catalyst including a palladium compound or a palladium complex such as bis(dibenzylideneacetone)palladium(0) or palladium (II) acetate and a ligand that coordinates to the palladium complex or the palladium compound, such as tri(tert-butyl)phosphine, tri(n-hexyl)phosphine, or tricyclohexylphosphine, is used. Examples of the base include organic bases such as sodium tert-butoxide, inorganic bases such as a potassium carbonate, and the like. In the case where a solvent is used, toluene, xylene, benzene, tetrahydrofuran, or the like can be used.

In the case where an Ullmann reaction is performed in Synthesis Scheme (A-1), Z represents a halogen. As the halogen, iodine, bromine, or chlorine is preferable. As a catalyst, copper or a copper compound is used. In the case where a copper compound is used as the catalyst, $R^{23}$ and $R^{24}$ in Synthesis Scheme (A-1) individually represent a halogen, an acetyl group, or the like. As the halogen, chlorine, bromine, or iodine can be given. Note that copper (I) iodide where $R^{23}$ is iodine or copper(II) acetate where $R^{24}$ is an acetyl group is preferably used. As the base which is used, an inorganic base such as potassium carbonate can be given. As a solvent, 1,3-dimethyl-3,4,5,6-tetrahydro-2 (1H)-pyrimidinone (DMPU), toluene, xylene, benzene, and the like can be employed. Note that the solvent is not limited thereto. In an Ullmann reaction, DMPU or xylene, which has a high boiling point, is preferably used, in which case the object of the synthesis can be obtained in a shorter time and a higher yield at a reaction temperature of 100° C. or more. A reaction temperature of 150° C. or more is further preferred and accordingly DMPU is more preferably used.

<Example of Method for Synthesizing Dibenzo[a,i]Carbazole Compound Represented by General Formula (G6)>

The dibenzo[a,i]carbazole compound represented by General Formula (G6) can be synthesized as in Synthesis Scheme (B-1). That is, a halide of an anthracene derivative (a1) is coupled with a dibenzo[a,i]carbazole derivative (a3) by using a metal catalyst, a metal, or a metal compound in the presence of a base, whereby the dibenzo[a,i]carbazole compound represented by General Formula (G6) can be obtained.

[Chemical Formula 43]

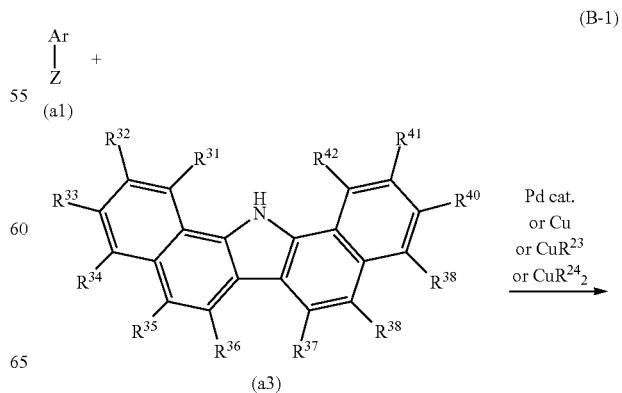

-continued

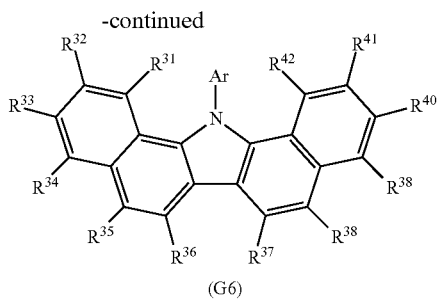

(G6)

In Synthesis Scheme (B-1), $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and Ar represents a substituted or unsubstituted aryl group which has 14 to 30 carbon atoms and at least an anthracene skeleton.

In the case where the Hartwig-Buchwald reaction is performed in Synthesis Scheme (B-1), Z represents a halogen or a triflate group. As the halogen, iodine, bromine, or chlorine is preferable. In this reaction, a palladium catalyst including a palladium compound or a palladium complex such as bis(dibenzylideneacetone)palladium(0) or palladium (II) acetate and a ligand that coordinates to the palladium complex or the palladium compound, such as tri(tert-butyl) phosphine, tri(n-hexyl)phosphine, or tricyclohexylphosphine, is used. Examples of the base include organic bases such as sodium tert-butoxide, inorganic bases such as a potassium carbonate, and the like. In the case where a solvent is used, toluene, xylene, benzene, tetrahydrofuran, or the like can be used.

In the case where an Ullmann reaction is performed in Synthesis Scheme (B-1), Z represents a halogen. As the halogen, iodine, bromine, or chlorine is preferable. As a catalyst, copper or a copper compound is used. In the case where a copper compound is used as the catalyst, $R^{23}$ and $R^{24}$ in Synthesis Scheme (B-1) individually represent a halogen, an acetyl group, or the like. As the halogen, chlorine, bromine, or iodine can be given. Note that copper (I) iodide where $R^{23}$ is iodine or copper(II) acetate where $R^{24}$ is an acetyl group is preferably used. As the base which is used, an inorganic base such as potassium carbonate can be given. As a solvent, 1,3-dimethyl-3,4,5,6-tetrahydro-2 (1H)-pyrimidinone (DMPU), toluene, xylene, benzene, and the like can be employed. Note that the solvent is not limited thereto. In an Ullmann reaction, DMPU or xylene, which has a high boiling point, is preferably used, in which case the object of the synthesis can be obtained in a shorter time and a higher yield at a reaction temperature of 100° C. or more. A reaction temperature of 150° C. or more is further preferred and accordingly DMPU is more preferably used.

In the above manner, the dibenzocarbazole compounds represented by General Formulae (G1) and (G6) can be synthesized.

Note that the compound described in this embodiment can be used in combination with any of the structures described in the other embodiments as appropriate.

Embodiment 3

In this embodiment, structure examples of a light-emitting element including any of the dibenzocarbazole compounds described in Embodiment 1 will be described with reference to FIGS. 2A to 2C.

Structure Example 1 of Light-Emitting Element

Figure 2A:
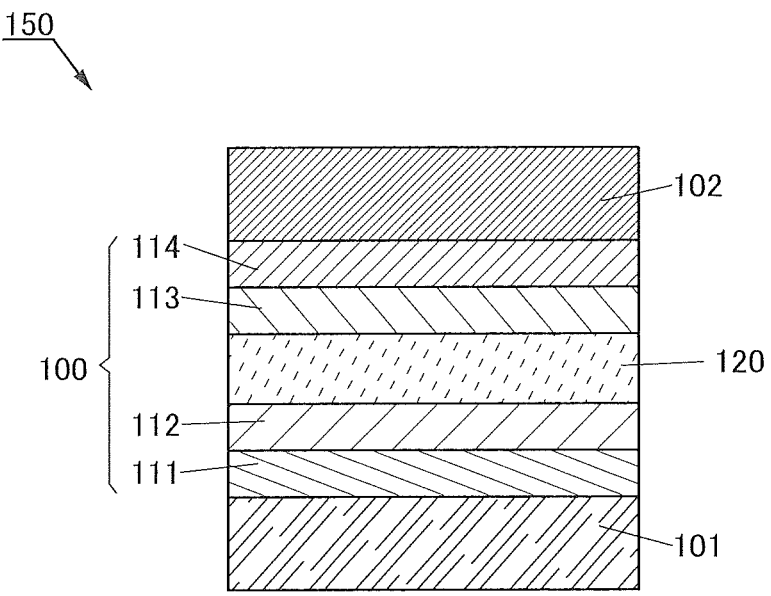
FIGS. 2A and 2B are schematic cross-sectional views of a light-emitting element of one embodiment of the present invention and FIG. 2C is a schematic diagram illustrating the correlation of energy levels.

FIG. 2A is a schematic cross-sectional view of a light-emitting element 150 of one embodiment of the present invention.

The light-emitting element 150 includes a pair of electrodes (an electrode 101 and an electrode 102) and an EL layer 100 therebetween. Any of the layers in the EL layer 100 includes any of the dibenzocarbazole compounds described in Embodiment 1.

The EL layer 100 includes at least a light-emitting layer 120.

The EL layer 100 illustrated in FIG. 2A includes functional layers such as a hole-injection layer 111, a hole-transport layer 112, an electron-transport layer 113, and an electron-injection layer 114, in addition to the light-emitting layer 120.

Note that in this embodiment, although description is given assuming that the electrode 101 and the electrode 102 of the pair of electrodes serve as an anode and a cathode, respectively, they are not limited thereto for the structure of the light-emitting element 150. That is, the electrode 101 may be a cathode, the electrode 102 may be an anode, and the stacking order of the layers between the electrodes may be reversed. In other words, the hole-injection layer 111, the hole-transport layer 112, the light-emitting layer 120, the electron-transport layer 113, and the electron-injection layer 114 may be stacked in this order from the anode side.

Note that the structure of the EL layer 100 is not limited to the structure illustrated in FIG. 2A, and a structure including at least one layer selected from the hole-injection layer 111, the hole-transport layer 112, the electron-transport layer 113, and the electron-injection layer 114 may be employed. Alternatively, the EL layer 100 may include a functional layer which is capable of lowering a hole- or electron-injection barrier, improving a hole- or electron-transport property, inhibiting transport of holes or electrons, or suppressing a quenching phenomenon by an electrode, for example. Note that the light-emitting layer 120 and the functional layers may each be a single layer or stacked layers.

Figure 2B:
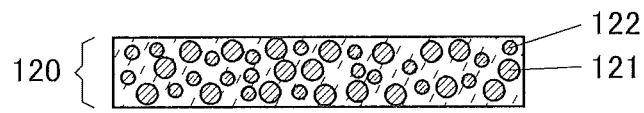

FIG. 2B is a schematic cross-sectional view illustrating an example of the light-emitting layer 120 in FIG. 2A. The light-emitting layer 120 in FIG. 2B includes at least a host material 121 and a guest material 122.

The dibenzocarbazole compounds described in Embodiment 1 have a high carrier-transport property and thus are suitable for the hole-transport layer 112 or the electron-transport layer 113. In addition, the dibenzocarbazole compound has a high carrier-transport property and a wide band gap, and thus is suitable as the host material 121. That is, when any of the dibenzocarbazole compounds described in Embodiment 1 is used for at least one of the host material 121, the hole-transport layer 112, and the electron-transport layer 113 of the light-emitting element 150, a light-emitting element with a low drive voltage can be fabricated. When the dibenzocarbazole compound is used as the host material 121 of the light-emitting element 150, a light-emitting element with a high emission efficiency can be fabricated. Note that the dibenzocarbazole compound is suitable for the host material and the carrier-transport material of a blue light-emitting element because of its wide band gap. Thus, with the structure illustrated in this embodiment, a light-emitting element that emits blue light and has a high emission efficiency can be fabricated. Furthermore, since the dibenzocarbazole compound is highly resistant to repetition of oxidation and reduction, a light-emitting element with a long driving lifetime can be fabricated.

Note that the dibenzocarbazole compounds described in Embodiment 1 have a wide band gap and thus are particularly suitable for a light-emitting element that emits deep blue light. In this specification and the like, deep blue refers to color having a chromaticity y of 0.01 to 0.15 on the CIE 1931 chromaticity coordinate.

Structure Example 2 of Light-Emitting Element

Next, a particularly preferable structure of the light-emitting element illustrated in FIGS. 2A and 2B will be described below with reference to FIG. 2C.

In the light-emitting element 150 illustrated in FIG. 2A, any of the dibenzocarbazole compounds described in Embodiment 1 is used as at least the host material 121.

The host material 121 preferably has a function of converting triplet excitation energy into singlet excitation energy by causing triplet-triplet annihilation (TTA), so that the triplet excitation energy generated in the light-emitting layer 120 can be partly converted into singlet excitation energy by TTA in the host material 121. The singlet excitation energy can be transferred to the guest material 122 and extracted as fluorescence. In order to achieve this, the lowest level of the singlet excitation energy (S1 level) of the host material 121 is preferably higher than the S1 level of the guest material 122. In addition, the lowest level of the triplet excitation energy (T1 level) of the host material 121 is preferably lower than the T1 level of the guest material 122.

Note that the host material 121 may be composed of a single compound or a plurality of compounds. The guest material 122 may be a light-emitting organic material, and the light-emitting organic material is preferably a material capable of emitting fluorescence (hereinafter also referred to as a fluorescent material). A structure in which a fluorescent material is used as the guest material 122 will be described below. The guest material 122 may be rephrased as the fluorescent material.

<Light Emission Mechanism of Light-Emitting Element>

First, the light emission mechanism of the light-emitting element 150 is described below.

In the light-emitting element 150 of one embodiment of the present invention, voltage application between the pair of electrodes (the electrodes 101 and 102) causes electrons and holes to be injected from the cathode and the anode, respectively, into the EL layer 100 and thus current flows. By recombination of the injected electrons and holes, excitons are formed. The ratio of singlet excitons to triplet excitons (hereinafter referred to as exciton generation probability) which are generated by carrier recombination is approximately 1:3 according to the statistically obtained probability. Hence, the probability of formation of singlet excitons is 25%.

Note that the term "exciton" refers to a carrier (electron and hole) pair. Since excitons have excitation energy, a material where excitons are generated is brought into an excited state.

Through the following two processes, singlet excitons are formed in the EL layer 100 and light emission from the guest material 122 can be obtained.

(α) Direct formation process
(β) TTA process.

<<(α) Direct Formation Process>>

Described first is the case where carriers (electrons and holes) recombine in the light-emitting layer 120 included in the EL layer 100 to form a singlet exciton.

When the carriers recombine in the host material 121, excitons are formed to bring the host material 121 into an excited state (a singlet excited state or a triplet excited state). At this time, in the case where the excited state of the host material 121 is a singlet excited state, singlet excitation energy transfers from the S1 level of the host material 121 to the S1 level of the guest material 122, thereby forming the singlet excited state of the guest material 122. Note that the case where the excited state of the host material 121 is a triplet excited state is described later in (β) TTA process.

When the carriers recombine in the guest material 122, excitons are formed to bring the guest material 122 into an excited state (a singlet excited state or a triplet excited state).

In the case where the formed excited state of the guest material 122 is a singlet excited state, light emission is obtained from the singlet excited state of the guest material 122. To obtain a high emission efficiency in this case, the fluorescence quantum yield of the guest material 122 is preferably high, specifically, 50% or higher, further preferably 70% or higher, and still further preferably 90% or higher.

In the case where the formed excited state of the guest material 122 is a triplet excited state, the triplet excited state of the guest material 122 is thermally deactivated and does not contribute to light emission because the guest material 122 is a fluorescent material. However, if the T1 level of the host material 121 is lower than the T1 level of the guest material 122, the triplet excitation energy of the guest material 122 can be transferred from the T1 level of the guest material 122 to the T1 level of the host material 121. In this case, the triplet excitation energy can be converted into singlet excitation energy by (β) TTA process described later.

<<(β) TTA Process>>

Described next is the case where a singlet exciton is formed from triplet excitons formed in the carrier recombination process in the light-emitting layer 120.

Here, the case where the T1 level of the host material 121 is lower than the T1 level of the guest material 122 is described. The correlation of energy levels in this case is schematically shown in FIG. 2C. What terms and numerals in FIG. 2C represent are listed below. Note that the T1 level of the host material 121 may be higher than the T1 level of the guest material 122.

Host (121): the host material 121
Guest (122): the guest material 122 (fluorescent material)
$S_{FH}$: the S1 level of the host material 121
$T_{FH}$: the T1 level of the host material 121
$S_{FG}$: the S1 level of the guest material 122 (fluorescent material)
$T_{FG}$: the T1 level of the guest material 122 (fluorescent material)

Carriers recombine in the host material 121 and excitons are formed to bring the host material 121 into an excited state. At this time, in the case where the formed excitons are triplet excitons and two of the formed triplet excitons approach each other, a reaction in which part of their triplet excitation energy is converted into singlet excitation energy and the triplet excitons are converted into a singlet exciton having energy of the S1 level ($S_{FH}$) of the host material 121 might be caused (see TTA in FIG. 2C). This is represented by General Formula (G11) or (G12).

$$^3H + {}^3H \rightarrow {}^1H^* + {}^1H \quad (G11)$$

$$^3H + {}^3H \rightarrow {}^3H^* + {}^1H \quad (G12)$$

General Formula (G11) represents a reaction in the host material 121 in which a singlet exciton ($^1H^*$) is formed from two triplet excitons ($^3H$) with a total spin quantum number of 0. General Formula (G12) represents a reaction in the host material 121 in which an electronically or oscillatorily excited triplet exciton ($^3H^*$) is formed from two triplet excitons ($^3H$) with a total spin quantum number of 1 (atomic unit). In General Formulae (G11) and (G12), $^1H$ represents the singlet ground state of the host material 121.

Although the reactions in General Formulae (G11) and (G12) occur at the same probability, there are three times as many pairs of triplet excitons with a total spin quantum number of 1 (atomic unit) as pairs of triplet excitons with a total spin quantum number of 0. In other words, when an exciton is formed from two triplet excitons, the singlet-triplet exciton formation ratio is 1:3 according to the statistically obtained probability. In the case where the density of the triplet excitons in the light-emitting layer 120 is sufficiently high (e.g., $1 \times 10^{-12}$ cm$^{-3}$ or more), only the reaction of two triplet excitons approaching each other can be considered whereas deactivation of a single triplet exciton is ignored.

Thus, by one reaction in General Formula (G11) and three reactions in General Formula (G12), one singlet exciton ($^1H^*$) and three triplet excitons ($^3H^*$) which are electronically or oscillatorily excited are formed from eight triplet excitons ($^3H$). This is represented by General Formula (G13).

$$8\,{}^3H \rightarrow {}^1H^* + 3\,{}^3H^* + 4\,{}^1H \quad (G13)$$

The electronically or oscillatorily excited triplet excitons ($^3H^*$), which are formed as General Formula (G13), become triplet excitons ($^3H$) by relaxation and then repeat the reaction in General Formula (G13) again with other triplet excitons. Hence, in General Formula (G13), if all the triplet excitons ($^3H$) are converted into singlet excitons ($^1H^*$), five triplet excitons ($^3H$) form one singlet exciton ($^1H^*$) (General Formula (G14)).

$$5\,{}^3H \rightarrow {}^1H^* + 4\,{}^1H \quad (G14)$$

The ratio of singlet excitons ($^1H^*$) to triplet excitons ($^3H$) which are directly formed by recombination of carriers injected from a pair of electrodes is statistically as follows: $^1H^*:^3H=1:3$. That is, the probability of singlet excitons being directly formed by recombination of carriers injected from a pair of electrodes is 25%.

When the singlet excitons directly formed by recombination of carriers injected from a pair of electrodes and the singlet excitons formed by TTA are put together, eight singlet excitons can be formed from twenty excitons (the sum of singlet excitons and triplet excitons) directly formed by recombination of carriers injected from a pair of electrodes (General Formula (G15)). That is, TTA can increase the probability of singlet exciton formation from 25%, which is the conventional value, to at most 40% (=8/20).

$$5\,{}^1H^* + 15\,{}^3H \rightarrow 5\,{}^1H^* + (3\,{}^1H^* + 12\,{}^1H) \quad (G15)$$

Figure 2C:
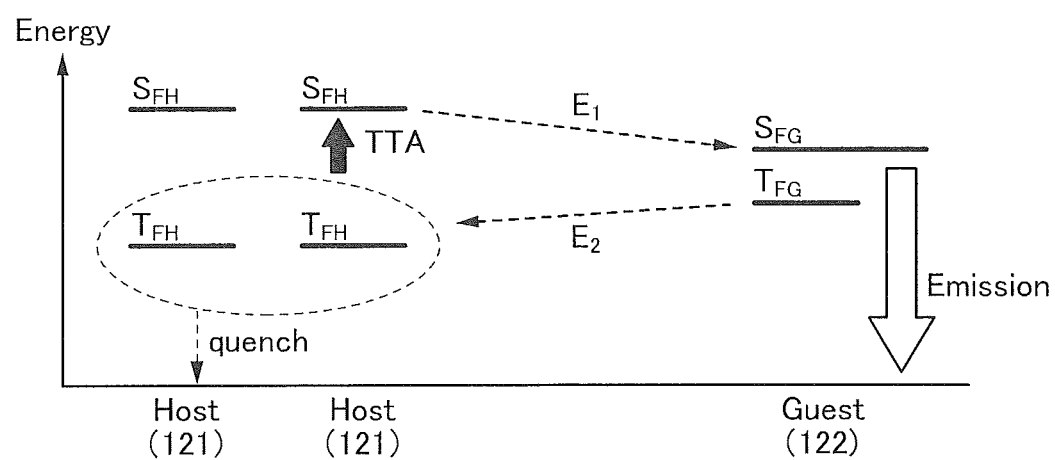

In the singlet excited state of the host material 121 which is formed by the singlet excitons formed through the above process, energy is transferred from the S1 level ($S_{FH}$) of the host material 121 to the S1 level ($S_{FG}$) of the guest material 122, which is lower than $S_{FH}$ (see Route $E_1$ in FIG. 2C). Then, the guest material 122 brought into a singlet excited state emits fluorescence.

In the case where carriers recombine in the guest material 122 and an excited state formed by the formed excitons is a triplet excited state, if the T1 level ($T_{FH}$) of the host material 121 is lower than the T1 level ($T_{FG}$) of the guest material 122, triplet excitation energy of $T_{FG}$ is not deactivated and transferred to $T_{FH}$ (see Route $E_2$ in FIG. 2C) to contribute to TTA.

In the case where the T1 level ($T_{FG}$) of the guest material 122 is lower than the T1 level ($T_{FH}$) of the host material 121, the weight percentage of the guest material 122 is preferably lower than that of the host material 121. Specifically, the weight ratio of the guest material 122 to the host material 121 is preferably greater than 0 and less than or equal to 0.05, which reduces the probability of carrier recombination in the guest material 122. In addition, the probability of energy transfer from the T1 level ($T_{FH}$) of the host material 121 to the T1 level ($T_{FG}$) of the guest material 122 can be reduced.

In the case where a guest material emitting blue light is used, the weight ratio of the guest material 122 to the host material 121 is preferably greater than 0 and less than 0.03, which allows deeper blue light to be emitted.

As described above, triplet excitons formed in the light-emitting layer 120 can be converted into singlet excitons by TTA, so that light emitted from the guest material 122 can be efficiently obtained.

Since TTA can increase the probability of formation of singlet excitons and the emission efficiency of a light-emitting element as described above, increasing the probability of occurrence of TTA (also referred to as TTA efficiency) is important for high emission efficiency. That is, it is important that a delayed fluorescence component due to TTA account for a large proportion of light emitted from the light-emitting element.

To increase the probability of occurrence of TTA, the host material 121 preferably has a higher singlet excitation energy and a lower triplet excitation energy than the guest material 122. Thus, the host material 121 is preferably a compound having a condensed aromatic ring skeleton, further preferably, a compound including an aryl group having at least an anthracene skeleton.

In a light-emitting element that emits blue light, a compound with high excitation energy needs to be used as the host material 121. That is, a compound including an aryl group having at least an anthracene skeleton is preferably used as the compound that emits delayed fluorescence due to TTA and can be used as a light-emitting material or the host material 121 in the light-emitting element that emits blue light.

When holes and electrons are injected from the anode and the cathode, respectively, into an EL layer so that current flows, the holes and the electrons are respectively injected to the highest occupied molecular orbital (HOMO) and the lowest unoccupied molecular orbital (LUMO) of a compound included in the EL layer, and then transferred.

In the case where the injected holes and electrons recombine in the host material and for example, the HOMO and the LUMO in the host material have molecular orbitals in the same region, an exciton to be generated has energy equivalent to the energy gap between the HOMO level and the LUMO level.

Hence, the compound preferably has a hole-transport skeleton and an electron-transport skeleton each with a wide band gap.

Any of the dibenzocarbazole compounds described in Embodiment 1 is preferably used as the above compound.

Benzo[a]anthracene skeleton is a tetracyclic aromatic hydrocarbon but has an S1 level and a T1 level that are approximately as high as those of anthracene, which is a tricyclic aromatic hydrocarbon. Thus, the dibenzocarbazole compound having the benzo[a]anthracene skeleton is suitable for the light-emitting element with a high TTA efficiency.

Note that a factor of delayed fluorescence in a light-emitting element, which is other than TTA, may be thermally activated delayed fluorescence due to reverse intersystem crossing from the triplet excited state to the singlet excited state. To efficiently cause reverse intersystem crossing, an energy difference between the S1 level and the T1 level is preferably 0.2 eV or less. In other words, an energy difference greater than 0.2 eV between the S1 level and the T1 level hardly causes reverse intersystem crossing. Therefore, to efficiently cause TTA, an energy difference between the lowest singlet excitation energy level and lowest triplet excitation energy level of a compound in which TTA occurs is preferably greater than 0.2 eV, further preferably greater than or equal to 0.5 eV.

The lowest singlet excitation energy level of an organic compound can be observed from an absorption spectrum at a transition from the singlet ground state to the lowest singlet excited state in the organic compound. Alternatively, the lowest singlet excitation energy level may be estimated from a peak wavelength of a fluorescence spectrum of the organic compound. Furthermore, the lowest triplet excitation energy level can be observed from an absorption spectrum at a transition from the singlet ground state to the lowest triplet excited state in the organic compound, but is difficult to observe in some cases because this transition is a forbidden transition. In such cases, the lowest triplet excitation energy level may be estimated from a peak wavelength of a phosphorescence spectrum of the organic compound. Thus, a difference in equivalent energy value between the peak wavelengths of the fluorescence and phosphorescence spectra of the organic compound is preferably greater than 0.2 eV, further preferably greater than or equal to 0.5 eV.

<Materials>

Next, components of a light-emitting element of one embodiment of the present invention are described in detail.

<<Light-Emitting Layer>>

In the light-emitting layer 120, the weight percentage of the host material 121 is higher than that of at least the guest material 122, and the guest material 122 (fluorescent material) is dispersed in the host material 121. Any of the dibenzocarbazole compounds described in Embodiment 1 is preferably used as the host material 121 in the light-emitting layer 120. Note that in the light-emitting layer 120, the host material 121 may be composed of one kind of compound or a plurality of compounds.

In the light-emitting layer 120, the guest material 122 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like, and for example, any of the following materials can be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)pyrene-1,6-diamine (abbreviation: 1,6tBuFLPAPrn), N,N'-diphenyl-N, [4-(9-phenyl-9H-fluoren-9-yl)phenyl]-3,8-dicyclohexylpyrene-1,6-diamine (abbreviation: ch-1,6FLPAPrn), [4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DO-TB), 2-(2,6-bis[2-[4-(dimethylamino)phenyl]ethenyl]-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd:1',2',3'-lm]perylene.

Note that the light-emitting layer 120 may include a material other than the host material 121 and the guest material 122.

Although there is no particular limitation on a material that can be used in the light-emitting layer 120, any of the following materials can be used, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)-tris(1-phenyl-1H-benzimidazole) (abbreviation: TPBI), bathophenantbroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be used. Specific examples thereof include 9,10-diphenylanthracene (abbreviation: DPAnth), N,N-diphenyl-9-[4-(10-phenyl-9-anthryl)phenyl]-9H-carbazol-3-amine (abbreviation: CzAlPA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N",N",N"',N"'-octaphenyldibenzo[g,p]chrysene-2,7,10,15-tetraamine (abbreviation: DBC1), 9-phenyl-3-[4-(10-phenyl-9-anthryl)phenyl]-9H-carbazol (abbreviation: PCzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). A plurality of dibenzocarbazole compounds described in Embodiment 1 may be included. One or more substances having a wider energy gap than the guest material 122 is preferably selected from these substances and known substances.

Note that the light-emitting layer 120 can have a structure in which two or more layers are stacked. For example, in the case where the light-emitting layer 120 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. Also in such a case, at least one light-emitting layer preferably includes any of the dibenzocarbazole compounds described in Embodiment 1.

Next, details of other components of the light-emitting element 150 in FIG. 2A are described.

<<Hole-Injection Layer>>

The hole-injection layer 111 has a function of reducing a barrier for hole injection from one of the pair of electrodes (the electrode 101 or the electrode 102) to promote hole injection and is formed using, for example, a transition metal oxide, a phthalocyanine derivative, or an aromatic amine. As the transition metal oxide, molybdenum oxide, vanadium oxide, ruthenium oxide, tungsten oxide, manganese oxide, or the like can be given. As the phthalocyanine derivative, phthalocyanine, metal phthalocyanine, or the like can be given. As the aromatic amine, a benzidine derivative, a phenylenediamine derivative, or the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. As examples of the material having an electron-accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: F$_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1 \times 10^{-6}$ cm$^2$/Vs or higher is preferable. Specifically, an aromatic amine, a carbazole derivative, an aromatic hydrocarbon, a stilbene derivative, or the like can be used. Furthermore, the hole-transport material may be a high molecular compound.

Examples of the aromatic amine compound, which has a high hole-transport property, include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Specific examples of the carbazole derivative are 3-[N-(4-diphenylaminophenyl)-N-phenylamino]-9-phenylcarbazole (abbreviation: PCzPCA1), 3,6-bis[N-(4-diphenylaminophenyl)-N-phenylamino]-9-phenylcarbazole (abbreviation: PCzPCA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole derivative include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples are pentacene and coronene. The aromatic hydrocarbon having a hole mobility of 1×10⁻ cm²/Vs or more and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation: DPVBi), and 9,10-bis[4-(2,2-diphenylvinyl)phenyl]anthracene (abbreviation: DPVPA).

Other examples are high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

Examples of the material having a high hole-transport property are aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N-bis(9-phenylcarbazol-3-yl)-N,N'-diphenylbenzene-1,3-diamine (abbreviation: PCA2B), N,N',N'-triphenyl-N,N,N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluor en-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N-diphenyl-9,9-dimethylfluorene-2,7-diamine (abbreviation: YGA2F). Other examples are amine compounds, carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di (9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). Among the above compounds, compounds including at least one of a pyrrole skeleton, a furan skeleton, a thiophene skeleton, and an aromatic amine skeleton are preferred because of their high stability and reliability. In addition, the compounds having such skeletons have a high hole-transport property to contribute to a reduction in driving voltage.

<<Hole-Transport Layer>>

The hole-transport layer 112 is a layer containing a hole-transport material and can be formed using any of the materials given as examples of the material of the hole-injection layer 111. In order that the hole-transport layer 112 has a function of transporting holes injected into the hole-injection layer 111 to the light-emitting layer 120, the highest occupied molecular orbital (HOMO) level of the hole-transport layer 112 is preferably equal or close to the HOMO level of the hole-injection layer 111.

As the hole-transport material, a substance having a hole mobility of 1×10 cm²/Vs or higher is preferably used. Note that any substance other than the substances listed here may be used as long as the hole-transport property is higher than the electron-transport property. The layer including a substance having a high hole-transport property is not limited to a single layer, and two or more layers containing the aforementioned substances may be stacked.

Any of the dibenzocarbazole compounds described in Embodiment 1 may be used as a material included in the hole-transport layer 112.

<<Electron-Transport Layer>>

The electron-transport layer 113 has a function of transporting, to the light-emitting layer 120, electrons injected from the other of the pair of electrodes (the electrode 101 or the electrode 102) through the electron-injection layer 114. A material having a property of transporting more electrons than holes can be used as an electron-transport material, and a material having an electron mobility of $1\times10^{-6}$ cm$^2$/Vs or higher is preferred. As the compound which easily accepts electrons (the material having an electron-transport property), a π-electron deficient heteroaromatic compound such as a nitrogen-containing heteroaromatic compound, a metal complex, or the like can be used. Specific examples include a metal complex having a quinoline ligand, a benzoquinoline ligand, an oxazole ligand, or a thiazole ligand; an oxadiazole derivative; a triazole derivative; a benzimidazole derivative; a quinoxaline derivative; a dibenzoquinoxaline derivative; a phenanthroline derivative; a pyridine derivative; a bipyridine derivative; a pyrimidine derivative; and a triazine derivative. Note that a substance other than the above substances may be used as long as it has a higher electron-transport property than a hole-transport property. The electron-transport layer 113 is not limited to a single layer, and may include stacked two or more layers containing the aforementioned substances.

Specific examples include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato) (4-phenylphenolato) aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolate]zinc(II) (abbreviation: ZnPBO) or bis[2-(2-benzothiazolyl)phenolato]zinc(II) (abbreviation: ZnBTZ) can be used. Other than the metal complexes, any of the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl) tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl) biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBT2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); heterocyclic compounds having a pyridine skeleton such as 3,5-bis[3-(9H-carbazol-9-yl)phenyl] pyridine (abbreviation: 35DCzPPy) and 1,3,5-tris[3-(3-pyridyl)-phenyl]benzene (abbreviation: TmPyPB); and heteroaromatic compounds such as 4,4'-bis(5-methylbenzoxazol-2-yl)stilbene (abbreviation: BzOs). Among the heterocyclic compounds, the heterocyclic compounds having at least one of a triazine skeleton, a diazine skeleton (pyrimidine, pyrazine, pyridazine), and a pyridine skeleton are preferred because of their high reliability and stability. In addition, the heterocyclic compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1\times10^{-6}$ cm$^2$/Vs or higher.

Any of the dibenzocarbazole compounds described in Embodiment 1 can also be used suitably. Note that a substance other than the above substances may be used as long as it has a higher electron-transport property than a hole-transport property. The electron-transport layer 113 is not limited to a single layer, and may include stacked two or more layers containing the aforementioned substances.

Between the electron-transport layer 113 and the light-emitting layer 120, a layer that controls the transport of electron carriers may be provided. This is a layer formed by the addition of a small amount of a substance having a high electron-trapping property to the aforementioned material having a high electron-transport property, and the layer is capable of adjusting carrier balance by retarding the transport of electron carriers. Such a structure is very effective in preventing a problem (such as a reduction in element lifetime) caused when electrons pass through the light-emitting layer.

An n-type compound semiconductor may also be used, and an oxide such as titanium oxide, zinc oxide, silicon oxide, tin oxide, tungsten oxide, tantalum oxide, barium titanate, barium zirconate, zirconium oxide, hafnium oxide, aluminum oxide, yttrium oxide, or zirconium silicate; a nitride such as silicon nitride; cadmium sulfide; zinc selenide; or zinc sulfide can be used, for example.

<<Electron-Injection Layer>>

The electron-injection layer 114 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, or the like can be given. Specifically, an alkali metal, an alkaline earth metal, or a compound thereof, such as lithium fluoride, sodium fluoride, cesium fluoride, calcium fluoride, or lithium oxide, can be used. Alternatively, a rare earth metal compound like erbium fluoride can be used. Electride may also be used for the electron-injection layer 114. Examples of the electride include a substance in which electrons are added at high concentration to calcium oxide-aluminum oxide. The electron-injection layer 114 can be formed using the substance that can be used for the electron-transport layer 113.

A composite material in which an organic compound and an electron donor (donor) are mixed may also be used for the electron-injection layer 114. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 113 (e.g., the metal complexes and heteroaromatic compounds) can be used, for example. As the electron donor, a substance showing an electron-donating property with respect to the organic compound may be used. Specifically, an alkali metal, an alkaline earth metal, and a rare earth metal are preferred; for example, lithium, sodium, cesium, magnesium, calcium, erbium, and ytterbium are given. In addition, an alkali metal oxide or an alkaline earth metal oxide is preferred; for example, lithium oxide, calcium oxide, and barium oxide are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, or a polymer) may be used in the light-emitting layer, the hole-injection layer, the hole-transport layer, the electron-transport layer, and the electron-injection layer.

<<Quantum Dot>>

A quantum dot is a semiconductor nanocrystal with a size of several nanometers to several tens of nanometers and contains approximately $1 \times 10^3$ to $1 \times 10^6$ atoms. Since the energy shift of quantum dots depends on their size, quantum dots made of the same substance emit light with different wavelengths depending on their size; thus, emission wavelengths can be easily adjusted by changing the size of quantum dots.

A quantum dot has an emission spectrum with a narrow peak, leading to emission with high color purity. In addition, a quantum dot is said to have a theoretical internal quantum efficiency of approximately 100%, which far exceeds that of a fluorescent organic compound, i.e., 25%, and is comparable to that of a phosphorescent organic compound. Therefore, a quantum dot can be used as a light-emitting material to obtain a light-emitting element having high light-emitting efficiency. Furthermore, since a quantum dot which is an inorganic material has high inherent stability, a light-emitting element which is favorable also in terms of lifetime can be obtained.

Examples of a material of a quantum dot include a Group 14 element, a Group element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; triiron tetraoxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur, a compound of cadmium, selenium, and tellurium; a compound of zinc, cadmium, and selenium; a compound of indium, gallium, and arsenic; a compound of indium, gallium, and selenium; a compound of indium, selenium, and sulfur, a compound of copper, indium, and sulfur, and combinations thereof. What is called an alloyed quantum dot, whose composition is represented by a given ratio, may be used. For example, an alloyed quantum dot of cadmium, selenium, and sulfur is an effective material to obtain blue light because the emission wavelength can be changed by changing the percentages of the elements.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether, trialkylphosphines such as tripropylphosphine, tributylphosphine, trihexylphosphine, and trioctylphoshine; polyoxyethylene alkylphenyl ethers such as polyoxyethylene n-octylphenyl ether and polyoxylethylene n-nonylphenyl ether, tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolones; animoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since quantum dots with a smaller size have a wider band gap, the size is adjusted as appropriate so that light with a desired wavelength can be obtained. Light emission from the quantum dots shifts to a blue color side, i.e., a high energy side, as the crystal size decreases; thus, the emission wavelengths of the quantum dots can be adjusted over a wavelength region of a spectrum of an ultraviolet region, a visible light region, and an infrared region by changing the size of the quantum dots. The range of size (diameter) of quantum dots which is usually used is 0.5 nm to 20 nm, preferably 1 nm to 10 nm. The emission spectra are narrowed as the size distribution of the quantum dots gets smaller, and thus light with high color purity can be obtained. The shape of the quantum dots is not particularly limited and may be a spherical shape, a rod shape, a circular shape, or the like. Quantum rods which are rod-like shape quantum dots have a function of emitting directional light; thus, quantum rods can be used as a light-emitting material to obtain a light-emitting element with higher external quantum efficiency.

In most organic EL elements, light-emitting materials are dispersed in host materials so that the concentration quenching of the light-emitting materials is suppressed to improve emission efficiency. The host material needs to have a singlet excitation energy level or a triplet excitation energy level higher than or equal to that of the light-emitting material. Particularly in the case where a blue phosphorescent material is used as a light-emitting material, it is not easy to develop a host material having a long lifetime and a triplet excitation energy level higher than or equal to that of the blue phosphorescent material. With use of quantum dots, a light-emitting layer can be obtained with no host material used while the emission efficiency is maintained, thereby offering a light-emitting element which is favorable in terms of a lifetime. In the case where the light-emitting layer is composed of only quantum dots, core-shell quantum dots (including core-multishell quantum dots) are preferably used.

In the case where quantum dots are used as the light-emitting material in the light-emitting layer, the thickness of the light-emitting layer is set to 3 nm to 100 nm, preferably 10 nm to 100 nm, and the light-emitting layer is made to contain 1 volume % to 100 volume % of the quantum dots. Note that it is preferable that the light-emitting layer be composed of only the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, blade coating method, a roll coating method, an ink-jet method, a printing method, a spray coating method, a curtain coating method, or a Langmuir-Blodgett method) may be performed. For a light-emitting layer containing a phosphorescent material, a vacuum evaporation method, as well as the wet process, can be suitably employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

<<Pair of Electrodes>>

The electrodes 101 and 102 function as an anode and a cathode of each light-emitting element. The electrodes 101 and 102 can be formed using a metal, an alloy, or a conductive compound, a mixture or a stack thereof, or the like.

One of the electrodes 101 and 102 is preferably formed using a conductive material having a function of reflecting light. Examples of the conductive material include aluminum (Al) and an alloy containing Al. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, a light-emitting element with aluminum can be manufactured at low costs. Alternatively, silver (Ag), an alloy of Ag and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrodes 101 and 102 is preferably formed using a conductive material having a function of transmitting light. Examples of the conductive material include a conductive material having a visible light transmittance higher than or equal to 40% and lower than or equal to 100%, preferably higher than or equal to 60% and lower than or equal to 100%, and a resistivity lower than or equal to $1 \times 10^{-2}$ $\Omega \cdot$cm.

The electrodes 101 and 102 may each be formed using a conductive material having functions of transmitting light and reflecting light. Examples of the conductive material include a conductive material having a visible light reflectivity higher than or equal to 20% and lower than or equal to 80%, preferably higher than or equal to 40% and lower than or equal to 70%, and a resistivity lower than or equal to $1 \times 10^{-2}$ $\Omega \cdot$cm. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, the material transmitting light may be a material that transmits visible light and has conductivity. Examples of the material include, in addition to the above-described oxide conductor typified by ITO, an oxide semiconductor and an organic conductor containing an organic substance. Examples of the organic conductor containing an organic substance include a composite material in which an organic compound and an electron donor (donor material) are mixed and a composite material in which an organic compound and an electron acceptor (acceptor material) are mixed. Alternatively, an inorganic carbon-based material such as graphene may be used. The resistivity of the material is preferably lower than or equal to $1\times10^5$ Ω·cm, further preferably lower than or equal to $1\times10^4$ Ω·cm.

Alternatively, the electrode 101 and/or the electrode 102 may be formed by stacking two or more of these materials.

Furthermore, to increase light extraction efficiency, a material having a higher refractive index than an electrode that has a function of transmitting light may be formed in contact with the electrode. Such a material may be a conductive material or a non-conductive material as long as having a function of transmitting visible light. For example, in addition to the above-described oxide conductor, an oxide semiconductor and an organic material are given as examples. As examples of the organic material, materials of the light-emitting layer, the hole-injection layer, the hole-transport layer, the electron-transport layer, and the electron-injection layer are given. Alternatively, an inorganic carbon-based material or a metal film thin enough to transmit light can be used. A plurality of layers each of which is formed using the material having a high refractive index and has a thickness of several nanometers to several tens of nanometers may be stacked.

In the case where the electrode 101 or the electrode 102 functions as the cathode, the electrode preferably contains a material having a low work function (lower than or equal to 3.8 eV). The examples include an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, and an alloy containing aluminum and silver.

In the case where the electrode 101 or the electrode 102 is used as an anode, a material having a high work function (higher than or equal to 4.0 eV) is preferably used.

Alternatively, the electrodes 101 and 102 may each be a stack of a conductive material having a function of reflecting light and a conductive material having a function of transmitting light. Such a structure is preferable because the electrodes 101 and 102 can each have a function of adjusting the optical path length so that desired light emitted from each light-emitting layer resonates and is intensified.

As the method for forming the electrodes 101 and 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element in one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element as long as it has a function of protecting the light-emitting element or the optical element.

In the present invention and the like, a light-emitting element can be formed using any of a variety of substrates, and there is no particular limitation on the type of substrate. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper which include a fibrous material, and a base material film. Examples of a glass substrate include a barium borosilicate glass substrate, an aluminoborosilicate glass substrate, and a soda lime glass substrate. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Alternatively, polypropylene, polyester, polyvinyl fluoride, polyvinyl chloride, or the like can be used. Further alternatively, polyamide, polyimide, aramid, epoxy, an inorganic vapor deposition film, paper, or the like can be used.

Alternatively, a flexible substrate may be used as the substrate such that the light-emitting element is provided directly on the flexible substrate. Further alternatively, a separation layer may be provided between the substrate and the light-emitting element. The separation layer can be used when part or the whole of a light-emitting element formed over the separation layer is separated from the substrate and transferred onto another substrate. In such a case, the light-emitting element can be transferred to a substrate having low heat resistance or a flexible substrate as well. Note that the above separation layer may have a structure in which inorganic films of a tungsten film and a silicon oxide film are stacked, a structure in which a resin film of polyimide or the like is formed over a substrate, or the like.

In other words, after the light-emitting element is formed using a substrate, the light-emitting element may be transferred to another substrate. Example of the substrate to which the light-emitting element is transferred are, in addition to the above substrates, a cellophane substrate, a stone substrate, a wood substrate, a cloth substrate (including a natural fiber (e.g., silk, cotton, and hemp), a synthetic fiber (e.g., nylon, polyurethane, and polyester), a regenerated fiber (e.g., acetate, cupra, rayon, and regenerated polyester), and the like), a leather substrate, and a rubber substrate. When such a substrate is used, a light-emitting element with high durability, high heat resistance, reduced weight, or reduced thickness can be formed.

The light-emitting element 150 may be formed over an electrode electrically connected to a field-effect transistor (FET), for example, which is formed over any of the above-described substrates. Accordingly, an active matrix display device in which the FET controls the driving of the light-emitting element 150 can be manufactured.

In this embodiment, one embodiment of the present invention has been described. Other embodiments of the present invention are described in the other embodiments. Note that one embodiment of the present invention is not limited to the above examples. In other words, various embodiments of the invention are described in this embodiment and the other embodiments, and one embodiment of the present invention is not limited to a particular embodiment. An example in which one embodiment of the present invention is used in a light-emitting element is described; however, one embodiment of the present invention is not limited thereto. Depending on circumstances or conditions, one embodiment of the present invention is not necessarily used in a light-emitting element, for example. For another example, one embodiment is not limited to the example in which the EL layer includes the dibenzocarbazole compound. Depending on circumstances, the EL layer does not necessarily include the dibenzocarbazole compound.

The structure described above in this embodiment can be combined with any of the other embodiments as appropriate.

Embodiment 4

In this embodiment, a light-emitting element having a structure different from that described in Embodiment 3 will be described below with reference to FIGS. 3A to 4C. In FIGS. 3A to 4C, a portion having a function similar to that in FIG. 2A is represented by the same hatch pattern as in FIG. 2A and not especially denoted by a reference numeral in some cases. In addition, common reference numerals are used for portions having similar functions, and a detailed description of the portions is omitted in some cases.

Structure Example 1 of Light-Emitting Element

Figure 3A:
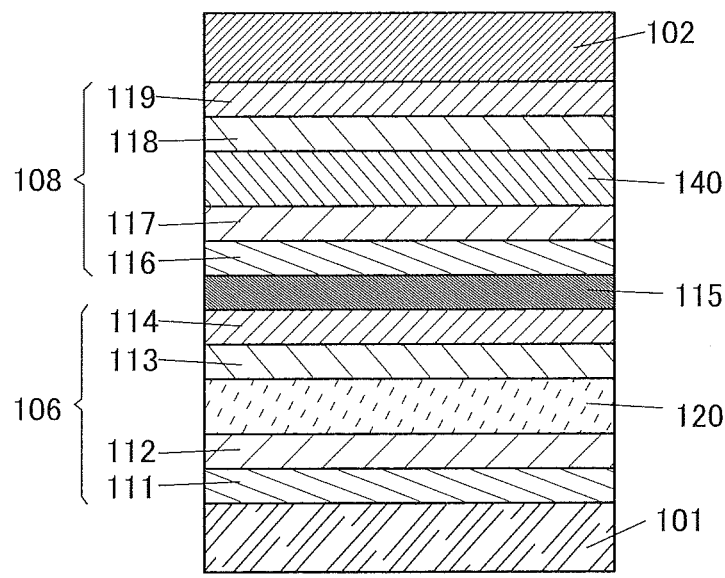
FIGS. 3A and 3B are each a schematic cross-sectional view of a light-emitting element of one embodiment of the present invention and FIG. 3C shows a correlation of energy levels.

FIG. 3A is a schematic cross-sectional view of a light-emitting element 250.

The light-emitting element 250 illustrated in FIG. 3A includes a plurality of light-emitting units (a light-emitting unit 106 and a light-emitting unit 108 in FIG. 3A) between a pair of electrodes (the electrode 101 and the electrode 102). One of the light-emitting units preferably has the same structure as the EL layer 100 illustrated in FIGS. 2A to 2C. That is, it is preferable that the light-emitting element 150 illustrated in FIGS. 2A to 2C include one light-emitting unit while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 3A, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable that the EL layer 100 illustrated in FIGS. 2A to 2C be used in the light-emitting unit 106.

The light-emitting element 250 includes the light-emitting layer 120 and a light-emitting layer 140. The light-emitting unit 106 includes the hole-injection layer 111, the hole-transport layer 112, the electron-transport layer 113, and the electron-injection layer 114 in addition to the light-emitting layer 120. The light-emitting unit 108 includes a hole-injection layer 116, a hole-transport layer 117, an electron-transport layer 118, and an electron-injection layer 119 in addition to the light-emitting layer 140.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 3 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A material having a hole mobility of $1 \times 10^{-6}$ cm$^2$/Vs or higher is preferably used as the organic compound. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115 as in the light-emitting unit 108, the charge-generation layer 115 can also serve as a hole-injection layer or a hole-transport layer of the light-emitting unit; thus, a hole-injection layer or a hole-transport layer is not necessarily included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive film.

The charge-generation layer 115 provided between the light-emitting unit 106 and the light-emitting unit 108 is configured so that electrons are injected into one of the light-emitting units and holes are injected into the other light-emitting unit when a voltage is applied between the electrode 101 and the electrode 102. For example, in FIG. 3A, the charge-generation layer 115 injects electrons into the light-emitting unit 106 and holes into the light-emitting unit 108 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even when having lower conductivity than the pair of electrodes (the electrodes 101 and 102).

The charge-generation layer 115 formed by using any of the above materials can suppress an increase in drive voltage caused by the stack of the light-emitting layers.

Although FIG. 3A illustrates the light-emitting element including the two light-emitting units, the light-emitting element can include three or more light-emitting units stacked. With a plurality of light-emitting units between a pair of electrodes, which are partitioned by the charge-generation layer as in the light-emitting element 250, it is possible to provide a light-emitting element which can emit high-luminance light with the current density kept low, has a long lifetime, and consumes low power.

When the structure described in Embodiment 3 is used for at least one of the plurality of units, a light-emitting element with a high emission efficiency can be provided.

When any of the dibenzocarbazole compounds described in Embodiment 1 is used for at least one of the light-emitting layers, a light-emitting element with a high emission efficiency can be provided.

In this embodiment, the light-emitting layer 120 included in the light-emitting unit 106 has a structure similar to that of the light-emitting layer 120 illustrated in FIG. 2B. That is, the light-emitting layer 120 includes the host material 121 and the guest material 122.

Figure 3B:
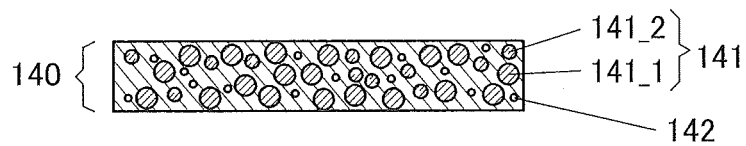

The light-emitting layer 140 included in the light-emitting unit 108 includes a host material 141 and a guest material 142 as illustrated in FIG. 3B. The host material 141 includes an organic compound 141_1 and an organic compound 141_2. Note that the guest material 142 is described below as a phosphorescent material.

<<Light Emission Mechanism of Light-Emitting Layer 140>>

The light emission mechanism of the light-emitting layer 140 is described below.

The organic compound 141_1 and the organic compound 141_2 which are included in the light-emitting layer 140 form an exciplex.

Although it is acceptable as long as the combination of the organic compound 141_1 and the organic compound 141_2 can form an exciplex, preferably, one of them is a compound having a hole-transport property and the other is a compound having an electron-transport property.

Figure 3C:
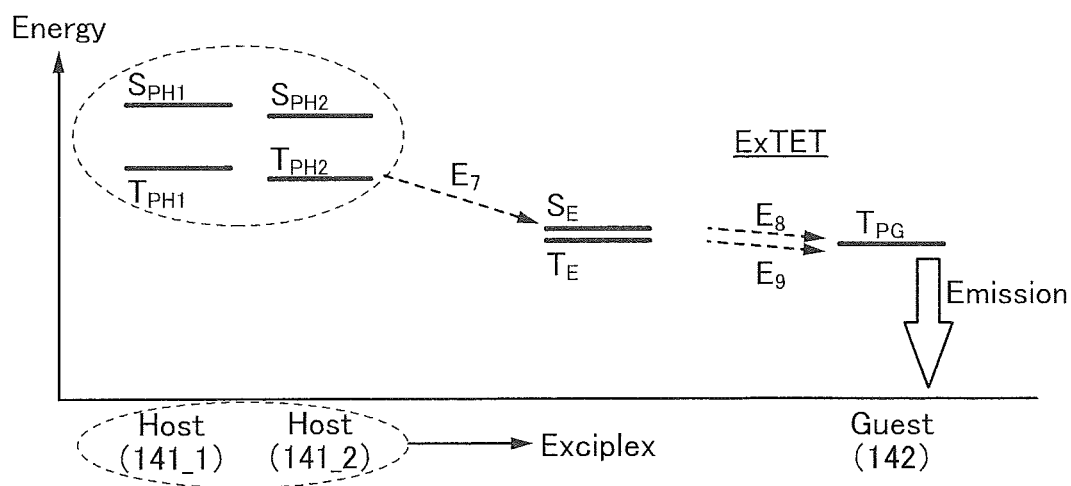

FIG. 3C shows a correlation between the energy levels of the organic compound 141_1, the organic compound 141_2, and the guest material 142 in the light-emitting layer 140. The following explains what terms and numerals in FIG. 3C represent:

Host (141_1): the organic compound 141_1 (host material);
Host (141_2): the organic compound 141_2 (host material);
Guest (142): the guest material 142 (phosphorescent material);
$S_{PH1}$: the S1 level of the organic compound 141_1 (host material);
$T_{PH1}$: the T1 level of the organic compound 141_1 (host material);
$S_{PH2}$: the S1 level of the organic compound 141_2 (host material);
$T_{PH2}$: the T1 level of the organic compound 141_2 (host material);
$T_{PG}$: the T1 level of the guest material 142 (phosphorescent material);
$S_E$: the S1 level of the exciplex; and
$T_E$: the T1 level of the exciplex.

The organic compound 141_1 and the organic compound 141_2 form an exciplex, and the S1 level ($S_E$) and the T1 level ($T_E$) of the exciplex are energy levels adjacent to each other (see Route $E_7$ in FIG. 3C).

One of the organic compound 141_1 and the organic compound 141_2 receives a hole and the other receives an electron to readily form an exciplex. Alternatively, when one of the organic compounds is brought into an excited state, it immediately interacts with the other to form an exciplex. Consequently, most excitons in the light-emitting layer 140 exist as exciplexes. Because the excitation energy levels ($S_E$ or $T_E$) of the exciplex are lower than the S1 levels ($S_{PH1}$ and $S_{PH2}$) of the host materials (the organic compounds 141_1 and 141_2) that form the exciplex, the excited state of the host material 141 can be formed with lower excitation energy. This can reduce the drive voltage of the light-emitting element.

Both of the energies $S_E$ and $T_E$ of the exciplex are then transferred to the T1 level of the guest material 142 (the phosphorescent material); thus, light emission is obtained (see Routes $E_8$ and $E_9$ in FIG. 3C).

Note that the T1 level ($T_E$) of the exciplex is preferably higher than the T1 level ($T_{PG}$) of the guest material 142. In that case, the singlet excitation energy and the triplet excitation energy of the formed exciplex can be transferred from the S1 level ($S_E$) and the T1 level ($T_E$) of the exciplex to the T1 level ($T_{PG}$) of the guest material 142.

In order to efficiently transfer excitation energy from the exciplex to the guest material 142, the T1 level ($T_E$) of the exciplex is preferably lower than or equal to the T1 levels ($T_{PH1}$ and $T_{PH2}$) of the organic compounds (the organic compound 141_1 and the organic compound 141_2) which form the exciplex. Thus, quenching of the triplet excitation energy of the exciplex due to the organic compounds (the organic compounds 141_1 and 141_2) is less likely to occur, resulting in efficient energy transfer from the exciplex to the guest material 142.

In order that the organic compound 141_1 and the organic compound 141_2 efficiently form an exciplex, it is preferable to satisfy the following: the HOMO level of one of the organic compound 141_1 and the organic compound 141_2 is higher than that of the other and the LUMO level of the one of the organic compound 141_1 and the organic compound 141_2 is higher than that of the other. For example, when the organic compound 141_1 has a hole-transport property and the organic compound 141_2 has an electron-transport property, it is preferable that the HOMO level of the organic compound 141_1 be higher than the HOMO level of the organic compound 141_2 and the LUMO level of the organic compound 141_1 be higher than the LUMO level of the organic compound 141_2. Alternatively, when the organic compound 141_2 has a hole-transport property and the organic compound 141_1 has an electron-transport property, it is preferable that the HOMO level of the organic compound 141_2 be higher than the HOMO level of the organic compound 141_1 and the LUMO level of the organic compound 141_2 be higher than the LUMO level of the organic compound 141_1. Specifically, the energy difference between the HOMO level of the organic compound 141_1 and the HOMO level of the organic compound 141_2 is preferably greater than or equal to 0.05 eV, further preferably greater than or equal to 0.1 eV, and still further preferably greater than or equal to 0.2 eV. Alternatively, the energy difference between the LUMO level of the organic compound 141_1 and the LUMO level of the organic compound 141_2 is preferably greater than or equal to 0.05 eV, more preferably greater than or equal to 0.1 eV, and still more preferably greater than or equal to 0.2 eV.

In the case where the combination of the organic compounds 141_1 and 141_2 is a combination of a compound having a hole-transport property and a compound having an electron-transport property, the carrier balance can be easily controlled by adjusting the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

<Energy Transfer Mechanism>

Next, factors controlling the processes of intermolecular energy transfer between the host material 141 and the guest material 142 will be described. As mechanisms of the intermolecular energy transfer, two mechanisms, i.e., Förster mechanism (dipole-dipole interaction) and Dexter mechanism (electron exchange interaction), have been proposed. Although the intermolecular energy transfer process between the host material 141 and the guest material 142 is described below, the same applies to the case where the host material 141 is an exciplex.

<<Förster Mechanism>>

In Förster mechanism, energy transfer does not require direct contact between molecules and energy is transferred through a resonant phenomenon of dipolar oscillation between the host material 141 and the guest material 142. By the resonant phenomenon of dipolar oscillation, the host material 141 provides energy to the guest material 142, and thus, the host material 141 in an excited state is brought to a ground state and the guest material 142 in a ground state is brought to an excited state. Note that the rate constant $k_{h^* \to g}$ of Förster mechanism is expressed by Formula (1).

[Formula 1]

$$k_{h^* \to g} = \frac{9000c^4 K^2 \phi \ln 10}{128\pi^5 n^4 N \tau R^2} \int \frac{f'_h(\nu)\varepsilon_g(\nu)}{\nu^4} d\nu \quad (1)$$

In Formula (1), $\nu$ denotes a frequency, $f'_h(\nu)$ denotes a normalized emission spectrum of the host material 141 (a fluorescent spectrum in energy transfer from a singlet excited state, and a phosphorescent spectrum in energy transfer from a triplet excited state), $\varepsilon_g(\nu)$ denotes a molar absorption coefficient of the guest material 142, N denotes Avogadro's number, n denotes a refractive index of a medium, R denotes an intermolecular distance between the host material 141 and the guest material 142, $\tau$ denotes a measured lifetime of an excited state (fluorescence lifetime or phosphorescence lifetime), c denotes the speed of light, $\phi$ denotes an emission quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the host material 141 and the guest material 142. Note that $K^2$ is 2/3 in random orientation.

<<Dexter Mechanism>>

In Dexter mechanism, the host material 141 and the guest material 142 are close to a contact effective range where their orbitals overlap, and the host material 141 in an excited state and the guest material 142 in a ground state exchange their electrons, which leads to energy transfer. Note that the rate constant $k_{h^* \to g}$ of Dexter mechanism is expressed by Formula (2).

[Formula 2]

$$k_{h^* \to g} = \left(\frac{2\pi}{h}\right) K^2 \exp\left(-\frac{2R}{L}\right) \int f'_h(\nu)\varepsilon'_g(\nu) d\nu \quad (2)$$

In Formula (2), h denotes a Planck constant, K denotes a constant having an energy dimension, $\nu$ denotes a frequency, $f'_h(\nu)$ denotes a normalized emission spectrum of the host material 141 (a fluorescent spectrum in energy transfer from a singlet excited state, and a phosphorescent spectrum in energy transfer from a triplet excited state), $\varepsilon'_g(\nu)$ denotes a normalized absorption spectrum of the guest material 142, L denotes an effective molecular radius, and R denotes an intermolecular distance between the host material 141 and the guest material 142.

Here, the efficiency of energy transfer from the host material 141 to the guest material 142 (energy transfer efficiency $\phi_{ET}$) is expressed by Formula (3). In the formula, $k_r$ denotes a rate constant of a light-emission process (fluorescence in energy transfer from a singlet excited state, and phosphorescence in energy transfer from a triplet excited state) of the host material 141, $k_n$ denotes a rate constant of a non-light-emission process (thermal deactivation or intersystem crossing) of the host material 141, and $\tau$ denotes a measured lifetime of an excited state of the host material 141.

[Formula 3]

$$\phi_{ET} = \frac{k_{h^* \to g}}{k_r + k_n + k_{h^* \to g}} = \frac{k_{h^* \to g}}{\left(\frac{1}{\tau}\right) + k_{h^* \to g}} \quad (3)$$

According to Formula (3), it is found that the energy transfer efficiency $\phi_{ET}$ can be increased by increasing the rate constant $k_{h^* \to g}$ of energy transfer so that another competing rate constant $k_r + k_n$ ($=1/\tau$) becomes relatively small.

<<Concept for Promoting Energy Transfer>>

In energy transfer by Förster mechanism, high energy transfer efficiency $\phi_{ET}$ is obtained when emission quantum yield $\phi$ (a fluorescence quantum yield in energy transfer from a singlet excited state, and a phosphorescence quantum yield in energy transfer from a triplet excited state) is high. Furthermore, it is preferable that the emission spectrum (the fluorescence spectrum in energy transfer from the singlet excited state) of the host material 141 largely overlap with the absorption spectrum (absorption corresponding to the transition from the singlet ground state to the triplet excited state) of the guest material 142. Moreover, it is preferable that the molar absorption coefficient of the guest material 142 be also high. This means that the emission spectrum of the host material 141 overlaps with the absorption band of the guest material 142 that is on the longest wavelength side.

In energy transfer by Dexter mechanism, in order to increase the rate constant $k_{h^* \to g}$, it is preferable that an emission spectrum of the host material 141 (a fluorescent spectrum in energy transfer from a singlet excited state, and a phosphorescent spectrum in energy transfer from a triplet excited state) largely overlap with an absorption spectrum of the guest material 142 (absorption corresponding to transition from a singlet ground state to a triplet excited state). Therefore, the energy transfer efficiency can be optimized by making the emission spectrum of the host material 141 overlap with the absorption band of the guest material 142 which is on the longest wavelength side.

In a manner similar to that of the energy transfer from the host material 141 to the guest material 142, the energy transfer by both Förster mechanism and Dexter mechanism also occurs in the energy transfer process from the exciplex to the guest material 142.

That is, the host material 141 includes the organic compounds 141_1 and 141_2 which are a combination for forming an exciplex functioning as an energy donor capable of efficiently transferring energy to the guest material 142. The excitation energy for forming the exciplex by the organic compounds 141_1 and 141_2 can be lower than the excitation energy of the organic compound 141_1 in the excited state and lower than the excitation energy of the organic compound 141_2 in the excited state. This results in a reduction in the driving voltage of the light-emitting element.

Furthermore, in order to facilitate the energy transfer from the S1 level of the exciplex to the T1 level of the guest material 142 serving as an energy acceptor, it is preferable that the emission spectrum of the exciplex overlap with the absorption band of the guest material 142 which is on the longest wavelength side (lowest energy side). Thus, the efficiency of generating the triplet excited state of the guest material 142 can be increased.

The exciplex generated in the light-emitting layer 140 has a feature in that the singlet excitation energy level is close to the triplet excitation energy level. Therefore, by overlapping the emission spectrum of the exciplex and the absorption band of the guest material 142 which is on the longest wavelength side (lowest energy side), energy can be easily transferred from the triplet excitation energy level of the exciplex to the triplet excitation energy level of the guest material 142.

When the light-emitting layer 140 has the above-described structure, light emission from the guest material 142 (the phosphorescent material) of the light-emitting layer 140 can be obtained efficiently.

Note that the above-described processes through Routes $E_7$ to $E_9$ may be referred to as exciplex-triplet energy transfer (ExTET) in this specification and the like. In other words, in the light-emitting layer 140, excitation energy is transferred from the exciplex to the guest material 142. In this case, the efficiency of reverse intersystem crossing from $T_E$ to $S_E$ and the emission quantum yield from $S_E$ are not necessarily high; thus, materials can be selected from a wide range of options.

Note that in each of the above-described structures, the emission colors of the guest materials used in the light-emitting unit 106 and the light-emitting unit 108 may be the same or different. In the case where the same guest materials emitting light of the same color are used for the light-emitting units 106 and 108, the light-emitting element 250 can exhibit a high emission luminance at a small current value, which is preferable. In the case where guest materials emitting light of different colors are used for the light-emitting units 106 and 108, the light-emitting element 250 can exhibit multi-color light emission, which is preferable. In that case, when a plurality of light-emitting materials with different emission wavelengths are used in one or both of the light-emitting layers 120 and 140, the light-emitting element 250 emits light obtained by synthesizing lights with different emission peaks. That is, the emission spectrum of the light-emitting element 250 has at least two local maximum values.

The above structure is also suitable for obtaining white light emission. When the light-emitting layer 120 and the light-emitting layer 140 emit light of complementary colors, white light emission can be obtained. It is particularly favorable to select the guest materials so that white light emission with high color rendering properties or light emission of at least red, green, and blue can be obtained.

One or both of the light-emitting layers 120 and 140 may be divided into layers and each of the divided layers may contain a different light-emitting material. That is, one or both of the light-emitting layers 120 and 140 may consist of two or more layers. For example, in the case where the light-emitting layer is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. In that case, a light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

In the case where the light-emitting units 106 and 108 contain guest materials whose emission colors are different, light emitted from the light-emitting layer 120 preferably has an emission peak on the shorter wavelength side than light emitted from the light-emitting layer 140. The luminance of a light-emitting element using a material having a high triplet excitation energy level tends to degrade quickly; thus, any of the dibenzocarbazole compounds described in Embodiment 1 is used in the light-emitting layer emitting light of a short wavelength so that a light-emitting element with less degradation of luminance can be provided.

Structure Example 2 of Light-Emitting Element

Next, a structure example different from that of the light-emitting element illustrated in FIGS. 3A to 3C will be described below with reference to FIGS. 4A to 4C.

Figure 4A:
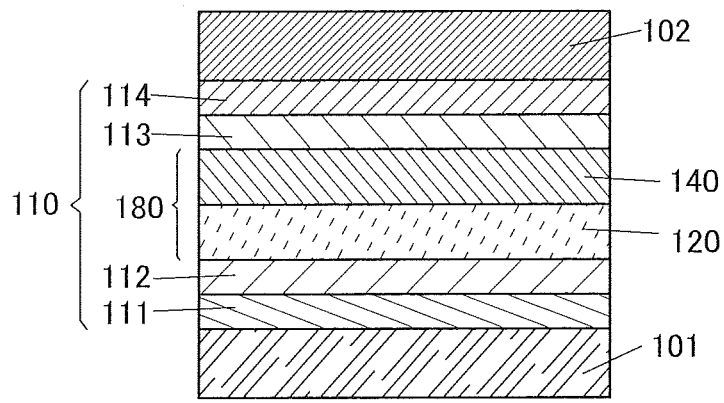
FIGS. 4A and 4B are each a schematic cross-sectional view of a light-emitting element of one embodiment of the present invention and FIG. 4C shows a correlation of energy levels.

FIG. 4A is a schematic cross-sectional view of a light-emitting element 252.

In the light-emitting element 252 shown in FIG. 4A, an EL layer 110 is between a pair of electrodes (the electrodes 101 and 102). Note that the electrode 101 functions as an anode and the electrode 102 functions as a cathode in the following description of the light-emitting element 252; however, the functions may be interchanged in the light-emitting element 252.

The EL layer 110 includes a light-emitting layer 180. The light-emitting layer 180 includes the light-emitting layer 120 and the light-emitting layer 140. In the light-emitting element 252, as the EL layer 110, the hole-injection layer 111, the hole-transport layer 112, the electron-transport layer 113, and the electron-injection layer 114 are illustrated in addition to the light-emitting layers. However, this stacked structure is an example, and the structure of the EL layer 110 in the light-emitting element 252 is not limited thereto. For example, the stacking order of the above layers of the EL layer 110 may be changed. Alternatively, in the EL layer 110, another functional layer other than the above layers may be provided. The functional layer may have a function of lowering a hole- or electron-injection barrier, a function of improving a hole- or electron-transport property, a function of inhibiting transport of holes or electrons, or a function of generating holes or electrons, for example.

Figure 4B:
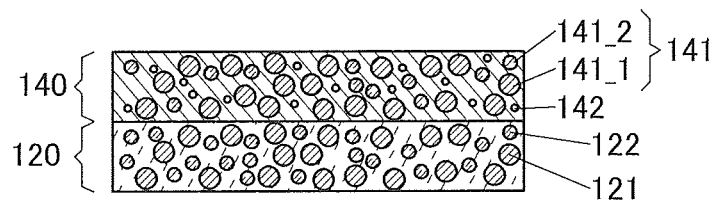

As illustrated in FIG. 4B, the light-emitting layer 120 contains the host material 121 and the guest material 122. The light-emitting layer 140 contains the host material 141 and the guest material 142. The host material 141 includes the organic compound 141_1 and the organic compound 141_2. Note that in the description below, the guest material 122 is a fluorescent material and the guest material 142 is a phosphorescent material.

<<Light Emission Mechanism of Light-Emitting Layer 180>>

The light emission mechanism of the light-emitting layer 120 is similar to that of the light-emitting layer 120 illustrated in FIGS. 2B and 2C. The light emission mechanism of the light-emitting layer 140 is similar to that of the light-emitting layer 140 illustrated in FIGS. 3B and 3C.

In the case where the light-emitting layers 120 and 140 are in contact with each other as illustrated in FIG. 4A, even when energy (in particular, triplet excitation energy) is transferred from the exciplex of the light-emitting layer 140 to the host material 121 of the light-emitting layer 120 at an interface between the light-emitting layer 120 and the light-emitting layer 140, triplet excitation energy can be converted into light emission in the light-emitting layer 120.

Note that the T1 level of the host material 121 of the light-emitting layer 120 is preferably lower than the T1 levels of the organic compounds 141_1 and 141_2 of the light-emitting layer 140. In the light-emitting layer 120, the S1 level of the host material 121 is preferably higher than the S1 level of the guest material 122 (fluorescent material) while the T1 level of the host material 121 is preferably lower than the T1 level of the guest material 122 (fluorescent material).

Figure 4C:
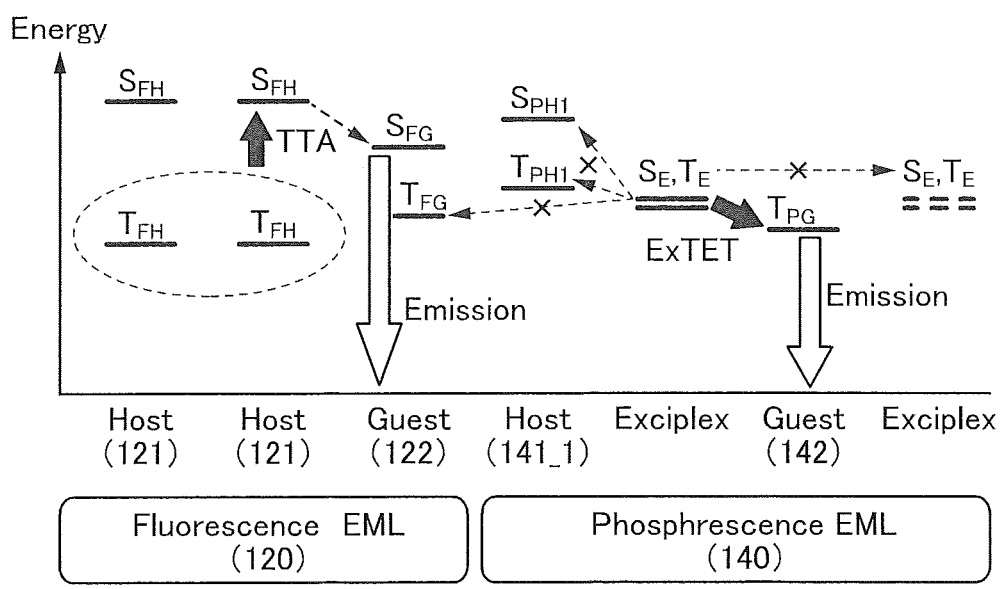

FIG. 4C shows a correlation of energy levels in the case where TTA is utilized in the light-emitting layer 120 and ExTET is utilized in the light-emitting layer 140. The following explains what terms and numerals in FIG. 4C represent:

Fluorescence EML (120): the light-emitting layer 120 (fluorescent light-emitting layer);
Phosphorescence EML (140): the light-emitting layer 140 (phosphorescent light-emitting layer);
Host (121): the host material 121;
Guest (122): the guest material 122 (fluorescent material);
Host (141_1): the host material (the organic compound 141_1);
Guest (142): the guest material 142 (phosphorescent material);
Exciplex: an exciplex (the organic compound 141_1 and the organic compound 141_2);
$S_{FH}$: the S1 level of the host material 121;
$T_{FH}$: the T1 level of the host material 121;
$S_{FG}$: the S1 level of the guest material 122 (fluorescent material);
$T_{FG}$: the T1 level of the guest material 122 (fluorescent material);
$S_{PH}$: the S1 level of the host material (the organic compound 141_1);
$T_{PH}$: the T1 level of the host material (the organic compound 141_1);
$T_{PG}$: the T1 level of the guest material 142 (phosphorescent material);
$S_E$: the S1 level of the exciplex; and
$T_E$: the T1 level of the exciplex.

As shown in FIG. 4C, the exciplex exists only in an excited state; thus, exciton diffusion between the exciplexes is less likely to occur. In addition, because the excitation energy levels ($S_E$ and $T_E$) of the exciplex are lower than the excitation energy levels ($S_{PH}$ and $T_{PH}$) of the organic compound 141_1 (i.e., the host material of the phosphorescent material) of the light-emitting layer 140, energy diffusion from the exciplex to the organic compound 141_1 does not occur. That is, the efficiency of the phosphorescent light-emitting layer (the light-emitting layer 140) can be maintained because an exciton diffusion distance of the exciplex is short in the phosphorescent light-emitting layer (the light-emitting layer 140). In addition, even when part of the triplet excitation energy of the exciplex of the phosphorescent light-emitting layer (the light-emitting layer 140) diffuses into the fluorescent light-emitting layer (the light-emitting layer 120) through the interface between the fluorescent light-emitting layer (the light-emitting layer 120) and the phosphorescent light-emitting layer (the light-emitting layer 140), energy loss can be reduced because the triplet excitation energy in the fluorescent light-emitting layer (the light-emitting layer 120) caused by the diffusion is converted into light emission through TTA.

As described above, ExTET is utilized in the light-emitting layer 140 and TTA is utilized in the light-emitting layer 120; thus, the light-emitting element 252 can have a reduced energy loss and a high emission efficiency. Furthermore, in the case where the light-emitting layer 120 and the light-emitting layer 140 are in contact with each other as in the light-emitting element 252, the number of the EL layers 110 as well as the energy loss can be reduced. Therefore, a light-emitting element with low manufacturing costs can be obtained.

Note that the light-emitting layer 120 and the light-emitting layer 140 are not necessarily in contact with each other. In that case, it is possible to prevent energy transfer by the Dexter mechanism (in particular, triplet energy transfer) from the organic compound 141_1 in an excited state, the organic compound 141_2 in an excited state, or the guest material 142 (phosphorescent material) in an excited state which is generated in the light-emitting layer 140 to the host material 121 or the guest material 122 (fluorescent material) in the light-emitting layer 120. Therefore, the thickness of a layer provided between the light-emitting layer 120 and the light-emitting layer 140 may be several nanometers. Specifically, the thickness is preferably more than or equal to 1 nm and less than or equal to 5 nm, in which case an increase in driving voltage can be inhibited.

The layer provided between the light-emitting layer 120 and the light-emitting layer 140 may contain a single material or both a hole-transport material and an electron-transport material. In the case of a single material, a bipolar material may be used. The bipolar material here refers to a material in which the ratio between the electron mobility and the hole mobility is 100 or less. Alternatively, the hole-transport material, the electron-transport material, or the like may be used. At least one of materials contained in the layer may be the same as the host material (the organic compound 141_1 or 141_2) of the light-emitting layer 140. This facilitates the manufacture of the light-emitting element and reduces the driving voltage. Furthermore, the hole-transport material and the electron-transport material may form an exciplex, which effectively prevents exciton diffusion. Specifically, it is possible to prevent energy transfer from the host material (the organic compound 141_1 or 141_2) in an excited state or the guest material 142 (phosphorescent material) in an excited state of the light-emitting layer 140 to the host material 121 or the guest material 122 (fluorescent material) in the light-emitting layer 120.

In the light-emitting element 252, the light-emitting layer 120 and the light-emitting layer 140 have been described as being positioned on the hole-transport layer 112 side and the electron-transport layer 113 side, respectively; however, the light-emitting element of one embodiment of the present invention is not limited to this structure. The light-emitting layer 120 and the light-emitting layer 140 may be positioned on the electron-transport layer 113 side and the hole-transport layer 112 side, respectively.

Note that in the light-emitting element 252, a carrier recombination region is preferably distributed to some extent. Therefore, it is preferable that the light-emitting layer 120 or 140 have an appropriate degree of carrier-trapping property. It is particularly preferable that the guest material 142 (phosphorescent material) in the light-emitting layer 140 have an electron-trapping property. Alternatively, the guest material 122 (fluorescent material) in the light-emitting layer 120 preferably has a hole-trapping property.

Note that light emitted from the light-emitting layer 120 preferably has an emission peak on the shorter wavelength side than light emitted from the light-emitting layer 140. The luminance of a light-emitting element using a phosphorescent material emitting light with a short wavelength tends to degrade quickly. By using fluorescence with a short wavelength, a light-emitting element with less degradation of luminance can be provided.

Furthermore, the light-emitting layer 120 and the light-emitting layer 140 may be made to emit light with different emission wavelengths, so that the light-emitting element can be a multicolor light-emitting element. In that case, the emission spectrum of the light-emitting element is formed by combining light having different emission peaks, and thus has at least two local maximum values.

The above structure is also suitable for obtaining white light emission. When the light-emitting layer 120 and the light-emitting layer 140 emit light of complementary colors, white light emission can be obtained.

In addition, white light emission with a high color rendering property that is formed of three primary colors or four or more colors can be obtained by using a plurality of light-emitting materials emitting light of different emission wavelengths for one of the light-emitting layers 120 and 140 or both. In that case, the light-emitting layer may be divided into layers and each of the divided layers may contain a light-emitting material different from the others.

<Example of Material that can be Used in Light-Emitting Layers>

Next, materials that can be used in the light-emitting layers 120 and 140 are described.

<<Material that can be Used in Light-Emitting Layer 120>>

In the light-emitting layer 120, the host material 121 is present in the largest proportion by weight, and the guest material 122 (fluorescent material) is dispersed in the host material 121. The S1 level of the host material 121 is preferably higher than the S1 level of the guest material 122 (fluorescent material) while the T1 level of the host material 121 is preferably lower than the T1 level of the guest material 122 (fluorescent material).

Any of the dibenzocarbazole compounds described in Embodiment 1 is preferably used as the host material 121. This allows the fabrication of a light-emitting element with a high emission efficiency.

In the light-emitting layer 120, the guest material 122 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like. For example, any of the materials described in Embodiment 3 can be used.

Note that the light-emitting layer 120 can have a structure in which two or more layers are stacked. For example, in the case where the light-emitting layer 120 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

In the light-emitting layer 120, the host material 121 may be composed of a single compound or a plurality of compounds. The light-emitting layer 120 may include a material other than the host material 121 and the guest material 122.

<<Material that can be Used in Light-Emitting Layer 140>>

In the light-emitting layer 140, the host material 141 is present in the largest proportion by weight, and the guest material 142 (fluorescent material) is dispersed in the host material 141. The T1 level of the host material 141 (organic compounds 141_1 and 141_2) is preferably higher than the T1 level of the guest material 142 in the light-emitting layer 140.

Examples of the organic compound 141_1 include a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative. Other examples are an aromatic amine and a carbazole derivative. Specifically, the electron-transport material and the hole-transport material described in Embodiment 3 can be used.

As the organic compound 141_2, a substance which can form an exciplex together with the organic compound 141_1 is preferably used. Specifically, the electron-transport material and the hole-transport material described in Embodiment 3 can be used. In that case, it is preferable that the organic compound 141_1, the organic compound 141_2, and the guest material 142 (phosphorescent material) be selected such that the emission peak of the exciplex formed by the organic compounds 141_1 and 141_2 overlaps with an absorption band, specifically an absorption band on the longest wavelength side, of a triplet metal to ligand charge transfer (MLCT) transition of the guest material 142 (phosphorescent material). This makes it possible to provide a light-emitting element with a drastically improved emission efficiency. Note that in the case where a thermally activated delayed fluorescence material is used instead of the phosphorescent material, it is preferable that the absorption band on the longest wavelength side be a singlet absorption band.

As the guest material 142 (phosphorescent material), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

Examples of the substance that has an emission peak in the blue or green wavelength range include organometallic iridium complexes having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium (HI) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having a 1H-triazole skeleton, such as tris[3-methyl-1-(2-methylphenyl)-5-phenyl-1H-1,2,4-triazolato]iridium (III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis {2-[3',5'-bis(trifluoromethyl)phenyl]pyridinato-N,$C^2$}iridium(III)picolinate (abbreviation: Ir(CF$_3$ppy)$_2$(pic)), and bis[2-(4',6'-difluorophenyl)pyridinato-N,$C^{2'}$]iridium(III) acetylacetonate (abbreviation: FIr(acac)).

Examples of the substance that has an emission peak in the green or yellow wavelength range include organometallic iridium complexes having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbomryl)-6-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), (acetylacetonato)bis{4,6-dimethyl-2-[6-(2,6-dimethylphenyl)-4-pyrimidinyl-κN3]phenyl-κC}iridium(I) (abbreviation: Ir(dmppm-dmp)$_2$(acac)), and (acetylacetonato)bis(4,6-diphenylpyrimidinato)iridium(III) (abbreviation: Ir(dppm)$_2$(acac)); organometallic iridium complexes having a pyrazine skeleton, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having a pyridine skeleton, such as tris(2-phenylpyridinato-N,$C^{2'}$)iridium(III) (abbreviation: Ir(ppy)$_3$), bis(2-phenylpyridinato-N,$C^{2'}$)iridium(II) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,$C^{2'}$)iridium(III) (abbreviation: Ir(pq)$_3$), and bis(2-phenylquinolinato-N,$C^{2'}$) iridium(III) acetylacetonate (abbreviation: Ir(pq)$_2$(acac)); organometallic iridium complexes such as bis(2,4-diphenyl-1,3-oxazolato-N,$C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), and bis(2-phenylbenzothiazolato-N,$C^{2'}$)iridium(III) acetylacetonate (abbreviation: Ir(bt)$_2$(acac)); and a rare earth metal complex such as tris(acetylacetonatoXmonophenanthroline)terbium(I) (abbreviation: Tb(acac)$_3$(Phen)). Among the materials given above, the organometallic iridium complexes having a pyrimidine skeleton have distinctively high reliability and emission efficiency and are thus particularly preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(d1npm)$_2$(dpm)); organometallic iridium complexes having a pyrazine skeleton, such as (acetylacetonato)bis(2,3,5-triphenylpyrazinato)iridium(I) (abbreviation: Ir(tppr)$_2$(acac)), bis(2,3,5-triphenylpyrazinato) (dipivaloylmethanato)iridium(III) (abbreviation: Ir(tpprh)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes having a pyridine skeleton, such as tris(1-phenylisoquinolinato-N,$C^{2'}$)iridium (III) (abbreviation: Ir(piq)$_3$) and bis(1-phenylisoquinolinato-N,$C^{2'}$)iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(II) (abbreviation: Eu(DBM)$_3$(Phen)) and tris[1-(2-thenoyl)-3,3,3-trifluoroacetonato](monophenanthroline)europium(III) (abbreviation: Eu(TTA)$_3$(Phen)). Among the materials given above, the organometallic iridium complexes having a pyrimidine skeleton have distinctively high reliability and emission efficiency and are thus particularly preferable. Further, the organometallic iridium complexes having a pyrazine skeleton can provide red light emission with favorable chromaticity.

Any material can be used as the light-emitting organic material included in the light-emitting layer as long as the material can convert the triplet excitation energy into light emission. As an example of the material that can convert triplet excitation energy into light emission, a thermally activated delayed fluorescence (TADF) material can be given in addition to the phosphorescent material. Therefore, the term "phosphorescent material" in the description can be rephrased as the term "thermally activated delayed fluorescence material". The thermally activated delayed fluorescence material is a material having a small energy difference between the singlet excitation energy level and the triplet excitation energy level and has a function of converting the triplet excitation energy into the singlet excitation energy by reverse intersystem crossing. Thus, the thermally activated delayed fluorescence material can up-convert a triplet excited state into a singlet excited state (i.e., reverse intersystem crossing is possible) using a little thermal energy and efficiently exhibit light emission (fluorescence) from the singlet excited state. Conditions for efficiently obtaining thermally activated delayed fluorescence are as follows: the energy difference between the singlet excitation energy level and the triplet excitation energy level is preferably greater than 0 eV and less than or equal to 0.2 eV, more preferably greater than 0 eV and less than or equal to 0.1 eV.

As examples of the thermally activated delayed fluorescence material, any of the following materials can be used. First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$(OEP)).

As the thermally activated delayed fluorescence material composed of one kind of material, a heterocyclic compound including a π-electron rich heteroaromatic ring and a π-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10 OH-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferably used because of having the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferable because the donor property of the π-electron rich heteroaromatic ring and the acceptor property of the π-electron deficient heteroaromatic ring are both increased and the difference between the level of the singlet excited state and the level of the triplet excited state becomes small. Note that an aromatic ring to which an electron-withdrawing group such as a cyano group is bonded may be used instead of the π-electron deficient heteroaromatic ring.

There is no limitation on the emission colors of the light-emitting materials contained in the light-emitting layers 120 and 140, and they may be the same or different. Light emitted from the light-emitting materials is mixed and extracted out of the element; therefore, for example, in the case where their emission colors are complementary colors, the light-emitting element can emit white light. In consideration of the reliability of the light-emitting element, the emission peak wavelength of the light-emitting material included in the light-emitting layer 120 is preferably shorter than that of the light-emitting material included in the light-emitting layer 140.

Note that the light-emitting units 106 and 108 and the charge-generation layer 115 can be formed by an evaporation method (including a vacuum evaporation method), an ink-jet method, a coating method, gravure printing, or the like.

The structure described in this embodiment can be used in combination with any of the structures described in the other embodiments as appropriate.

Embodiment 5

In this embodiment, examples of light-emitting elements having structures different from those described in Embodiments 3 and 4 are described below with reference to FIGS. 5A and 5B, FIGS. 6A and 6B, FIGS. 7A to 7C, and FIGS. 8A to 8C.

Structure Example 1 of Light-Emitting Element

Figure 5A:
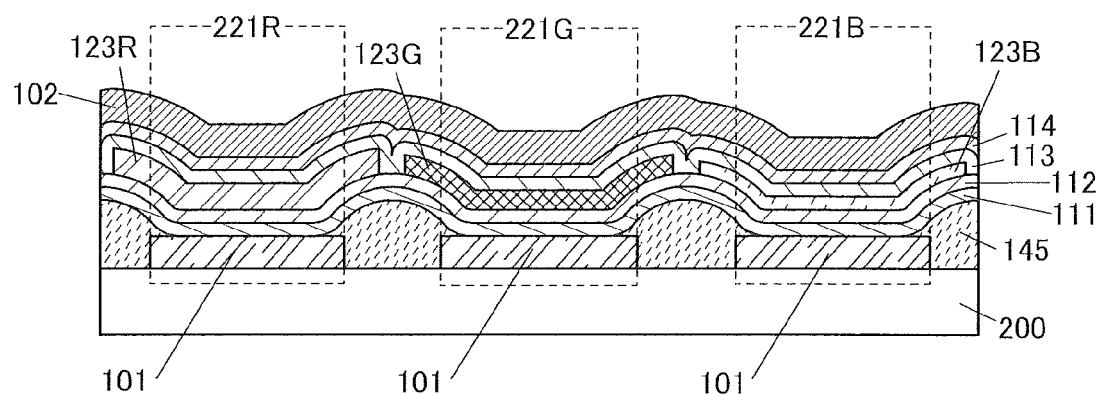
FIGS. 5A and 5B are each a schematic cross-sectional view of a light-emitting element of one embodiment of the present invention.
Figure 5B:
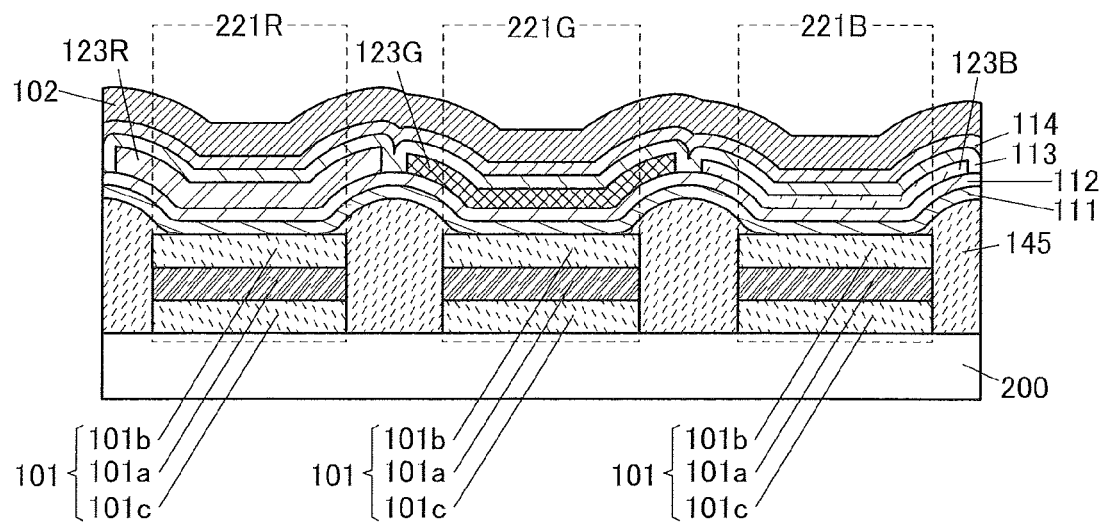

FIGS. 5A and 5B are cross-sectional views each illustrating a light-emitting element of one embodiment of the present invention. In FIGS. 5A and 5B, a portion having a function similar to that in FIG. 2A is represented by the same hatch pattern as in FIG. 2A and not especially denoted by a reference numeral in some cases. In addition, common reference numerals are used for portions having similar functions, and a detailed description of the portions is omitted in some cases.

Light-emitting elements 260a and 260b in FIGS. 5A and 5B may have a bottom-emission structure in which light is extracted through the substrate 200 or may have a top-emission structure in which light emitted from the light-emitting element is extracted in the direction opposite to the substrate 200. However, one embodiment of the present invention is not limited to this structure, and a light-emitting element having a dual-emission structure in which light emitted from the light-emitting element is extracted in both top and bottom directions of the substrate 200 may be used.

In the case where the light-emitting elements 260a and 260b each have a bottom emission structure, the electrode 101 preferably has a function of transmitting light and the electrode 102 preferably has a function of reflecting light. Alternatively, in the case where the light-emitting elements 260a and 260b each have a top emission structure, the electrode 101 preferably has a function of reflecting light and the electrode 102 preferably has a function of transmitting light.

The light-emitting elements 260a and 260b each include the electrode 101 and the electrode 102 over the substrate 200. Between the electrodes 101 and 102, a light-emitting layer 123B, a light-emitting layer 123G, and a light-emitting layer 123R are provided. The hole-injection layer 111, the hole-transport layer 112, the electron-transport layer 113, and the electron-injection layer 114 are also provided.

The light-emitting element 260b includes, as part of the electrode 101, a conductive layer 101a, a conductive layer 101b over the conductive layer 101a, and a conductive layer 101c under the conductive layer 101a. In other words, the light-emitting element 260b includes the electrode 101 having a structure in which the conductive layer 101a is sandwiched between the conductive layer 101b and the conductive layer 101c.

In the light-emitting element 260b, the conductive layer 101b and the conductive layer 101c may be formed of different materials or the same material. The conductive layers 101b and 101c are preferably formed of the same conductive material, in which case patterning by etching in the process for forming the electrode 101 can be performed easily.

In the light-emitting element 260b, the electrode 101 may include one of the conductive layer 101b and the conductive layer 101c.

For each of the conductive layers 101a, 101b, and 101c, which are included in the electrode 101, the structure and materials of the electrode 101 or 102 described in Embodiment 3 can be used.

In FIGS. 5A and 5B, a partition wall 145 is provided between a region 221B, a region 221G, and a region 221R, which are sandwiched between the electrode 101 and the electrode 102. The partition wall 145 has an insulating property. The partition wall 145 covers end portions of the electrode 101 and has openings overlapping with the electrode. With the partition wall 145, the electrode 101 provided over the substrate 200 in the regions can be divided into island shapes.

Note that the light-emitting layer 123B and the light-emitting layer 123G may overlap with each other in a region where they overlap with the partition wall 145. The light-emitting layer 123G and the light-emitting layer 123R may overlap with each other in a region where they overlap with the partition wall 145. The light-emitting layer 123R and the light-emitting layer 123B may overlap with each other in a region where they overlap with the partition wall 145.

The partition wall 145 has an insulating property and is formed using an inorganic or organic material. Examples of the inorganic material include silicon oxide, silicon oxynitride, silicon nitride oxide, silicon nitride, aluminum oxide, and aluminum nitride. Examples of the organic material include photosensitive resin materials such as an acrylic resin and a polyimide resin.

Note that a silicon oxynitride film refers to a film in which the proportion of oxygen is higher than that of nitrogen. The silicon oxynitride film preferably contains oxygen, nitrogen, silicon, and hydrogen in the ranges of 55 atomic % to 65 atomic %, 1 atomic % to 20 atomic %, 25 atomic % to 35 atomic %, and 0.1 atomic % to 10 atomic %, respectively. A silicon nitride oxide film refers to a film in which the proportion of nitrogen is higher than that of oxygen. The silicon nitride oxide film preferably contains nitrogen, oxygen, silicon, and hydrogen in the ranges of 55 atomic % to 65 atomic %, 1 atomic % to 20 atomic %, 25 atomic % to 35 atomic %, and 0.1 atomic % to 10 atomic %, respectively.

The light-emitting layers 123R, 123G, and 123B preferably contain light-emitting materials having functions of emitting light of different colors. For example, when the light-emitting layer 123R contains a light-emitting material having a function of emitting red, the region 221R emits red light. When the light-emitting layer 123G contains a light-emitting material having a function of emitting green, the region 221G emits green light. When the light-emitting layer 123B contains a light-emitting material having a function of emitting blue, the region 221B emits blue light. The light-emitting element 260a or 260b having such a structure is used in a pixel of a display device, whereby a full-color display device can be fabricated. The thicknesses of the light-emitting layers may be the same or different.

One or more of the light-emitting layer 123B, the light-emitting layer 123G, and the light-emitting layer 123R preferably have at least one of the structures of the light-emitting layer 120 described in Embodiment 3. In that case, a light-emitting element with high emission efficiency can be fabricated.

One or more of the light-emitting layers 123B, 123G, and 123R may include two or more stacked layers.

When at least one light-emitting layer includes the light-emitting layer described in Embodiment 3 and the light-emitting element 260a or 260b including the light-emitting layer is used in pixels in a display device, a display device with high emission efficiency can be fabricated. The display device including the light-emitting element 260a or 260b can thus have reduced power consumption.

By providing an optical element (e.g., a color filter, a polarizing plate, and an anti-reflection film) on the light extraction side of the electrode through which light is extracted, the color purity of each of the light-emitting elements 260a and 260b can be improved. Therefore, the color purity of a display device including the light-emitting element 260a or 260b can be improved. Alternatively, the reflection of external light by each of the light-emitting elements 260a and 260b can be reduced. Therefore, the contrast ratio of a display device including the light-emitting element 260a or 260b can be improved.

For the other components of the light-emitting elements 260a and 260b, the components of the light-emitting element in Embodiments 3 and 4 may be referred to.

Structure Example 2 of Light-Emitting Element

Next, structure examples different from the light-emitting elements illustrated in FIGS. 5A and 5B will be described below with reference to FIGS. 6A and 6B.

Figure 6A:
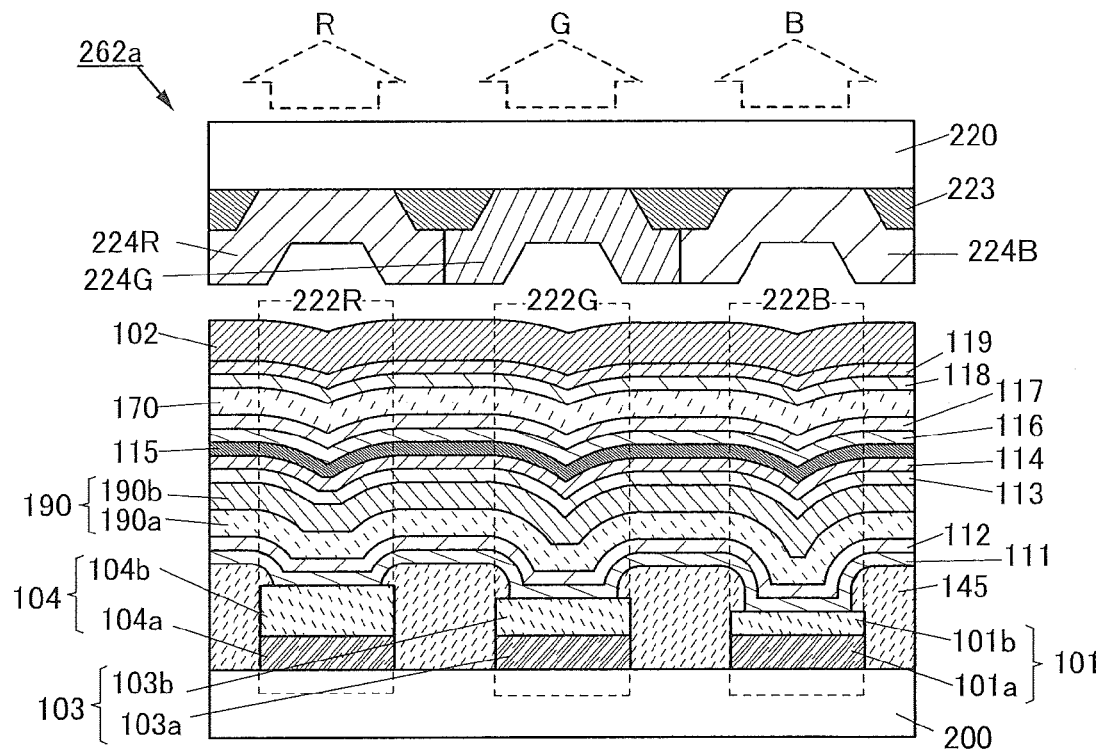
FIGS. 6A and 6B are each a schematic cross-sectional view of a light-emitting element of one embodiment of the present invention.
Figure 6B:
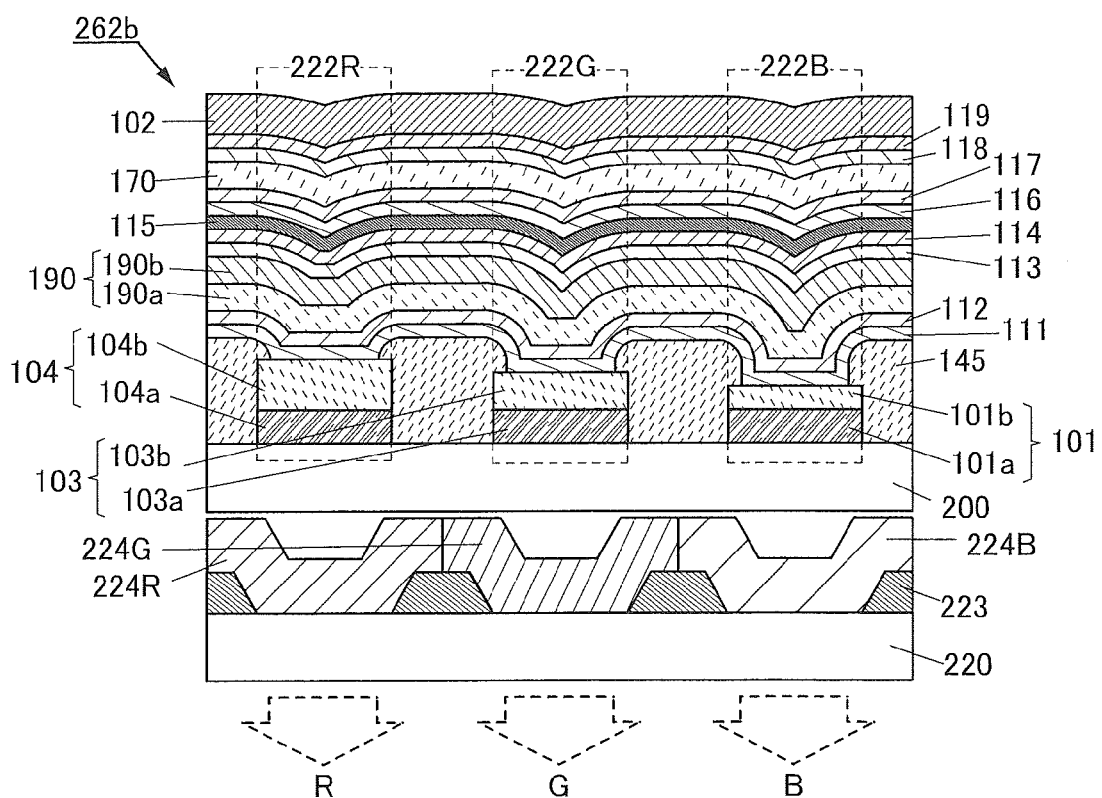

FIGS. 6A and 6B are cross-sectional views of a light-emitting element of one embodiment of the present invention. In FIGS. 6A and 6B, a portion having a function similar to that in FIGS. 5A and 5B is represented by the same hatch pattern as in FIGS. 5A and 5B and not especially denoted by a reference numeral in some cases. In addition, common reference numerals are used for portions having similar functions, and a detailed description of such portions is not repeated in some cases.

FIGS. 6A and 6B illustrate structure examples of a light-emitting element including the light-emitting layer between a pair of electrodes. A light-emitting element 262a illustrated in FIG. 6A has a top-emission structure in which light is extracted in a direction opposite to the substrate 200, and a light-emitting element 262b illustrated in FIG. 6B has a bottom-emission structure in which light is extracted to the substrate 200 side. However, one embodiment of the present invention is not limited to these structures and may have a dual-emission structure in which light emitted from the light-emitting element is extracted in both top and bottom directions with respect to the substrate 200 over which the light-emitting element is formed.

The light-emitting elements 262a and 262b each include the electrode 101, the electrode 102, an electrode 103, and an electrode 104 over the substrate 200. At least a light-emitting layer 170, a light-emitting layer 190, and the charge-generation layer 115 are provided between the electrode 101 and the electrode 102, between the electrode 102 and the electrode 103, and between the electrode 102 and the electrode 104. The hole-injection layer 111, the hole-transport layer 112, the electron-transport layer 113, the electron-injection layer 114, the hole-injection layer 116, the hole-transport layer 117, the electron-transport layer 118, and the electron-injection layer 119 are further provided.

The electrode 101 includes a conductive layer 101a and a conductive layer 101b over and in contact with the conductive layer 101a. The electrode 103 includes a conductive layer 103a and a conductive layer 103b over and in contact with the conductive layer 103a. The electrode 104 includes a conductive layer 104a and a conductive layer 104b over and in contact with the conductive layer 104a.

The light-emitting element 262a illustrated in FIG. 6A and the light-emitting element 262b illustrated in FIG. 6B each include a partition wall 145 between a region 222B sandwiched between the electrode 101 and the electrode 102, a region 222G sandwiched between the electrode 102 and the electrode 103, and a region 222R sandwiched between the electrode 102 and the electrode 104. The partition wall 145 has an insulating property. The partition wall 145 covers end portions of the electrodes 101, 103, and 104 and has openings overlapping with the electrodes. With the partition wall 145, the electrodes provided over the substrate 200 in the regions can be separated into island shapes.

The charge-generation layer 115 can be formed with a material obtained by adding an electron acceptor (acceptor) to a hole-transport material or a material obtained by adding an electron donor (donor) to an electron-transport material. Note that when the conductivity of the charge-generation layer 115 is as high as that of the pair of electrodes, carriers generated in the charge-generation layer 115 might transfer to an adjacent pixel and light emission might occur in the pixel. In order to prevent such false light emission from an adjacent pixel, the charge-generation layer 115 is preferably formed with a material whose conductivity is lower than that of the pair of electrodes.

The light-emitting elements 262a and 262b each include a substrate 220 provided with an optical element 224B, an optical element 224G, and an optical element 224R in the direction in which light emitted from the region 222B, light emitted from the region 222G, and light emitted from the region 222R are extracted. The light emitted from each region is emitted outside the light-emitting element through each optical element. In other words, the light from the region 222B, the light from the region 222G, and the light from the region 222R are emitted through the optical element 224B, the optical element 224G, and the optical element 224R, respectively.

The optical elements 224B, 224G, and 224R each have a function of selectively transmitting light of a particular color out of incident light. For example, the light emitted from the region 222B through the optical element 224B is blue light, the light emitted from the region 222G through the optical element 224G is green light, and the light emitted from the region 222R through the optical element 224R is red light.

For example, a coloring layer (also referred to as color filter), a band pass filter, a multilayer filter, or the like can be used for the optical elements 224R, 224G, and 224B. Alternatively, color conversion elements can be used as the optical elements. A color conversion element is an optical element that converts incident light into light having a longer wavelength than the incident light. As the color conversion elements, quantum-dot elements can be favorably used. The usage of the quantum dot can increase color reproducibility of the display device.

One or more optical elements may be stacked over each of the optical elements 224R, 224G, and 224B. As another optical element, a circularly polarizing plate, an anti-reflective film, or the like can be provided, for example. A circularly polarizing plate provided on the side where light emitted from the light-emitting element of the display device is extracted can prevent a phenomenon in which light entering from the outside of the display device is reflected inside the display device and returned to the outside. An anti-reflective film can weaken external light reflected by a surface of the display device. This leads to clear observation of light emitted from the display device.

Note that in FIGS. 6A and 6B, blue light (B), green light (G), and red light (R) emitted from the regions through the optical elements are schematically illustrated by arrows of dashed lines.

A light-blocking layer 223 is provided between the optical elements. The light-blocking layer 223 has a function of blocking light emitted from the adjacent regions. Note that a structure without the light-blocking layer 223 may also be employed.

The light-blocking layer 223 has a function of reducing the reflection of external light. The light-blocking layer 223 has a function of preventing mixture of light emitted from an adjacent light-emitting element. As the light-blocking layer 223, a metal, a resin containing black pigment, carbon black, a metal oxide, a composite oxide containing a solid solution of a plurality of metal oxides, or the like can be used.

Note that the optical element 224B and the optical element 224G may overlap with each other in a region where they overlap with the light-blocking layer 223. In addition, the optical element 224G and the optical element 224R may overlap with each other in a region where they overlap with the light-blocking layer 223. In addition, the optical element 224R and the optical element 224B may overlap with each other in a region where they overlap with the light-blocking layer 223.

As for the structures of the substrate 200 and the substrate 220 provided with the optical elements, Embodiment 3 can be referred to.

Furthermore, the light-emitting elements 262a and 262b have a microcavity structure.

<<Microcavity Structure>>

Light emitted from the light-emitting layer 170 and the light-emitting layer 190 resonates between a pair of electrodes (e.g., the electrode 101 and the electrode 102). The light-emitting layer 170 and the light-emitting layer 190 are formed at such a position as to intensify the light of a desired wavelength among light to be emitted. For example, by adjusting the optical length from a reflective region of the electrode 101 to the light-emitting region of the light-emitting layer 170 and the optical length from a reflective region of the electrode 102 to the light-emitting region of the light-emitting layer 170, the light of a desired wavelength among light emitted from the light-emitting layer 170 can be intensified. By adjusting the optical length from the reflective region of the electrode 101 to the light-emitting region of the light-emitting layer 190 and the optical length from the reflective region of the electrode 102 to the light-emitting region of the light-emitting layer 190, the light of a desired wavelength among light emitted from the light-emitting layer 190 can be intensified. In the case of a light-emitting element in which a plurality of light-emitting layers (here, the light-emitting layers 170 and 190) are stacked, the optical lengths of the light-emitting layers 170 and 190 are preferably optimized.

In each of the light-emitting elements 262a and 262b, by adjusting the thicknesses of the conductive layers (the conductive layer 101b, the conductive layer 103b, and the conductive layer 104b) in each region, the light of a desired wavelength among light emitted from the light-emitting layers 170 and 190 can be increased. Note that the thickness of at least one of the hole-injection layer 111 and the hole-transport layer 112 or at least one of the electron-injection layer 119 and the electron-transport layer 118 may differ between the regions to increase the light emitted from the light-emitting layers 170 and 190.

For example, in the case where the refractive index of the conductive material having a function of reflecting light in the electrodes 101 to 104 is lower than the refractive index of the light-emitting layer 170 or 190, the thickness of the conductive layer 101b of the electrode 101 is adjusted so that the optical length between the electrode 101 and the electrode 102 is $m_B\lambda_B/2$ ($m_B$ is a natural number and $\lambda_B$ is the wavelength of light intensified in the region 222B). Similarly, the thickness of the conductive layer 103b of the electrode 103 is adjusted so that the optical length between the electrode 103 and the electrode 102 is $m_G\lambda_G/2$ ($m_G$ is a natural number and $\lambda_G$ is the wavelength of light intensified in the region 222G). Furthermore, the thickness of the conductive layer 104b of the electrode 104 is adjusted so that the optical length between the electrode 104 and the electrode 102 is $m_R\lambda_R/2$ ($m_R$ is a natural number and $\lambda_R$ is the wavelength of light intensified in the region 222R).

In the case where it is difficult to precisely determine the reflective regions of the electrodes 101 to 104, the optical length for increasing the intensity of light emitted from the light-emitting layer 170 or the light-emitting layer 190 may be derived on the assumption that certain regions of the electrodes 101 to 104 are the reflective regions. In the case where it is difficult to precisely determine the light-emitting regions of the light-emitting layer 170 and the light-emitting layer 190, the optical length for increasing the intensity of light emitted from the light-emitting layer 170 and the light-emitting layer 190 may be derived on the assumption that certain regions of the light-emitting layer 170 and the light-emitting layer 190 are the light-emitting regions.

In the above manner, with the microcavity structure, in which the optical length between the pair of electrodes in the respective regions is adjusted, scattering and absorption of light in the vicinity of the electrodes can be suppressed, resulting in high light extraction efficiency.

In the above structure, the conductive layers 101b, 103b, and 104b preferably have a function of transmitting light. The materials of the conductive layers 101b, 103b, and 104b may be the same or different. It is preferable to use the same material for the conductive layer 101b, the conductive layer 103b, and the conductive layer 104b because patterning by etching in the formation process of the electrode 101, the electrode 103, and the electrode 104 can be performed easily. Each of the conductive layers 101b, 103b, and 104b may have a stacked structure of two or more layers.

Since the light-emitting element 262a illustrated in FIG. 6A has a top-emission structure, it is preferable that the conductive layer 101a, the conductive layer 103a, and the conductive layer 104a have a function of reflecting light. In addition, it is preferable that the electrode 102 have functions of transmitting light and reflecting light.

Since the light-emitting element 262b illustrated in FIG. 6B has a bottom-emission structure, it is preferable that the conductive layer 101a, the conductive layer 103a, and the conductive layer 104a have functions of transmitting light and reflecting light. In addition, it is preferable that the electrode 102 have a function of reflecting light.

In each of the light-emitting elements 262a and 262b, the conductive layers 101a, 103a, and 104a may be formed of different materials or the same material. When the conductive layers 101a, 103a, and 104a are formed of the same material, manufacturing cost of the light-emitting elements 262a and 262b can be reduced. Note that each of the conductive layers 101a, 103a, and 104a may have a stacked structure including two or more layers.

At least one of the structures described in Embodiments 3 and 4 is preferably used for at least one of the light-emitting layers 170 and 190 included in the light-emitting elements 262a and 262b. In this way, the light-emitting elements can have high emission efficiency.

Either or both of the light-emitting layers 170 and 190 may have a stacked structure of two layers like the light-emitting layers 190a and 190b, for example. Two kinds of light-emitting materials (a first compound and a second compound) for emitting light of different colors are used in the two light-emitting layers, so that light of a plurality of colors can be obtained at the same time. It is particularly preferable to select the light-emitting materials of the light-emitting layers so that white light can be obtained by combining light emissions from the light-emitting layers 170 and 190.

Either or both of the light-emitting layers 170 and 190 may have a stacked structure of three or more layers, in which a layer not including a light-emitting material may be included.

In the above-described manner, by using the light-emitting element 262a or 262b including the light-emitting layer having at least one of the structures described in Embodiments 3 and 4 in pixels in a display device, a display device with high emission efficiency can be fabricated. Accordingly, the display device including the light-emitting element 262a or 262b can have low power consumption.

For the other components of the light-emitting elements 262a and 262b, the components of the light-emitting element 260a or 260b or the light-emitting element in Embodiments 3 and 4 may be referred to.

<Fabrication Method of Light-Emitting Element>

Next, a method for fabricating a light-emitting element of one embodiment of the present invention is described below with reference to FIGS. 7A to 7C and FIGS. 8A to 8C. Here, a method for fabricating the light-emitting element 262a illustrated in FIG. 6A is described.

FIGS. 7A to 7C and FIGS. 8A to 8C are cross-sectional views illustrating a method for fabricating the light-emitting element of one embodiment of the present invention.

The method for fabricating the light-emitting element 262a described below includes first to seventh steps.

<<First Step>>

Figure 7A:
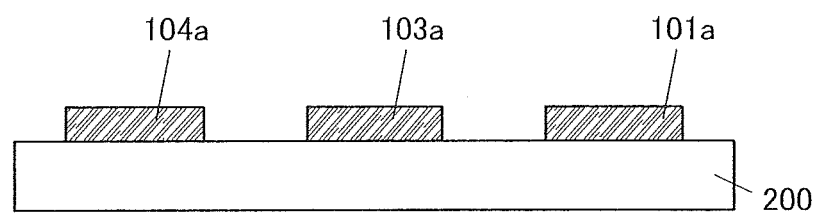
FIGS. 7A to 7C are schematic cross-sectional views illustrating a method for fabricating a light-emitting element of one embodiment of the present invention.

In the first step, the electrodes (specifically the conductive layer 101a of the electrode 101, the conductive layer 103a of the electrode 103, and the conductive layer 104a of the electrode 104) of the light-emitting elements are formed over the substrate 200 (see FIG. 7A).

In this embodiment, a conductive layer having a function of reflecting light is formed over the substrate 200 and processed into a desired shape; whereby the conductive layers 101a, 103a, and 104a are formed. As the conductive layer having a function of reflecting light, an alloy film of silver, palladium, and copper (also referred to as an Ag—Pd—Cu film or APC) is used. The conductive layers 101a, 103a, and 104a are preferably formed through a step of processing the same conductive layer, because the manufacturing cost can be reduced.

Note that a plurality of transistors may be formed over the substrate 200 before the first step. The plurality of transistors may be electrically connected to the conductive layers 101a, 103a, and 104a.

<<Second Step>>

Figure 7B:
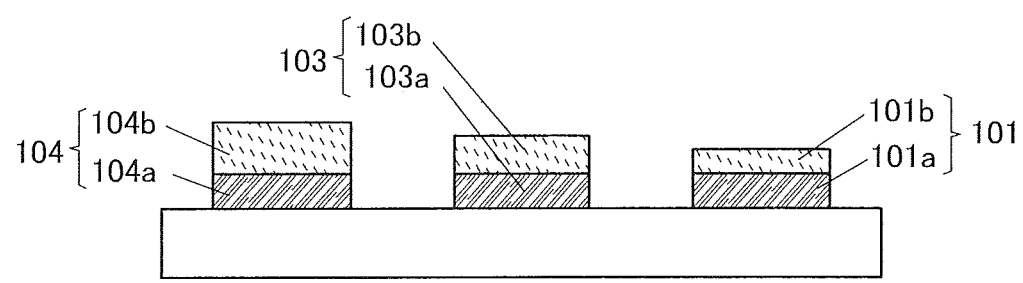

In the second step, the conductive layer 101b having a function of transmitting light is formed over the conductive layer 101a of the electrode 101, the conductive layer 103b having a function of transmitting light is formed over the conductive layer 103a of the electrode 103, and the conductive layer 104b having a function of transmitting light is formed over the conductive layer 104a of the electrode 104 (see FIG. 7B).

In this embodiment, the conductive layers 101b, 103b, and 104b each having a function of transmitting light are formed over the conductive layers 101a, 103a, and 104a each having a function of reflecting light, respectively, whereby the electrode 101, the electrode 103, and the electrode 104 are formed. As the conductive layers 101b, 103b, and 104b, ITSO films are used.

The conductive layers 101b, 103b, and 104b having a function of transmitting light may be formed in a plurality of steps. When the conductive layers 101b, 103b, and 104b having a function of transmitting light are formed in a plurality of steps, they can be formed to have thicknesses which enable microcavity structures appropriate in the respective regions.

<<Third Step>>

Figure 7C:
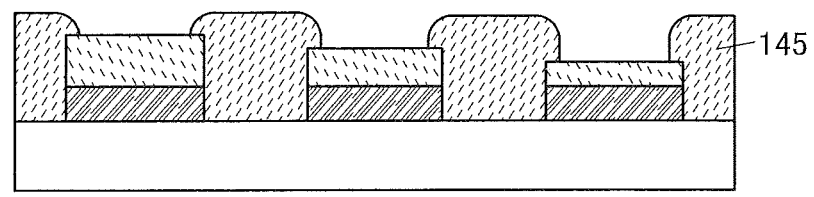

In the third step, the partition wall 145 that covers end portions of the electrodes of the light-emitting element is formed (see FIG. 7C).

The partition wall 145 includes an opening overlapping with the electrode. The conductive film exposed by the opening functions as the anode of the light-emitting element. As the partition wall 145, a polyimide-based resin is used in this embodiment.

In the first to third steps, since there is no possibility of damaging the EL layer (a layer containing an organic compound), a variety of film formation methods and micromachining technologies can be employed. In this embodiment, a reflective conductive layer is formed by a sputtering method, a pattern is formed over the conductive layer by a lithography method, and then the conductive layer is processed into an island shape by a dry etching method or a wet etching method to form the conductive layer 101a of the electrode 101, the conductive layer 103a of the electrode 103, and the conductive layer 104a of the electrode 104. Then, a transparent conductive film is formed by a sputtering method, a pattern is formed over the transparent conductive film by a lithography method, and then the transparent conductive film is processed into island shapes by a wet etching method to form the electrodes 101, 103, and 104.

<<Fourth Step>>

Figure 8A:
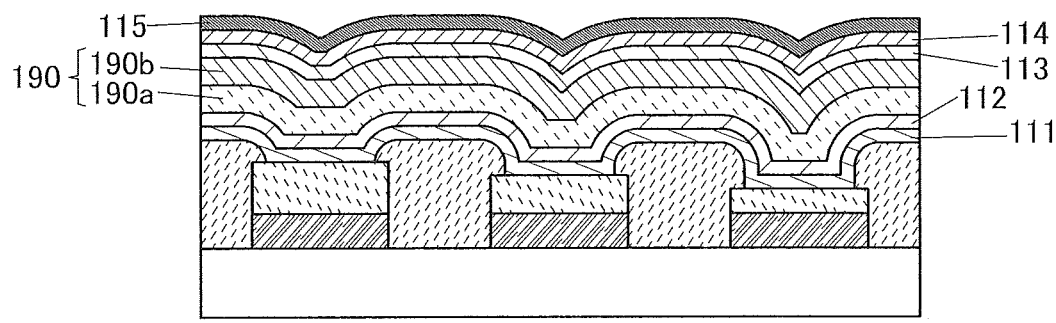
FIGS. 8A to 8C are schematic cross-sectional views illustrating a method for fabricating a light-emitting element of one embodiment of the present invention.

In the fourth step, the hole-injection layer 111, the hole-transport layer 112, the light-emitting layer 190, the electron-transport layer 113, the electron-injection layer 114, and the charge-generation layer 115 are formed (see FIG. 8A).

The hole-injection layer 111 can be formed by co-evaporating a hole-transport material and a material containing an acceptor substance. Note that a co-evaporation method is an evaporation method in which a plurality of different substances are concurrently vaporized from respective different evaporation sources. The hole-transport layer 112 can be formed by evaporating a hole-transport material.

The light-emitting layer 190 can be formed by evaporating a guest material that emits light of at least one color selected from violet, blue, blue green, green, yellow green, yellow, orange, and red. As the guest material, a fluorescent or phosphorescent organic material can be used. The structure of the light-emitting layer described in Embodiments 3 and 4 is preferably employed. The light-emitting layer 190 may have a two-layer structure. In such a case, the two light-emitting layers each preferably contain a light-emitting material that emits light of a different color.

The electron-transport layer 113 can be formed by evaporating a substance having a high electron-transport property. The electron-injection layer 114 can be formed by evaporating a substance having a high electron-injection property.

The charge-generation layer 115 can be formed by evaporating a material obtained by adding an electron acceptor (acceptor) to a hole-transport material or a material obtained by adding an electron donor (donor) to an electron-transport material.

<<Fifth Step>>

Figure 8B:
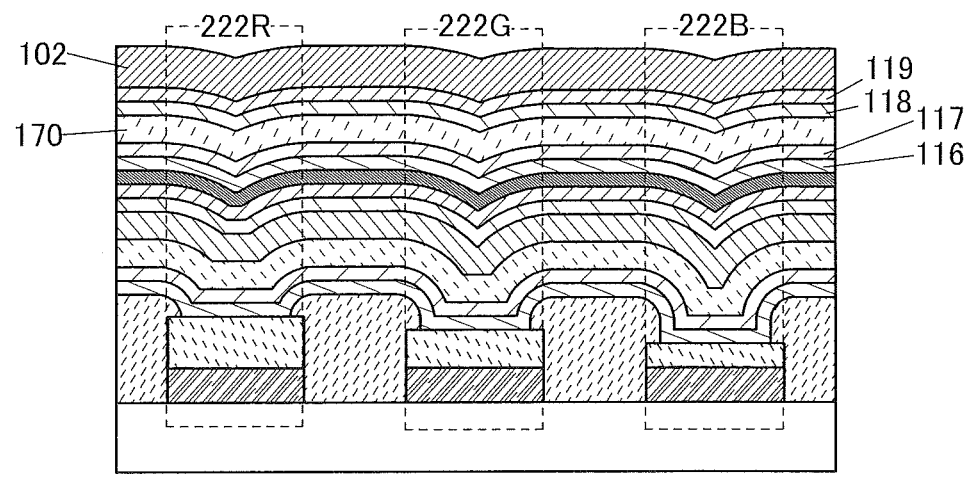

In the fifth step, the hole-injection layer 116, the hole-transport layer 117, the light-emitting layer 170, the electron-transport layer 118, the electron-injection layer 119, and the electrode 102 are formed (see FIG. 8B).

The hole-injection layer 116 can be formed by using a material and a method which are similar to those of the hole-injection layer 111. The hole-transport layer 117 can be formed by using a material and a method which are similar to those of the hole-transport layer 112.

The light-emitting layer 170 can be formed by evaporating a guest material that emits light of at least one color selected from violet, blue, blue green, green, yellow green, yellow, orange, and red. As the guest material, a fluorescent or phosphorescent organic compound can be used. The structure of the light-emitting layer described in Embodiments 3 and 4 is preferably employed. Note that at least one of the light-emitting layer 170 and the light-emitting layer 190 preferably includes any of the dibenzocarbazole compounds described in Embodiment 1. The light-emitting layer 170 and the light-emitting layer 190 preferably include light-emitting organic compounds exhibiting light of different colors.

The electron-transport layer 118 can be formed by using a material and a method which are similar to those of the electron-transport layer 113. The electron-injection layer 119 can be formed by using a material and a method which are similar to those of the electron-injection layer 114.

The electrode 102 can be formed by stacking a reflective conductive film and a light-transmitting conductive film. The electrode 102 may have a single-layer structure or a stacked-layer structure.

Through the above-described steps, the light-emitting element including the region 222B, the region 222G, and the region 222R over the electrode 101, the electrode 103, and the electrode 104, respectively, are formed over the substrate 200.

<<Sixth Step>>

Figure 8C:
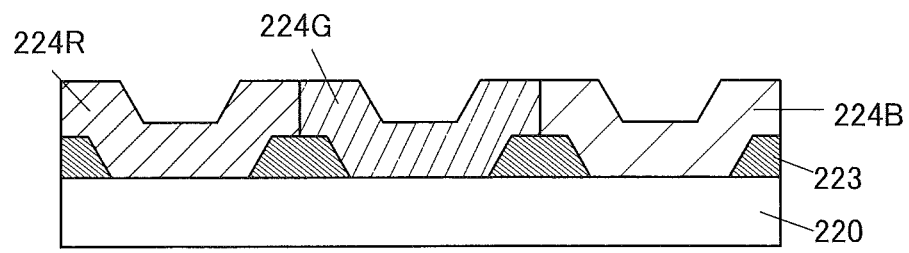

In the sixth step, the light-blocking layer 223, the optical element 224B, the optical element 224G, and the optical element 224R are formed over the substrate 220 (see FIG. 8C).

As the light-blocking layer 223, a resin film containing black pigment is formed in a desired region. Then, the optical element 224B, the optical element 224G, and the optical element 224R are formed over the substrate 220 and the light-blocking layer 223. As the optical element 224B, a resin film containing blue pigment is formed in a desired region. As the optical element 224G, a resin film containing green pigment is formed in a desired region. As the optical element 224R, a resin film containing red pigment is formed in a desired region.

<<Seventh Step>>

In the seventh step, the light-emitting element formed over the substrate 200 is attached to the light-blocking layer 223, the optical element 224B, the optical element 224G, and the optical element 224R formed over the substrate 220, and sealed with a sealant (not illustrated).

Through the above-described steps, the light-emitting element 262a illustrated in FIG. 6A can be formed.

The structure described in this embodiment can be used in combination with any of the structures described in the other embodiments as appropriate.

Embodiment 6

This embodiment shows an example of a mode where any of the dibenzocarbazole compounds described in Embodiment 1 is used in an active layer of a vertical transistor (a static induction transistor (SIT)), which is a kind of an organic semiconductor element.

Figure 9:
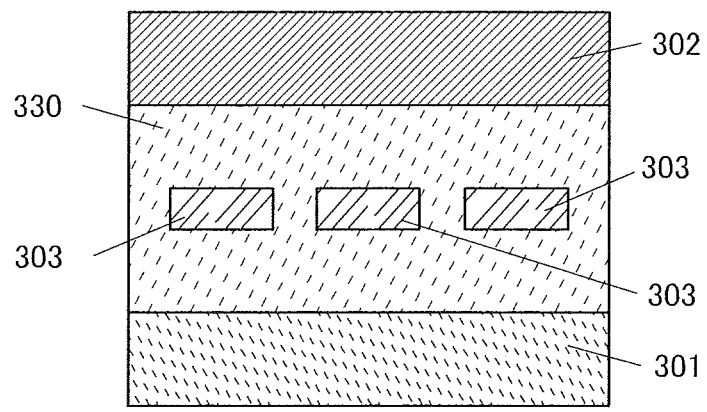
FIG. 9 is a schematic cross-sectional view of a semiconductor element of one embodiment of the present invention.

In an element structure, between a source electrode 301 and a drain electrode 302, a thin-film active layer 330 including any of the dibenzocarbazole compounds described in Embodiment 1 is provided and gate electrodes 303 are embedded in the active layer 330, as illustrated in FIG. 9. The gate electrodes 303 are electrically connected to a means for applying a gate voltage, and the source electrode 301 and the drain electrode 302 are electrically connected to a means for controlling a voltage between the source electrode and the drain electrode.

In such an element structure, when a voltage is applied between the source electrode and the drain electrode without applying a voltage to the gate electrodes 303, a current flows (the element is turned on). Then, when a voltage is applied to the gate electrodes 303 in that state, a depletion layer is formed in the periphery of the gate electrodes 303, so that the current ceases flowing (the element is turned off). With such a mechanism, an organic semiconductor element 300 operates as a transistor.

In a vertical transistor, a material having both a carrier-transport property and a favorable film quality is required for an active layer like in a light-emitting element. Since each of the dibenzocarbazole compounds described in Embodiment 1 sufficiently meets these requirements, it can be suitably used.

Note that the structure described in this embodiment can be combined as appropriate with any of the structures described in the other embodiments.

Embodiment 7

In this embodiment, a display device of one embodiment of the present invention will be described below with reference to FIGS. 10A and 10B, FIGS. 11A and 11B, FIG. 12, FIGS. 13A and 13B, FIGS. 14A and 14B, FIG. 15, FIGS. 16A and 16B, FIG. 17, and FIGS. 18A and 18B.

Structure Example 1 of Display Device

Figure 10A:
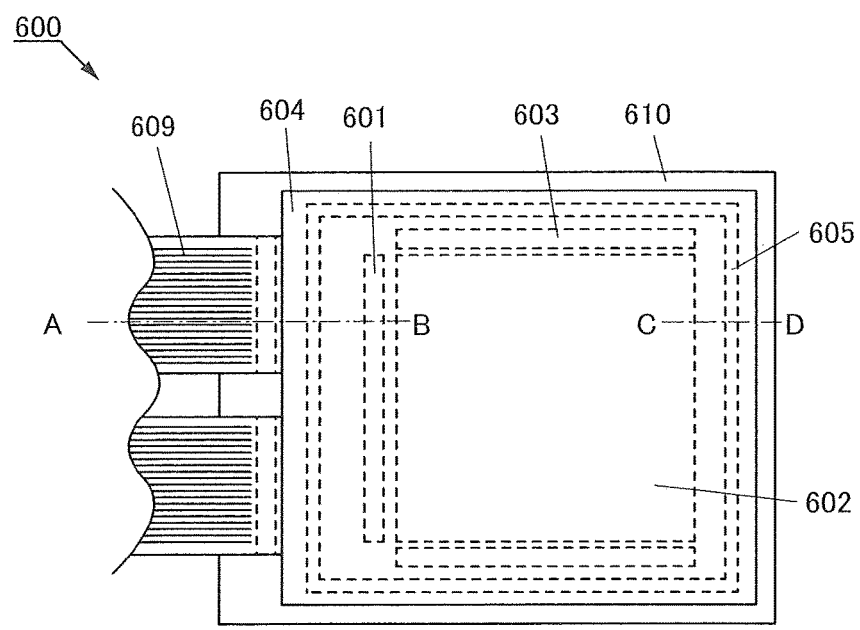
FIGS. 10A and 10B are a top view and a schematic cross-sectional view illustrating a display device of one embodiment of the present invention.
Figure 10B:
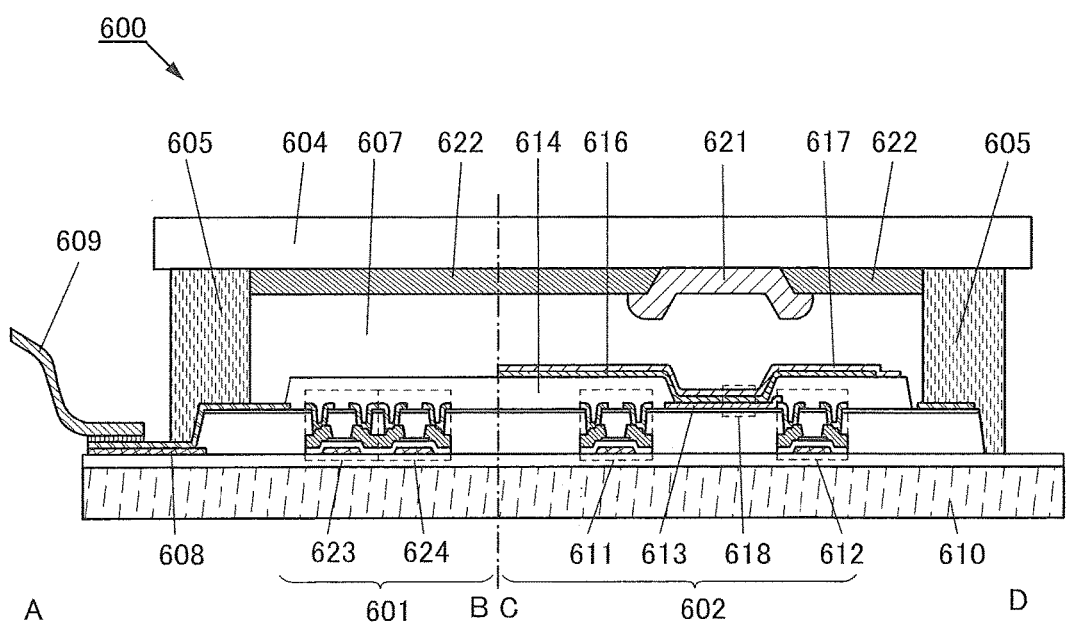

FIG. 10A is a top view illustrating a display device 600 and FIG. 10B is a cross-sectional view taken along the dashed-dotted line A-B and the dashed-dotted line C-D in FIG. 10A. The display device 600 includes driver circuit portions (a signal line driver circuit portion 601 and a scan line driver circuit portion 603) and a pixel portion 602. Note that the signal line driver circuit portion 601, the scan line driver circuit portion 603, and the pixel portion 602 have a function of controlling light emission from a light-emitting element.

The display device 600 also includes an element substrate 610, a sealing substrate 604, a sealant 605, a region 607 surrounded by the sealant 605, a lead wiring 608, and an FPC 609.

Note that the lead wiring 608 is a wiring for transmitting signals to be input to the signal line driver circuit portion 601 and the scan line driver circuit portion 603 and for receiving a video signal, a clock signal, a start signal, a reset signal, and the like from the FPC 609 serving as an external input terminal. Although only the FPC 609 is illustrated here, the FPC 609 may be provided with a printed wiring board (PWB).

As the signal line driver circuit portion 601, a CMOS circuit in which an n-channel transistor 623 and a p-channel transistor 624 are combined is formed. As the signal line driver circuit portion 601 or the scan line driver circuit portion 603, various types of circuits such as a CMOS circuit, a PMOS circuit, or an NMOS circuit can be used. Although a driver in which a driver circuit portion is formed and a pixel are formed over the same surface of a substrate in the display device of this embodiment, the driver circuit portion is not necessarily formed over the substrate and can be formed outside the substrate.

The pixel portion 602 includes a switching transistor 611, a current control transistor 612, and a lower electrode 613 electrically connected to a drain of the current control transistor 612. Note that a partition wall 614 is formed to cover end portions of the lower electrode 613. As the partition wall 614, for example, a positive type photosensitive acrylic resin film can be used.

In order to obtain favorable coverage, the partition wall 614 is formed to have a curved surface with curvature at its upper or lower end portion. For example, in the case of using a positive photosensitive acrylic as a material of the partition wall 614, it is preferable that only the upper end portion of the partition wall 614 have a curved surface with curvature (the radius of the curvature being 0.2 µm to 3 µm). As the partition wall 614, either a negative photosensitive resin or a positive photosensitive resin can be used.

Note that there is no particular limitation on a structure of each of the transistors (the transistors 611, 612, 623, and 624). For example, a staggered transistor can be used. In addition, there is no particular limitation on the polarity of these transistors. For these transistors, n-channel and p-channel transistors may be used, or either n-channel transistors or p-channel transistors may be used, for example. Furthermore, there is no particular limitation on the crystallinity of a semiconductor film used for these transistors. For example, an amorphous semiconductor film or a crystalline semiconductor film may be used. Examples of a semiconductor material include Group 14 semiconductors (e.g., a semiconductor including silicon), compound semiconductors (including oxide semiconductors), organic semiconductors, and the like. For example, it is preferable to use an oxide semiconductor that has an energy gap of 2 eV or more, preferably 2.5 eV or more and further preferably 3 eV or more, for the transistors, so that the off-state current of the transistors can be reduced. Examples of the oxide semiconductor include an In—Ga oxide and an In-M-Zn oxide (M is aluminum (Al), gallium (Ga), yttrium (Y), zirconium (Zr), lanthanum (La), cerium (Ce), tin (Sn), hafnium (Hf), or neodymium (Nd)).

An EL layer 616 and an upper electrode 617 are formed over the lower electrode 613. Here, the lower electrode 613 functions as an anode and the upper electrode 617 functions as a cathode.

In addition, the EL layer 616 is formed by various methods such as an evaporation method with an evaporation mask, an ink-jet method, or a spin coating method. As another material included in the EL layer 616, a low molecular compound or a high molecular compound (including an oligomer or a dendrimer) may be used.

Note that a light-emitting element 618 is formed with the lower electrode 613, the EL layer 616, and the upper electrode 617. The light-emitting element 618 preferably has any of the structures described in Embodiments 3 to 5. In the case where the pixel portion includes a plurality of light-emitting elements, the pixel portion may include both any of the light-emitting elements described in Embodiments 3 to 5 and a light-emitting element having a different structure.

When the sealing substrate 604 and the element substrate 610 are attached to each other with the sealant 605, the light-emitting element 618 is provided in the region 607 surrounded by the element substrate 610, the sealing substrate 604, and the sealant 605. The region 607 is filled with a filler. In some cases, the region 607 is filled with an inert gas (nitrogen, argon, or the like) or filled with an ultraviolet curable resin or a thermosetting resin which can be used for the sealant 605. For example, a polyvinyl chloride (PVC)-based resin, an acrylic-based resin, a polyimide-based resin, an epoxy-based resin, a silicone-based resin, a polyvinyl butyral (PVB)-based resin, or an ethylene vinyl acetate (EVA)-based resin can be used. It is preferable that the sealing substrate be provided with a recessed portion and a desiccant be provided in the recessed portion, in which case deterioration due to influence of moisture can be inhibited.

An optical element 621 is provided below the sealing substrate 604 to overlap with the light-emitting element 618. A light-blocking layer 622 is provided below the sealing substrate 604. The structures of the optical element 621 and the light-blocking layer 622 can be the same as those of the optical element and the light-blocking layer in Embodiment 5, respectively.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), polyester, acrylic, or the like can be used.

In the above-described manner, the display device including any of the light-emitting elements and the optical elements which are described in Embodiments 3 to 5 can be obtained.

Structure Example 2 of Display Device

Next, another example of the display device is described with reference to FIGS. 11A and 11B and FIG. 12. Note that FIGS. 11A and 11B and FIG. 12 are each a cross-sectional view of a display device of one embodiment of the present invention.

Figure 11A:
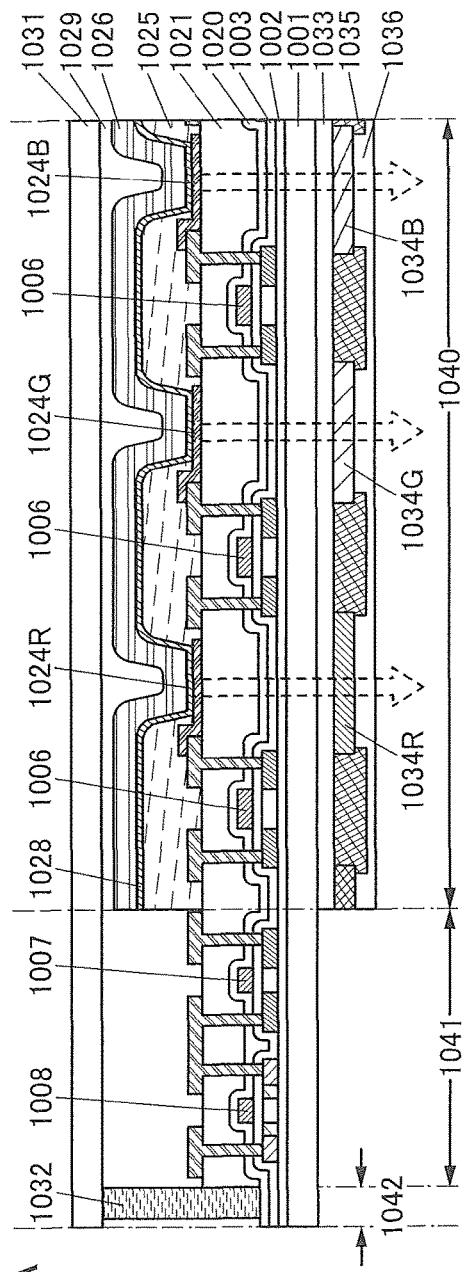
FIGS. 11A and 11B are each a schematic cross-sectional view illustrating a display device of one embodiment of the present invention.
Figure 12:
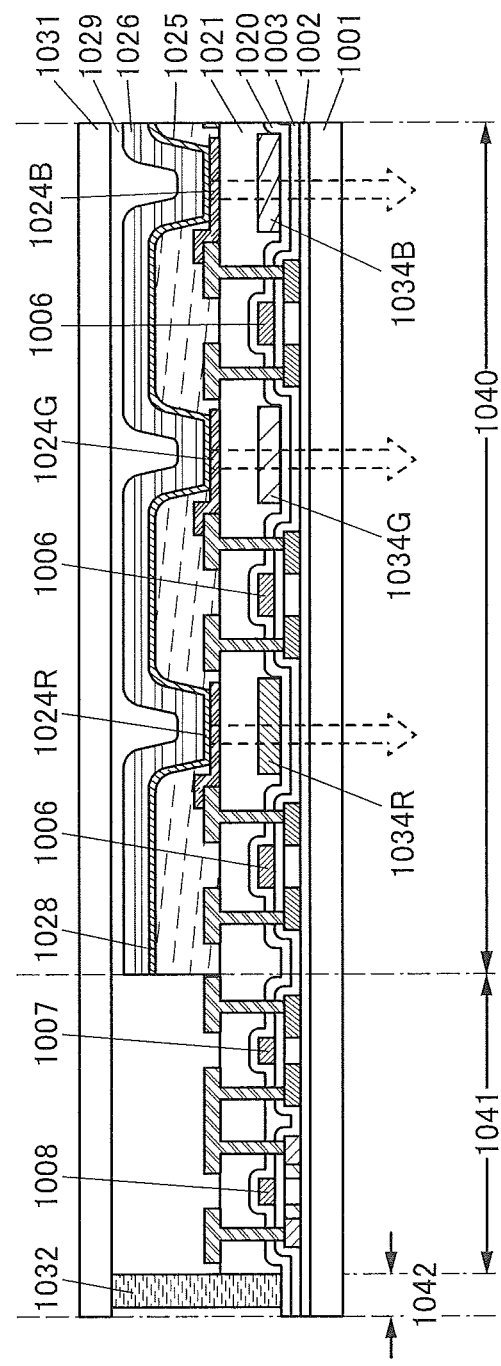
FIG. 12 is a schematic cross-sectional view illustrating a display device of one embodiment of the present invention.

In FIG. 11A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, lower electrodes 1024R, 1024G, and 1024B of light-emitting elements, a partition wall 1025, an EL layer 1028, an upper electrode 1026 of the light-emitting elements, a sealing layer 1029, a sealing substrate 1031, a sealant 1032, and the like are illustrated.

In FIG. 11A, examples of the optical elements, coloring layers (a red coloring layer 1034R, a green coloring layer 1034G, and a blue coloring layer 1034B) are provided on a transparent base material 1033. Further, a light-blocking layer 1035 may be provided. The transparent base material 1033 provided with the coloring layers and the light-blocking layer is positioned and fixed to the substrate 1001. Note that the coloring layers and the light-blocking layer are covered with an overcoat layer 1036. In the structure in FIG. 11A, red light, green light, and blue light transmit the coloring layers, and thus an image can be displayed with the use of pixels of three colors.

Figure 11B:
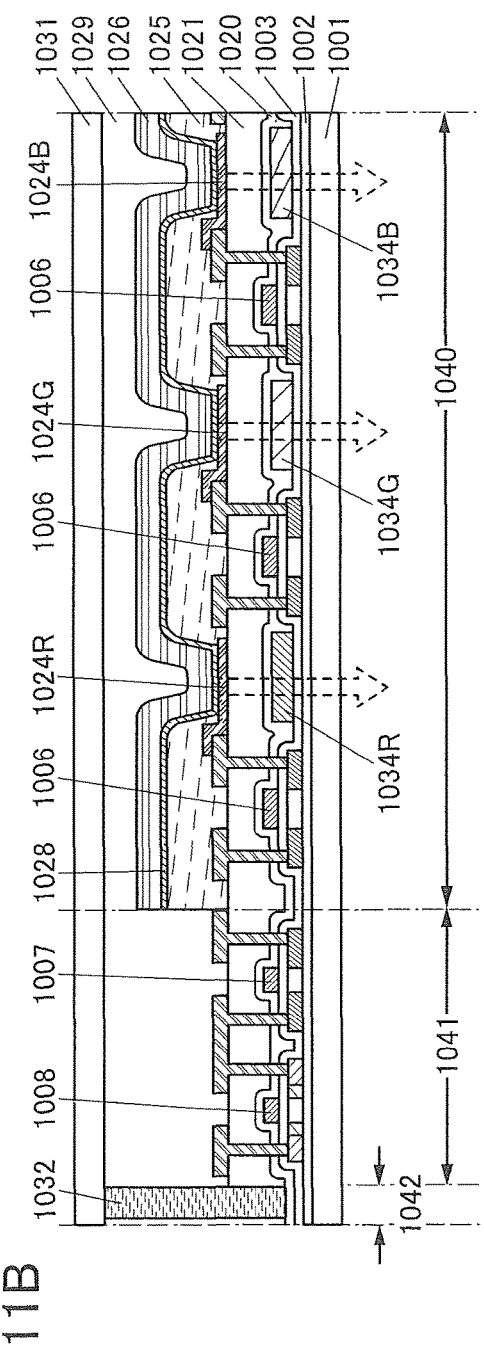

FIG. 11B illustrates an example in which, as examples of the optical elements, the coloring layers (the red coloring layer 1034R, the green coloring layer 1034G, and the blue coloring layer 1034B) are provided between the gate insulating film 1003 and the first interlayer insulating film 1020. As in this structure, the coloring layers may be provided between the substrate 1001 and the sealing substrate 1031.

FIG. 12 illustrates an example in which, as examples of the optical elements, the coloring layers (the red coloring layer 1034R, the green coloring layer 1034G, and the blue coloring layer 1034B) are provided between the first interlayer insulating film 1020 and the second interlayer insulating film 1021. As in this structure, the coloring layers may be provided between the substrate 1001 and the sealing substrate 1031.

The above-described display device has a structure in which light is extracted from the substrate 1001 side where the transistors are formed (a bottom-emission structure), but may have a structure in which light is extracted from the sealing substrate 1031 side (a top-emission structure).

Structure Example 3 of Display Device

Figure 13A:
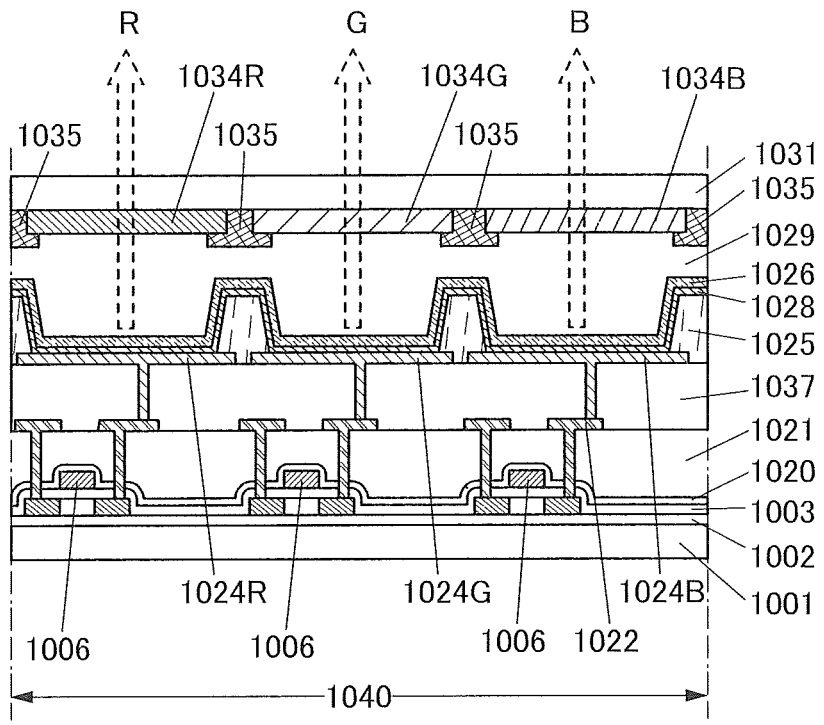
FIGS. 13A and 13B are schematic cross-sectional views each illustrating a display device of one embodiment of the present invention.
Figure 13B:
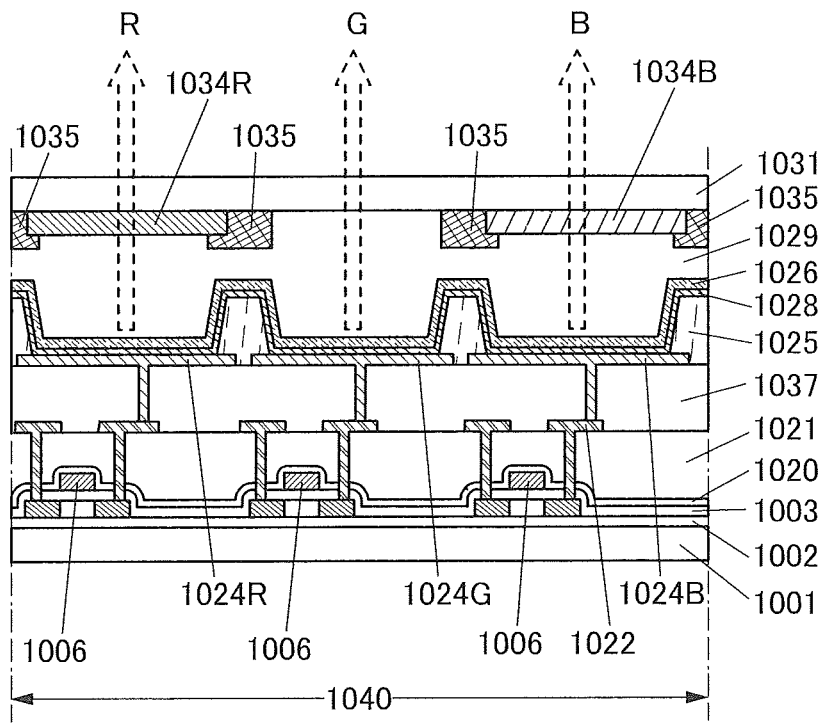

FIGS. 13A and 13B are each an example of a cross-sectional view of a display device having a top emission structure. Note that FIGS. 13A and 13B are each a cross-sectional view illustrating the display device of one embodiment of the present invention, and the driver circuit portion 1041, the peripheral portion 1042, and the like, which are illustrated in FIGS. 11A and 11B and FIG. 12, are not illustrated therein.

In this case, as the substrate 1001, a substrate that does not transmit light can be used. The process up to the step of forming a connection electrode which connects the transistor and the anode of the light-emitting element is performed in a manner similar to that of the display device having a bottom-emission structure. Then, a third interlayer insulating film 1037 is formed to cover an electrode 1022. This insulating film may have a planarization function. The third interlayer insulating film 1037 can be formed using a material similar to that of the second interlayer insulating film, or can be formed using any other various materials.

The lower electrodes 1024R, 1024G, and 1024B of the light-emitting elements each function as an anode here, but may function as a cathode. Further, in the case of a display device having a top-emission structure as illustrated in FIGS. 13A and 13B, the lower electrodes 1024R, 1024G, and 1024B preferably have a function of reflecting light. The upper electrode 1026 is provided over the EL layer 1028. It is preferable that the upper electrode 1026 have a function of reflecting light and a function of transmitting light and that a microcavity structure be used between the upper electrode 1026 and the lower electrodes 1024R, 1024G, and 1024B, in which case the intensity of light having a specific wavelength is increased.

In the case of a top-emission structure as illustrated in FIG. 13A, sealing can be performed with the sealing substrate 1031 on which the coloring layers (the red coloring layer 1034R, the green coloring layer 1034G, and the blue coloring layer 1034B) are provided. The sealing substrate 1031 may be provided with the light-blocking layer 1035 which is positioned between pixels. Note that a light-transmitting substrate is favorably used as the sealing substrate 1031.

FIG. 13A illustrates the structure provided with the light-emitting elements and the coloring layers for the light-emitting elements as an example; however, the structure is not limited thereto. For example, as shown in FIG. 13B, a structure including the red coloring layer 1034R and the blue coloring layer 1034B but not including a green coloring layer may be employed to achieve full color display with the three colors of red, green, and blue. The structure as illustrated in FIG. 13A where the light-emitting elements are provided with the coloring layers is effective to suppress reflection of external light. In contrast, the structure as illustrated in FIG. 13B where the light-emitting elements are provided with the red coloring layer and the blue coloring layer and without the green coloring layer is effective to reduce power consumption because of small energy loss of light emitted from the green light-emitting element.

Structure Example 4 of Display Device

Figure 15:
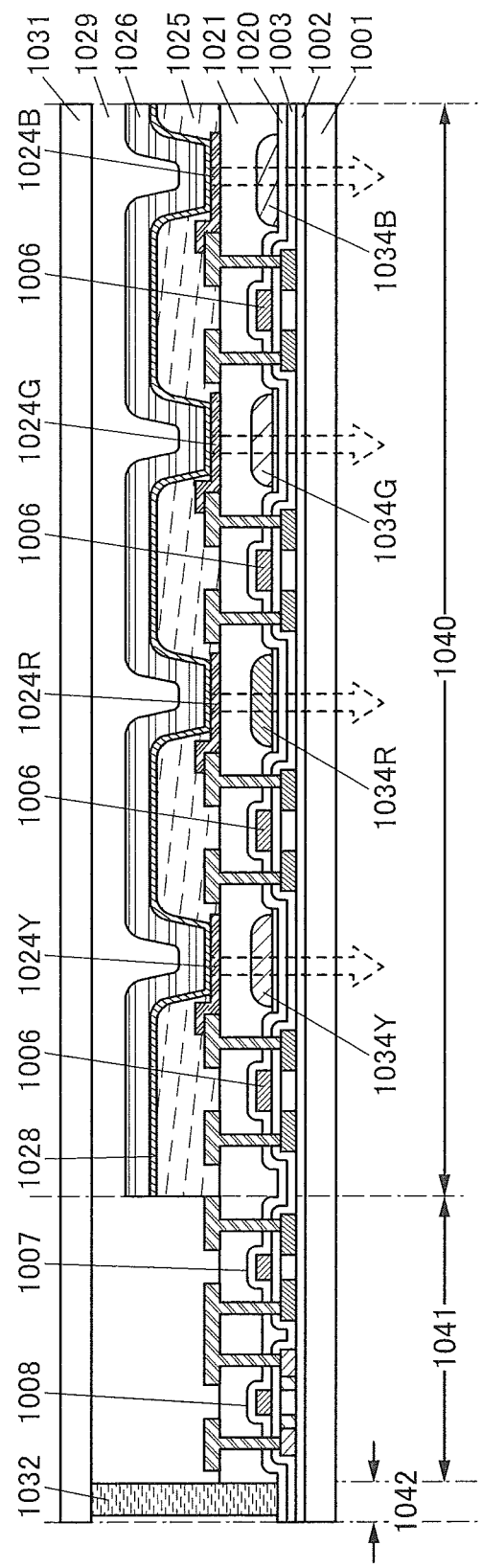
FIG. 15 is a schematic cross-sectional view illustrating a display device of one embodiment of the present invention.

Although a display device including sub-pixels of three colors (red, green, and blue) is described above, the number of colors of sub-pixels may be four (red, green, blue, and yellow, or red, green, blue, and white). FIGS. 14A and 14B, FIG. 15, and FIGS. 16A and 16B illustrate structures of display devices each including the lower electrodes 1024R, 1024G, 1024B, and 1024Y. FIGS. 14A and 14B and FIG. 15 each illustrate a display device having a structure in which light is extracted from the substrate 1001 side on which transistors are formed (bottom-emission structure), and FIGS. 16A and 16B each illustrate a display device having a structure in which light is extracted from the sealing substrate 1031 side (top-emission structure).

FIG. 14A illustrates an example of a display device in which optical elements (the coloring layer 1034R, the coloring layer 1034G, the coloring layer 1034B, and a coloring layer 1034Y) are provided on the transparent base material 1033. FIG. 14B illustrates an example of a display device in which optical elements (the coloring layer 1034R, the coloring layer 1034G, and the coloring layer 1034B) are provided between the gate insulating film 1003 and the first interlayer insulating film 1020. FIG. 15 illustrates an example of a display device in which optical elements (the coloring layer 1034R, the coloring layer 1034G, the coloring layer 1034B, and the coloring layer 1034Y) are provided between the first interlayer insulating film 1020 and the second interlayer insulating film 1021.

The coloring layer 1034R transmits red light, the coloring layer 1034G transmits green light, and the coloring layer 1034B transmits blue light. The coloring layer 1034Y transmits yellow light or transmits light of a plurality of colors selected from blue, green, yellow, and red. When the coloring layer 1034Y can transmit light of a plurality of colors selected from blue, green, yellow, and red, light released from the coloring layer 1034Y may be white light. Since the light-emitting element which transmits yellow or white light has high emission efficiency, the display device including the coloring layer 1034Y can have lower power consumption.

Figure 16A:
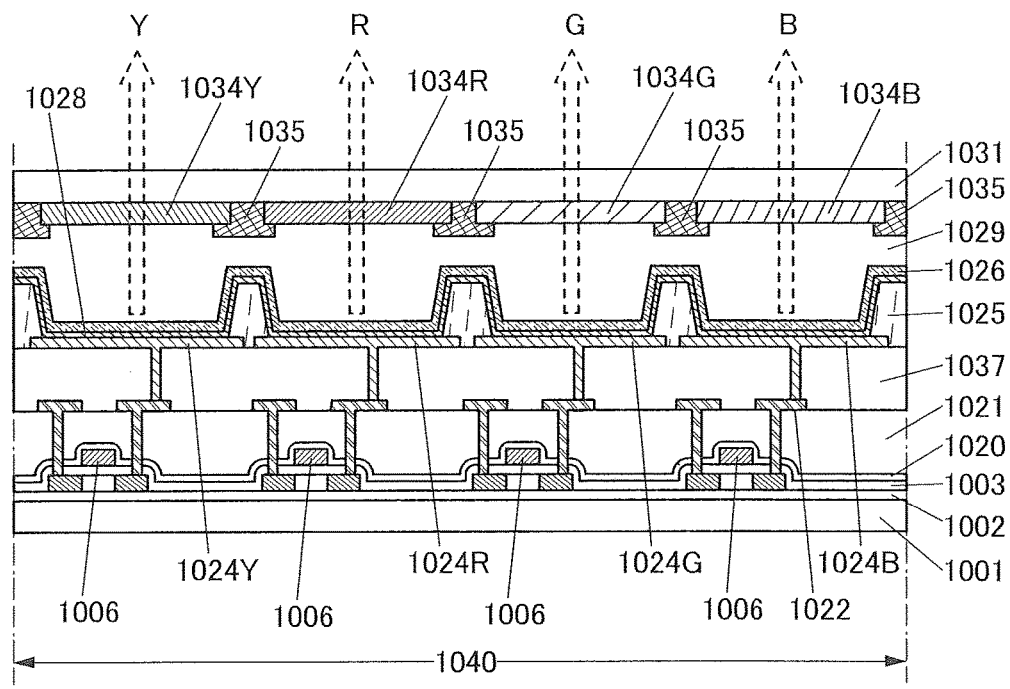
FIGS. 16A and 16B are schematic cross-sectional views each illustrating a display device of one embodiment of the present invention.
Figure 16B:
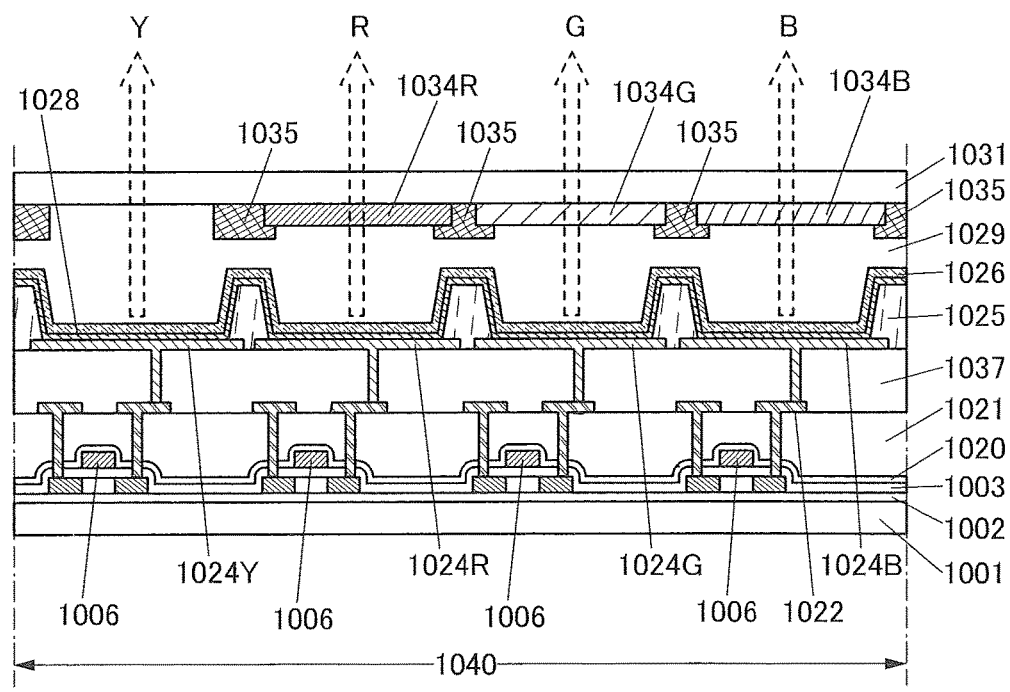

In the top-emission display devices illustrated in FIGS. 16A and 16B, a light-emitting element including the lower electrode 1024Y preferably has a microcavity structure between the lower electrode 1024Y and the upper electrode 1026 as in the display device illustrated in FIG. 13A. In the display device illustrated in FIG. 16A, sealing can be performed with the sealing substrate 1031 on which the coloring layers (the red coloring layer 1034R, the green coloring layer 1034G, the blue coloring layer 1034B, and the yellow coloring layer 1034Y) are provided.

Light emitted through the microcavity and the yellow coloring layer 1034Y has an emission spectrum in a yellow region. Since yellow is a color with a high luminosity factor, a light-emitting element emitting yellow light has high emission efficiency. Therefore, the display device of FIG. 16A can reduce power consumption.

FIG. 16A illustrates the structure provided with the light-emitting elements and the coloring layers for the light-emitting elements as an example; however, the structure is not limited thereto. For example, as shown in FIG. 16B, a structure including the red coloring layer 1034R, the green coloring layer 1034G, and the blue coloring layer 1034B but not including a yellow coloring layer may be employed to achieve full color display with the four colors of red, green, blue, and yellow or of red, green, blue, and white. The structure as illustrated in FIG. 16A where the light-emitting elements are provided with the coloring layers is effective to suppress reflection of external light. In contrast, the structure as illustrated in FIG. 16B where the light-emitting elements are provided with the red coloring layer, the green coloring layer, and the blue coloring layer and without the yellow coloring layer is effective to reduce power consumption because of small energy loss of light emitted from the yellow or white light-emitting element.

Structure Example 5 of Display Device

Figure 17:
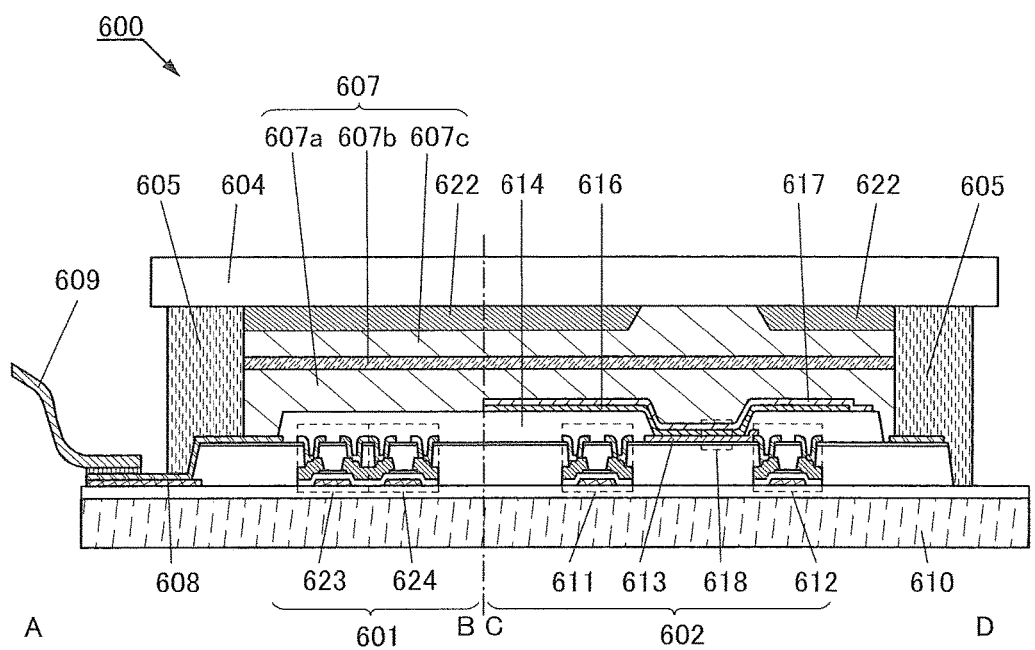
FIG. 17 is a schematic cross-sectional view illustrating a display device of one embodiment of the present invention.

Next, a display device of another embodiment of the present invention is described with reference to FIG. 17. FIG. 17 is a cross-sectional view taken along the dashed-dotted line A-B and the dashed-dotted line C-D in FIG. 10A. Note that in FIG. 17, portions having functions similar to those of portions in FIG. 10B are given the same reference numerals as in FIG. 10B, and a detailed description of the portions is omitted.

The display device 600 in FIG. 17 includes a sealing layer 607a, a sealing layer 607b, and a sealing layer 607c in a region 607 surrounded by the element substrate 610, the sealing substrate 604, and the sealant 605. For one or more of the sealing layer 607a, the sealing layer 607b, and the sealing layer 607c, a resin such as a polyvinyl chloride (PVC) based resin, an acrylic-based resin, a polyimide-based resin, an epoxy-based resin, a silicone-based resin, a polyvinyl butyral (PVB) based resin, or an ethylene vinyl acetate (EVA) based resin can be used. Alternatively, an inorganic material such as silicon oxide, silicon oxynitride, silicon nitride oxide, silicon nitride, aluminum oxide, or aluminum nitride can be used. The formation of the sealing layers 607a, 607b, and 607c can prevent deterioration of the light-emitting element 618 due to impurities such as water, which is preferable. In the case where the sealing layers 607a, 607b, and 607c are formed, the sealant 605 is not necessarily provided.

Alternatively, any one or two of the sealing layers 607a, 607b, and 607c may be provided or four or more sealing layers may be formed. When the sealing layer has a multi-layer structure, the impurities such as water can be effectively prevented from entering the light-emitting element 618 which is inside the display device from the outside of the display device 600. In the case where the sealing layer has a multilayer structure, a resin and an inorganic material are preferably stacked.

Structure Example 6 of Display Device

Although the display devices in the structure examples 1 to 4 in this embodiment each have a structure including optical elements, one embodiment of the present invention does not necessarily include an optical element.

Figure 18A:
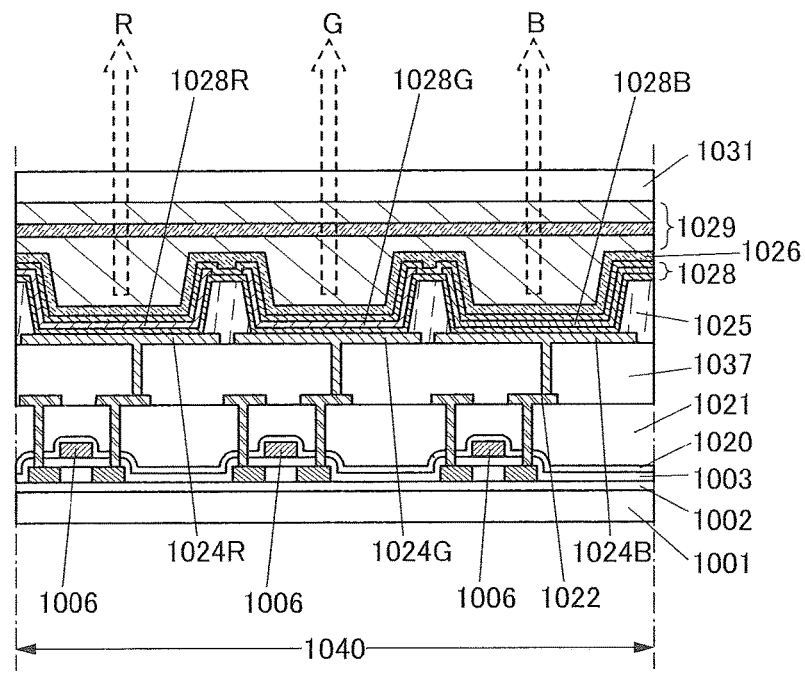
FIGS. 18A and 18B are schematic cross-sectional views each illustrating a display device of one embodiment of the present invention.
Figure 18B:
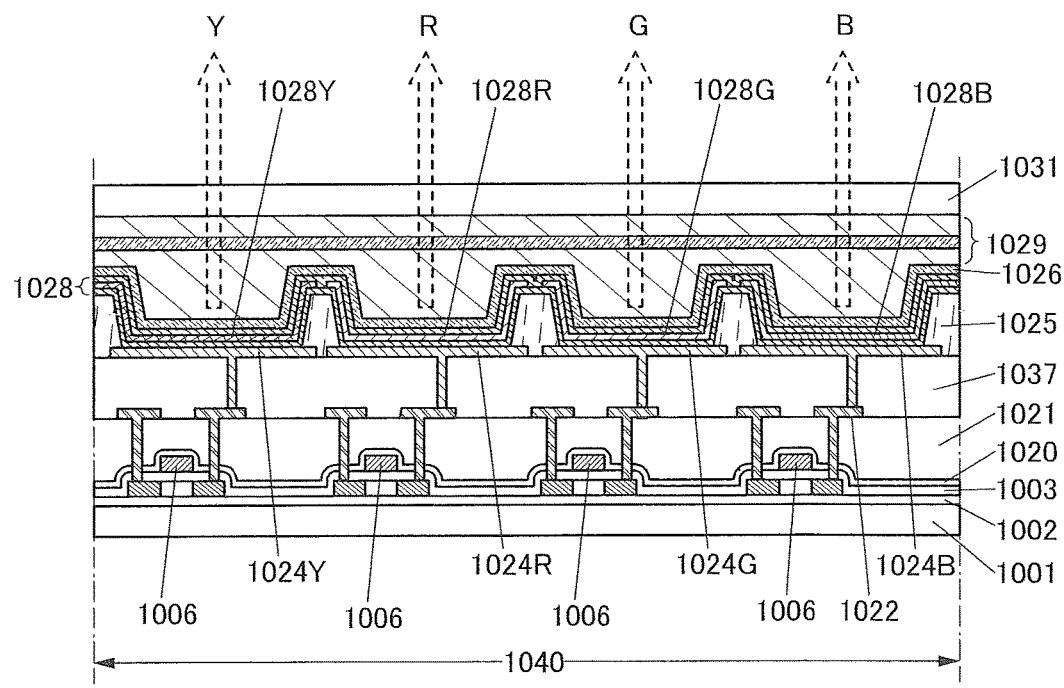

FIGS. 18A and 18B each illustrate a display device having a structure in which light is extracted from the sealing substrate 1031 side (a top-emission display device). FIG. 18A illustrates an example of a display device including a light-emitting layer 1028R, a light-emitting layer 1028G, and a light-emitting layer 1028B. FIG. 18B illustrates an example of a display device including a light-emitting layer 1028R, a light-emitting layer 1028G, a light-emitting layer 1028B, and a light-emitting layer 1028Y.

The light-emitting layer 1028R has a function of exhibiting red light, the light-emitting layer 1028G has a function of exhibiting green light, and the light-emitting layer 1028B has a function of exhibiting blue light. The light-emitting layer 1028Y has a function of exhibiting yellow light or a function of exhibiting light of a plurality of colors selected from blue, green, and red. The light-emitting layer 1028Y may exhibit white light. Since the light-emitting element which exhibits yellow or white light has high light emission efficiency, the display device including the light-emitting layer 1028Y can have lower power consumption.

Each of the display devices in FIGS. 18A and 18B does not necessarily include coloring layers serving as optical elements because EL layers exhibiting light of different colors are included in sub-pixels.

For the sealing layer 1029, a resin such as a polyvinyl chloride (PVC) based resin, an acrylic-based resin, a polyimide-based resin, an epoxy-based resin, a silicone-based resin, a polyvinyl butyral (PVB) based resin, or an ethylene vinyl acetate (EVA) based resin can be used. Alternatively, an inorganic material such as silicon oxide, silicon oxynitride, silicon nitride oxide, silicon nitride, aluminum oxide, or aluminum nitride can be used. The formation of the sealing layer 1029 can prevent deterioration of the light-emitting element due to impurities such as water, which is preferable.

Alternatively, the sealing layer 1029 may have a single-layer or two-layer structure, or four or more sealing layers may be formed as the sealing layer 1029. When the sealing layer has a multilayer structure, the impurities such as water can be effectively prevented from entering the inside of the display device from the outside of the display device. In the case where the sealing layer has a multilayer structure, a resin and an inorganic material are preferably stacked.

Note that the sealing substrate 1031 has a function of protecting the light-emitting element. Thus, for the sealing substrate 1031, a flexible substrate or a film can be used.

The structures described in this embodiment can be combined as appropriate with any of the other structures in this embodiment and the other embodiments.

Embodiment 8

In this embodiment, a display device including a light-emitting element of one embodiment of the present invention will be described with reference to FIGS. 19A and 19B, FIGS. 20A and 20B, and FIGS. 21A and 21B.

Figure 19A:
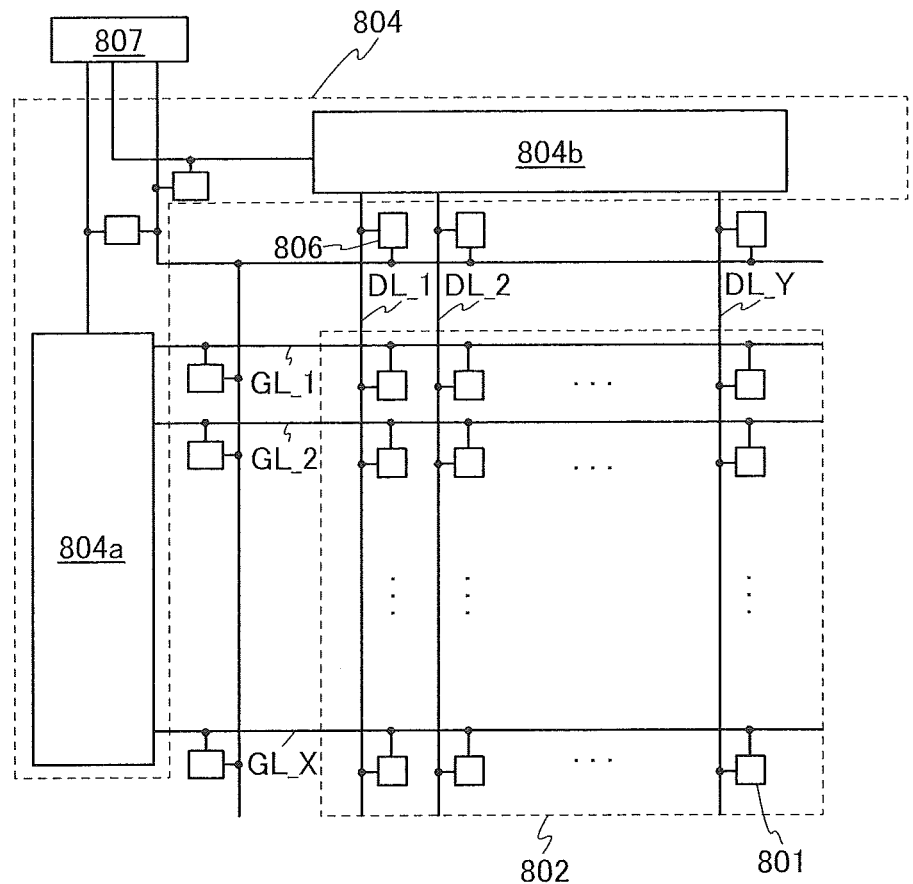
FIGS. 19A and 19B are a block diagram and a circuit diagram illustrating a display device of one embodiment of the present invention.
Figure 19B:
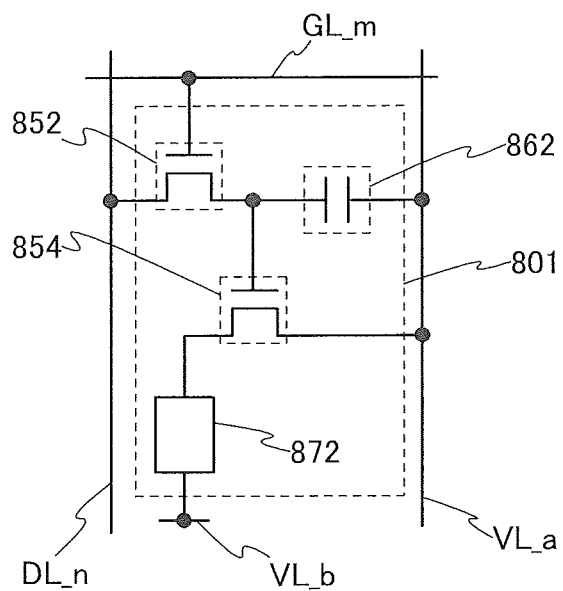

FIG. 19A is a block diagram illustrating the display device of one embodiment of the present invention, and FIG. 19B is a circuit diagram illustrating a pixel circuit of the display device of one embodiment of the present invention.
<Description of Display Device>

The display device illustrated in FIG. 19A includes a region including pixels of display elements (the region is hereinafter referred to as a pixel portion 802), a circuit portion provided outside the pixel portion 802 and including circuits for driving the pixels (the portion is hereinafter referred to as a driver circuit portion 804), circuits having a function of protecting elements (the circuits are hereinafter referred to as protection circuits 806), and a terminal portion 807. Note that the protection circuits 806 are not necessarily provided.

A part or the whole of the driver circuit portion 804 is preferably formed over a substrate over which the pixel portion 802 is formed, in which case the number of components and the number of terminals can be reduced. When a part or the whole of the driver circuit portion 804 is not formed over the substrate over which the pixel portion 802 is formed, the part or the whole of the driver circuit portion 804 can be mounted by COG or tape automated bonding (TAB).

The pixel portion 802 includes a plurality of circuits for driving display elements arranged in X rows (X is a natural number of 2 or more) and Y columns (Y is a natural number of 2 or more) (such circuits are hereinafter referred to as pixel circuits 801). The driver circuit portion 804 includes driver circuits such as a circuit for supplying a signal (scan signal) to select a pixel (the circuit is hereinafter referred to as a scan line driver circuit 804*a*) and a circuit for supplying a signal (data signal) to drive a display element in a pixel (the circuit is hereinafter referred to as a signal line driver circuit 804*b*).

The scan line driver circuit 804*a* includes a shift register or the like. Through the terminal portion 807, the scan line driver circuit 804*a* receives a signal for driving the shift register and outputs a signal. For example, the scan line driver circuit 804*a* receives a start pulse signal, a clock signal, or the like and outputs a pulse signal. The scan line driver circuit 804*a* has a function of controlling the potentials of wirings supplied with scan signals (such wirings are hereinafter referred to as scan lines GL_1 to GL_X). Note that a plurality of scan line driver circuits 804*a* may be provided to control the scan lines GL_1 to GL_X separately. Alternatively, the scan line driver circuit 804*a* has a function of supplying an initialization signal. Without being limited thereto, the scan line driver circuit 804*a* can supply another signal.

The signal line driver circuit 804*b* includes a shift register or the like. The signal line driver circuit 804*b* receives a signal (image signal) from which a data signal is derived, as well as a signal for driving the shift register, through the terminal portion 807. The signal line driver circuit 804*b* has a function of generating a data signal to be written to the pixel circuit 801 which is based on the image signal. In addition, the signal line driver circuit 804*b* has a function of controlling output of a data signal in response to a pulse signal produced by input of a start pulse signal, a clock signal, or the like. Furthermore, the signal line driver circuit 804*b* has a function of controlling the potentials of wirings supplied with data signals (such wirings are hereinafter referred to as data lines DL_1 to DL_Y). Alternatively, the signal line driver circuit 804*b* has a function of supplying an initialization signal. Without being limited thereto, the signal line driver circuit 804*b* can supply another signal.

The signal line driver circuit 804*b* includes a plurality of analog switches or the like, for example. The signal line driver circuit 804*b* can output, as the data signals, signals obtained by time-dividing the image signal by sequentially turning on the plurality of analog switches. The signal line driver circuit 804*b* may include a shift register or the like.

A pulse signal and a data signal are input to each of the plurality of pixel circuits 801 through one of the plurality of scan lines GL supplied with scan signals and one of the plurality of data lines DL supplied with data signals, respectively. Writing and holding of the data signal to and in each of the plurality of pixel circuits 801 are controlled by the scan line driver circuit 804*a*. For example, to the pixel circuit 801 in the m-th row and the n-th column (m is a natural number of less than or equal to X, and n is a natural number of less than or equal to Y), a pulse signal is input from the scan line driver circuit 804*a* through the scan line GL_m, and a data signal is input from the signal line driver circuit 804*b* through the data line DL_n in accordance with the potential of the scan line GL_m.

The protection circuit 806 shown in FIG. 19A is connected to, for example, the scan line GL between the scan line driver circuit 804*a* and the pixel circuit 801. Alternatively, the protection circuit 806 is connected to the data line DL between the signal line driver circuit 804*b* and the pixel circuit 801. Alternatively, the protection circuit 806 can be connected to a wiring between the scan line driver circuit 804*a* and the terminal portion 807. Alternatively, the protection circuit 806 can be connected to a wiring between the signal line driver circuit 804*b* and the terminal portion 807. Note that the terminal portion 807 means a portion having terminals for inputting power, control signals, and image signals to the display device from external circuits.

The protection circuit 806 is a circuit that electrically connects a wiring connected to the protection circuit to another wiring when a potential out of a certain range is applied to the wiring connected to the protection circuit.

As illustrated in FIG. 19A, the protection circuits 806 are connected to the pixel portion 802 and the driver circuit portion 804, so that the resistance of the display device to overcurrent generated by electrostatic discharge (ESD) or the like can be improved. Note that the configuration of the protection circuits 806 is not limited to that, and for example, a configuration in which the protection circuits 806 are connected to the scan line driver circuit 804*a* or a configuration in which the protection circuits 806 are connected to the signal line driver circuit 804*b* may be employed. Alternatively, the protection circuits 806 may be configured to be connected to the terminal portion 807.

In FIG. 19A, an example in which the driver circuit portion 804 includes the scan line driver circuit 804*a* and the signal line driver circuit 804*b* is shown; however, the structure is not limited thereto. For example, only the scan line driver circuit 804*a* may be formed and a separately prepared substrate where a signal line driver circuit is formed (e.g., a driver circuit substrate formed with a single crystal semiconductor film or a polycrystalline semiconductor film) may be mounted.

Structure Example of Pixel Circuit

Each of the plurality of pixel circuits 801 in FIG. 19A can have a structure illustrated in FIG. 19B, for example.

The pixel circuit 801 illustrated in FIG. 19B includes transistors 852 and 854, a capacitor 862, and a light-emitting element 872.

One of a source electrode and a drain electrode of the transistor 852 is electrically connected to a wiring to which a data signal is supplied (a data line DL_n). A gate electrode of the transistor 852 is electrically connected to a wiring to which a gate signal is supplied (a scan line GL_m).

The transistor 852 has a function of controlling whether to write a data signal.

One of a pair of electrodes of the capacitor 862 is electrically connected to a wiring to which a potential is supplied (hereinafter referred to as a potential supply line VL_a), and the other is electrically connected to the other of the source electrode and the drain electrode of the transistor 852.

The capacitor 862 functions as a storage capacitor for storing written data.

One of a source electrode and a drain electrode of the transistor 854 is electrically connected to the potential supply line VL_a. Furthermore, a gate electrode of the transistor 854 is electrically connected to the other of the source electrode and the drain electrode of the transistor 852.

One of an anode and a cathode of the light-emitting element 872 is electrically connected to a potential supply line VL_b, and the other is electrically connected to the other of the source electrode and the drain electrode of the transistor 854.

As the light-emitting element 872, any of the light-emitting elements described in Embodiments 3 to 5 can be used.

Note that a high power supply potential VDD is supplied to one of the potential supply line VL_a and the potential supply line VL_b, and a low power supply potential VSS is supplied to the other.

In the display device including the pixel circuits 801 in FIG. 19B, the pixel circuits 801 are sequentially selected row by row by the scan line driver circuit 804*a* in FIG. 19A, for example, whereby the transistors 852 are turned on and a data signal is written.

When the transistors 852 are turned off, the pixel circuits 801 in which the data has been written are brought into a holding state. Furthermore, the amount of current flowing between the source electrode and the drain electrode of the transistor 854 is controlled in accordance with the potential of the written data signal. The light-emitting element 872 emits light with a luminance corresponding to the amount of flowing current. This operation is sequentially performed row by row; thus, an image is displayed.

Alternatively, the pixel circuit can have a function of compensating variation in threshold voltages or the like of a transistor. FIGS. 20A and 20B and FIGS. 21A and 21B illustrate examples of the pixel circuit.

Figure 20A:
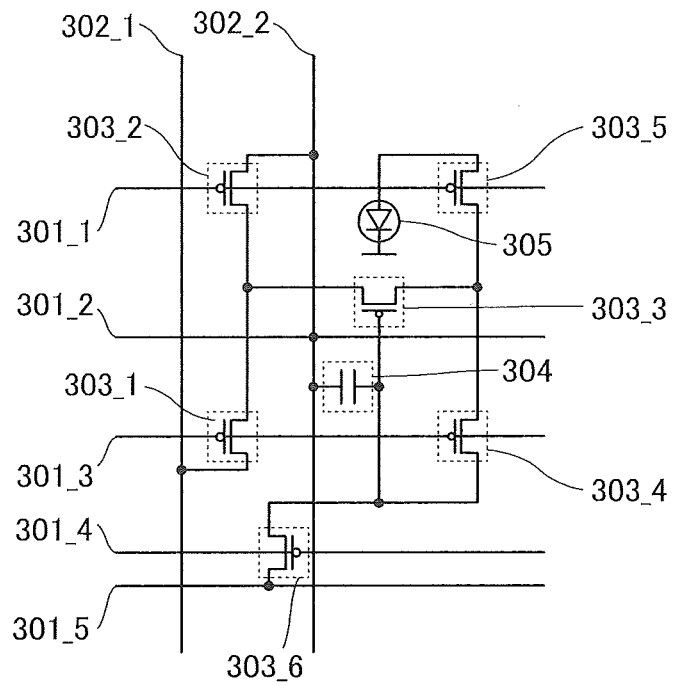
FIGS. 20A and 20B are circuit diagrams each illustrating a pixel circuit of a display device of one embodiment of the present invention.

The pixel circuit illustrated in FIG. 20A includes six transistors (transistors 303_1 to 303_6), a capacitor 304, and a light-emitting element 305. The pixel circuit illustrated in FIG. 20A is electrically connected to wirings 301_1 to 301_5 and wirings 302_1 and 302_2. Note that as the transistors 303_1 to 303_6, for example, p-channel transistors can be used.

Figure 20B:
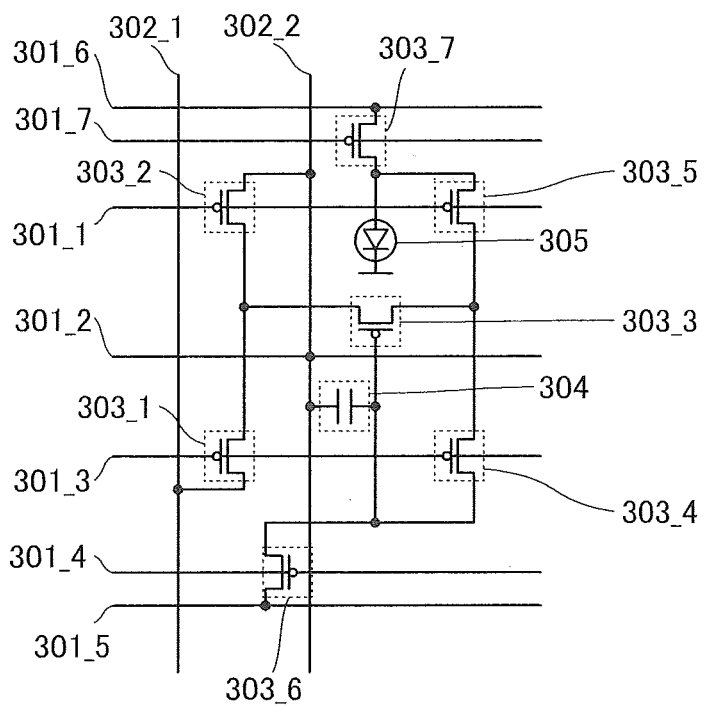

The pixel circuit shown in FIG. 20B has a configuration in which a transistor 303_7 is added to the pixel circuit shown in FIG. 20A. The pixel circuit illustrated in FIG. 20B is electrically connected to wirings 301_6 and 301_7. The wirings 301_5 and 301_6 may be electrically connected to each other. Note that as the transistor 303_7, for example, a p-channel transistor can be used.

Figure 21A:
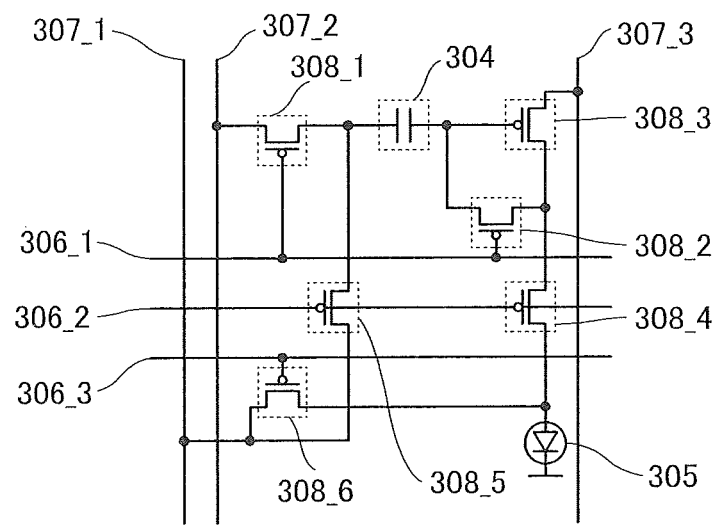
FIGS. 21A and 21B are circuit diagrams each illustrating a pixel circuit of a display device of one embodiment of the present invention.

The pixel circuit shown in FIG. 21A includes six transistors (transistors 308_1 to 308_6), the capacitor 304, and the light-emitting element 305. The pixel circuit illustrated in FIG. 21A is electrically connected to wirings 306_1 to 306_3 and wirings 307_1 to 307_3. The wirings 306_1 and 306_3 may be electrically connected to each other. Note that as the transistors 308_1 to 308_6, for example, p-channel transistors can be used.

Figure 21B:
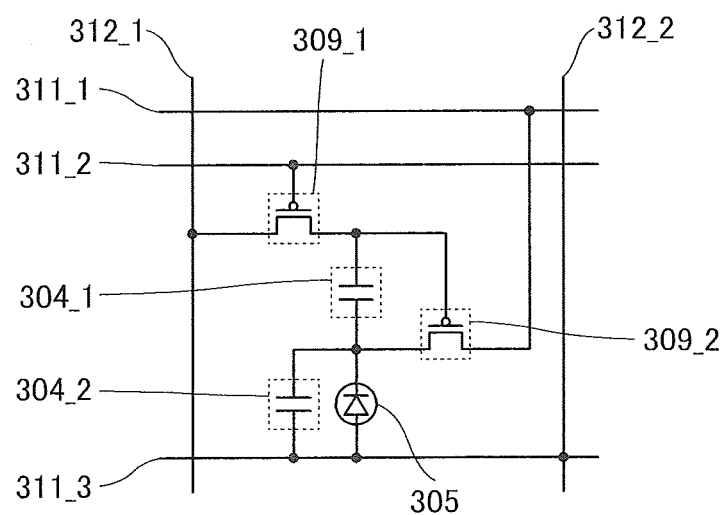

The pixel circuit illustrated in FIG. 21B includes two transistors (transistors 309_1 and 309_2), two capacitors (capacitors 304_1 and 304_2), and the light-emitting element 305. The pixel circuit illustrated in FIG. 21B is electrically connected to wirings 311_1 to 311_3 and wirings 312_1 and 312_2. With the configuration of the pixel circuit illustrated in FIG. 21B, the pixel circuit can be driven by a voltage inputting current driving method (also referred to as CVCC). Note that as the transistors 309_1 and 309_2, for example, p-channel transistors can be used.

A light-emitting element of one embodiment of the present invention can be used for an active matrix method in which an active element is included in a pixel of a display device or a passive matrix method in which an active element is not included in a pixel of a display device.

In the active matrix method, as an active element (a non-linear element), not only a transistor but also a variety of active elements (non-linear elements) can be used. For example, a metal insulator metal (MIM), a thin film diode (TFD), or the like can also be used. Since these elements can be formed with a smaller number of manufacturing steps, manufacturing cost can be reduced or yield can be improved. Alternatively, since the size of these elements is small, the aperture ratio can be improved, so that power consumption can be reduced and higher luminance can be achieved.

As a method other than the active matrix method, the passive matrix method in which an active element (a non-linear element) is not used can also be used. Since an active element (a non-linear element) is not used, the number of manufacturing steps is small, so that manufacturing cost can be reduced or yield can be improved. Alternatively, since an active element (a non-linear element) is not used, the aperture ratio can be improved, so that power consumption can be reduced or higher luminance can be achieved, for example.

The structure described in this embodiment can be used in combination with any of the structures described in the other embodiments as appropriate.

Embodiment 9

In this embodiment, a display device including a light-emitting element of one embodiment of the present invention and an electronic device in which the display device is provided with an input device will be described with reference to FIGS. 22A and 22B, FIGS. 23A to 23C, FIGS. 24A and 24B, FIGS. 25A and 25B, and FIG. 26.
<Description 1 of Touch Panel>
In this embodiment, a touch panel 2000 including a display device and an input device will be described as an example of an electronic device. In addition, an example in which a touch sensor is included as an input device will be described.

Figure 22A:
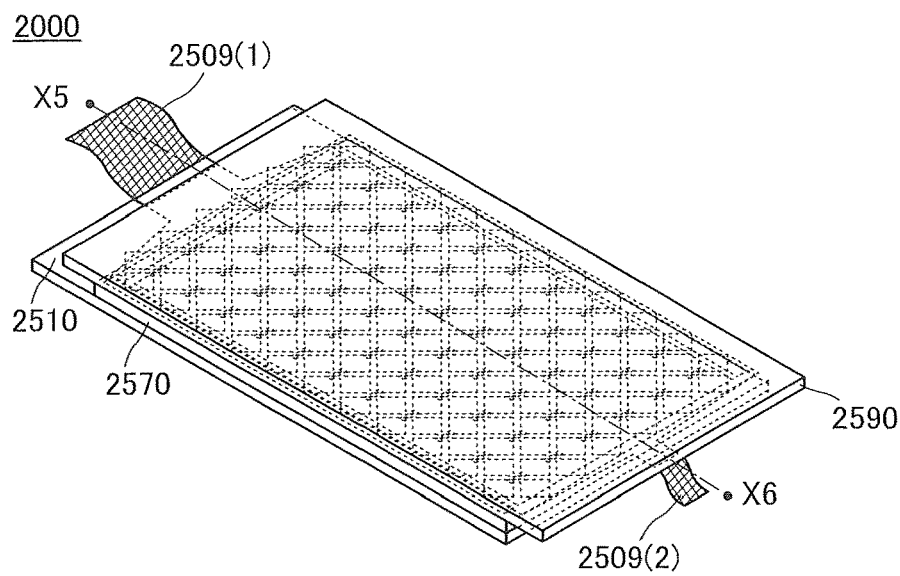
FIGS. 22A and 22B are perspective views of an example of a touch panel of one embodiment of the present invention.
Figure 22B:
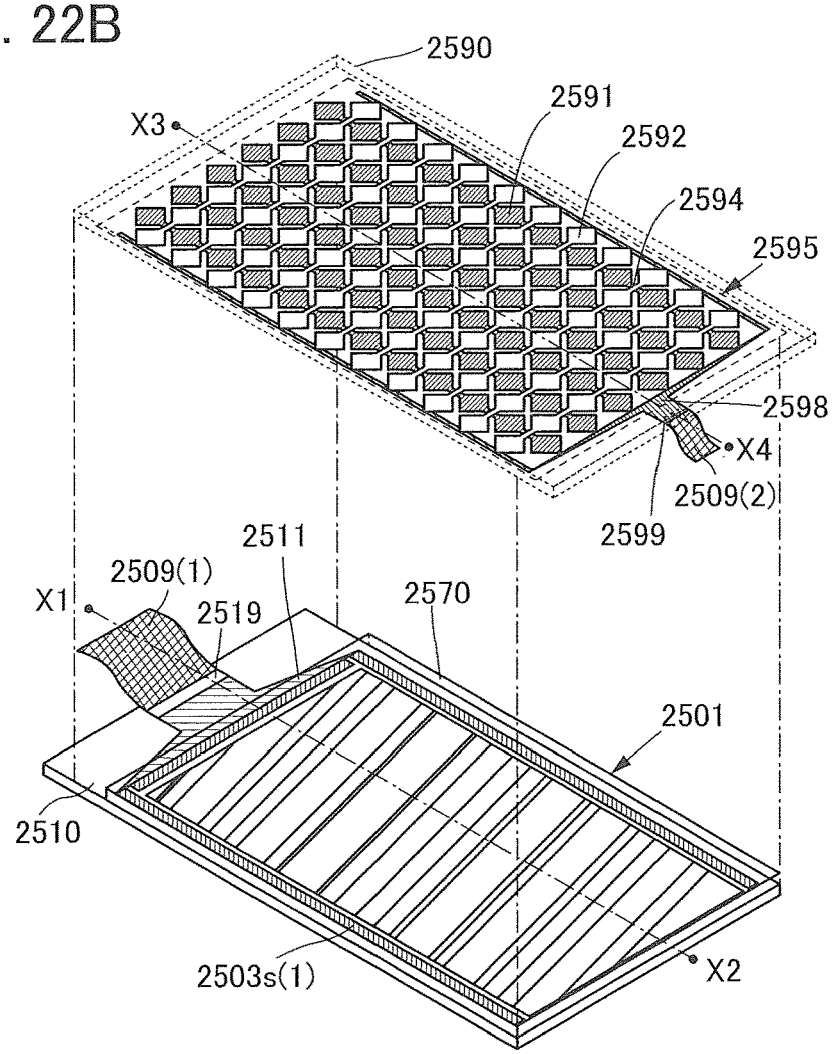

FIGS. 22A and 22B are perspective views of the touch panel 2000. Note that FIGS. 22A and 22B illustrate only main components of the touch panel 2000 for simplicity.

The touch panel 2000 includes a display device 2501 and a touch sensor 2595 (see FIG. 22B). The touch panel 2000 also includes a substrate 2510, a substrate 2570, and a substrate 2590. The substrate 2510, the substrate 2570, and the substrate 2590 each have flexibility. Note that one or all of the substrates 2510, 2570, and 2590 may be inflexible.

The display device 2501 includes a plurality of pixels over the substrate 2510 and a plurality of wirings 2511 through which signals are supplied to the pixels. The plurality of wirings 2511 are led to a peripheral portion of the substrate 2510, and parts of the plurality of wirings 2511 form a terminal 2519. The terminal 2519 is electrically connected to an FPC 2509(1). The plurality of wirings 2511 can supply signals from a signal line driver circuit 2503s(1) to the plurality of pixels.

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal. The terminal is electrically connected to an FPC 2509(2). Note that in FIG. 22B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used. Examples of the capacitive touch sensor are a surface capacitive touch sensor and a projected capacitive touch sensor.

Examples of the projected capacitive touch sensor are a self capacitive touch sensor and a mutual capacitive touch sensor, which differ mainly in the driving method. The use of a mutual capacitive type is preferable because multiple points can be sensed simultaneously.

Note that the touch sensor 2595 illustrated in FIG. 22B is an example of using a projected capacitive touch sensor.

Note that a variety of sensors that can sense proximity or touch of a sensing target such as a finger can be used as the touch sensor 2595.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598.

The electrodes 2592 each have a shape of a plurality of quadrangles arranged in one direction with one corner of a quadrangle connected to one corner of another quadrangle as illustrated in FIGS. 22A and 22B.

The electrodes 2591 each have a quadrangular shape and are arranged in a direction intersecting with the direction in which the electrodes 2592 extend.

A wiring 2594 electrically connects two electrodes 2591 between which the electrode 2592 is positioned. The intersecting area of the electrode 2592 and the wiring 2594 is preferably as small as possible. Such a structure allows a reduction in the area of a region where the electrodes are not provided, reducing variation in transmittance. As a result, variation in luminance of light passing through the touch sensor 2595 can be reduced.

Figure 23A:
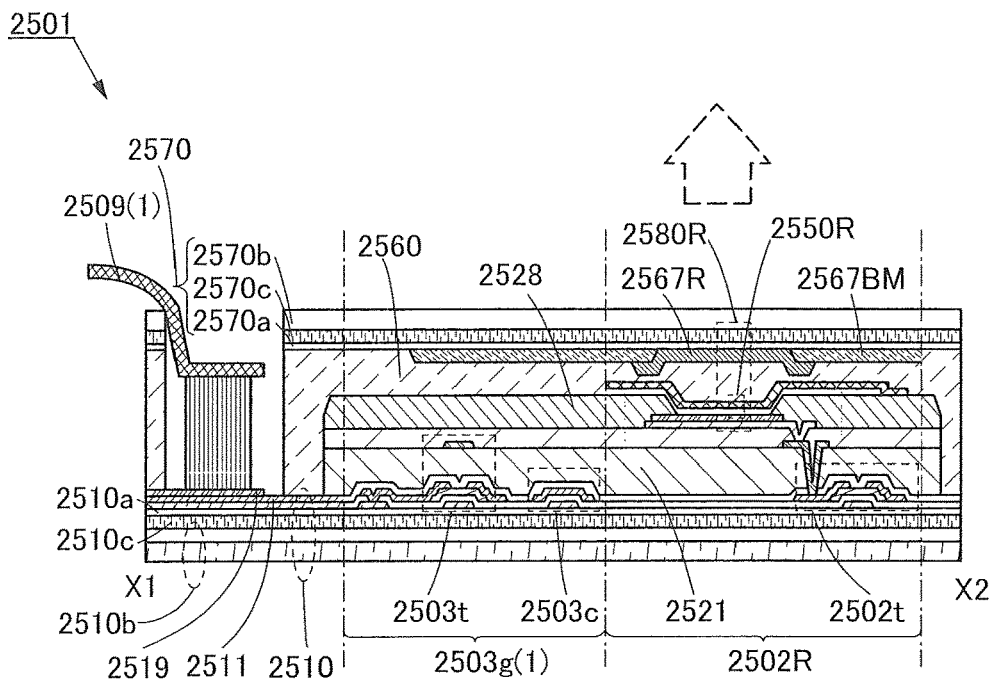
FIGS. 23A to 23C are cross-sectional views of examples of a display device and a touch sensor of one embodiment of the present invention.

Note that the shapes of the electrodes 2591 and the electrodes 2592 are not limited thereto and can be any of a variety of shapes. For example, a structure may be employed in which the plurality of electrodes 2591 are arranged so that gaps between the electrodes 2591 are reduced as much as possible, and the electrodes 2592 are spaced apart from the electrodes 2591 with an insulating layer interposed therebetween to have regions not overlapping with the electrodes 2591. In this case, it is preferable to provide, between two adjacent electrodes 2592, a dummy electrode electrically insulated from these electrodes because the area of regions having different transmittances can be reduced.
<Description of Display Device>
Next, the display device 2501 will be described in detail with reference to FIG. 23A. FIG. 23A corresponds to a cross-sectional view taken along dashed-dotted line X1-X2 in FIG. 22B.

The display device 2501 includes a plurality of pixels arranged in a matrix. Each of the pixels includes a display element and a pixel circuit for driving the display element.

In the following description, an example of using a light-emitting element that emits white light as a display element will be described; however, the display element is not limited to such an element. For example, light-emitting elements that emit light of different colors may be included so that the light of different colors can be emitted from adjacent pixels.

For the substrate 2510 and the substrate 2570, for example, a flexible material with a vapor permeability of lower than or equal to $1\times10^{-5}$ g·m$^{-2}$·day$^{-1}$, preferably lower than or equal to $1\times10^{-6}$ g·m$^{-2}$·day$^{-1}$ can be favorably used. Alternatively, materials whose thermal expansion coefficients are substantially equal to each other are preferably used for the substrate 2510 and the substrate 2570. For example, the coefficients of linear expansion of the materials are preferably lower than or equal to $1\times10^{-3}$/K, further preferably lower than or equal to $5\times10^{-5}$/K, and still further preferably lower than or equal to $1\times10^{-5}$/K.

Note that the substrate 2510 is a stacked body including an insulating layer 2510a for preventing impurity diffusion into the light-emitting element, a flexible substrate 2510b, and an adhesive layer 2510c for attaching the insulating layer 2510a and the flexible substrate 2510b to each other. The substrate 2570 is a stacked body including an insulating layer 2570a for preventing impurity diffusion into the light-emitting element, a flexible substrate 2570b, and an adhesive layer 2570c for attaching the insulating layer 2570a and the flexible substrate 2570b to each other.

For the adhesive layer 2510c and the adhesive layer 2570c, for example, polyester, polyolefin, polyamide (e.g., nylon, aramid), polyimide, polycarbonate, or an acrylic resin, polyurethane, or an epoxy resin can be used. Alternatively, a material that includes a resin having a siloxane bond such as silicone can be used.

A sealing layer 2560 is provided between the substrate 2510 and the substrate 2570. The sealing layer 2560 preferably has a refractive index higher than that of air. In the case where light is extracted to the sealing layer 2560 side as illustrated in FIG. 23A, the sealing layer 2560 can also serve as an optical adhesive layer.

A sealant may be formed in the peripheral portion of the sealing layer 2560. With the use of the sealant, a light-emitting element 2550R can be provided in a region surrounded by the substrate 2510, the substrate 2570, the sealing layer 2560, and the sealant. Note that an inert gas (such as nitrogen and argon) may be used instead of the sealing layer 2560. A drying agent may be provided in the inert gas so as to adsorb moisture or the like. A resin such as an acrylic resin or an epoxy resin may be used. An epoxy-based resin or a glass frit is preferably used as the sealant. As a material used for the sealant, a material which is impermeable to moisture and oxygen is preferably used.

The display device 2501 includes a pixel 2502R. The pixel 2502R includes a light-emitting module 2580R.

The pixel 2502R includes the light-emitting element 2550R and a transistor 2502t that can supply electric power to the light-emitting element 2550R. Note that the transistor 2502t functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode. As the light-emitting element 2550R, any of the light-emitting elements described in Embodiments 3 to 5 can be used.

A microcavity structure may be employed between the lower electrode and the upper electrode so as to increase the intensity of light having a specific wavelength.

In the case where the sealing layer 2560 is provided on the light extraction side, the sealing layer 2560 is in contact with the light-emitting element 2550R and the coloring layer 2567R.

The coloring layer 2567R is positioned in a region overlapping with the light-emitting element 2550R. Accordingly, part of light emitted from the light-emitting element 2550R passes through the coloring layer 2567R and is emitted to the outside of the light-emitting module 2580R as indicated by an arrow in the drawing.

The display device 2501 includes a light-blocking layer 2567BM on the light extraction side. The light-blocking layer 2567BM is provided so as to surround the coloring layer 2567R.

The coloring layer 2567R is a coloring layer having a function of transmitting light in a particular wavelength region. For example, a color filter for transmitting light in a red wavelength region, a color filter for transmitting light in a green wavelength region, a color filter for transmitting light in a blue wavelength region, a color filter for transmitting light in a yellow wavelength region, or the like can be used. Each color filter can be formed with any of various materials by a printing method, an inkjet method, an etching method using a photolithography technique, or the like.

An insulating layer 2521 is provided in the display device 2501. The insulating layer 2521 covers the transistor 2502t. Note that the insulating layer 2521 has a function of covering unevenness caused by the pixel circuit. The insulating layer 2521 may have a function of suppressing impurity diffusion. This can prevent the reliability of the transistor 2502t or the like from being lowered by impurity diffusion.

The light-emitting element 2550R is formed over the insulating layer 2521. A partition 2528 is provided so as to overlap with an end portion of the lower electrode of the light-emitting element 2550R. Note that a spacer for controlling the distance between the substrate 2510 and the substrate 2570 may be formed over the partition 2528.

A scan line driver circuit 2503g(1) includes a transistor 2503t and a capacitor 2503c. Note that the driver circuit can be formed in the same process and over the same substrate as those of the pixel circuits.

The wirings 2511 through which signals can be supplied are provided over the substrate 2510. The terminal 2519 is provided over the wirings 2511. The FPC 2509(1) is electrically connected to the terminal 2519. The FPC 2509(1) has a function of supplying a video signal, a clock signal, a start signal, a reset signal, or the like. Note that the FPC 2509(1) may be provided with a PWB.

Figure 23B:
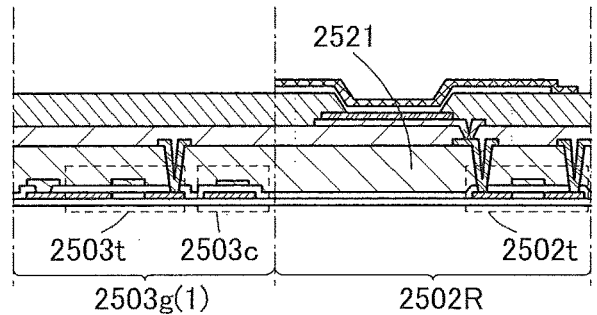

In the display device 2501, transistors with any of a variety of structures can be used. FIG. 23A illustrates an example of using bottom-gate transistors; however, the present invention is not limited to this example, and top-gate transistors may be used in the display device 2501 as illustrated in FIG. 23B.

In addition, there is no particular limitation on the polarity of the transistor 2502t and the transistor 2503t. For these transistors, n-channel and p-channel transistors may be used, or either n-channel transistors or p-channel transistors may be used, for example. Furthermore, there is no particular limitation on the crystallinity of a semiconductor film used for the transistors 2502t and 2503t. For example, an amorphous semiconductor film or a crystalline semiconductor film may be used. Examples of semiconductor materials include Group 14 semiconductors (e.g., a semiconductor including silicon), compound semiconductors (including oxide semiconductors), organic semiconductors, and the like. An oxide semiconductor that has an energy gap of 2 eV or more, preferably 2.5 eV or more, further preferably 3 eV or more is preferably used for one of the transistors 2502t and 2503t or both, so that the off-state current of the transistors can be reduced. Examples of the oxide semiconductors include an In—Ga oxide, an In-M-Zn oxide (M represents Al, Ga, Y, Zr, La, Ce, Sn, Hf, or Nd), and the like.

<Description of Touch Sensor>

Figure 23C:
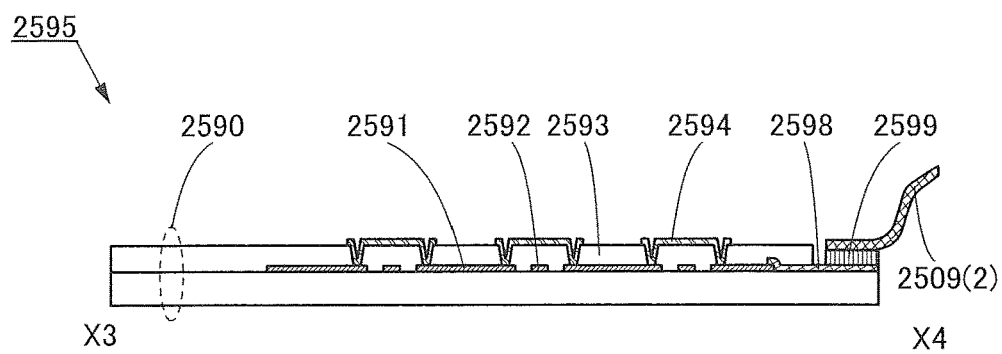

Next, the touch sensor 2595 will be described in detail with reference to FIG. 23C. FIG. 23C corresponds to a cross-sectional view taken along dashed-dotted line X3-X4 in FIG. 22B.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film containing graphene oxide. As a reducing method, a method with application of heat or the like can be employed.

The electrodes 2591 and the electrodes 2592 may be formed by, for example, depositing a light-transmitting conductive material on the substrate 2590 by a sputtering method and then removing an unnecessary portion by any of various pattern forming techniques such as photolithography.

Examples of a material for the insulating layer 2593 are a resin such as an acrylic resin or an epoxy resin, a resin having a siloxane bond such as silicone, and an inorganic insulating material such as silicon oxide, silicon oxynitride, or aluminum oxide.

Openings reaching the electrodes 2591 are formed in the insulating layer 2593, and the wiring 2594 electrically connects the adjacent electrodes 2591. A light-transmitting conductive material can be favorably used as the wiring 2594 because the aperture ratio of the touch panel can be increased. Moreover, a material with higher conductivity than the conductivities of the electrodes 2591 and 2592 can be favorably used for the wiring 2594 because electric resistance can be reduced.

One electrode 2592 extends in one direction, and a plurality of electrodes 2592 are provided in the form of stripes. The wiring 2594 intersects with the electrode 2592.

Adjacent electrodes 2591 are provided with one electrode 2592 provided therebetween. The wiring 2594 electrically connects the adjacent electrodes 2591.

Note that the plurality of electrodes 2591 are not necessarily arranged in the direction orthogonal to one electrode 2592 and may be arranged to intersect with one electrode 2592 at an angle of more than 0 degrees and less than 90 degrees.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Note that an insulating layer that covers the insulating layer 2593 and the wiring 2594 may be provided to protect the touch sensor 2595.

A connection layer 2599 electrically connects the wiring 2598 to the FPC 2509(2).

As the connection layer 2599, any of various anisotropic conductive films (ACF), anisotropic conductive pastes (ACP), or the like can be used.

<Description 2 of Touch Panel>

Figure 24A:
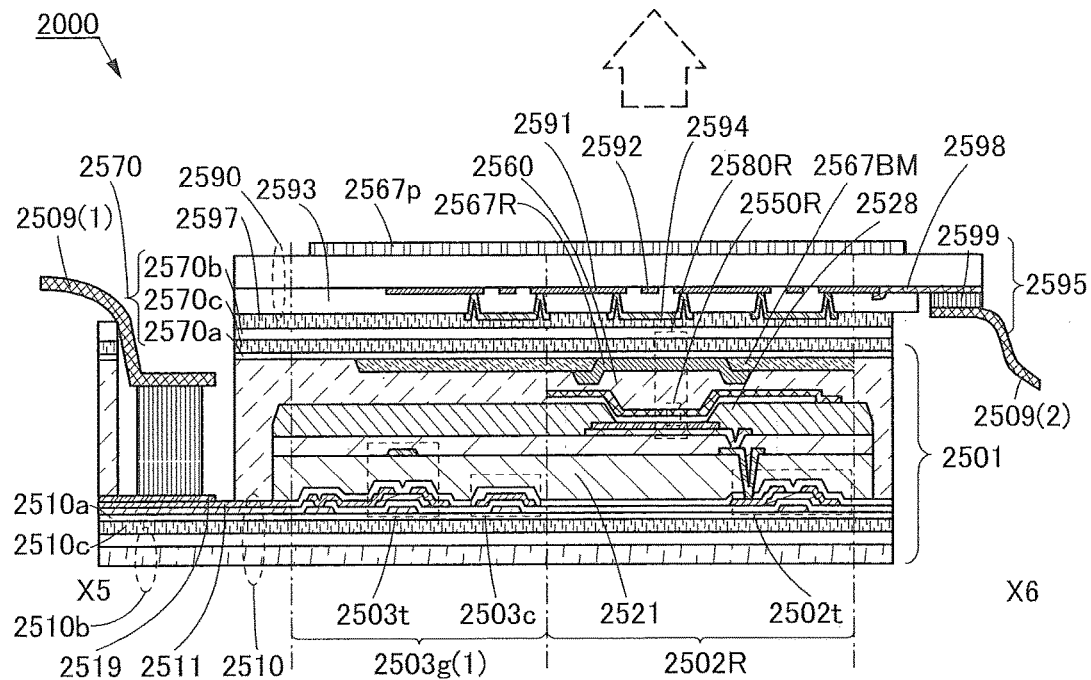
FIGS. 24A and 24B are cross-sectional views each illustrating an example of a touch panel of one embodiment of the present invention.

Next, the touch panel 2000 will be described in detail with reference to FIG. 24A. FIG. 24A corresponds to a cross-sectional view taken along dashed-dotted line X5-X6 in FIG. 22A.

In the touch panel 2000 illustrated in FIG. 24A, the display device 2501 described with reference to FIG. 23A and the touch sensor 2595 described with reference to FIG. 23C are attached to each other.

The touch panel 2000 illustrated in FIG. 24A includes an adhesive layer 2597 and an anti-reflective layer 2567p in addition to the components described with reference to FIGS. 23A and 23C.

The adhesive layer 2597 is provided in contact with the wiring 2594. Note that the adhesive layer 2597 attaches the substrate 2590 to the substrate 2570 so that the touch sensor 2595 overlaps with the display device 2501. The adhesive layer 2597 preferably has a light-transmitting property. A heat curable resin or an ultraviolet curable resin can be used for the adhesive layer 2597. For example, an acrylic resin, a urethane-based resin, an epoxy-based resin, or a siloxane-based resin can be used.

The anti-reflective layer 2567p is positioned in a region overlapping with pixels. As the anti-reflective layer 2567p, a circularly polarizing plate can be used, for example.

Next, a touch panel having a structure different from that illustrated in FIG. 24A will be described with reference to FIG. 24B.

Figure 24B:
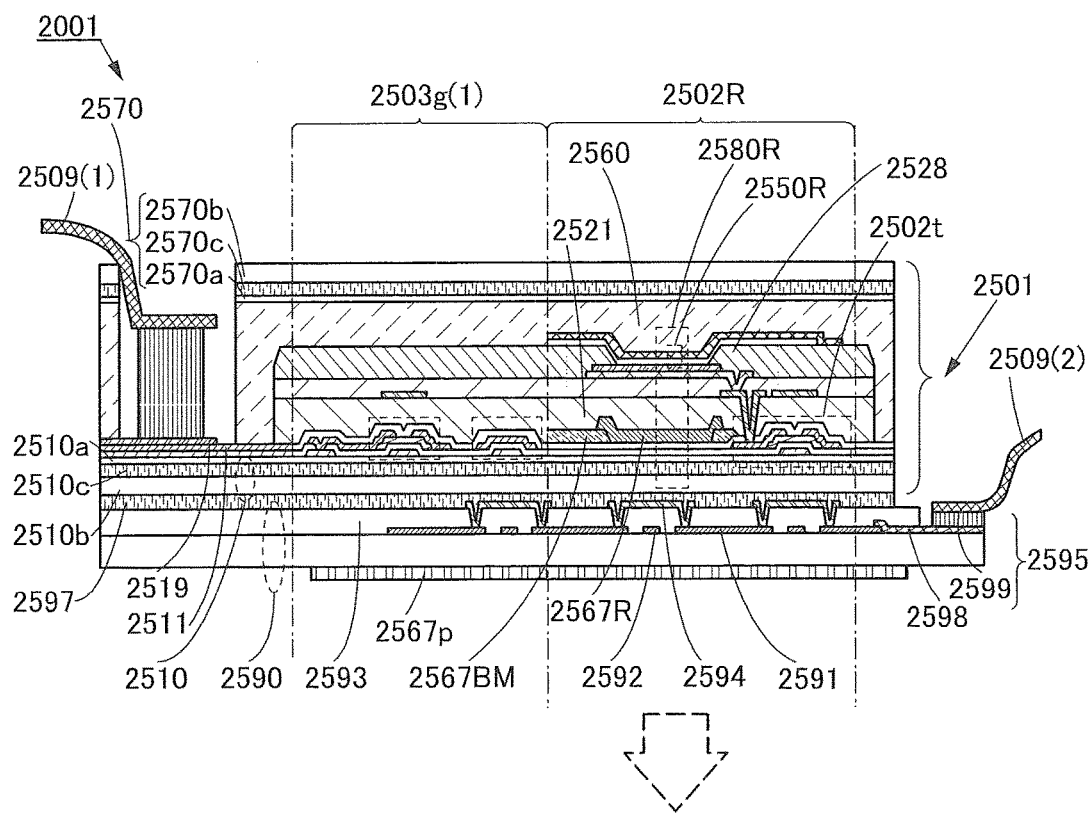

FIG. 24B is a cross-sectional view of a touch panel 2001. The touch panel 2001 illustrated in FIG. 24B differs from the touch panel 2000 illustrated in FIG. 24A in the position of the touch sensor 2595 relative to the display device 2501. Different parts are described in detail below, and the above description of the touch panel 2000 is referred to for the other similar parts.

The coloring layer 2567R is positioned in a region overlapping with the light-emitting element 2550R. The light-emitting element 2550R illustrated in FIG. 24B emits light to the side where the transistor 2502t is provided. Accordingly, part of light emitted from the light-emitting element 2550R passes through the coloring layer 2567R and is emitted to the outside of the light-emitting module 2580R as indicated by an arrow in FIG. 24B.

The touch sensor 2595 is provided on the substrate 2510 side of the display device 2501.

The adhesive layer 2597 is provided between the substrate 2510 and the substrate 2590 and attaches the touch sensor 2595 to the display device 2501.

As illustrated in FIG. 24A or 24B, light may be emitted from the light-emitting element through one or both of the substrate 2510 and the substrate 2570.

<Description of Method for Driving Touch Panel>

Next, an example of a method for driving a touch panel will be described with reference to FIGS. 25A and 25B.

Figure 25A:
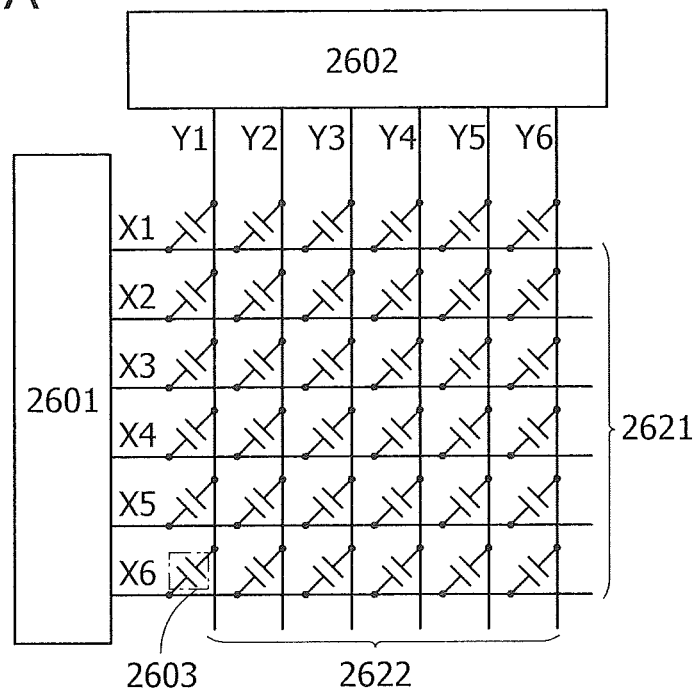
FIGS. 25A and 25B are a block diagram and a timing chart of a touch sensor of one embodiment of the present invention.

FIG. 25A is a block diagram illustrating the structure of a mutual capacitive touch sensor. FIG. 25A illustrates a pulse voltage output circuit 2601 and a current sensing circuit 2602. Note that in FIG. 25A, six wirings X1 to X6 represent the electrodes 2621 to which a pulse voltage is applied, and six wirings Y1 to Y6 represent the electrodes 2622 that detect changes in current. FIG. 25A also illustrates capacitors 2603 that are each formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for sensing of current values.

Figure 25B:
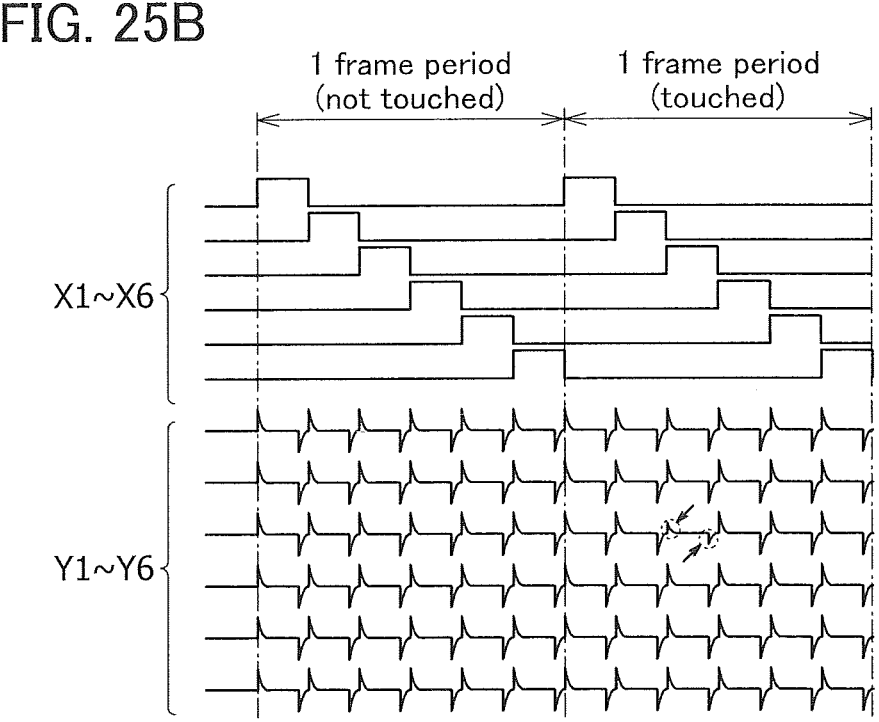

FIG. 25B is a timing chart showing input and output waveforms in the mutual capacitive touch sensor illustrated in FIG. 25A. In FIG. 25B, sensing of a sensing target is performed in all the rows and columns in one frame period. FIG. 25B shows a period when a sensing target is not sensed (not touched) and a period when a sensing target is sensed (touched). In FIG. 25B, sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6. The current value is decreased at the point of approach or contact of a sensing target and accordingly the waveform of the voltage value changes.

By detecting a change in mutual capacitance in this manner, the approach or contact of a sensing target can be sensed.

<Description of Sensor Circuit>

Figure 26:
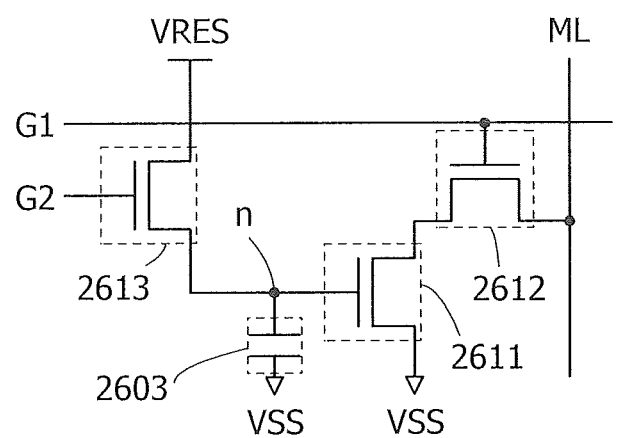
FIG. 26 is a circuit diagram of a touch sensor of one embodiment of the present invention.

Although FIG. 25A illustrates a passive matrix type touch sensor in which only the capacitor 2603 is provided at the intersection of wirings as a touch sensor, an active matrix type touch sensor including a transistor and a capacitor may be used. FIG. 26 illustrates an example of a sensor circuit included in an active matrix type touch sensor.

The sensor circuit in FIG. 26 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 26 will be described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained.

Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613 so that the potential of the node n can be held for a long time and the frequency of operation of resupplying VRES to the node n (refresh operation) can be reduced.

The structure described in this embodiment can be used in combination with any of the structures described in the other embodiments as appropriate.

Embodiment 10

In this embodiment, a display module and electronic devices including a light-emitting element of one embodiment of the present invention will be described with reference to FIG. 27, FIGS. 28A to 28G, FIGS. 29A to 29F, FIGS. 30A to 30D, and FIGS. 31A and 31B.

<Display Module>

Figure 27:
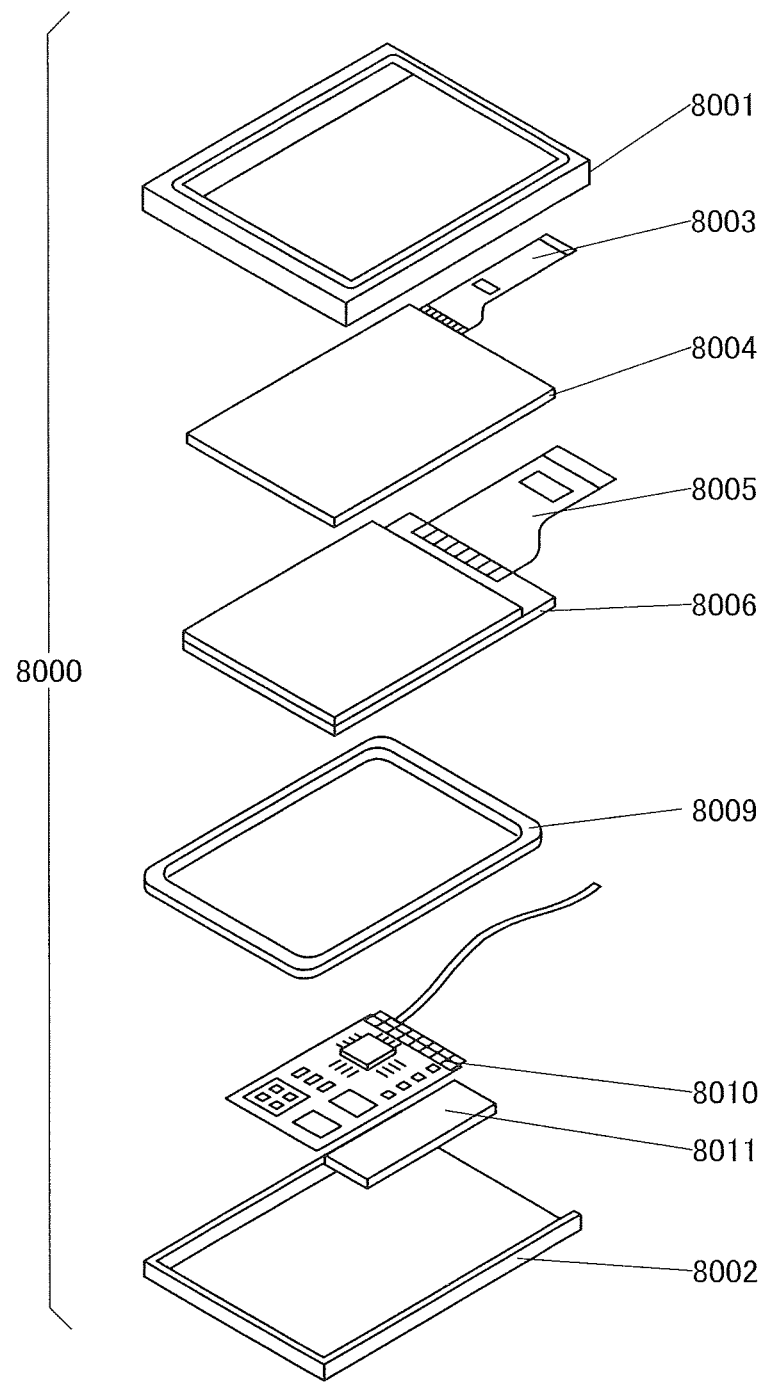
FIG. 27 is a perspective view of a display module of one embodiment of the present invention.

In a display module 8000 in FIG. 27, a touch sensor 8004 connected to an FPC 8003, a display device 8006 connected to an FPC 8005, a frame 8009, a printed board 8010, and a battery 8011 are provided between an upper cover 8001 and a lower cover 8002.

The light-emitting element of one embodiment of the present invention can be used for the display device 8006, for example.

The shapes and sizes of the upper cover 8001 and the lower cover 8002 can be changed as appropriate in accordance with the sizes of the touch sensor 8004 and the display device 8006.

The touch sensor 8004 can be a resistive touch sensor or a capacitive touch sensor and may be formed to overlap with the display device 8006. A counter substrate (sealing substrate) of the display device 8006 can have a touch sensor function. A photosensor may be provided in each pixel of the display device 8006 so that an optical touch sensor is obtained.

The frame 8009 protects the display device 8006 and also serves as an electromagnetic shield for blocking electromagnetic waves generated by the operation of the printed board 8010. The frame 8009 may serve as a radiator plate.

The printed board 8010 has a power supply circuit and a signal processing circuit for outputting a video signal and a clock signal. As a power source for supplying power to the power supply circuit, an external commercial power source or the battery 8011 provided separately may be used. The battery 8011 can be omitted in the case of using a commercial power source.

The display module 8000 can be additionally provided with a member such as a polarizing plate, a retardation plate, or a prism sheet.

<Electronic Devices>

FIGS. 28A to 28G illustrate electronic devices. These electronic devices can include a housing 9000, a display portion 9001, a speaker 9003, operation keys 9005 (including a power switch or an operation switch), a connection terminal 9006, a sensor 9007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 9008, and the like. In addition, the sensor 9007 may have a function of measuring biological information like a pulse sensor and a finger print sensor.

The electronic devices illustrated in FIGS. 28A to 28G can have a variety of functions, for example, a function of displaying a variety of data (a still image, a moving image, a text image, and the like) on the display portion, a touch sensor function, a function of displaying a calendar, date, time, and the like, a function of controlling a process with a variety of software (programs), a wireless communication function, a function of being connected to a variety of computer networks with a wireless communication function, a function of transmitting and receiving a variety of data with a wireless communication function, a function of reading a program or data stored in a memory medium and displaying the program or data on the display portion, and the like. Note that functions that can be provided for the electronic devices illustrated in FIGS. 28A to 28G are not limited to those described above, and the electronic devices can have a variety of functions. Although not illustrated in FIGS. 28A to 28G, the electronic devices may include a plurality of display portions. The electronic devices may have a camera or the like and a function of taking a still image, a function of taking a moving image, a function of storing the taken image in a memory medium (an external memory medium or a memory medium incorporated in the camera), a function of displaying the taken image on the display portion, or the like.

The electronic devices illustrated in FIGS. 28A to 28G will be described in detail below.

Figure 28A:
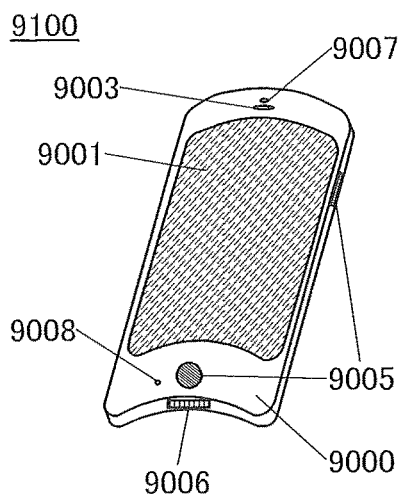
FIGS. 28A to 28G each illustrate an electronic device of one embodiment of the present invention.

FIG. 28A is a perspective view of a portable information terminal 9100. The display portion 9001 of the portable information terminal 9100 is flexible. Therefore, the display portion 9001 can be incorporated along a bent surface of a bent housing 9000. In addition, the display portion 9001 includes a touch sensor, and operation can be performed by touching the screen with a finger, a stylus, or the like. For example, when an icon displayed on the display portion 9001 is touched, an application can be started.

Figure 28D:
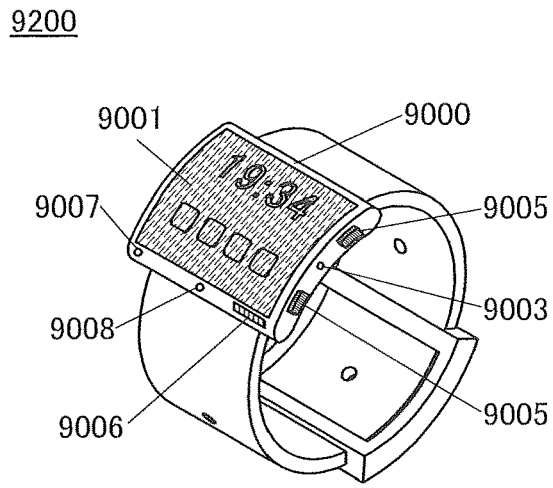
Figure 28B:
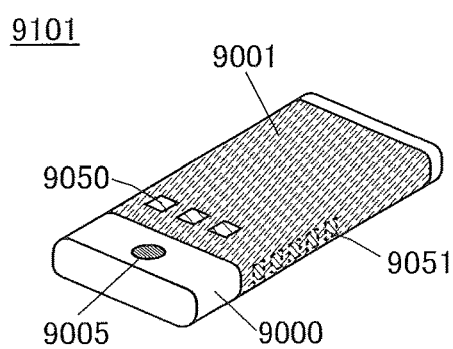

FIG. 28B is a perspective view of a portable information terminal 9101. The portable information terminal 9101 functions as, for example, one or more of a telephone set, a notebook, and an information browsing system. Specifically, the portable information terminal can be used as a smartphone. Note that the speaker 9003, the connection terminal 9006, the sensor 9007, and the like, which are not shown in FIG. 28B, can be positioned in the portable information terminal 9101 as in the portable information terminal 9100 shown in FIG. 28A. The portable information terminal 9101 can display characters and image information on its plurality of surfaces. For example, three operation buttons 9050 (also referred to as operation icons, or simply, icons) can be displayed on one surface of the display portion 9001. Furthermore, information 9051 indicated by dashed rectangles can be displayed on another surface of the display portion 9001. Examples of the information 9051 include display indicating reception of an incoming email, social networking service (SNS) message, call, and the like; the title and sender of an email and SNS message; the date; the time; remaining battery; and display indicating the strength of a received signal such as a radio wave. Instead of the information 9051, the operation buttons 9050 or the like may be displayed on the position where the information 9051 is displayed.

As a material of the housing 9000, an alloy, plastic, ceramic, or a material containing carbon fiber can be used. As the material containing carbon fiber, carbon fiber reinforced plastic (CFRP) has advantages of lightweight and corrosion-free; however, it is black and thus limits the exterior and design of the housing. The CFRP can be regarded as a kind of reinforced plastic, which may use glass fiber or aramid fiber. Since the fiber might be separated from a resin by high impact, the alloy is preferred. As the alloy, an aluminum alloy and a magnesium alloy can be given. An amorphous alloy (also referred to as metallic glass) containing zirconium, copper, nickel, and titanium especially has high elastic strength. This amorphous alloy has a glass transition region at room temperature, which is also referred to as a bulk-solidifying amorphous alloy and substantially has an amorphous atomic structure. An alloy material is molded in a mold of at least the part of the housing and coagulated by a solidification casting method, whereby part of the housing is formed with the bulk-solidifying amorphous alloy. The amorphous alloy may contain beryllium, silicon, niobium, boron, gallium, molybdenum, tungsten, manganese, iron, cobalt, yttrium, vanadium, phosphorus, carbon, or the like in addition to zirconium, copper, nickel, and titanium. The amorphous alloy may be formed by a vacuum evaporation method, a sputtering method, an electroplating method, an electroless plating method, or the like instead of the solidification casting method. The amorphous alloy may include a microcrystal or a nanocrystal as long as a state without a long-range order (a periodic structure) is maintained as a whole. Note that the term alloy includes both a complete solid solution alloy having a single solid-phase structure and a partial solution having two or more phases. The housing 9000 using the amorphous alloy can have high elastic strength. Even if the portable information terminal 9101 is dropped and the impact causes temporary deformation, the use of the amorphous alloy in the housing 9000 allows a return to the original shape; thus, the impact resistance of the portable information terminal 9101 can be improved.

Figure 29A:
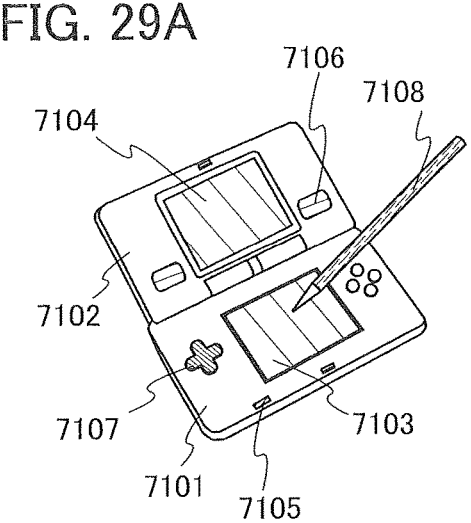
FIGS. 29A to 29F each illustrate an electronic device of one embodiment of the present invention.
Figure 29B:
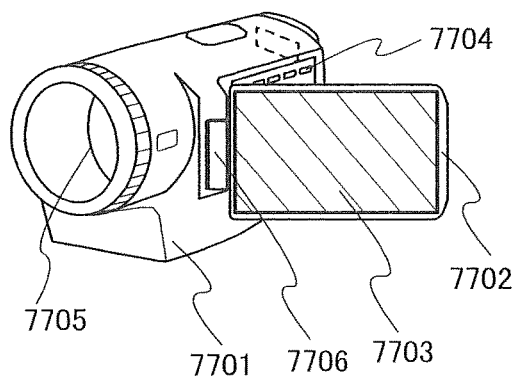
Figure 29C:
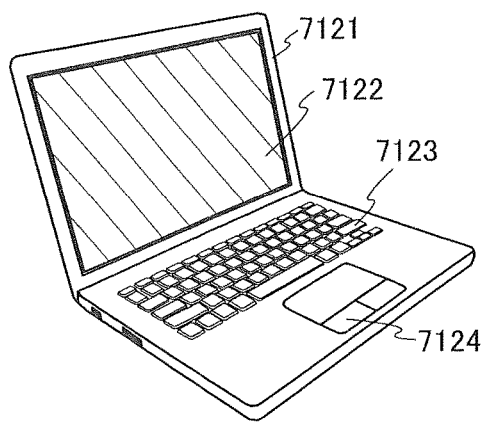

FIG. 29C is a perspective view of a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can see the display (here, the information 9053) with the portable information terminal 9102 put in a breast pocket of his/her clothes. Specifically, a caller's phone number, name, or the like of an incoming call is displayed in a position that can be seen from above the portable information terminal 9102. Thus, the user can see the display without taking out the portable information terminal 9102 from the pocket and decide whether to answer the call.

FIG. 28D is a perspective view of a watch-type portable information terminal 9200. The portable information terminal 9200 is capable of executing a variety of applications such as mobile phone calls, e-mailing, viewing and editing texts, music reproduction, Internet communication, and computer games. The display surface of the display portion 9001 is bent, and images can be displayed on the bent display surface. The portable information terminal 9200 can employ near field communication that is a communication method based on an existing communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is possible. Note that the charging operation may be performed by wireless power feeding without using the connection terminal 9006.

Figure 28E:
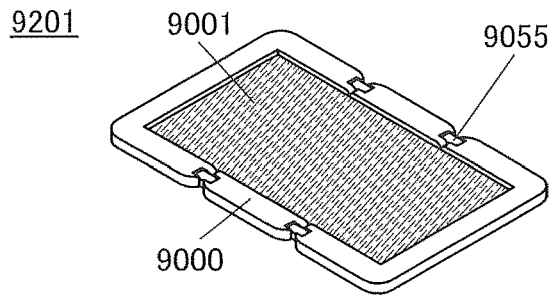
Figure 28C:
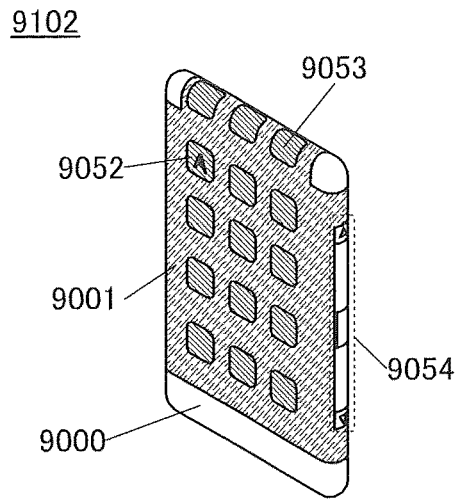
Figure 28F:
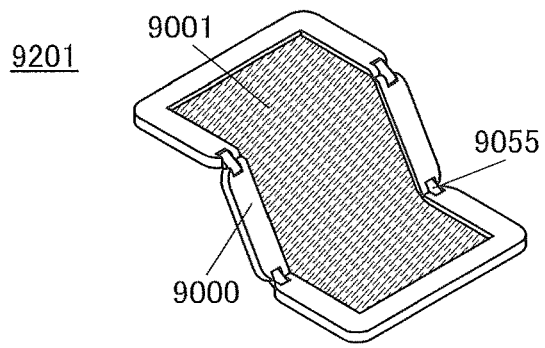
Figure 28G:
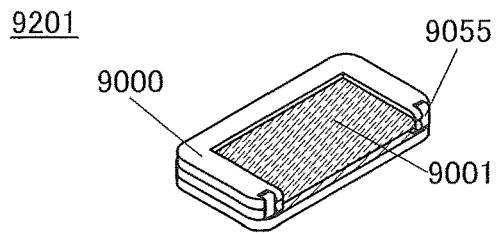

FIGS. 28E, 28F, and 28G are perspective views of a foldable portable information terminal 9201. FIG. 28E is a perspective view illustrating the portable information terminal 9201 that is opened. FIG. 28F is a perspective view illustrating the portable information terminal 9201 that is being opened or being folded. FIG. 28G is a perspective view illustrating the portable information terminal 9201 that is folded. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. By folding the portable information terminal 9201 at a connection portion between two housings 9000 with the hinges 9055, the portable information terminal 9201 can be reversibly changed in shape from an opened state to a folded state. For example, the portable information terminal 9201 can be bent with a radius of curvature of greater than or equal to 1 mm and less than or equal to 150 mm.

Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a goggle-type display (head mounted display), a portable game machine, a portable information terminal, an audio reproducing device, and a large-sized game machine such as a pachinko machine.

Furthermore, the electronic device of one embodiment of the present invention may include a secondary battery. It is preferable that the secondary battery be capable of being charged by non-contact power transmission.

Examples of the secondary battery include a lithium ion secondary battery such as a lithium polymer battery using a gel electrolyte (lithium ion polymer battery), a lithium-ion battery, a nickel-hydride battery, a nickel-cadmium battery, an organic radical battery, a lead storage battery, an air secondary battery, a nickel-zinc battery, and a silver-zinc battery.

The electronic device of one embodiment of the present invention may include an antenna. When a signal is received by the antenna, the electronic device can display an image, data, or the like on a display portion. When the electronic device includes a secondary battery, the antenna may be used for non-contact power transmission.

FIG. 29A illustrates a portable game machine including a housing 7101, a housing 7102, display portions 7103 and 7104, a microphone 7105, speakers 7106, an operation key 7107, a stylus 7108, and the like. When the light-emitting device of one embodiment of the present invention is used as the display portion 7103 or 7104, it is possible to provide a user-friendly portable game machine with quality that hardly deteriorates. Although the portable game machine illustrated in FIG. 29A includes two display portions, the display portions 7103 and 7104, the number of display portions included in the portable game machine is not limited to two.

FIG. 29B illustrates a video camera including a housing 7701, a housing 7702, a display portion 7703, operation keys 7704, a lens 7705, a joint 7706, and the like. The operation keys 7704 and the lens 7705 are provided for the housing 7701, and the display portion 7703 is provided for the housing 7702. The housing 7701 and the housing 7702 are connected to each other with the joint 7706, and the angle between the housing 7701 and the housing 7702 can be changed with the joint 7706. Images displayed on the display portion 7703 may be switched in accordance with the angle at the joint 7706 between the housing 7701 and the housing 7702.

FIG. 29C illustrates a notebook personal computer including a housing 7121, a display portion 7122, a keyboard 7123, a pointing device 7124, and the like. Note that the display portion 7122 is small- or medium-sized but can perform 8 k display because it has greatly high pixel density and high resolution; therefore, a significantly clear image can be obtained.

Figure 29D:
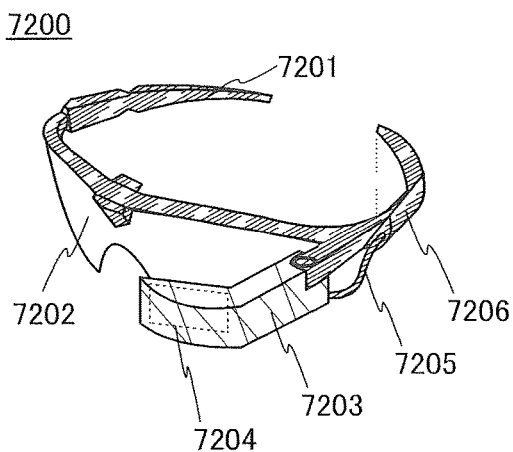

FIG. 29D is an external view of a head-mounted display 7200.

The head-mounted display 7200 includes a mounting portion 7201, a lens 7202, a main body 7203, a display portion 7204, a cable 7205, and the like. The mounting portion 7201 includes a battery 7206.

Power is supplied from the battery 7206 to the main body 7203 through the cable 7205. The main body 7203 includes a wireless receiver or the like to receive video data, such as image data, and display it on the display portion 7204. The movement of the eyeball and the eyelid of a user is captured by a camera in the main body 7203 and then coordinates of the points the user looks at are calculated using the captured data to utilize the eye point of the user as an input means.

The mounting portion 7201 may include a plurality of electrodes so as to be in contact with the user. The main body 7203 may be configured to sense current flowing through the electrodes with the movement of the user's eyeball to recognize the direction of his or her eyes. The main body 7203 may be configured to sense current flowing through the electrodes to monitor the user's pulse. The mounting portion 7201 may include sensors, such as a temperature sensor, a pressure sensor, or an acceleration sensor, so that the user's biological information can be displayed on the display portion 7204. The main body 7203 may be configured to sense the movement of the user's head or the like to move an image displayed on the display portion 7204 in synchronization with the movement of the user's head or the like.

Figure 29E:
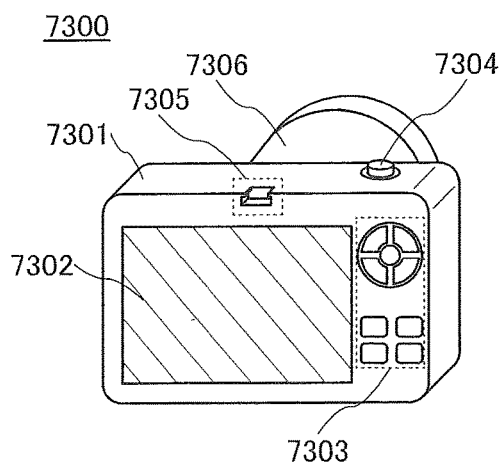

FIG. 29E is an external view of a camera 7300. The camera 7300 includes a housing 7301, a display portion 7302, an operation button 7303, a shutter button 7304, a connection portion 7305, and the like. A lens 7306 can be put on the camera 7300.

The connection portion 7305 includes an electrode to connect with a finder 7400, which is described below, a stroboscope, or the like.

Although the lens 7306 of the camera 7300 here is detachable from the housing 7301 for replacement, the lens 7306 may be included in the housing 7301.

Images can be taken at the touch of the shutter button 7304. In addition, images can be taken by operation of the display portion 7302 including a touch sensor.

In the display portion 7302, the display device of one embodiment of the present invention or a touch sensor can be used.

Figure 29F:
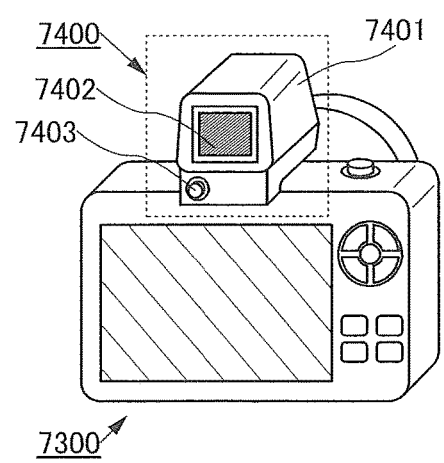

FIG. 29F shows the camera 7300 with the finder 7400 connected.

The finder 7400 includes a housing 7401, a display portion 7402, and a button 7403.

The housing 7401 includes a connection portion for engagement with the connection portion 7305 of the camera 7300 so that the finder 7400 can be connected to the camera 7300. The connection portion includes an electrode, and an image or the like received from the camera 7300 through the electrode can be displayed on the display portion 7402.

The button 7403 has a function of a power button, and the display portion 7402 can be turned on and off with the button 7403.

Although the camera 7300 and the finder 7400 are separate and detachable electronic devices in FIGS. 29E and 29F, the housing 7301 of the camera 7300 may include a finder having a display device of one embodiment of the present invention or a touch sensor.

Figure 30A:
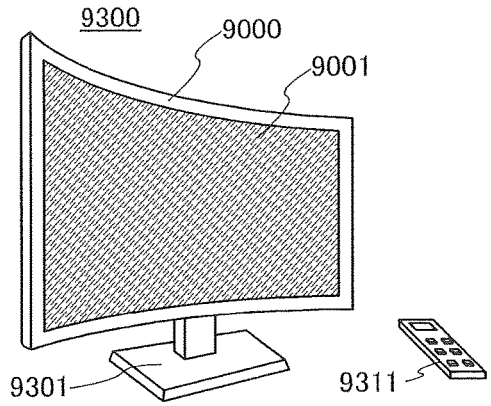
FIGS. 30A to 30D each illustrate an electronic device of one embodiment of the present invention.

FIG. 30A illustrates an example of a television set. In the television set 9300, the display portion 9001 is incorporated into the housing 9000. Here, the housing 9000 is supported by a stand 9301.

The television set 9300 illustrated in FIG. 30A can be operated with an operation switch of the housing 9000 or a separate remote controller 9311. The display portion 9001 may include a touch sensor. The television set 9300 can be operated by touching the display portion 9001 with a finger or the like. The remote controller 9311 may be provided with a display portion for displaying data output from the remote controller 9311. With operation keys or a touch panel of the remote controller 9311, channels or volume can be controlled and images displayed on the display portion 9001 can be controlled.

The television set 9300 is provided with a receiver, a modem, or the like. A general television broadcast can be received with the receiver. When the television set is connected to a communication network with or without wires via the modem, one-way (from a transmitter to a receiver) or two-way (between a transmitter and a receiver or between receivers) data communication can be performed.

The electronic device or the lighting device of one embodiment of the present invention has flexibility and therefore can be incorporated along a curved inside/outside wall surface of a house or a building or a curved interior/exterior surface of a car.

Figure 30B:
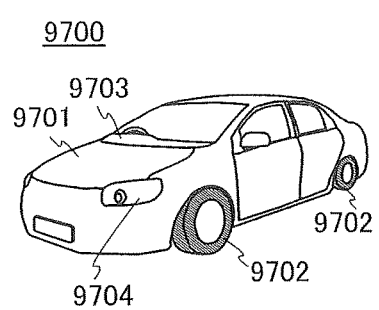
Figure 30C:
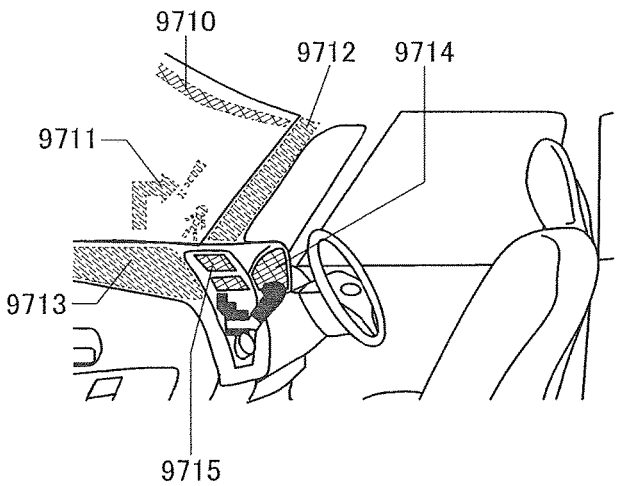

FIG. 30B is an external view of an automobile 9700. FIG. 30C illustrates a driver's seat of the automobile 9700. The automobile 9700 includes a car body 9701, wheels 9702, a dashboard 9703, lights 9704, and the like. The display device, the light-emitting device, or the like of one embodiment of the present invention can be used in a display portion or the like of the automobile 9700. For example, the display device, the light-emitting device, or the like of one embodiment of the present invention can be used in display portions 9710 to 9715 illustrated in FIG. 30C.

The display portion 9710 and the display portion 9711 are each a display device provided in an automobile windshield. The display device, the light-emitting device, or the like of one embodiment of the present invention can be a see-through display device, through which the opposite side can be seen, using a light-transmitting conductive material for its electrodes and wirings. Such a see-through display portion 9710 or 9711 does not hinder driver's vision during driving the automobile 9700. Thus, the display device, the light-emitting device, or the like of one embodiment of the present invention can be provided in the windshield of the automobile 9700. Note that in the case where a transistor or the like for driving the display device, the light-emitting device, or the like is provided, a transistor having a light-transmitting property, such as an organic transistor using an organic semiconductor material or a transistor using an oxide semiconductor, is preferably used.

The display portion 9712 is a display device provided on a pillar portion. For example, an image taken by an imaging unit provided in the car body is displayed on the display portion 9712, whereby the view hindered by the pillar portion can be compensated. The display portion 9713 is a display device provided on the dashboard. For example, an image taken by an imaging unit provided in the car body is displayed on the display portion 9713, whereby the view hindered by the dashboard can be compensated. That is, by displaying an image taken by an imaging unit provided on the outside of the automobile, blind areas can be eliminated and safety can be increased. Displaying an image to compensate for the area which a driver cannot see, makes it possible for the driver to confirm safety easily and comfortably.

Figure 30D:
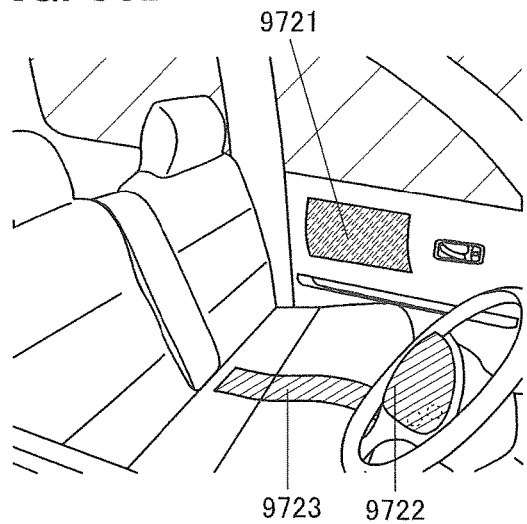

FIG. 30D illustrates the inside of a car in which bench seats are used for a driver seat and a front passenger seat. A display portion 9721 is a display device provided in a door portion. For example, an image taken by an imaging unit provided in the car body is displayed on the display portion 9721, whereby the view hindered by the door can be compensated. A display portion 9722 is a display device provided in a steering wheel. A display portion 9723 is a display device provided in the middle of a seating face of the bench seat. Note that the display device can be used as a seat heater by providing the display device on the seating face or backrest and by using heat generation of the display device as a heat source.

The display portion 9714, the display portion 9715, and the display portion 9722 can provide a variety of kinds of information such as navigation data, a speedometer, a tachometer, a mileage, a fuel meter, a gearshift indicator, and air-condition setting. The content, layout, or the like of the display on the display portions can be changed freely by a user as appropriate. The information listed above can also be displayed on the display portions 9710 to 9713, 9721, and 9723. The display portions 9710 to 9715 and 9721 to 9723 can also be used as lighting devices. The display portions 9710 to 9715 and 9721 to 9723 can also be used as heating devices.

Figure 31A:
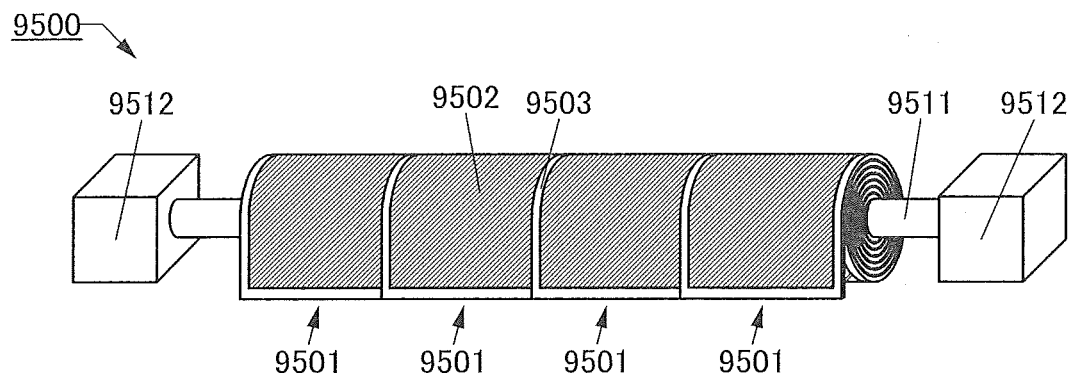
FIGS. 31A and 31B are perspective views illustrating a display device of one embodiment of the present invention.
Figure 31B:
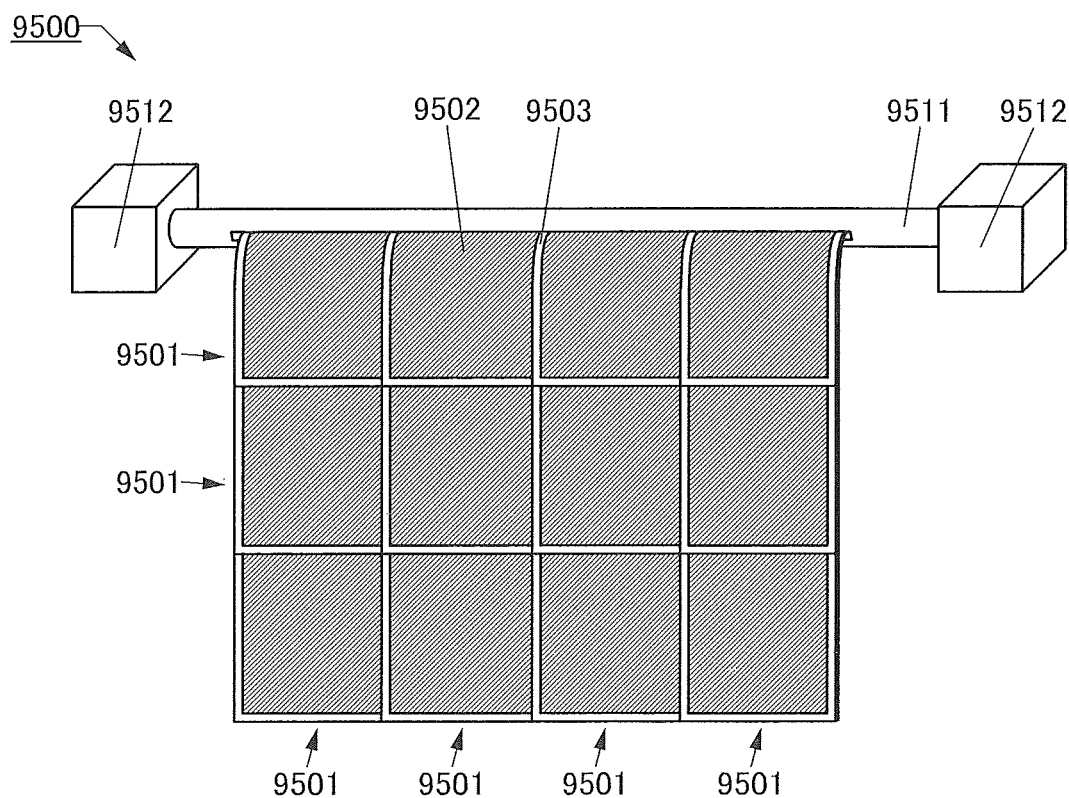

A display device 9500 illustrated in FIGS. 31A and 31B includes a plurality of display panels 9501, a hinge 9511, and a bearing 9512. The plurality of display panels 9501 each include a display region 9502 and a light-transmitting region 9503.

Each of the plurality of display panels 9501 is flexible. Two adjacent display panels 9501 are provided so as to partly overlap with each other. For example, the light-transmitting regions 9503 of the two adjacent display panels 9501 can be overlapped each other. A display device having a large screen can be obtained with the plurality of display panels 9501. The display device is highly versatile because the display panels 9501 can be wound depending on its use.

Moreover, although the display regions 9502 of the adjacent display panels 9501 are separated from each other in FIGS. 31A and 31B, without limitation to this structure, the display regions 9502 of the adjacent display panels 9501 may overlap with each other without any space so that a continuous display region 9502 is obtained, for example.

The electronic devices described in this embodiment each include the display portion for displaying some sort of data. Note that the light-emitting element of one embodiment of the present invention can also be used for an electronic device which does not have a display portion. The structure in which the display portion of the electronic device described in this embodiment is flexible and display can be performed on the bent display surface or the structure in which the display portion of the electronic device is foldable is described as an example; however, the structure is not limited thereto and a structure in which the display portion of the electronic device is not flexible and display is performed on a plane portion may be employed.

The structure described in this embodiment can be used in combination with any of the structures described in the other embodiments as appropriate.

Embodiment 11

In this embodiment, a light-emitting device including the light-emitting element of one embodiment of the present invention will be described with reference to FIGS. 32A to 32C and FIGS. 33A to 33D.

Figure 32A:
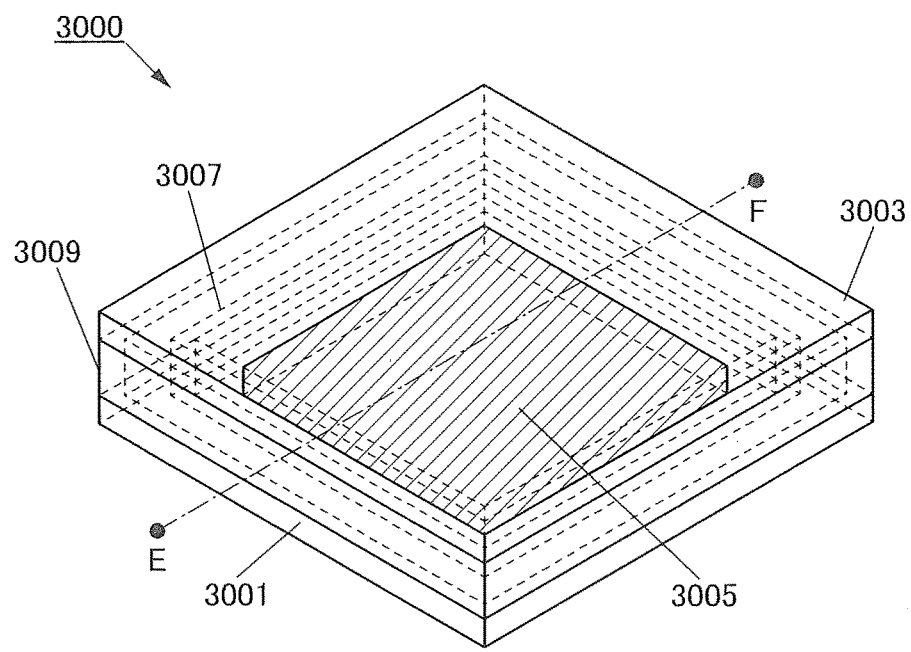
FIGS. 32A to 32C are a perspective view and cross-sectional views illustrating light-emitting devices of one embodiment of the present invention.
Figure 32B:
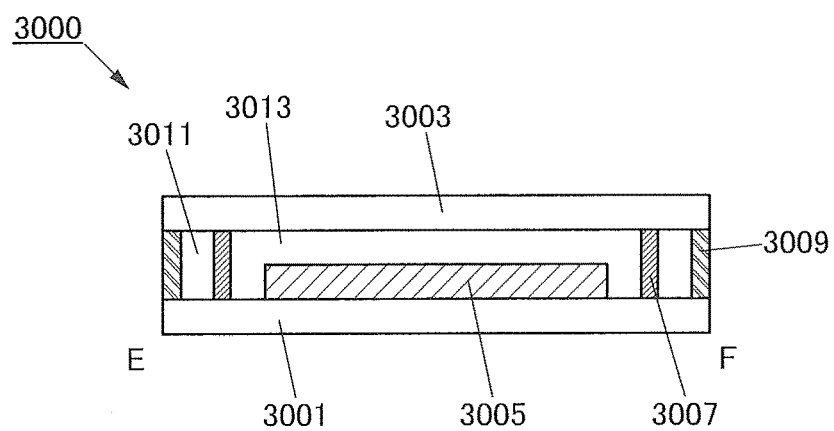

FIG. 32A is a perspective view of a light-emitting device 3000 shown in this embodiment, and FIG. 32B is a cross-sectional view along dashed-dotted line E-F in FIG. 32A. Note that in FIG. 32A, some components are illustrated by broken lines in order to avoid complexity of the drawing.

The light-emitting device 3000 illustrated in FIGS. 32A and 32B includes a substrate 3001, a light-emitting element 3005 over the substrate 3001, a first sealing region 3007 provided around the light-emitting element 3005, and a second sealing region 3009 provided around the first sealing region 3007.

Light is emitted from the light-emitting element 3005 through one or both of the substrate 3001 and a substrate 3003. In FIGS. 32A and 32B, a structure in which light is emitted from the light-emitting element 3005 to the lower side (the substrate 3001 side) is illustrated.

As illustrated in FIGS. 32A and 32B, the light-emitting device 3000 has a double sealing structure in which the light-emitting element 3005 is surrounded by the first sealing region 3007 and the second sealing region 3009. With the double sealing structure, entry of impurities (e.g., water, oxygen, and the like) from the outside into the light-emitting element 3005 can be favorably suppressed. Note that it is not necessary to provide both the first sealing region 3007 and the second sealing region 3009. For example, only the first sealing region 3007 may be provided.

Note that in FIG. 32B, the first sealing region 3007 and the second sealing region 3009 are each provided in contact with the substrate 3001 and the substrate 3003. However, without limitation to such a structure, for example, one or both of the first sealing region 3007 and the second sealing region 3009 may be provided in contact with an insulating film or a conductive film provided on the substrate 3001. Alternatively, one or both of the first sealing region 3007 and the second sealing region 3009 may be provided in contact with an insulating film or a conductive film provided on the substrate 3003.

The substrate 3001 and the substrate 3003 can have structures similar to those of the substrate 200 and the substrate 220 described in the above embodiment, respectively. The light-emitting element 3005 can have a structure similar to that of any of the light-emitting elements described in the above embodiments.

For the first sealing region 3007, a material containing glass (e.g., a glass fit, a glass ribbon, and the like) can be used. For the second sealing region 3009, a material containing a resin can be used. With the use of the material containing glass for the first sealing region 3007, productivity and a sealing property can be improved. Moreover, with the use of the material containing a resin for the second sealing region 3009, impact resistance and heat resistance can be improved. However, the materials used for the first sealing region 3007 and the second sealing region 3009 are not limited to such, and the first sealing region 3007 may be formed using the material containing a resin and the second sealing region 3009 may be formed using the material containing glass.

The glass frit may contain, for example, magnesium oxide, calcium oxide, strontium oxide, barium oxide, cesium oxide, sodium oxide, potassium oxide, boron oxide, vanadium oxide, zinc oxide, tellurium oxide, aluminum oxide, silicon dioxide, lead oxide, tin oxide, phosphorus oxide, ruthenium oxide, rhodium oxide, iron oxide, copper oxide, manganese dioxide, molybdenum oxide, niobium oxide, titanium oxide, tungsten oxide, bismuth oxide, zirconium oxide, lithium oxide, antimony oxide, lead borate glass, tin phosphate glass, vanadate glass, or borosilicate glass. The glass frit preferably contains at least one kind of transition metal to absorb infrared light.

As the above glass frits, for example, a frit paste is applied to a substrate and is subjected to heat treatment, laser light irradiation, or the like. The frit paste contains the glass frit and a resin (also referred to as a binder) diluted by an organic solvent. Note that an absorber which absorbs light having the wavelength of laser light may be added to the glass frit. For example, an Nd:YAG laser or a semiconductor laser is preferably used as the laser. The shape of laser light may be circular or quadrangular.

As the above material containing a resin, for example, polyester, polyolefin, polyamide (e.g., nylon, aramid), polyimide, polycarbonate, or an acrylic resin, polyurethane, or an epoxy resin can be used. Alternatively, a material that includes a resin having a siloxane bond such as silicone can be used.

Note that in the case where the material containing glass is used for one or both of the first sealing region 3007 and the second sealing region 3009, the material containing glass preferably has a thermal expansion coefficient close to that of the substrate 3001. With the above structure, generation of a crack in the material containing glass or the substrate 3001 due to thermal stress can be suppressed.

For example, the following advantageous effect can be obtained in the case where the material containing glass is used for the first sealing region 3007 and the material containing a resin is used for the second sealing region 3009.

The second sealing region 3009 is provided closer to an outer portion of the light-emitting device 3000 than the first sealing region 3007 is. In the light-emitting device 3000, distortion due to external force or the like increases toward the outer portion. Thus, the light-emitting device 3000 is sealed using the material containing a resin for the outer portion of the light-emitting device 3000 where a larger amount of distortion is generated, that is, the second sealing region 3009, and the light-emitting device 3000 is sealed using the material containing glass for the first sealing region 3007 provided on an inner side of the second sealing region 3009, whereby the light-emitting device 3000 is less likely to be damaged even when distortion due to external force or the like is generated.

Furthermore, as illustrated in FIG. 32B, a first region 3011 corresponds to the region surrounded by the substrate 3001, the substrate 3003, the first sealing region 3007, and the second sealing region 3009. A second region 3013 corresponds to the region surrounded by the substrate 3001, the substrate 3003, the light-emitting element 3005, and the first sealing region 3007.

The first region 3011 and the second region 3013 are preferably filled with, for example, an inert gas such as a rare gas or a nitrogen gas. Alternatively, the first region 3011 and the second region 3013 are preferably filled with a resin such as an acrylic resin or an epoxy resin. Note that for the first region 3011 and the second region 3013, a reduced pressure state is preferred to an atmospheric pressure state.

Figure 32C:
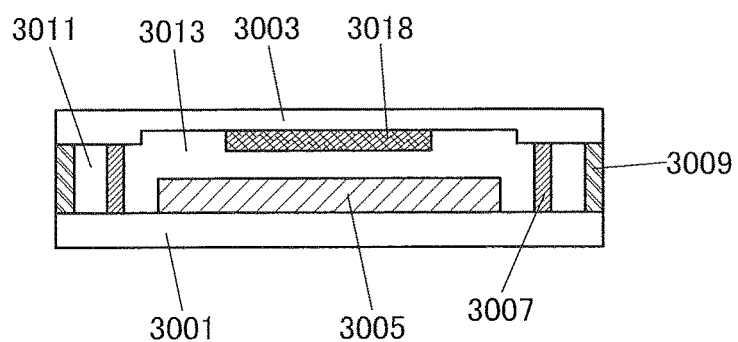

FIG. 32C illustrates a modification example of the structure in FIG. 32B. FIG. 32C is a cross-sectional view illustrating the modification example of the light-emitting device 3000.

FIG. 32C illustrates a structure in which a desiccant 3018 is provided in a recessed portion provided in part of the substrate 3003. The other components are the same as those of the structure illustrated in FIG. 32B.

As the desiccant 3018, a substance which adsorbs moisture and the like by chemical adsorption or a substance which adsorbs moisture and the like by physical adsorption can be used. Examples of the substance that can be used as the desiccant 3018 include alkali metal oxides, alkaline earth metal oxide (e.g., calcium oxide, barium oxide, and the like), sulfate, metal halides, perchlorate, zeolite, silica gel, and the like.

Next, modification examples of the light-emitting device 3000 which is illustrated in FIG. 32B are described with reference to FIGS. 33A to 33D. Note that FIGS. 33A to 33D are cross-sectional views illustrating the modification examples of the light-emitting device 3000 illustrated in FIG. 32B.

In each of the light-emitting devices illustrated in FIGS. 33A to 33D, the second sealing region 3009 is not provided but only the first sealing region 3007 is provided. Moreover, in each of the light-emitting devices illustrated in FIGS. 33A to 33D, a region 3014 is provided instead of the second region 3013 illustrated in FIG. 32B.

For the region 3014, for example, polyester, polyolefin, polyamide (e.g., nylon, aramid), polyimide, polycarbonate, or an acrylic resin, polyurethane, or an epoxy resin can be used. Alternatively, a material that includes a resin having a siloxane bond such as silicone can be used.

When the above-described material is used for the region 3014, what is called a solid-sealing light-emitting device can be obtained.

Figure 33A:
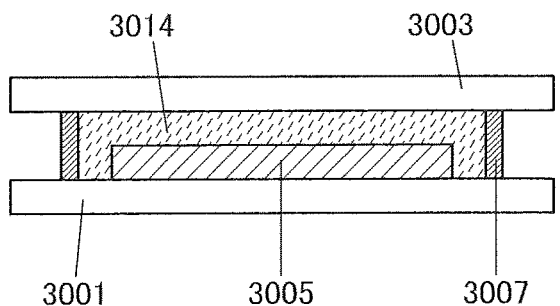
FIGS. 33A and 33D are each a cross-sectional view illustrating a light-emitting device of one embodiment of the present invention.
Figure 33B:
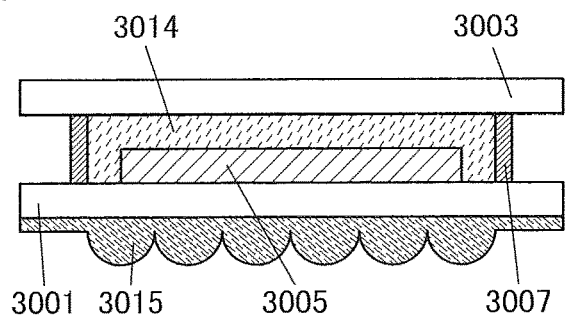

In the light-emitting device illustrated in FIG. 33B, a substrate 3015 is provided on the substrate 3001 side of the light-emitting device illustrated in FIG. 33A.

The substrate 3015 has unevenness as illustrated in FIG. 33B. With a structure in which the substrate 3015 having unevenness is provided on the side through which light emitted from the light-emitting element 3005 is extracted, the efficiency of extraction of light from the light-emitting element 3005 can be improved. Note that instead of the structure having unevenness and illustrated in FIG. 33B, a substrate having a function as a diffusion plate may be provided.

Figure 33C:
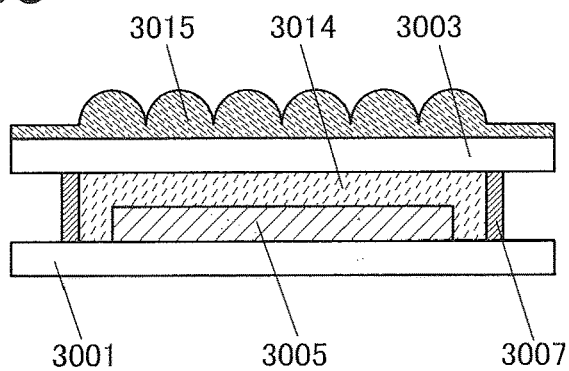

In the light-emitting device illustrated in FIG. 33C, light is extracted through the substrate 3003 side, unlike in the light-emitting device illustrated in FIG. 33A, in which light is extracted through the substrate 3001 side.

The light-emitting device illustrated in FIG. 33C includes the substrate 3015 on the substrate 3003 side. The other components are the same as those of the light-emitting device illustrated in FIG. 33B.

Figure 33D:
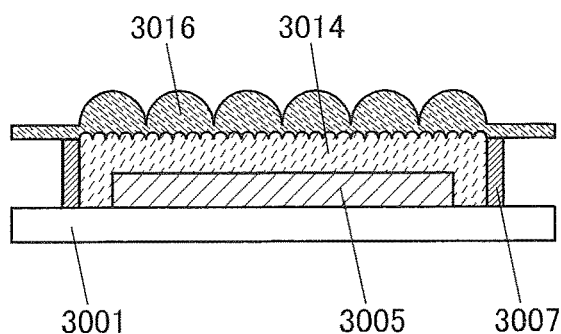

In the light-emitting device illustrated in FIG. 33D, the substrate 3003 and the substrate 3015 included in the light-emitting device illustrated in FIG. 33C are not provided but a substrate 3016 is provided.

The substrate 3016 includes first unevenness positioned closer to the light-emitting element 3005 and second unevenness positioned farther from the light-emitting element 3005. With the structure illustrated in FIG. 33D, the efficiency of extraction of light from the light-emitting element 3005 can be further improved.

Thus, the use of the structure described in this embodiment can provide a light-emitting device in which deterioration of a light-emitting element due to impurities such as moisture and oxygen is suppressed. Alternatively, with the structure described in this embodiment, a light-emitting device having high light extraction efficiency can be obtained.

Note that the structure described in this embodiment can be combined as appropriate with any of the structures described in the other embodiments.

Embodiment 12

In this embodiment, examples in which the light-emitting element of one embodiment of the present invention is used for various lighting devices and electronic devices will be described with reference to FIGS. 34A to 34C and FIG. 35.

An electronic device or a lighting device that has a light-emitting region with a curved surface can be obtained with the use of the light-emitting element of one embodiment of the present invention which is manufactured over a substrate having flexibility.

Furthermore, a light-emitting device to which one embodiment of the present invention is applied can also be used for lighting for motor vehicles, examples of which are lighting for a dashboard, a windshield, a ceiling, and the like.

Figure 34A:
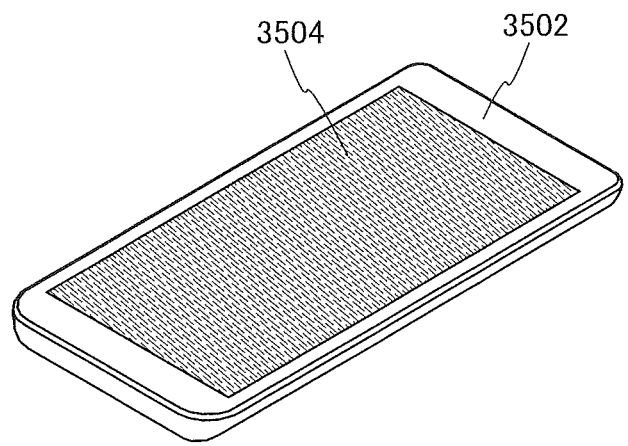
FIGS. 34A to 34C illustrate an electronic device and a lighting device of one embodiment of the present invention.
Figure 34B:
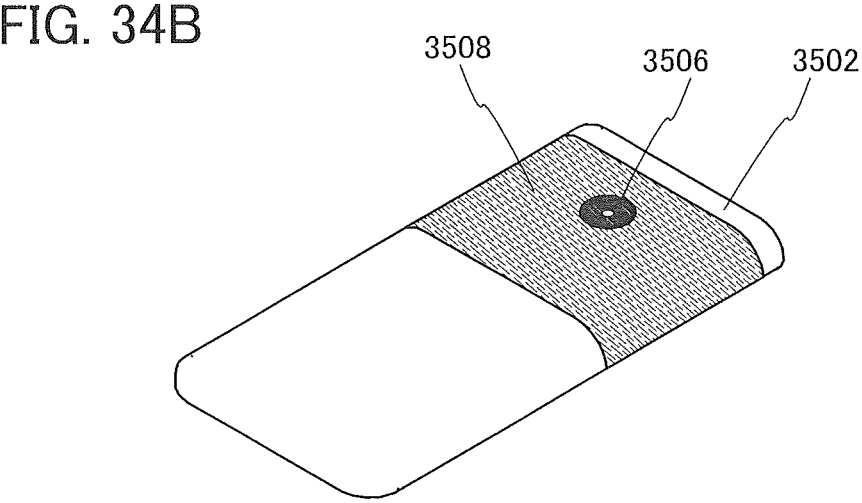

FIG. 34A is a perspective view illustrating one surface of a multifunction terminal 3500, and FIG. 34B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 34A and 34B can have a variety of functions as in the electronic devices illustrated in FIGS. 28A to 28G.

The housing 3502 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. When a detection device including a sensor for detecting inclination, such as a gyroscope or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 34C:
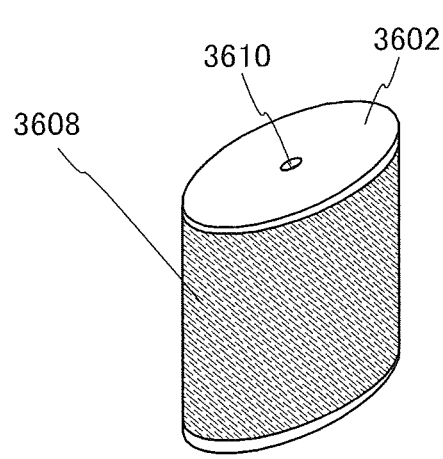

FIG. 34C is a perspective view of a security light 3600. The security light 3600 includes lighting 3608 on the outside of the housing 3602, and a speaker 3610 and the like are incorporated in the housing 3602. The light-emitting device of one embodiment of the present invention can be used for the lighting 3608.

The security light 3600 emits light when the lighting 3608 is gripped or held, for example. An electronic circuit that can control the manner of light emission from the security light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The security light 3600 can emit light in various directions; therefore, it is possible to intimidate a thug or the like with light, or light and sound. Moreover, the security light 3600 may include a camera such as a digital still camera to have a photography function.

Figure 35:
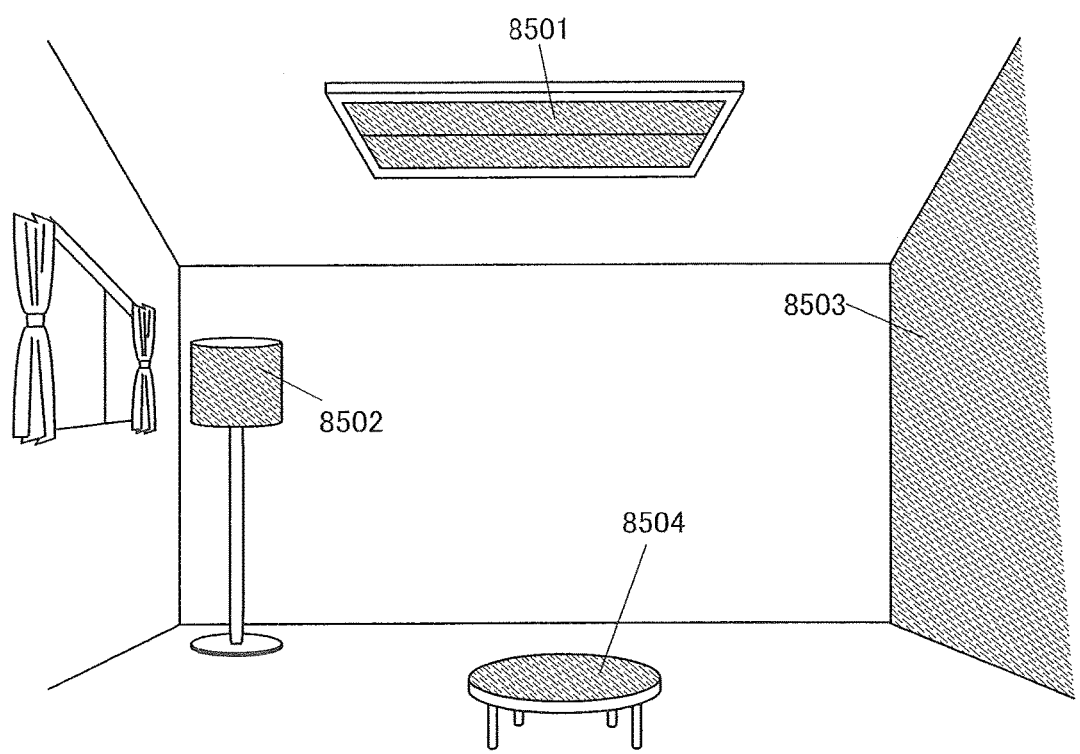
FIG. 35 illustrates lighting devices each of which is one embodiment of the present invention.

FIG. 35 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting device of one embodiment of the present invention. Note that the light-emitting device can be used for electronic devices in a variety of fields without being limited to the lighting devices and the electronic devices described in this embodiment.

The structure described in this embodiment can be used in combination with any of the structures described in the other embodiments as appropriate.

Example 1

Described in this example is a method of synthesizing 7-[4-(10-phenyl-9-anthryl)phenyl]-7H-dibenzo[a,g]carbazole (abbreviation: agDBCzPA, Structural Formula (100)), which is a dibenzocarbazole compound represented by General Formula (G1) described in Embodiment 1.

<Synthesis of agDBCzPA>

In a 200-mL three-neck flask were put 3.0 g (7.5 mmol) of 9-(4-bromophenyl)-10-phenylanthracene, 2.0 g (7.5 mol) of 7H-dibenzo[a,g]carbazole, and 1.4 g (15 mmol) of sodium tert-butoxide, and the air in the flask was replaced with nitrogen. To this mixture were added 38 mL of mesitylene and 0.30 mL of tri-tert-butylphosphine (10 wt % hexane solution), and the mixture was stirred to be degassed while the pressure in the flask was reduced. After the degassing, 43 mg (0.075 mol) of bis(dibenzylideneacetone)palladium(0) was added to the mixture, and the mixture was stirred at 150° C. for 6 hours under a nitrogen stream. After the stirring, the mixture was cooled to room temperature, and approximately 20 mL of water was added to the mixture and then stirred. Then, this mixture was suction-filtered to collect a solid. The collected solid was dissolved in approximately 50 mL of toluene heated, and the solution was suction-filtered through Celite, aluminum oxide, and Florisil. The obtained filtrate was concentrated to give a solid. The obtained solid was recrystallized from toluene, so that 3.5 g of a pale yellow powder, which was the object of the synthesis, was obtained with a yield of 78%. This reaction scheme is shown below.

[Chemical Formula 44]

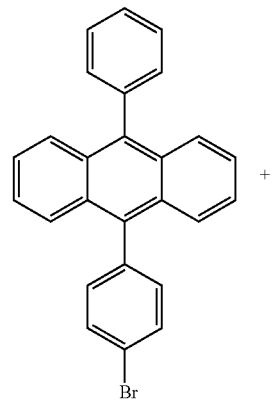

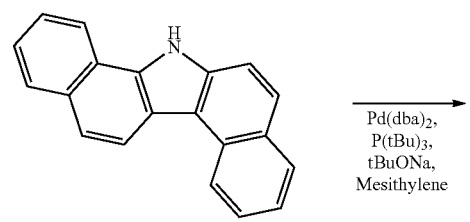

-continued

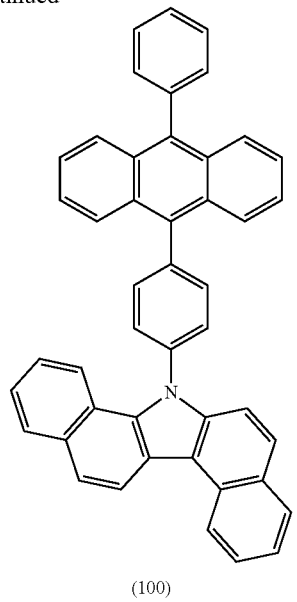

(100)

Then, 3.5 g of the obtained pale yellow powdered solid was sublimated and purified by a train sublimation method. In the sublimation purification, agDBCzPA was heated at 290° C. under a pressure of 2.7 Pa with a flow rate of argon gas of 5.0 mL/min. After the sublimation purification, 3.3 g of a pale yellow solid of agDBCzPA was obtained at a collection rate of 96%.

The resulting substance was measured by $^1$H NMR (nuclear magnetic resonance). The measurement data are shown below.

$^1$H NMR (CDCl$_3$, 500 MHz): δ=7.42-7.45 (m, 3H), 7.50-7.67 (m, 10H), 7.74 (d, J=8.5z, 1H), 7.74-7.83 (m, 3H), 7.84 (s, 4H), 7.92 (t, J=9.0z, 3H), 7.97 (d, J=9.0z, 1H), 8.10 (dd, J=7.5z, J$_2$=2.5z, 2H), 8.85 (d, J=8.5 Hz, 1H), 9.04 (d, J$_1$=8.5 Hz, 1H).

Figure 36A:
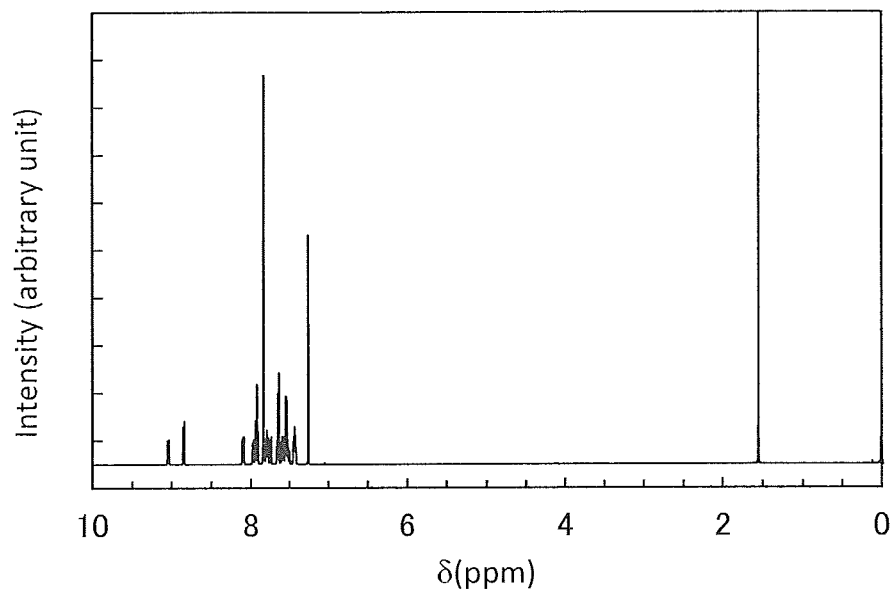
FIGS. 36A and 36B show NMR charts of a compound of Example.
Figure 36B:
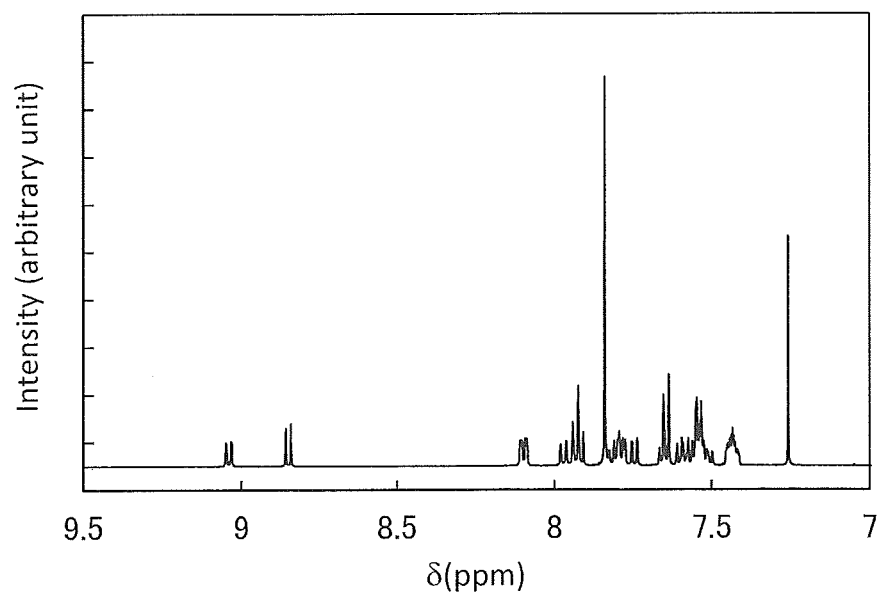

FIGS. 36A and 36B are $^1$H NMR charts. FIG. 36B is an enlarged chart showing a range of 7.00 ppm to 9.50 ppm of FIG. 36A. These results indicate that agDBCzPA, which is the dibenzocarbazole compound of one embodiment of the present invention represented by Structural Formula (100), was obtained.

<Properties of agDBCzPA>

Next, the obtained agDBCzPA was analyzed by liquid chromatography mass spectrometry (LC/MS).

The LC/MS analysis was carried out with Acquity UPLC (produced by Waters Corporation) and Xevo G2 Tof MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above conditions was made to collide with an argon gas in a collision cell to dissociate into product ions. The energy (collision energy) for the collision with argon was 70 eV. The mass range in the measurement was m/z=100 to 1200.

Figure 37:
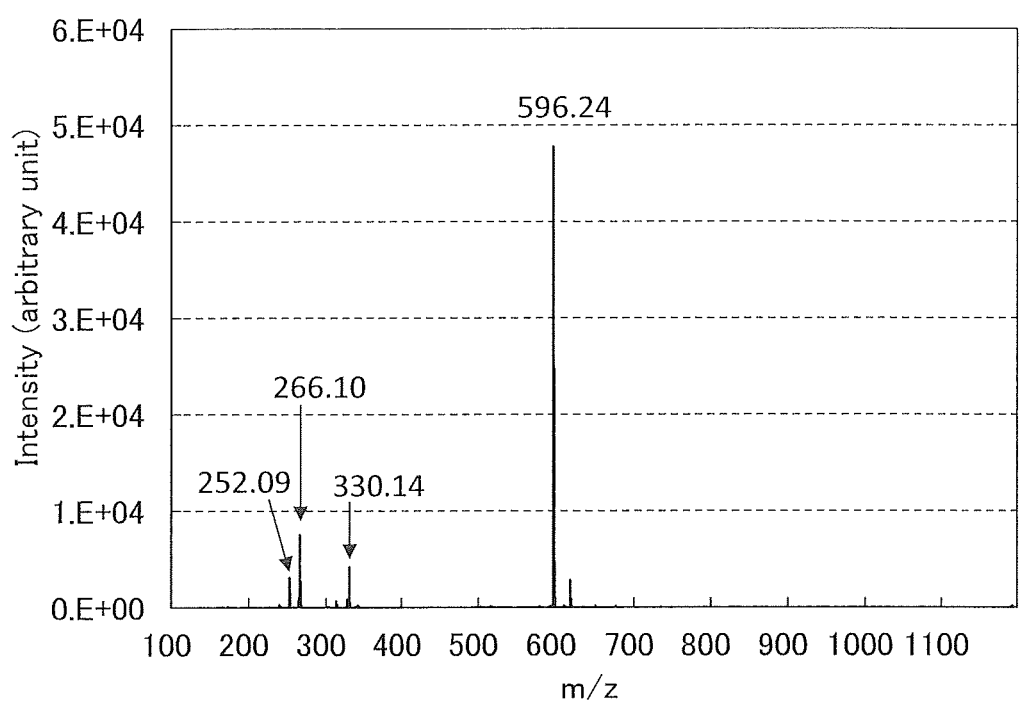
FIG. 37 is a graph showing an MS spectrum of a compound of Example.

FIG. 37 shows the measurement results. According to the results in FIG. 37, product ions are detected mainly around m/z=596, m/z=330, and m/z=266 in agDBCzPA, which is the dibenzocarbazole compound of one embodiment of the present invention represented by Structural Formula (100).

Note that the results in FIG. 37 show typical features derived from agDBCzPA and therefore can be regarded as important data for identifying agDBCzPA contained in the mixture.

An N—C bond between dibenzo[a,g]carbazole and a phenylene group is cut and electric charge remains on the dibenzo[a,g]carbazole side; thus, the product ions around m/z=266 are useful because they probably include data on a state where the N—C bond between dibenzo[a,g]carbazole and a phenylene group of the compound represented by Structural Formula (100) is cut. In addition, the product ions around m/z=330 can be presumed to be product ions including diphenylanthracene, which indicates that agDBCzPA, which is the dibenzocarbazole compound of one embodiment of the present invention, includes dibenzo[a,g]carbazole and diphenylanthracene.

Thermogravimetry-differential thermal analysis (TG-DTA) was performed on the obtained agDBCzPA. The measurement was conducted by using a high vacuum differential type differential thermal balance (TG-DTA 2410SA, manufactured by Bruker AXS K.K.). The measurement was conducted under a nitrogen stream (flow rate: 200 mL/min) at normal pressure at a temperature increase rate of 10° C./min. It was found from the relationship between weight and temperature (thermogravimetry) that the 5% weight loss temperature of agDBCzPA was approximately 475° C. This indicates that agDBCzPA has high heat resistance.

Next, ultraviolet-visible absorption spectra (hereinafter simply referred to as "absorption spectra") and emission spectra of a thin film of agDBCzPA and a toluene solution of agDBCzPA were measured.

The absorption spectrum of agDBCzPA in a toluene solution was obtained by subtraction of the absorption spectrum of toluene and a quartz cell from the absorption spectrum of the toluene solution of agDBCzPA put in the quartz cell. The absorption spectrum of the thin film was obtained by subtraction of the absorption spectrum of a quartz substrate from the absorption spectrum of a sample formed by vacuum evaporation of agDBCzPA on the quartz substrate. Note that the absorption spectra were measured using an ultraviolet-visible spectrophotometer (V-550 type manufactured by JASCO Corporation).

The emission spectra were measured with a fluorescence spectrophotometer (FS920 manufactured by Hamamatsu Photonics K.K.).

Figure 38:
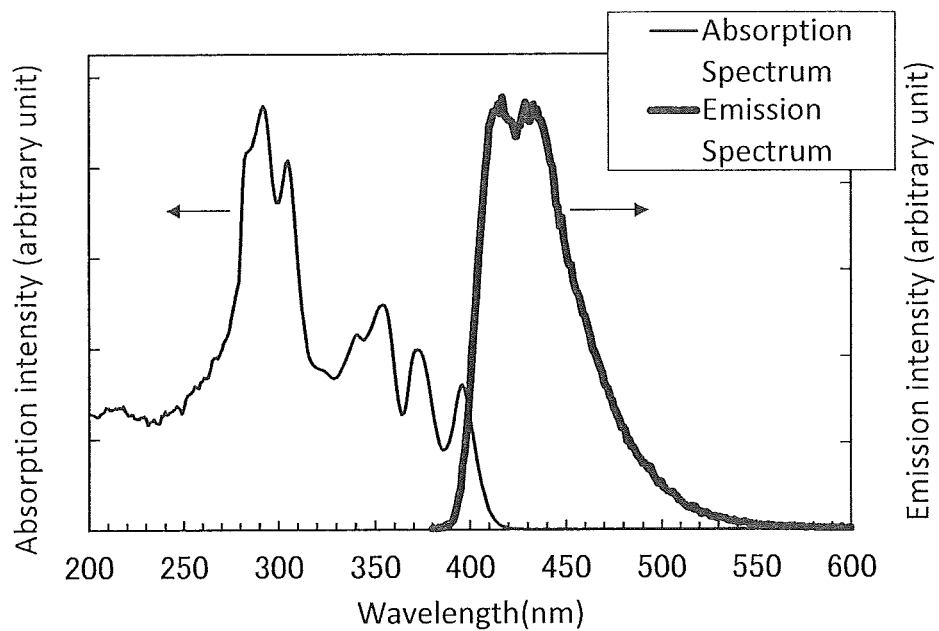
FIG. 38 is a graph showing absorption and emission spectra of a compound of Example.
Figure 39:
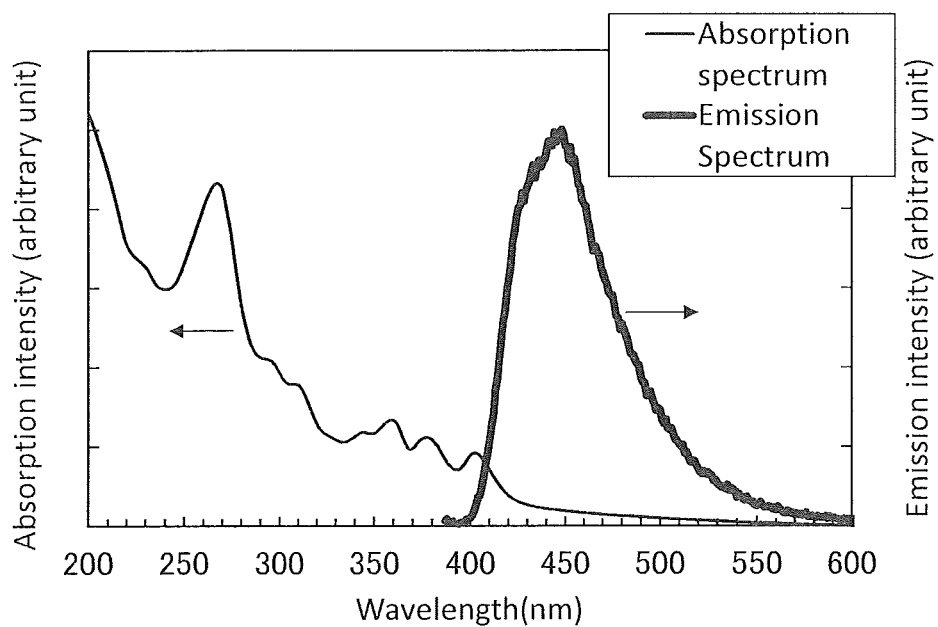
FIG. 39 is a graph showing absorption and emission spectra of a compound of Example.

FIG. 38 shows the measurement results of the absorption and emission spectra of agDBCzPA in the toluene solution, and FIG. 39 shows the measurement results of the absorption and emission spectra of agDBCzPA in the thin film.

As shown in FIG. 38, in the toluene solution of agDBCzPA, the absorption maxima were observed at approximately 292 nm, 305 nm, 341 nm, 354 nm, 372 nm, and 396 nm, and the emission peaks were observed at 417 nm and 429 nm.

As shown in FIG. 39, in the thin film of agDBCzPA, the absorption maxima were observed at approximately 228 nm, 267 nm, 295 nm, 308 nm, 345 nm, 359 nm, 377 nm, and 402 nm, and the emission peaks were observed at 433 nm and 447 nm (excitation wavelength: 371 nm).

The ionization potential of the thin film of agDBCzPA was measured in the air with a photoelectron spectrometer (AC-3, produced by Riken Keiki, Co., Ltd.). The obtained value of the ionization potential was converted into a negative value, and the HOMO level of agDBCzPA was −5.93 eV. From the data of the absorption spectrum of the thin film in FIG. 39, the absorption edge of agDBCzPA, which was obtained from Tauc plot with an assumption of direct transition, was 2.95 eV. Thus, the optical energy gap of agDBCzPA in the solid state was estimated to be 2.95 eV; from the values of the HOMO level obtained above and this energy gap, the LUMO level of agDBCzPA can be estimated to be −2.98 eV. This reveals that agDBCzPA in the solid state has an energy gap as wide as 2.95 eV.

Then, the electrochemical characteristics (oxidation reaction characteristics and reduction reaction characteristics) of agDBCzPA were measured by cyclic voltammetry (CV) measurement. Note that for the measurement, an electrochemical analyzer (ALS model 600A or 600C, produced by BAS Inc.) was used, and the measurement was performed on a solution in which agDBCzPA is dissolved in N,N-dimethylformamide (abbreviation: DMF). In the measurement, the potential of a working electrode with respect to the reference electrode was changed within an appropriate range, so that the oxidation peak potential and the reduction peak potential were obtained. In addition, the HOMO and LUMO levels of agDBCzPA were calculated from the obtained peak potentials and the redox potential of the reference electrode estimated to be −4.94 eV.

According to the CV measurement results, the oxidation potential of agDBCzPA was 0.76 V and the reduction potential was −2.21 V. In addition, the HOMO level and LUMO level of agDBCzPA, which were calculated from the CV measurement results, were −5.70 eV and −2.74 eV, respectively. Thus, agDBCzPA was found to have a large energy difference between the HOMO level and the LUMO level.

Example 2

Described in this example is a method of synthesizing 11-[4-(10-phenyl-9-anthryl)phenyl]-11H-dibenzo[a,i]carbazole (abbreviation: aiDBCzPA, Structural Formula (136)), which is a dibenzocarbazole compound represented by General Formula (G6) described in Embodiment 1.

<Synthesis of aiDBCzPA>

In a 200-mL three-neck flask were put 3.0 g (7.5 mmol) of 9-(4-bromophenyl)-10-phenylanthracene, 2.0 g (7.5 mol) of 11H-dibenzo[a,i]carbazole, and 1.4 g (15 mmol) of sodium tert-butoxide, and the air in the flask was replaced with nitrogen. To this mixture were added 38 mL of mesitylene and 0.30 mL of tri(tert-butyl)phosphine (10 wt % hexane solution), and the mixture was stirred to be degassed while the pressure in the flask was reduced. After the degassing, 43 mg (0.075 mol) of bis(dibenzylideneacetone)palladium(0) was added to the mixture, and the mixture was stirred at 150° C. for 6 hours under a nitrogen stream. After the stirring, the aqueous layer of this mixture was subjected to extraction with toluene, and the solution of the extract and the organic layer were combined and washed with saturated brine. The organic layer was dried over magnesium sulfate, and after that, this mixture was gravity-filtered. A solid obtained by concentrating the obtained filtrate was dissolved in approximately 30 mL of toluene, and the resulting solution was purified by silica gel column chromatography (developing solvent, hexane:toluene=4:1) to give a solid. The solid obtained by the purification was recrystallized from toluene/hexane, so that 3.8 g of a pale yellow powder, which was the object of the synthesis, was obtained with a yield of 85%. This reaction scheme is shown below.

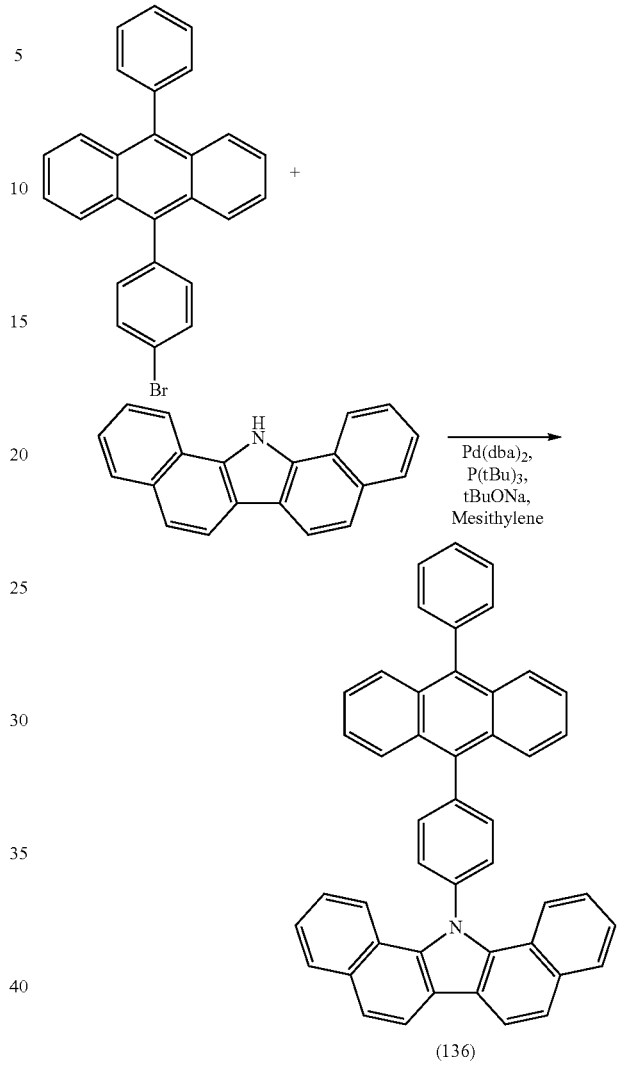

[Chemical Formula 45]

(136)

Then, 3.7 g of the obtained pale yellow powdered solid was sublimated and purified by a train sublimation method. In the sublimation purification, aiDBCzPA was heated at 280° C. under a pressure of 2.8 Pa with a flow rate of argon gas of 5.0 mL/min. After the sublimation purification, 2.0 g of a pale yellow solid of aiDBCzPA was obtained at a collection rate of 55%.

The resulting substance was measured by $^1$H NMR (nuclear magnetic resonance). The measurement data are shown below.

$^1$H NMR (CDCl$_3$, 500 MHz): δ=7.41-7.46 (m, 4H), 7.50-7.61 (m, 7H), 7.64-7.67 (m, 2H), 7.70 (d, J=8.5z, 2H), 7.80 (d, J=8.5 Hz, 2H), 7.83 (d, J$_1$=8.0 Hz, 2H), 7.89 (d, J$_1$=8.0 Hz, 2H), 7.99 (d, J$_1$=8.0 Hz, 2H), 8.03 (d, J=8.5z, 2H), 8.07 (d, J=8.0 Hz, 2H), 8.35 (d, J$_1$=8.5 Hz, 2H).

Figure 40A:
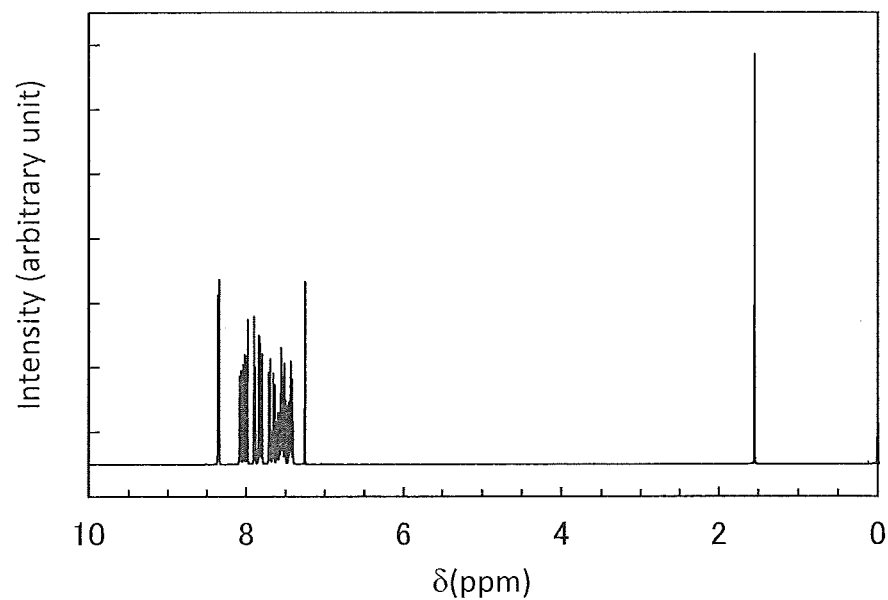
FIGS. 40A and 40B show NMR charts of a compound of Example.
Figure 40B:
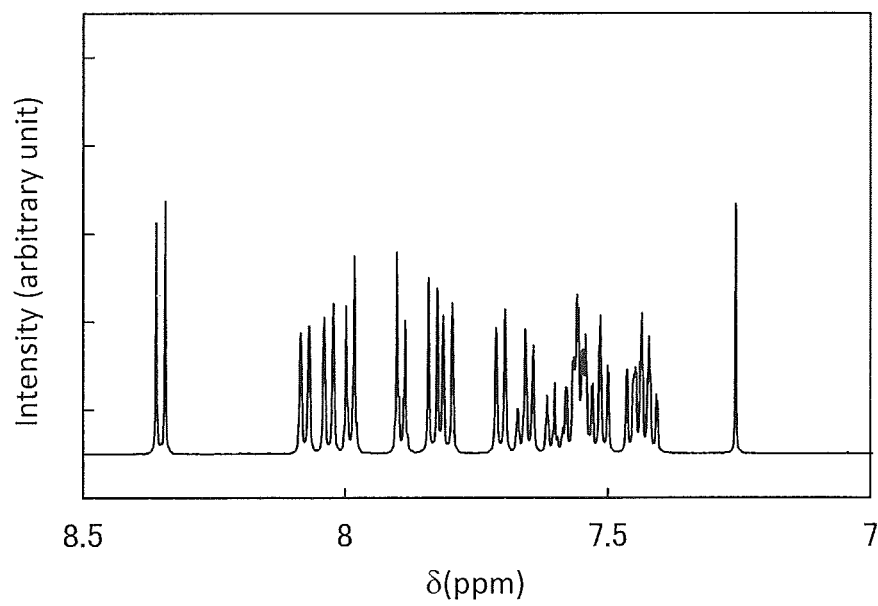

FIGS. 40A and 40B are $^1$H NMR charts. FIG. 40B is an enlarged chart showing a range of 7.00 ppm to 8.50 ppm of FIG. 40A. These results indicate that aiDBCzPA, which is the dibenzocarbazole compound of one embodiment of the present invention represented by Structural Formula (136), was obtained.

<Properties of aiDBCzPA>

Next, the obtained aiDBCzPA was analyzed by liquid chromatography mass spectrometry (LC/MS).

The LC/MS analysis was carried out with Acquity UPLC (produced by Waters Corporation) and Xevo G2 Tof MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above conditions was made to collide with an argon gas in a collision cell to dissociate into product ions. The energy (collision energy) for the collision with argon was 70 eV. The mass range in the measurement was m/z=100 to 1200.

Figure 41:
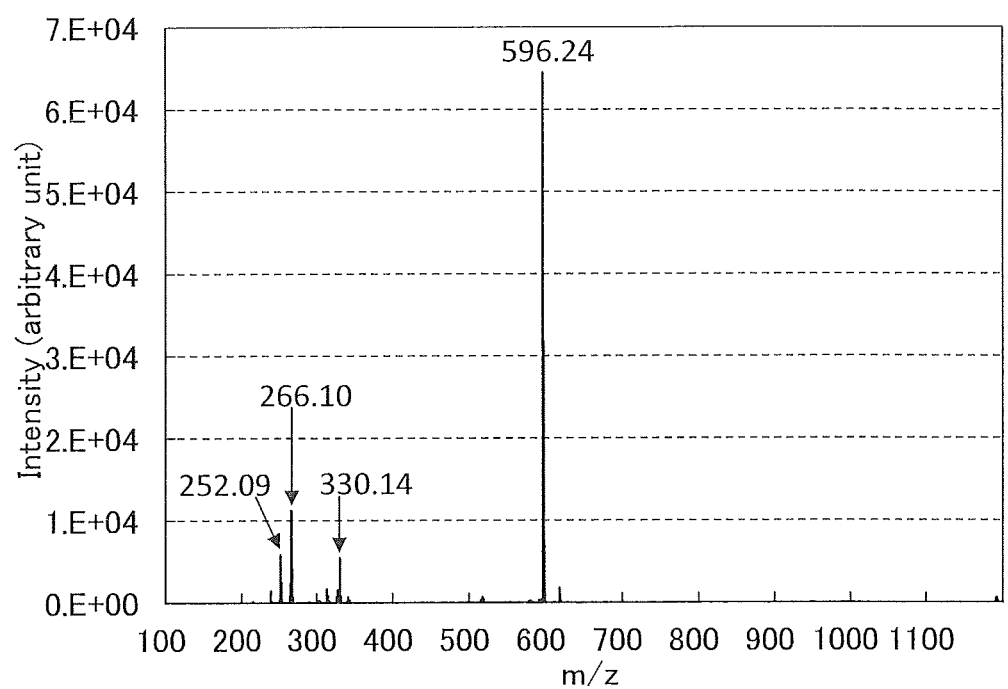
FIG. 41 is a graph showing an MS spectrum of a compound of Example.

FIG. 41 shows the measurement results. According to the results in FIG. 41, product ions are detected mainly around m/z=596, m/z=330, and m/z=266 in aiDBCzPA, which is the dibenzocarbazole compound of one embodiment of the present invention represented by Structural Formula (136). Note that the results in FIG. 41 show typical features derived from aiDBCzPA and therefore can be regarded as important data for identifying aiDBCzPA contained in the mixture.

An N—C bond between dibenzo[a,i]carbazole and a phenylene group is cut and electric charge remains on the dibenzo[a,i]carbazole side; thus, the product ions around m/z=266 are useful because they probably include data on a state where the N—C bond between dibenzo[a,i]carbazole and a phenylene group of the compound represented by Structural Formula (136) is cut. In addition, the product ions around m/z=330 can be presumed to be product ions including diphenylanthracene, which indicates that aiDBCzPA, which is the dibenzocarbazole compound of one embodiment of the present invention, includes dibenzo[a,i]carbazole and diphenylanthracene.

Thermogravimetry-differential thermal analysis (TG-DTA) was performed on the obtained aiDBCzPA. The measurement was conducted by using a high vacuum differential type differential thermal balance (TG-DTA 2410SA, manufactured by Bruker AXS K.K.). The measurement was conducted under a nitrogen stream (flow rate: 200 ml/min) at normal pressure at a temperature increase rate of 10° C./min. It was found from the relationship between weight and temperature (thermogravimetry) that the 5% weight loss temperature of aiDBCzPA was approximately 442° C. This indicates that aiDBCzPA has high heat resistance.

Next, ultraviolet-visible absorption spectra (hereinafter simply referred to as "absorption spectra") and emission spectra of a thin film of aiDBCzPA and a toluene solution of aiDBCzPA were measured. The measurement method is similar to that in Example 1.

Figure 42:
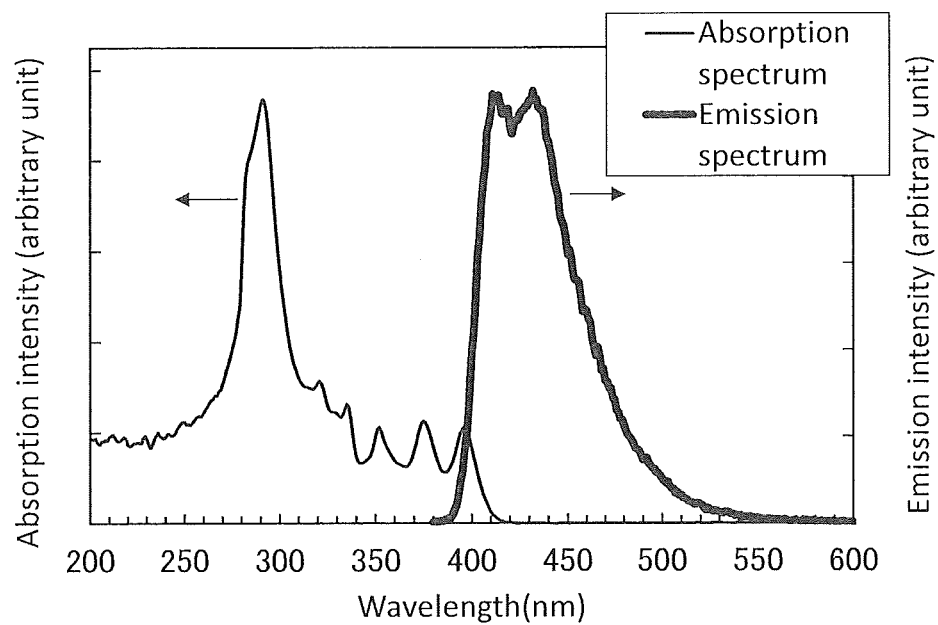
FIG. 42 is a graph showing absorption and emission spectra of a compound of Example.
Figure 43:
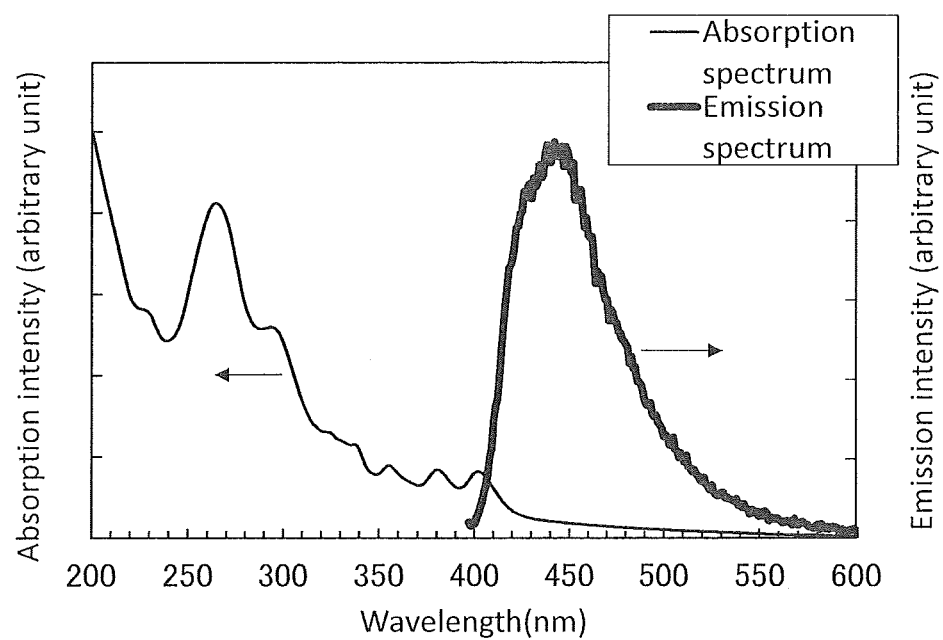
FIG. 43 is a graph showing absorption and emission spectra of a compound of Example.

FIG. 42 shows the measurement results of the absorption and emission spectra of aiDBCzPA in the toluene solution, and FIG. 43 shows the measurement results of the absorption and emission spectra of aiDBCzPA in the thin film.

As shown in FIG. 42, in the toluene solution of aiDBCzPA, the absorption maxima were observed at approximately 291 nm, 321 nm, 335 nm, 352 nm, 375 nm, and 396 nm, and the emission peaks were observed at 413 nm and 432 nm.

As shown in FIG. 43, in the thin film of aiDBCzPA, the absorption maxima were observed at approximately 228 nm, 264 nm, 294 nm, 324 nm, 335 nm, 381 nm, and 402 nm, and the emission peaks were observed at 429 nm and 442 nm (excitation wavelength: 381 nm).

The ionization potential of the thin film of aiDBCzPA was measured in the air with a photoelectron spectrometer (AC-3, produced by Riken Keiki, Co., Ltd.). The obtained value of the ionization potential was converted into a negative value, and the HOMO level of aiDBCzPA was −5.91 eV. From the data of the absorption spectrum of the thin film in FIG. 43, the absorption edge of aiDBCzPA, which was obtained from Tauc plot with an assumption of direct transition, was 2.95 eV. Thus, the optical energy gap of aiDBCzPA in the solid state was estimated to be 2.95 eV; from the values of the HOMO level obtained above and this energy gap, the LUMO level of aiDBCzPA can be estimated to be −2.96 eV. This reveals that aiDBCzPA in the solid state has an energy gap as wide as 2.95 eV.

Then, the electrochemical characteristics (oxidation reaction characteristics and reduction reaction characteristics) of aiDBCzPA were measured by cyclic voltammetry (CV) measurement. Note that the measurement method is similar to that in Example 1.

According to the CV measurement results, the oxidation potential of aiDBCzPA was 0.73 V and the reduction potential was −2.21 V. In addition, the HOMO level and LUMO level of aiDBCzPA, which were calculated from the CV measurement results, were −5.77 eV and −2.74 eV, respectively. Thus, aiDBCzPA was found to have a large energy difference between the HOMO level and the LUMO level.

Example 3

In this example, a fabrication example of a light-emitting element including a compound of one embodiment of the present invention and the characteristics of the light-emitting element will be described. FIG. 2A can be referred to for a schematic cross-sectional view of the light-emitting element fabricated in this example. Table 1 shows details of the element structure. In addition, structures and abbreviations of compounds used are given below. Note that the above examples are referred to for other compounds.

[Chemical Formula 46]

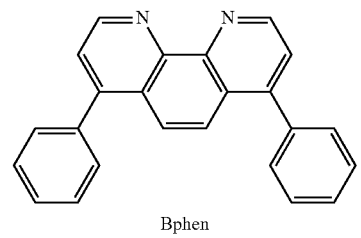

Bphen

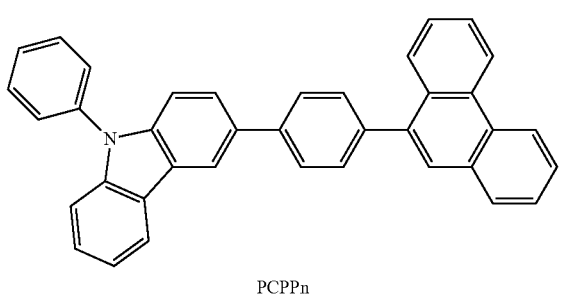

PCPPn

-continued

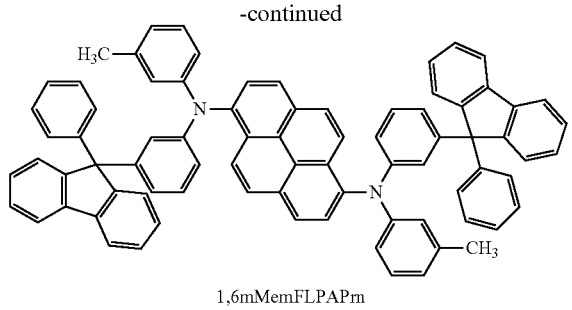

1,6mMemFLPAPrn were deposited by co-evaporation to a thickness of 10 nm such that the weight ratio of PCPPn to $MoO_3$ was 1:0.5. Note that co-evaporation is an evaporation method in which a plurality of different substances are concurrently vaporized from the respective evaporation sources.

Next, as the hole-transport layer 112 over the hole-injection layer 111, PCPPn was deposited by evaporation to a thickness of 20 nm.

Next, as the light-emitting layer 120 over the hole-transport layer 112, 7-[4-(10-phenyl-9-anthryl)phenyl]-7H-dibenzo[a,g]carbazole (abbreviation: agDBCzPA) and N,N'-bis(3-methylphenyl)-N,N-bis[3-(9-phenyl-9H-fluoren-9-yl)phenyl]pyrene-1,6-diamine (abbreviation: 1,6mMemFLPAPrn) were deposited by co-evaporation to a

TABLE 1

| | Layer | Reference numeral | Film thickness | Material | Weight ratio |
|---|---|---|---|---|---|
| Light-emitting element 1 | Electrode | 102 | 200 | Al | — |
| | Electron-injection layer | 114 | 1 | LiF | — |
| | Electron-transport layer | 113(2) | 15 | Bphen | — |
| | | 113(1) | 10 | agDBCzPA | — |
| | Light-emitting layer | 120 | 25 | agDBCzPA:1,6mMemFLPAPrn | 1:0.01 |
| | Hole-transport layer | 112 | 20 | PCPPn | — |
| | Hole-injection layer | 111 | 10 | PCPPn:$MoO_3$ | 1:0.5 |
| | Electrode | 101 | 70 | ITSO | — |
| Light-emitting element 2 | Electrode | 102 | 200 | Al | — |
| | Electron-injection layer | 114 | 1 | LiF | — |
| | Electron-transport layer | 113(2) | 15 | Bphen | — |
| | | 113(1) | 10 | agDBCzPA | — |
| | Light-emitting layer | 120 | 25 | agDBCzPA:1,6mMemFLPAPrn | 1:0.03 |
| | Hole-transport layer | 112 | 20 | PCPPn | — |
| | Hole-injection layer | 111 | 10 | PCPPn:$MoO_3$ | 1:0.5 |
| | Electrode | 101 | 70 | ITSO | — |
| Light-emitting element 3 | Electrode | 102 | 200 | Al | — |
| | Electron-injection layer | 114 | 1 | LiF | — |
| | Electron-transport layer | 113(2) | 15 | Bphen | — |
| | | 113(1) | 10 | aiDBCzPA | — |
| | Light-emitting layer | 120 | 25 | aiDBCzPA:1,6mMemFLPAPrn | 1:0.01 |
| | Hole-transport layer | 112 | 20 | PCPPn | — |
| | Hole-injection layer | 111 | 10 | PCPPn:$MoO_3$ | 1:0.5 |
| | Electrode | 101 | 70 | ITSO | — |
| Light-emitting element 4 | Electrode | 102 | 200 | Al | — |
| | Electron-injection layer | 114 | 1 | LiF | — |
| | Electron-transport layer | 113(2) | 15 | Bphen | — |
| | | 113(1) | 10 | aiDBCzPA | — |
| | Light-emitting layer | 120 | 25 | aiDBCzPA:1,6mMemFLPAPrn | 1:0.03 |
| | Hole-transport layer | 112 | 20 | PCPPn | — |
| | Hole-injection layer | 111 | 10 | PCPPn:$MoO_3$ | 1:0.5 |
| | Electrode | 101 | 70 | ITSO | — |

<Fabrication of Light-Emitting Element>
<<Fabrication of Light-Emitting Element 1>>

As the electrode 101, an ITSO film was formed to a thickness of 70 nm over a substrate. The electrode area of the electrode 101 was set to 4 $mm^2$ (2 mm×2 mm).

Then, as the hole-injection layer 111 over the electrode 101, 3-[4-(9-phenanthryl)-phenyl]-9-phenyl-9H-carbazole (abbreviation: PCPPn) and molybdenum oxide ($MoO_3$)

thickness of 25 nm such that the weight ratio of agDBCzPA to 1,6mMemFLPAPrn was 1:0.01. Note that in the light-emitting layer 120, agDBCzPA is a host material and 1,6mMemFLPAPrn is a guest material (fluorescent material).

Then, as the electron-transport layer 113 over the light-emitting layer 120, agDBCzPA and bathophenanthroline (abbreviation: BPhen) were sequentially deposited by evaporation to thicknesses of 10 nm and 15 nm, respectively. After that, as the electron-injection layer 114 over the electron-transport layer 113, lithium fluoride (LiF) was deposited by evaporation to a thickness of 1 nm.

Next, as the electrode 102 over the electron-injection layer 114, aluminum (Al) was deposited to a thickness of 200 nm.

Next, in a glove box containing a nitrogen atmosphere, a sealing substrate was fixed to the substrate over which the organic materials were deposited using a sealant for an organic EL device, so that the light-emitting element 1 was sealed. Through the above steps, the light-emitting element 1 was obtained.

<<Fabrication of Light-Emitting Element 2>>

A light-emitting element 2 was fabricated through the same steps as those for the above-mentioned light-emitting element 1 except for the step of forming the light-emitting layer 120.

As the light-emitting layer 120 in the light-emitting element 2, agDBCzPA and 1,6mMemFLPAPrn were deposited by co-evaporation to a thickness of 25 nm such that the weight ratio of agDBCzPA to 1,6mMemFLPAPrn was 1:0.03. Note that in the light-emitting layer 120, agDBCzPA is a host material and 1,6mMemFLPAPrn is a guest material (fluorescent material).

<<Fabrication of Light-Emitting Element 3>>

A light-emitting element 3 was fabricated through the same steps as those for the above-mentioned light-emitting element 1 except for the steps of forming the light-emitting layer 120 and the electron-transport layer 113.

As the light-emitting layer 120 in the light-emitting element 3,11-[4-(10-phenyl-9-anthryl)phenyl]-11H-dibenzo[a,i]carbazole (abbreviation: aiDBCzPA) and 1,6mMemFLPAPrn were deposited by co-evaporation to a thickness of 25 nm such that the weight ratio of aiDBCzPA to 1,6mMemFLPAPrn was 1:0.01. Note that in the light-emitting layer 120, aiDBCzPA is a host material and 1,6mMemFLPAPrn is a guest material (fluorescent material).

As the electron-transport layer 113 in the light-emitting element 3, aiDBCzPA and BPhen were sequentially deposited by evaporation to thicknesses of 10 nm and 15 nm, respectively.

<<Fabrication of Light-Emitting Element 4>>

A light-emitting element 4 was fabricated through the same steps as those for the above-mentioned light-emitting element 3 except for the step of forming the light-emitting layer 120.

As the light-emitting layer 120 in the light-emitting element 4, aiDBCzPA and 1,6mMemFLPAPrn were deposited by co-evaporation to a thickness of 25 nm such that the weight ratio of aiDBCzPA to 1,6mMemFLPAPrn was 1:0.03. Note that in the light-emitting layer 120, aiDBCzPA is a host material and 1,6mMemFLPAPrn is a guest material (fluorescent material).

<Emission Characteristics of Light-Emitting Elements>

Next, the emission characteristics of the fabricated light-emitting elements 1 to 4 were measured. The luminance and CIE chromaticity were measured with a luminance colorimeter (BM-5A manufactured by TOPCON TECHNOHOUSE CORPORATION), and the electroluminescence spectrum was measured with a multi-channel spectrometer (PMA-11 manufactured by Hamamatsu Photonics K.K.). Note that the measurement was performed at room temperature (in an atmosphere maintained at 25° C.).

Figure 44:
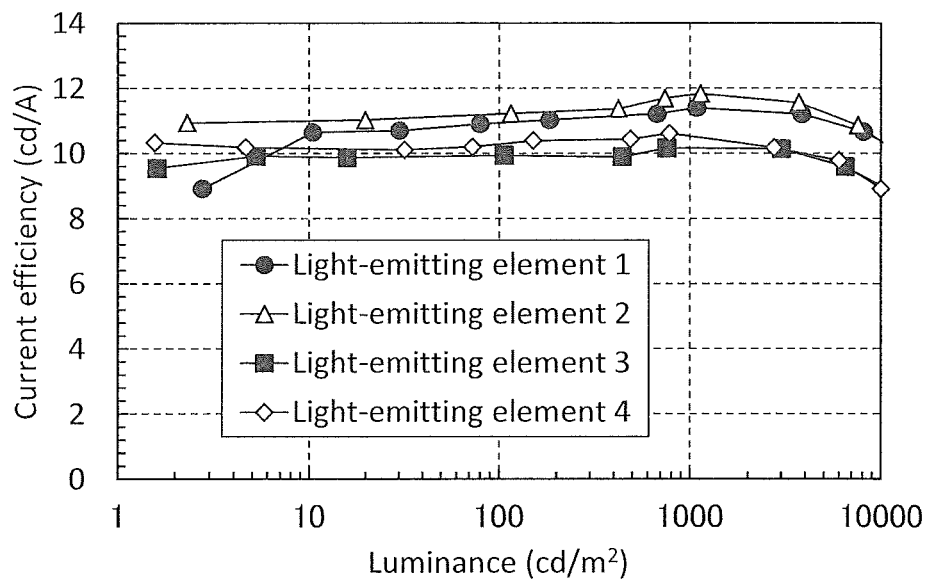
FIG. 44 is a graph showing current efficiency-luminance characteristics of light-emitting elements in Example.
Figure 45:
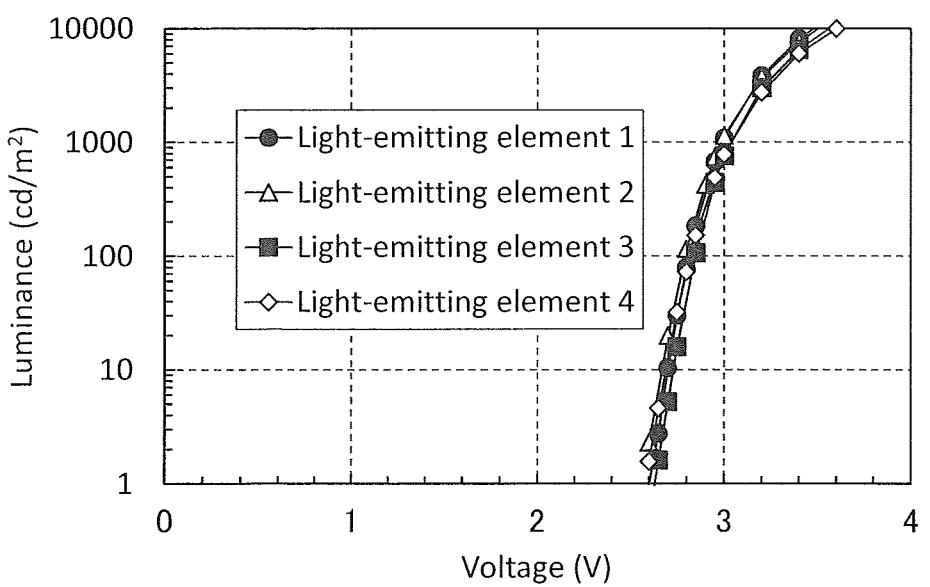
FIG. 45 is a graph showing luminance-voltage characteristics of light-emitting elements in Example.
Figure 46:
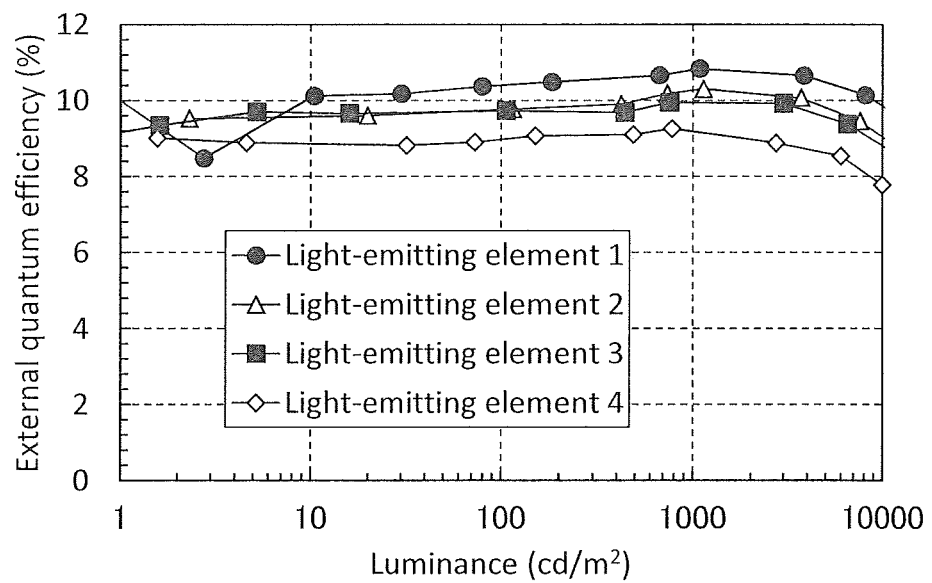
FIG. 46 is a graph showing external quantum efficiency-luminance characteristics of light-emitting elements in Example.
Figure 47:
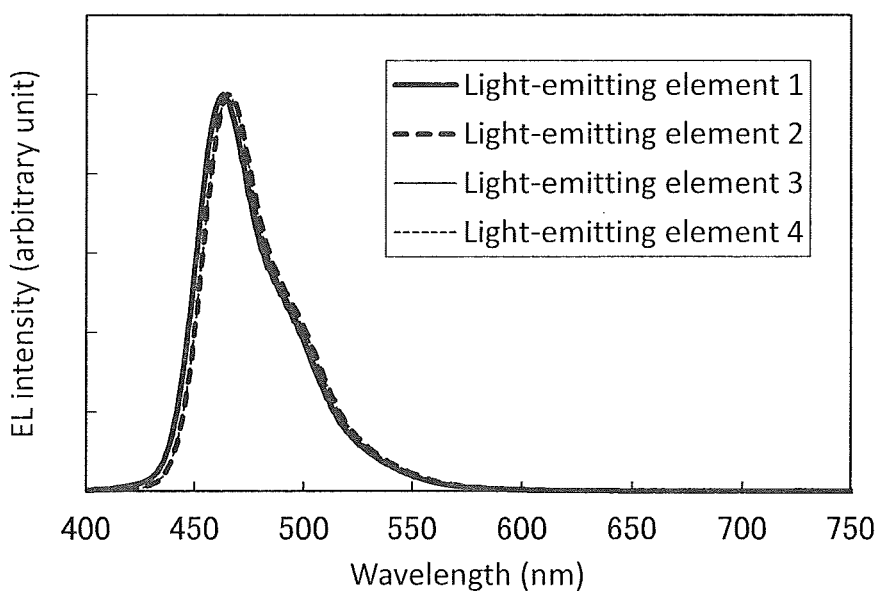
FIG. 47 is a graph showing electroluminescence spectra of light-emitting elements in Example.

FIG. 44 shows the current efficiency-luminance characteristics of the light-emitting elements 1 to 4, FIG. 45 shows the luminance-voltage characteristics thereof, and FIG. 46 shows the external quantum efficiency-luminance characteristics thereof. FIG. 47 shows the electroluminescence spectra when a current with a current density of 2.5 mA/cm$^2$ was supplied to the light-emitting elements 1 to 4.

Table 2 shows the emission characteristics of the light-emitting elements at a luminance around 1000 cd/m$^2$.

TABLE 2

| | Voltage (V) | Current density (mA/cm$^2$) | CIE chromaticity (x, y) | Luminance (cd/m$^2$) | Current efficiency (cd/A) | External quantum efficiency (%) |
|---|---|---|---|---|---|---|
| Light-emitting element 1 | 3.00 | 9.55 | (0.138, 0.142) | 1090 | 11.4 | 10.8 |
| Light-emitting element 2 | 3.00 | 9.63 | (0.138, 0.163) | 1140 | 11.8 | 10.3 |
| Light-emitting element 3 | 3.00 | 7.47 | (0.139, 0.135) | 760 | 10.2 | 10.0 |
| Light-emitting element 4 | 3.00 | 7.38 | (0.138, 0.161) | 783 | 10.6 | 9.3 |

As shown in FIG. 47, the light-emitting elements 1 to 4 exhibited blue light emission derived from the guest material (1,6mMemFLPAPrn).

FIG. 44 to FIG. 47 and Table 2 show that the light-emitting elements 1 to 4, which include a fluorescent material as a light-emitting material, have a high current efficiency and a high external quantum efficiency. The light-emitting elements 1 to 4 also exhibited an external quantum efficiency as high as more than 9%.

Since the probability of formation of singlet excitons which are generated by recombination of carriers (holes and electrons) injected from a pair of electrodes is at most 25%, the external quantum efficiency in the case where the light extraction efficiency to the outside is 25% is at most 6.25%. The light-emitting elements 1 to 4 have an external quantum efficiency higher than 6.25%. This is because in addition to light emission derived from singlet excitons generated by recombination of carriers (holes and electrons) injected from a pair of electrodes, light emission derived from singlet excitons generated by TTA was obtained from the light-emitting elements 1 to 4.

Note that the light-emitting element 1 has a chromaticity y of 0.142, i.e., exhibits deeper blue emission than the light-emitting element 2 and also has a higher external quantum efficiency than the light-emitting element 2. In addition, the light-emitting element 3 has a chromaticity y of 0.135, i.e., exhibits deeper blue emission than the light-emitting element 4 and also has a higher external quantum efficiency than the light-emitting element 4.

In the light-emitting element that emits blue light, a high emission energy needs to be confined in the light-emitting layer, which makes it difficult to obtain a high emission efficiency particularly in the light-emitting element that exhibits deep blue emission. However, the light-emitting element including the dibenzocarbazole compound of one embodiment of the present invention as the host material emits deep blue light while exhibiting a high efficiency. This indicates that the dibenzocarbazole compound of one embodiment of the present invention can be suitably used for light-emitting elements that emit deep blue light.

Furthermore, the light-emitting elements 1 to 4 are driven at a low voltage and therefore consume low power. That is, a light-emitting element driven at a low voltage can be fabricated when the dibenzocarbazole compound of one embodiment of the present invention, which has a high carrier-transport property, is used as a host material and an electron-transport material.

Figure 48:
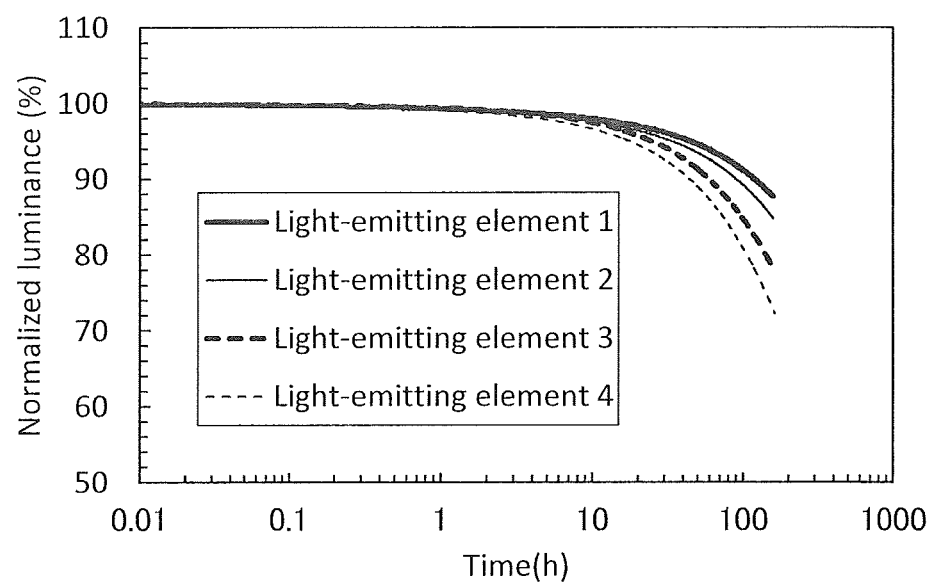
FIG. 48 is a graph showing test results of the driving lifetime of light-emitting elements of Example.

Next, the driving lifetime of the light-emitting elements 1 to 4 was measured. FIG. 48 shows the measurement results of the driving lifetime test. Note that the driving lifetime test was performed while each of the light-emitting elements 1 to 4 was continuously driven with a constant current density, which was set so that each light-emitting element had an initial luminance of 5000 cd.

As shown in FIG. 48, the light-emitting elements 1 to 4, which include a blue fluorescent material as a light-emitting material, have a long driving lifetime. In addition, the light-emitting element 1 has a longer driving lifetime than the light-emitting element 2, and the light-emitting element 3 has a longer driving lifetime than the light-emitting element 4.

In the light-emitting element that emits blue light, a high emission energy needs to be confined in the light-emitting layer, which makes it difficult to obtain a long driving lifetime particularly in the light-emitting element that exhibits deep blue emission. However, the light-emitting element including the dibenzocarbazole compound of one embodiment of the present invention as the host material emits deep blue light while exhibiting a long driving lifetime. This indicates that the dibenzocarbazole compound of one embodiment of the present invention can be suitably used for light-emitting elements that emit deep blue light. Specifically, the dibenzocarbazole compound of one embodiment of the present invention can be suitably used for a light-emitting element that emits deep blue having a chromaticity y of 0.01 to 0.15.

The above results also indicate that in the light-emitting element including the dibenzocarbazole compound of one embodiment of the present invention as the host material, the weight percentage of the guest material is preferably lower than that of the host material; specifically, the weight ratio of the guest material to the host material is preferably greater than 0 and less than 0.03.

As described above, the dibenzocarbazole compound of one embodiment of the present invention can be suitably used for a light-emitting element that emits deep blue light. With the dibenzocarbazole compound of one embodiment of the present invention, a light-emitting element with a high emission efficiency can be fabricated. With the dibenzocarbazole compound of one embodiment of the present invention, a light-emitting element with lower power consumption can be fabricated. With the dibenzocarbazole compound of one embodiment of the present invention, a light-emitting element with a long driving lifetime can be fabricated.

The structures described in this example can be used in combination with any of the structures described in the other embodiments as appropriate.

Example 4

In this example, a fabrication example of light-emitting elements 5 and 6 including a compound of one embodiment of the present invention and the characteristics of the light-emitting elements will be described. For comparison, light-emitting elements 7 and 8 including a compound different from that of one embodiment of the present invention were also fabricated. FIG. 2A can be referred to for a schematic cross-sectional view of the light-emitting element fabricated in this example. Table 3 shows details of the element structure. In addition, structures and abbreviations of compounds used are given below. Note that the above examples are referred to for other compounds.

[Chemical Formula 47]

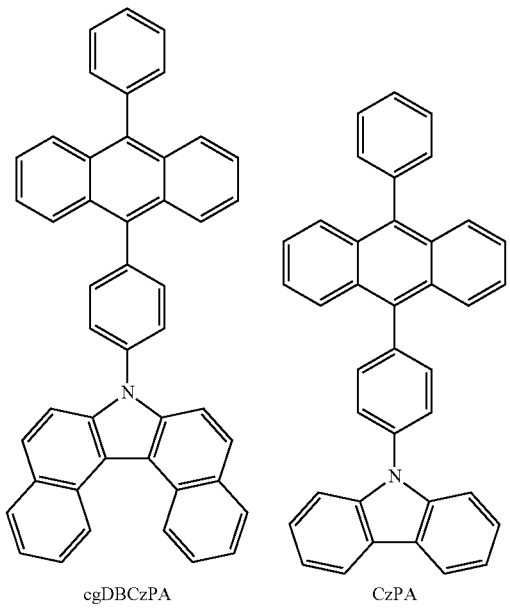

cgDBCzPA        CzPA

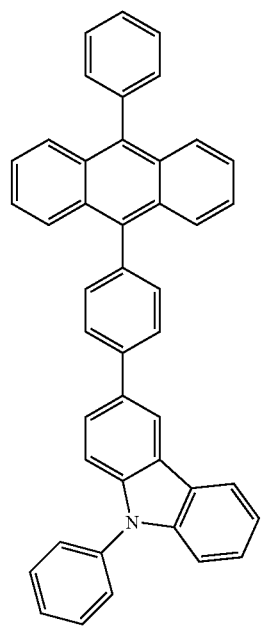

PCzPA

TABLE 3

| Layer | Reference Numeral | Film thickness | Material | Weight ratio |
|---|---|---|---|---|
| Light-emitting element 5 | | | | |
| Electrode | 102 | 200 | Al | — |
| Electron-injection layer | 114 | 1 | LiF | — |
| Electron-transport layer | 113(2) | 15 | Bphen | — |
| | 113(1) | 10 | agDBCzPA | — |
| Light-emitting layer | 120 | 25 | agDBCzPA:1,6mMemFLPAPrn | 1:0.01 |
| Hole-transport layer | 112 | 20 | PCzPA | — |
| Hole-injection layer | 111 | 10 | PCzPA:MoO$_3$ | 1:0.5 |
| Electrode | 101 | 70 | ITSO | — |
| Light-emitting element 6 | | | | |
| Electrode | 102 | 200 | Al | — |
| Electron-injection layer | 114 | 1 | LiF | — |
| Electron-transport layer | 113(2) | 15 | Bphen | — |
| | 113(1) | 10 | aiDBCzPA | — |
| Light-emitting layer | 120 | 25 | aiDBCzPA:1,6mMemFLPAPrn | 1:0.01 |
| Hole-transport layer | 112 | 20 | PCzPA | — |
| Hole-injection layer | 111 | 10 | PCzPA:MoO$_3$ | 1:0.5 |
| Electrode | 101 | 70 | ITSO | — |
| Light-emitting element 7 | | | | |
| Electrode | 102 | 200 | Al | — |
| Electron-injection layer | 114 | 1 | LiF | — |
| Electron-transport layer | 113(2) | 15 | Bphen | — |
| | 113(1) | 10 | cgDBCzPA | — |
| Light-emitting layer | 120 | 25 | cgDBCzPA:1,6mMemFLPAPrn | 1:0.03 |
| Hole-transport layer | 112 | 20 | PCzPA | — |
| Hole-injection layer | 111 | 10 | PCzPA:MoO$_3$ | 1:0.5 |
| Electrode | 101 | 70 | ITSO | — |
| Light-emitting element 8 | | | | |
| Electrode | 102 | 200 | Al | — |
| Electron-injection layer | 114 | 1 | LiF | — |
| Electron-transport layer | 113(2) | 15 | Bphen | — |
| | 113(1) | 10 | CzPA | — |
| Light-emitting layer | 120 | 25 | CzPA:1,6mMemFLPAPrn | 1:0.04 |
| Hole-transport layer | 112 | 20 | PCzPA | — |
| Hole-injection layer | 111 | 10 | PCzPA:MoO$_3$ | 1:0.5 |
| Electrode | 101 | 70 | ITSO | — |

<Fabrication of Light-Emitting Element>
<<Fabrication of Light-Emitting Element 5>>

As the electrode 101, an ITSO film was formed to a thickness of 70 nm over a substrate. The electrode area of the electrode 101 was set to 4 mm$^2$ (2 mm×2 mm).

Then, as the hole-injection layer 111 over the electrode 101, 9-phenyl-3-[4-(10-phenyl-9-anthryl)phenyl]-9H-carbazole (abbreviation: PCzPA) and molybdenum oxide (MoO$_3$) were deposited by co-evaporation to a thickness of 10 nm such that the weight ratio of PCzPA to MoO$_3$ was 1:0.5.

Next, as the hole-transport layer 112 over the hole-injection layer 111, PCzPA was deposited by evaporation to a thickness of 20 nm.

Then, as the light-emitting layer 120 over the hole-transport layer 112, agDBCzPA and 1,6mMemFLPAPrn were deposited by co-evaporation to a thickness of 25 nm such that the weight ratio of agDBCzPA to 1,6mMemFL-PAPrn was 1:0.01. Note that in the light-emitting layer 120, agDBCzPA is a host material and 1,6mMemFLPAPrn is a guest material (fluorescent material).

Then, as the electron-transport layer 113 over the light-emitting layer 120, agDBCzPA and BPhen were sequentially deposited by evaporation to thicknesses of 1Q nm and 15 nm, respectively. After that, as the electron-injection layer 114 over the electron-transport layer 113, lithium fluoride (LiF) was deposited by evaporation to a thickness of 1 nm.

Next, as the electrode 102 over the electron-injection layer 114, aluminum (Al) was deposited to a thickness of 200 nm.

Next, in a glove box containing a nitrogen atmosphere, a sealing substrate was fixed to the substrate over which the organic materials were deposited using a sealant for an organic EL device, so that the light-emitting element 5 was sealed. Through the above steps, the light-emitting element 5 was obtained.

<<Fabrication of Light-Emitting Element 6>>

The light-emitting element 6 was fabricated through the same steps as those for the above-mentioned light-emitting element 5 except for the steps of forming the light-emitting layer 120 and the electron-transport layer 113.

As the light-emitting layer 120 in the light-emitting element 6, aiDBCzPA and 1,6mMemFLPAPrn were deposited by co-evaporation to a thickness of 25 nm such that the weight ratio of aiDBCzPA to 1,6mMemFLPAPrn was 1:0.01. Note that in the light-emitting layer 120, aiDBCzPA is a host material and 1,6mMemFLPAPrn is a guest material (fluorescent material).

Figure 52:
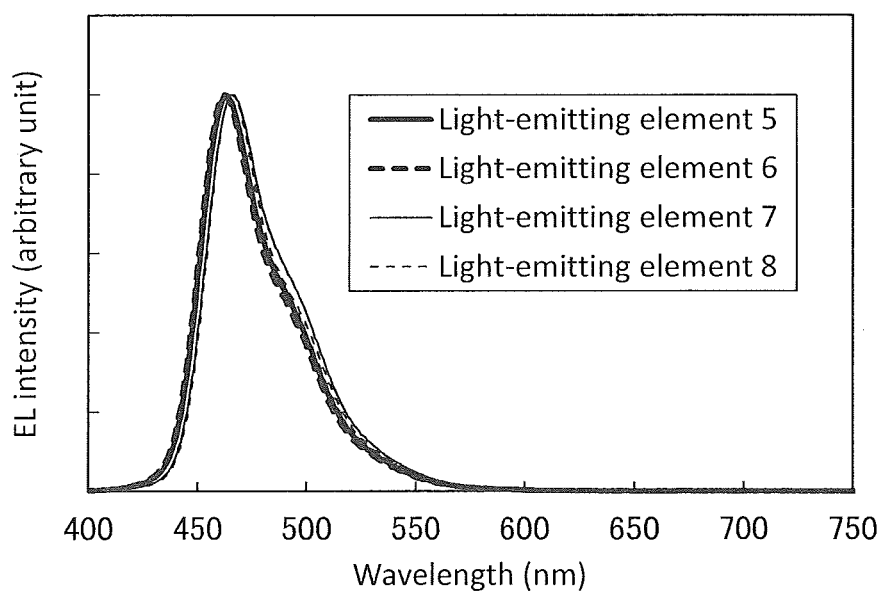
FIG. 52 is a graph showing electroluminescence spectra of light-emitting elements in Example.

As the electron-transport layer 113 in the light-emitting element 6, aiDBCzPA and BPhen were sequentially deposited by evaporation to thicknesses of 10 nm and 15 nm, respectively.

nal quantum efficiency-luminance characteristics thereof. FIG. 52 shows the electroluminescence spectra when a current with a current density of 2.5 mA/cm$^2$ was supplied to the light-emitting elements 5 to 8.

Table 4 shows the emission characteristics of the light-emitting elements at a luminance around 1000 cd/m$^2$.

TABLE 4

|  | Voltage (V) | Current density (mA/cm$^2$) | CIE chromaticity (x, y) | Luminance (cd/m$^2$) | Current efficiency (cd/A) | External quantum efficiency (%) |
|---|---|---|---|---|---|---|
| Light-emitting element 5 | 3.00 | 14.6 | (0.139, 0.143) | 1410 | 9.69 | 9.19 |
| Light-emitting element 6 | 3.00 | 9.18 | (0.138, 0.135) | 818 | 8.92 | 8.78 |
| Light-emitting element 7 | 3.00 | 14.5 | (0.138, 0.169) | 1700 | 11.7 | 9.97 |
| Light-emitting element 8 | 3.00 | 6.34 | (0.138, 0.165) | 689 | 10.9 | 9.43 |

<<Fabrication of Light-Emitting Element 7>>

The light-emitting element 7 for comparison was fabricated through the same steps as those for the above-mentioned light-emitting element 5 except for the steps of forming the light-emitting layer 120 and the electron-transport layer 113.

As the light-emitting layer 120 in the light-emitting element 7,7-[4-(10-phenyl-9-anthryl)phenyl]-7H-dibenzo[c,g]carbazole (abbreviation: cgDBCzPA) and 1,6mMemFLPAPrn were deposited by co-evaporation to a thickness of 25 nm such that the weight ratio of cgDBCzPA to 1,6mMemFLPAPrn was 1:0.03. Note that in the light-emitting layer 120, cgDBCzPA is a host material and 1,6mMemFLPAPrn is a guest material (fluorescent material).

As the electron-transport layer 113 in the light-emitting element 7, cgDBCzPA and BPhen were sequentially deposited by evaporation to thicknesses of 10 nm and 15 nm, respectively.

<<Fabrication of Light-Emitting Element 8>>

The light-emitting element 8 for comparison was fabricated through the same steps as those for the above-mentioned light-emitting element 5 except for the steps of forming the light-emitting layer 120 and the electron-transport layer 113.

As the light-emitting layer 120 in the light-emitting element 8,9-[4-(10-phenyl-9-anthryl)phenyl]-9H-carbazole (abbreviation: CzPA) and 1,6mMemFLPAPrn were deposited by co-evaporation to a thickness of 25 nm such that the weight ratio of CzPA to 1,6mMemFLPAPrn was 1:0.04. Note that in the light-emitting layer 120, CzPA is a host material and 1,6mMemFLPAPrn is a guest material (fluorescent material).

As the electron-transport layer 113 in the light-emitting element 8, CzPA and BPhen were sequentially deposited by evaporation to thicknesses of 10 nm and 15 nm, respectively.

<Emission Characteristics of Light-Emitting Elements>

Figure 49:
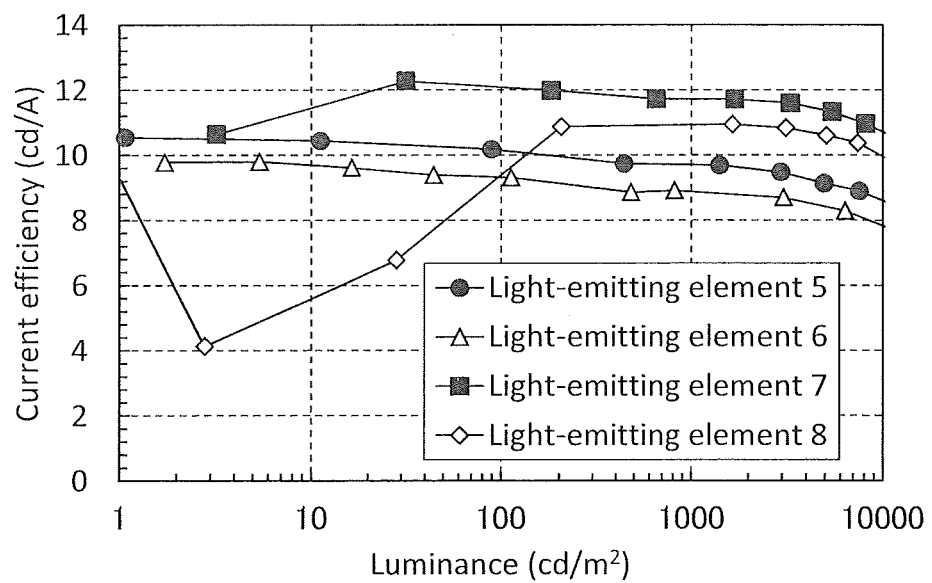
FIG. 49 shows current efficiency-luminance characteristics of light-emitting elements in Example.
Figure 50:
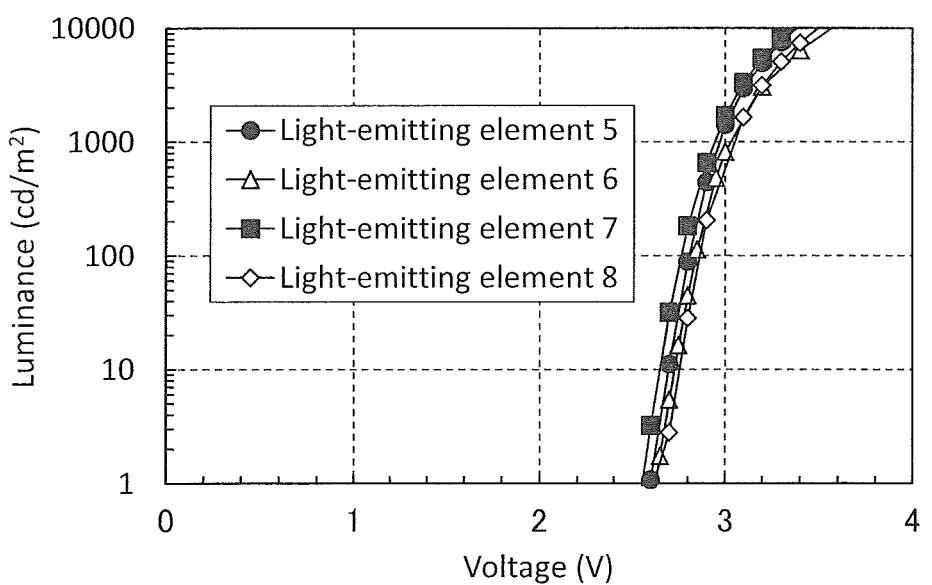
FIG. 50 is a graph showing luminance-voltage characteristics of light-emitting elements in Example.
Figure 51:
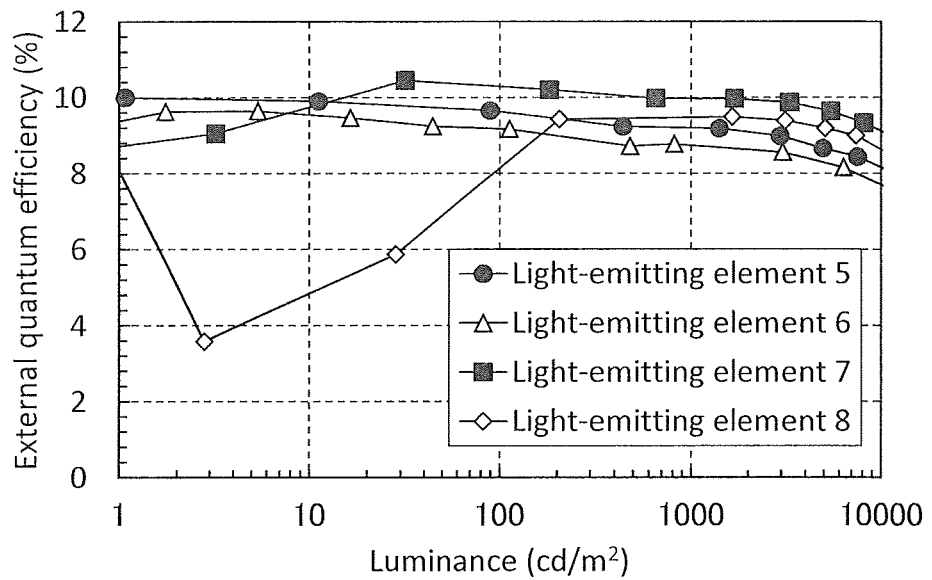
FIG. 51 is a graph showing external quantum efficiency-luminance characteristics of light-emitting elements in Example.

Next, the emission characteristics of the fabricated light-emitting elements 5 to 8 were measured. Note that the measurement was performed at room temperature (in an atmosphere maintained at 25° C.) as in Example 3. FIG. 49 shows the current efficiency-luminance characteristics of the light-emitting elements 5 to 8, FIG. 50 shows the luminance-voltage characteristics thereof, and FIG. 51 shows the exter- As shown in FIG. 52, the light-emitting elements 5 to 8 exhibited blue light emission derived from the guest material (1,6mMemFLPAPrn).

FIG. 49 to FIG. 52 and Table 4 show that the light-emitting elements 5 to 8, which include a fluorescent material as a light-emitting material, have a high current efficiency and a high external quantum efficiency.

The light-emitting elements 5 and 6 have a high current efficiency and a high external quantum efficiency although they exhibit deep blue emission with a chromaticity y of 0.143 and 0.135. That is, a light-emitting element including the dibenzocarbazole compound of one embodiment of the present invention as a host material can be suitably used for a light-emitting element that emits deep blue light.

Furthermore, the light-emitting elements 5 and 6 are driven at a low voltage and therefore consume low power. That is, a light-emitting element driven at a low voltage can be fabricated when the dibenzocarbazole compound of one embodiment of the present invention, which has a high carrier-transport property, is used as a host material and an electron-transport material.

Figure 53:
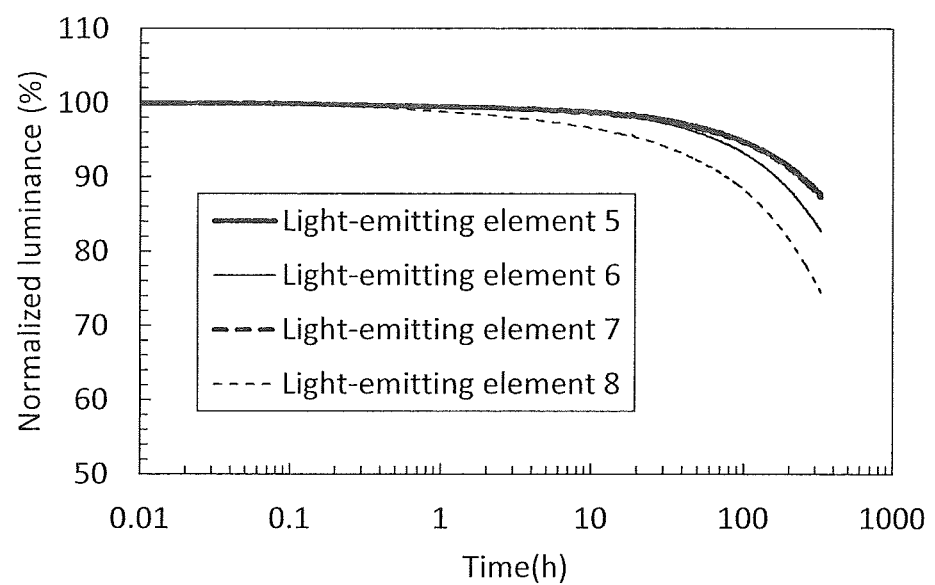
FIG. 53 is a graph showing test results of the driving lifetime of light-emitting elements of Example.

Next, the driving lifetime of the light-emitting elements 5 to 8 was measured. FIG. 53 shows the measurement results of the driving lifetime test. Note that the driving lifetime test was performed while the light-emitting elements 5 to 8 were continuously driven with a constant current density, which was set to 44.87 mA/cm$^2$ so that the light-emitting element 7 had an initial luminance of 5000 cd.

As shown in FIG. 53, the light-emitting elements 5 and 6, which include a blue fluorescent material as a light-emitting material, have a long driving lifetime. In addition, the light-emitting element 5 has a driving lifetime equal to that of the light-emitting element 7 and longer than that of the light-emitting element 8 although it emits deeper blue light than the light-emitting elements 7 and 8. The light-emitting element 6 has a longer driving lifetime than the light-emitting element 8 although it emits deeper blue light than the light-emitting element 8.

In the light-emitting element that emits blue light, a high emission energy needs to be confined in the light-emitting layer, which makes it difficult to obtain a long driving lifetime particularly in the light-emitting element that exhibits deep blue emission. However, the light-emitting element including the dibenzocarbazole compound of one embodiment of the present invention as the host material emits deep blue light while exhibiting a long driving lifetime. This indicates that the dibenzocarbazole compound of one embodiment of the present invention can be suitably used for light-emitting elements that emit deep blue light. Specifically, the dibenzocarbazole compound of one embodiment of the present invention can be suitably used for a light-emitting element that emits deep blue having a chromaticity y of 0.01 to 0.15.

As described above, the dibenzocarbazole compound of one embodiment of the present invention can be suitably used for a light-emitting element that emits deep blue light. With the dibenzocarbazole compound of one embodiment of the present invention, a light-emitting element with a high emission efficiency can be fabricated. With the dibenzocarbazole compound of one embodiment of the present invention, a light-emitting element with lower power consumption can be fabricated. With the dibenzocarbazole compound of one embodiment of the present invention, a light-emitting element with a long driving lifetime can be fabricated.

The structures described in this example can be used in combination with any of the structures described in the other embodiments as appropriate.

This application is based on Japanese Patent Application serial No. 2015-214392 filed with Japan Patent Office on Oct. 30, 2015, the entire contents of which are hereby incorporated by reference.

What is claimed is:

1. A dibenzocarbazole compound,
wherein an aryl group is bonded to a dibenzo[a,g]carbazole skeleton or a dibenzo[a,i] carbazole skeleton,
wherein the aryl group is an aryl group which has 14 to 30 carbon atoms and at least an anthracene skeleton, and
wherein the aryl group is bonded to a 7-position of the dibenzo[a,g]carbazole skeleton or a 11-position of the dibenzo[a,i]carbazole skeleton.

2. The dibenzocarbazole compound according to claim 1,
wherein the 7-position of the dibenzo[a,g]carbazole skeleton or the 11-position of the dibenzo[a,i]carbazole skeleton is bonded to the anthracene skeleton through a phenylene group.

3. The dibenzocarbazole compound according to claim 2,
wherein the 7-position of the dibenzo[a,g]carbazole skeleton or the 11-position of the dibenzo[a,i]carbazole skeleton is bonded to a 9-position of the anthracene skeleton through the phenylene group.

4. The dibenzocarbazole compound according to claim 1,
wherein the 7-position of the dibenzo[a,g]carbazole skeleton or the 11-position of the dibenzo[a,i]carbazole skeleton is bonded to a substituted or unsubstituted anthryl phenyl group having 20 to 30 carbon atoms.

5. The dibenzocarbazole compound according to claim 1,
wherein the 7-position of the dibenzo[a,g]carbazole skeleton or the 11-position of the dibenzo[a,i]carbazole skeleton is bonded to a substituted or unsubstituted (9-anthryl) phenyl group having 20 to 30 carbon atoms.

6. A dibenzocarbazole compound represented by General Formula (G1):

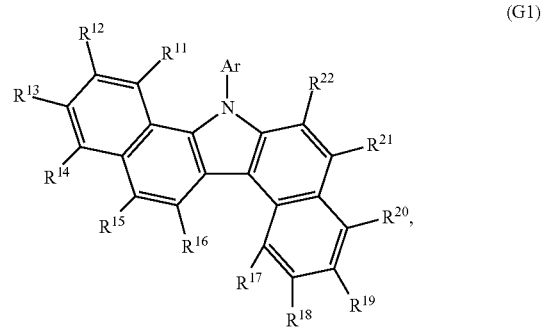

(G1)

wherein $R^{11}$ to $R^{22}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and Ar represents a substituted or unsubstituted aryl group which has 14 to 30 carbon atoms and at least an anthracene skeleton.

7. The dibenzocarbazole compound represented by General Formula (G1) according to claim 6, wherein the dibenzocarbazole compound is represented by General Formula (G2):

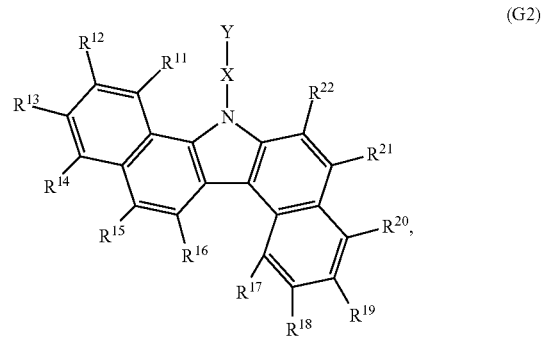

(G2)

wherein X represents a substituted or unsubstituted arylene group having 6 to 13 carbon atoms; and Y represents a substituted or unsubstituted anthryl group.

8. The dibenzocarbazole compound according to claim 7, wherein the total number of carbon atoms of X and Y is 20 to 30.

9. The dibenzocarbazole compound according to claim 7, wherein X represents a substituted or unsubstituted phenylene group.

10. The dibenzocarbazole compound represented by General Formula (G1) according to claim 6, wherein the dibenzocarbazole compound is represented by General Formula (G3):

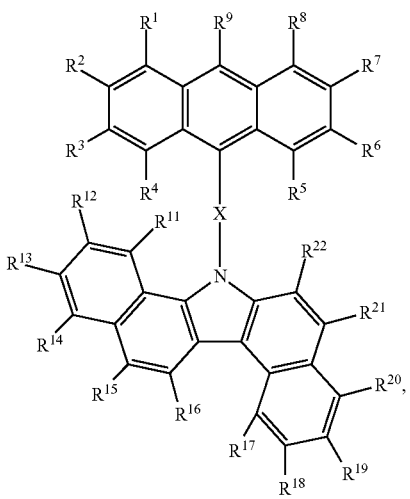

(G3)

wherein R¹ to R⁸ each independently represent hydrogen or an alkyl group having 1 to 4 carbon atoms; R⁹ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted arylene group having 6 to 13 carbon atoms.

11. The dibenzocarbazole compound according to claim 10, wherein the total number of carbon atoms of R¹ to R⁹ and X is 6 to 16.

12. The dibenzocarbazole compound according to claim 10, wherein X represents a substituted or unsubstituted phenylene group.

13. The dibenzocarbazole compound represented by General Formula (G1) according to claim 6, wherein the dibenzocarbazole compound is represented by General Formula (G4):

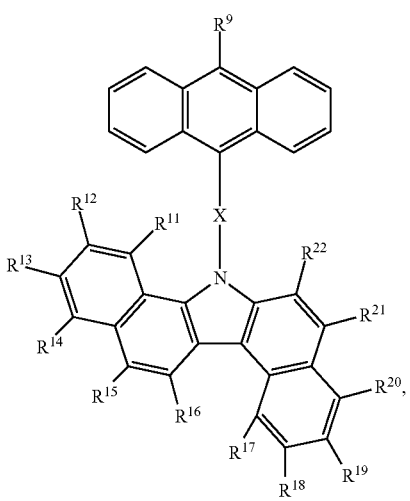

(G4)

wherein R⁹ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted phenylene group.

14. The dibenzocarbazole compound according to claim 13, wherein the total number of carbon atoms of R⁹ and X is 6 to 16.

15. The dibenzocarbazole compound represented by General Formula (G1) according to claim 6, wherein the dibenzocarbazole compound is represented by General Formula (G5):

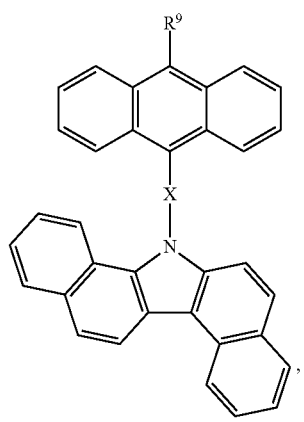

(G5)

wherein R⁹ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted phenylene group.

16. The dibenzocarbazole compound according to claim 15, wherein the total number of carbon atoms of R⁹ and X is 6 to 16.

17. The dibenzocarbazole compound represented by General Formula (G1) according to claim 6, wherein the dibenzocarbazole compound is represented by Structural Formula (100):

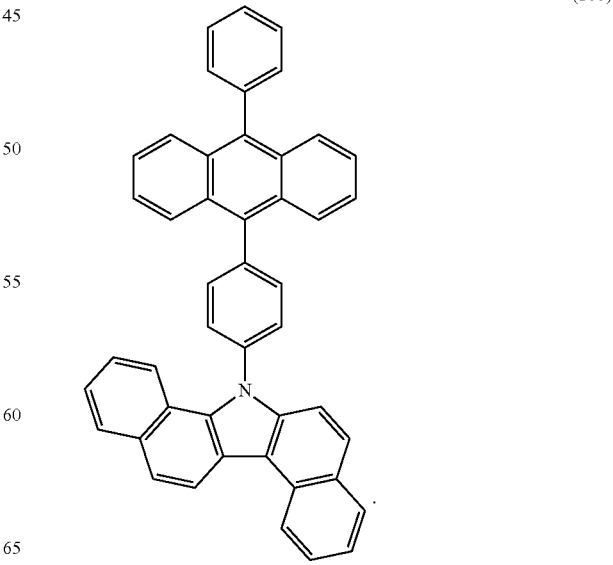

(100)

18. A dibenzocarbazole compound represented by General Formula (G6):

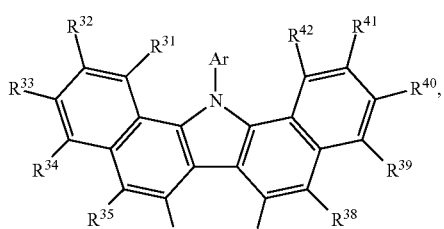

(G6)

wherein $R^{31}$ to $R^{42}$ each independently represent any of hydrogen, an alkyl group having 1 to 6 carbon atoms, a substituted or unsubstituted cycloalkyl group having 3 to 6 carbon atoms, and a substituted or unsubstituted aryl group having 6 to 13 carbon atoms; and Ar represents a substituted or unsubstituted aryl group which has 14 to 30 carbon atoms and at least an anthracene skeleton.

19. The dibenzocarbazole compound represented by General Formula (G6) according to claim 18, wherein the dibenzocarbazole compound is represented by General Formula (G7):

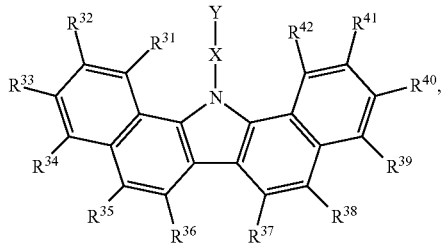

(G7)

wherein X represents a substituted or unsubstituted arylene group having 6 to 13 carbon atoms; and Y represents a substituted or unsubstituted anthryl group.

20. The dibenzocarbazole compound according to claim 19, wherein the total number of carbon atoms of X and Y is 20 to 30.

21. The dibenzocarbazole compound according to claim 19, wherein X represents a substituted or unsubstituted phenylene group.

22. The dibenzocarbazole compound represented by General Formula (G6) according to claim 18, wherein the dibenzocarbazole compound is represented by General Formula (G8):

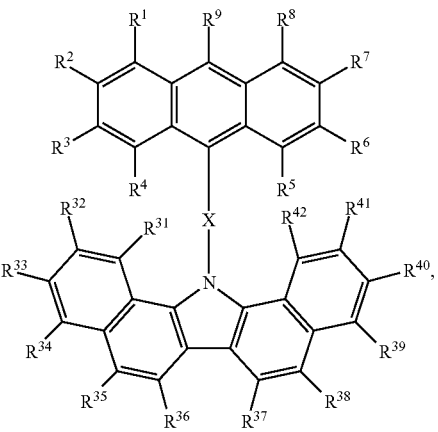

(G8)

wherein $R^1$ to $R^8$ each independently represent hydrogen or an alkyl group having 1 to 4 carbon atoms; $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted arylene group having 6 to 13 carbon atoms.

23. The dibenzocarbazole compound according to claim 22, wherein the total number of carbon atoms of $R^1$ to $R^9$ and X is 6 to 16.

24. The dibenzocarbazole compound according to claim 22, wherein X represents a substituted or unsubstituted phenylene group.

25. The dibenzocarbazole compound represented by General Formula (G6) according to claim 18, wherein the dibenzocarbazole compound is represented by General Formula (G9):

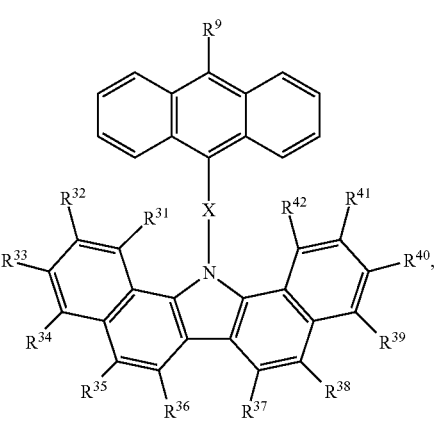

(G9)

wherein $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted phenylene group.

26. The dibenzocarbazole compound according to claim 25, wherein the total number of carbon atoms of $R^9$ and X is 6 to 16.

27. The dibenzocarbazole compound represented by General Formula (G6) according to claim 18, wherein the dibenzocarbazole compound is represented by General Formula (G10):

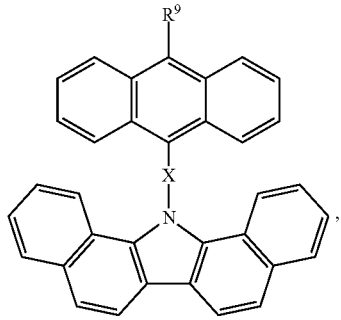

(G10)

wherein $R^9$ represents any of hydrogen, an alkyl group having 1 to 6 carbon atoms, a substituted or unsubstituted cycloalkyl group having 3 to 6 carbon atoms, and a substituted or unsubstituted aryl group having 6 to 10 carbon atoms; and X represents a substituted or unsubstituted phenylene group.

28. The dibenzocarbazole compound according to claim 27, wherein the total number of carbon atoms of $R^9$ and X is 6 to 16.

29. The dibenzocarbazole compound represented by General Formula (G6) according to claim 18, wherein the dibenzocarbazole compound is represented by Structural Formula (136):

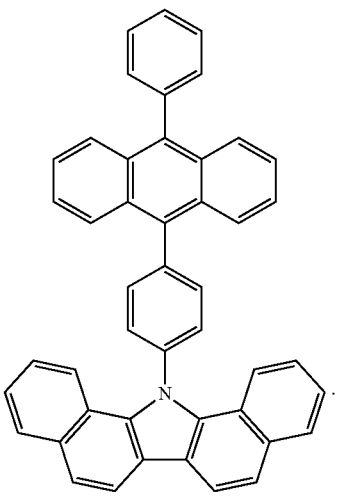

(136)

* * * * *